US012648855B2

(12) United States Patent
Greenhalgh et al.

(10) Patent No.: US 12,648,855 B2
(45) Date of Patent: Jun. 9, 2026

(54) JOINT STABILIZATION SYSTEM

(71) Applicant: SurGenTec, LLC, Boca Raton, FL (US)

(72) Inventors: Travis Greenhalgh, Boca Raton, FL (US); Andrew Shoup, Boca Raton, FL (US); John Souza, Monroe, NC (US); Bryan Hellriegel, Boynton Beach, FL (US); Richard Sharp, Tamarac, FL (US)

(73) Assignee: SurGenTec, LLC, Boca Raton, FL (US)

( * ) Notice: Subject to any disclaimer, the term of this patent is extended or adjusted under 35 U.S.C. 154(b) by 0 days.

(21) Appl. No.: 18/905,921

(22) Filed: Oct. 3, 2024

(65) Prior Publication Data

US 2025/0025310 A1      Jan. 23, 2025

Related U.S. Application Data

(60) Continuation-in-part of application No. 18/339,150, filed on Jun. 21, 2023, now Pat. No. 12,186,195, which is a division of application No. 18/095,981, filed on Jan. 11, 2023, now Pat. No. 11,951,010, which is a continuation of application No. 18/079,710, filed on Dec. 12, 2022.

(60) Provisional application No. 63/562,650, filed on Mar. 7, 2024, provisional application No. 63/587,666, filed on Oct. 3, 2023, provisional application No. 63/342,518, filed on May 16, 2022, provisional application No. 63/288,495, filed on Dec. 10, 2021.

(51) Int. Cl.
*A61F 2/30*      (2006.01)
*A61F 2/46*      (2006.01)

(52) U.S. Cl.
CPC ..................... *A61F 2/30988* (2013.01); *A61F 2002/30299* (2013.01); *A61F 2002/30433* (2013.01); *A61F 2002/30518* (2013.01); *A61F 2002/30593* (2013.01); *A61F 2002/30845* (2013.01); *A61F 2002/3085* (2013.01); *A61F 2002/3092* (2013.01); *A61F 2002/30995* (2013.01); *A61F 2002/4627* (2013.01)

(58) Field of Classification Search
CPC .... A61F 2002/30995; A61F 2002/3085; A61F 2002/30299

See application file for complete search history.

(56) References Cited

U.S. PATENT DOCUMENTS

| | | | |
|---|---|---|---|
| 6,517,542 | B1 | 2/2003 | Papay |
| 7,648,509 | B2 | 1/2010 | Stark |
| 8,062,270 | B2 | 11/2011 | Sweeney |

(Continued)

FOREIGN PATENT DOCUMENTS

WO      WO 00/62684      10/2000

*Primary Examiner* — Javier G Blanco
(74) *Attorney, Agent, or Firm* — Knobbe, Martens, Olson & Bear, LLP

(57) ABSTRACT

A sacroiliac joint implant system includes a primary implant configured to be received in a sacroiliac joint of a patient and a secondary implant configured to couple with the primary implant. The primary implant includes a body extending from a proximal end to a distal end and a plurality of threads extending from the body. The secondary implant includes a first anchor configured to anchor within a sacrum of the patient and a second anchor configured to anchor within an ilium of the patient.

19 Claims, 153 Drawing Sheets

(56) References Cited

U.S. PATENT DOCUMENTS

| | | | |
|---|---|---|---|
| 8,267,966 | B2 | 9/2012 | McCormack et al. |
| 8,361,152 | B2 | 1/2013 | McCormack et al. |
| 8,425,558 | B2 | 4/2013 | McCormack et al. |
| 8,512,347 | B2 | 8/2013 | McCormack et al. |
| 8,623,054 | B2 | 1/2014 | McCormack et al. |
| 8,753,347 | B2 | 6/2014 | McCormack et al. |
| 8,753,377 | B2 | 6/2014 | McCormack et al. |
| 8,821,506 | B2 | 9/2014 | Mitchell |
| 8,828,062 | B2 | 9/2014 | McCormack et al. |
| 8,834,472 | B2 | 9/2014 | McCormack et al. |
| 9,011,492 | B2 | 4/2015 | McCormack et al. |
| 9,333,086 | B2 | 5/2016 | McCormack et al. |
| 9,381,049 | B2 | 7/2016 | McCormack et al. |
| 9,492,284 | B2 | 11/2016 | Ginn et al. |
| 9,603,644 | B2 | 3/2017 | Sweeney |
| 9,615,856 | B2 | 4/2017 | Arnett et al. |
| 9,622,791 | B2 | 4/2017 | McCormack et al. |
| 9,622,874 | B2 | 4/2017 | McCormack et al. |
| 9,629,665 | B2 | 4/2017 | McCormack et al. |
| 9,668,781 | B2 | 6/2017 | Stark |
| 9,943,342 | B2 | 4/2018 | Tanaka et al. |
| 10,039,649 | B2 | 8/2018 | McCormack et al. |
| 10,149,673 | B2 | 12/2018 | McCormack et al. |
| 10,172,721 | B2 | 1/2019 | McCormack et al. |
| 10,226,285 | B2 | 3/2019 | McCormack et al. |
| 10,238,501 | B2 | 3/2019 | McCormack et al. |
| 10,456,175 | B2 | 10/2019 | McCormack et al. |
| 10,568,666 | B2 | 2/2020 | McCormack et al. |
| 10,588,672 | B2 | 3/2020 | McCormack et al. |
| 10,596,003 | B2 | 3/2020 | Donner et al. |
| 10,646,236 | B2 | 5/2020 | Donner et al. |
| 10,653,458 | B2 | 5/2020 | Tanaka et al. |
| 10,653,535 | B2 | 5/2020 | McCormack et al. |
| 10,682,243 | B2 | 6/2020 | Phan et al. |
| 10,856,922 | B2 | 12/2020 | Loke |
| 10,874,447 | B2 | 12/2020 | Tanaka et al. |
| 11,045,231 | B2 | 6/2021 | Stark |
| 11,058,553 | B2 | 7/2021 | McCormack et al. |
| 11,065,039 | B2 | 7/2021 | McCormack et al. |
| 11,141,144 | B2 | 10/2021 | McCormack et al. |
| 11,147,675 | B2 | 10/2021 | Ginn et al. |
| 11,224,521 | B2 | 1/2022 | McCormack et al. |
| 11,272,964 | B2 | 3/2022 | McCormack et al. |
| 11,344,339 | B2 | 5/2022 | McCormack et al. |
| 11,571,245 | B2 | 2/2023 | Stuart |
| 11,648,128 | B2 | 5/2023 | Tanaka et al. |
| 11,813,172 | B2 | 11/2023 | Tanaka et al. |
| 11,890,038 | B2 | 2/2024 | McCormack et al. |
| 11,951,010 | B2 | 4/2024 | Greenhalgh |
| 12,004,781 | B2 | 6/2024 | McCormack et al. |
| 12,186,195 | B2 | 1/2025 | Greenhalgh |
| 2001/0031968 | A1 | 10/2001 | Dorchak |
| 2002/0072805 | A1 | 6/2002 | Sullivan |
| 2003/0018391 | A1 | 1/2003 | Evans |
| 2004/0225292 | A1 | 11/2004 | Sasso |
| 2005/0273168 | A1* | 12/2005 | Crozet ................. A61B 17/861 623/17.11 |
| 2008/0234758 | A1 | 9/2008 | Fisher |
| 2009/0138053 | A1 | 5/2009 | Assell |
| 2009/0192551 | A1 | 7/2009 | Cianfrani |
| 2010/0030135 | A1 | 2/2010 | Mitchell |
| 2011/0313462 | A1 | 12/2011 | Alleyne |
| 2012/0116454 | A1 | 5/2012 | Edidin |
| 2013/0013070 | A1 | 1/2013 | McCormack et al. |
| 2013/0110183 | A1* | 5/2013 | Duggal ................ A61B 17/809 606/328 |
| 2013/0123863 | A1* | 5/2013 | Hollis .................... A61B 17/68 606/328 |
| 2013/0144343 | A1* | 6/2013 | Arnett ................ A61B 17/7055 606/279 |
| 2013/0144353 | A1 | 6/2013 | Arnett |
| 2014/0046381 | A1 | 2/2014 | Asfora |
| 2016/0100870 | A1 | 4/2016 | Lavigne et al. |
| 2016/0310188 | A1 | 10/2016 | Marino |
| 2016/0361096 | A1 | 12/2016 | van der Pol |
| 2018/0280067 | A1 | 10/2018 | Bjork |
| 2018/0325570 | A1* | 11/2018 | Kuntz .................... A61B 17/70 |
| 2019/0083271 | A1 | 3/2019 | Donner et al. |
| 2020/0121373 | A1 | 4/2020 | Biedermann |
| 2020/0268518 | A1 | 8/2020 | Suh et al. |
| 2023/0038914 | A1 | 2/2023 | Muller |
| 2023/0039837 | A1 | 2/2023 | Greenhalgh |
| 2023/0048409 | A1* | 2/2023 | Mangone ........... A61B 17/8014 |
| 2023/0173146 | A1 | 6/2023 | Brubaker et al. |
| 2023/0181322 | A1 | 6/2023 | Greenhalgh |

* cited by examiner

330

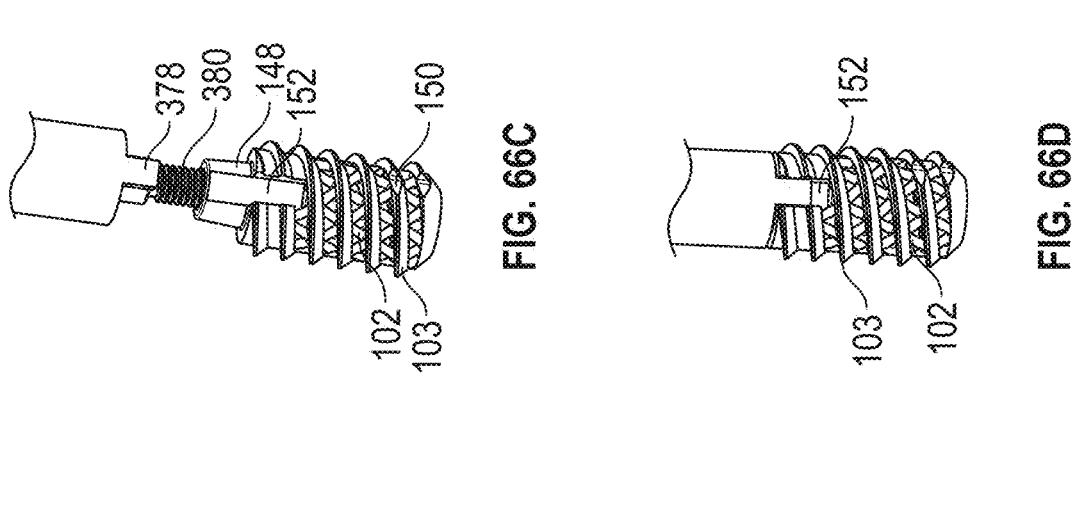
FIG. 66C
FIG. 66D
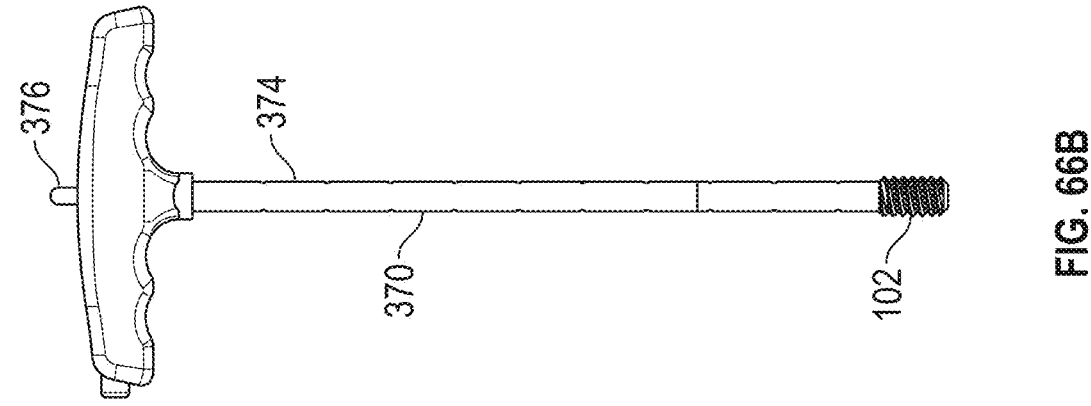
FIG. 66B
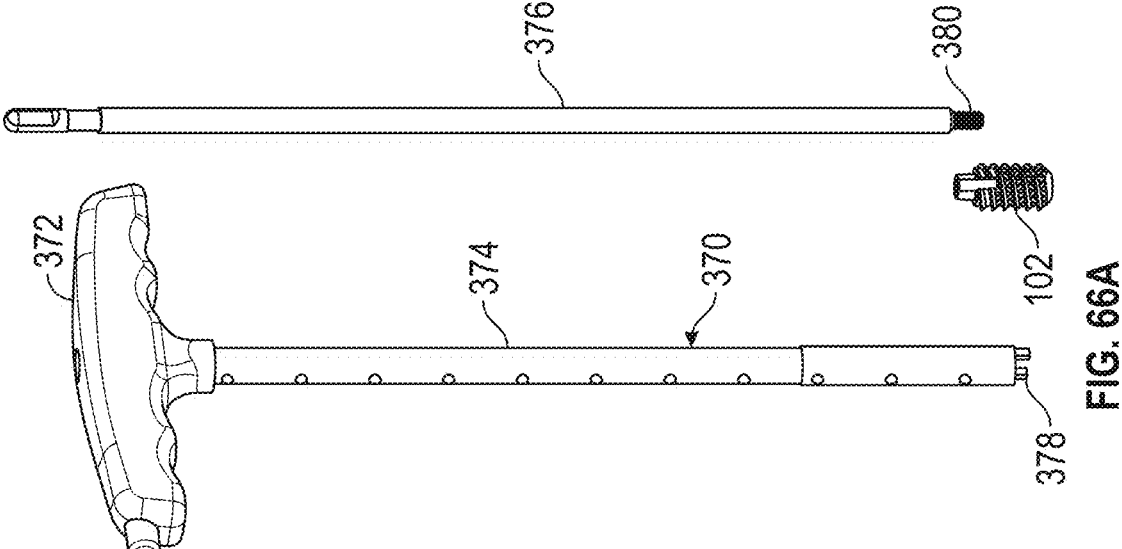
FIG. 66A

370

330

102

372

374

376

330

102

376

372

106                         106

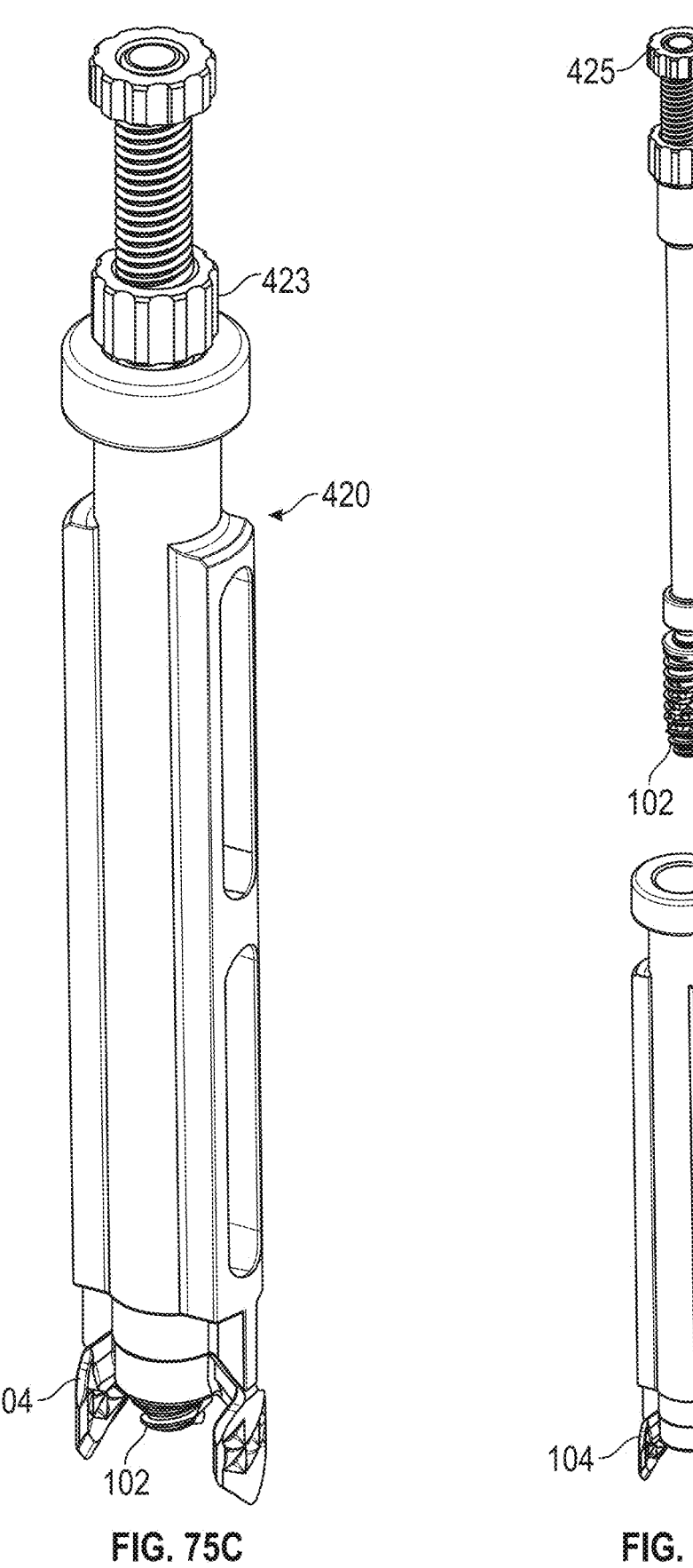
FIG. 75C                    FIG. 75D

330

331

331

330

335

104

JOINT STABILIZATION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims priority benefit of U.S. Provisional Application Ser. No. 63/562,650, entitled JOINT STABILIZATION SYS-TEM, filed Mar. 7, 2024, and U.S. Provisional Application Ser. No. 63/587,666, entitled SACROILIAC JOINT STA-BILIZATION SYSTEM, filed Oct. 3, 2023, and this appli-cation is a continuation-in-part of U.S. application Ser. No. 18/339,150, entitled SACROILIAC JOINT STABILIZA-TION SYSTEM, filed Jun. 21, 2023, which is a divisional of U.S. application Ser. No. 18/095,981, entitled SACRO-ILIAC JOINT STABILIZATION SYSTEM, filed Jan. 11, 2023, which is a continuation of U.S. application Ser. No. 18/079,710, entitled SACROILIAC JOINT STABILIZA-TION SYSTEM, filed Dec. 12, 2022, which claims priority benefit of U.S. Provisional Application Ser. No. 63/288,495, entitled SACROILIAC JOINT STABILIZATION SYS-TEM, filed Dec. 10, 2021, and U.S. Provisional Application Ser. No. 63/342,518, entitled SACROILIAC JOINT STA-BILIZATION SYSTEM, filed May 16, 2022, the entire contents of which are incorporated by reference herein in their entirety and for all purposes.

BACKGROUND

Field

The present application relates to orthopedic surgery in general, and more particularly, to methods, systems, and apparatuses for joint stabilization.

Description of the Related Art

The sacroiliac ("SI") joint is formed between the ilium and sacrum, connecting the spine and hips. The SI joints are considered true diarthrodial joints which contain hyaline cartilage on the sacral side and fibrocartilage on the iliac side. The two SI joints provide stability and support while also playing a role in absorbing impact with movement. The joint is re-enforced with thick ligaments surrounding it, some of which extend across the joint in the back of the pelvis. Too much movement may cause the joint to become unstable and lead to pain. Too little movement can cause muscle tension or pain and limit mobility. Inflammation of the joint can lead to chronic pain and the need for treatments ranging from conservative care to surgery.

5

Figure 47A:
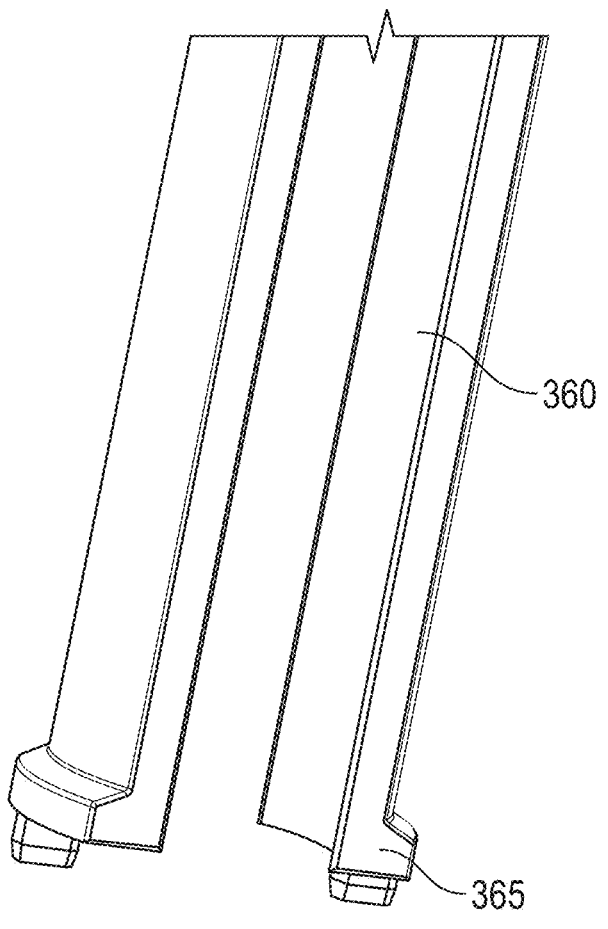
FIG. 47A illustrates an enlarged perspective view of an end of an implant inserter and implant of an implant system.
Figure 47A:
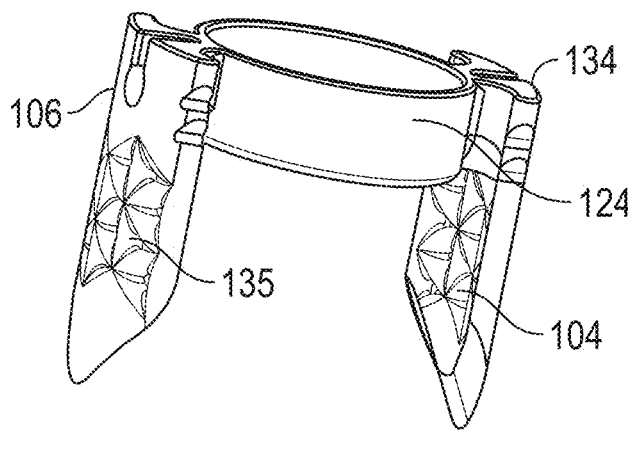
Figures 47B, 47C:
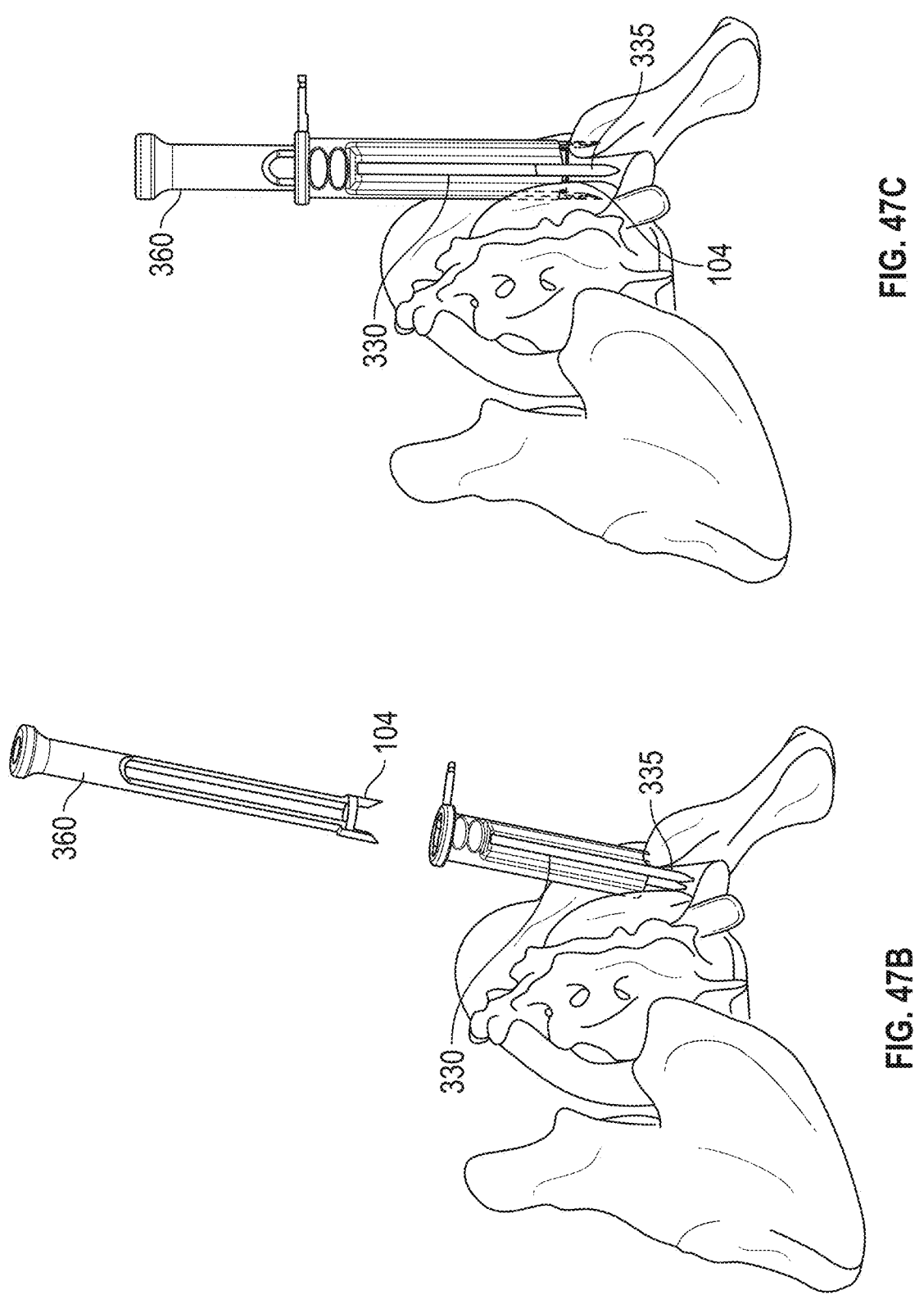

FIG. 47B illustrates a perspective view of a guide and an implant inserter as part of an embodiment of an implant system inserted into the SI joint.

FIG. 47C illustrates a perspective view of an implant inserter inserted into a guide within the SI joint.

Figure 48:
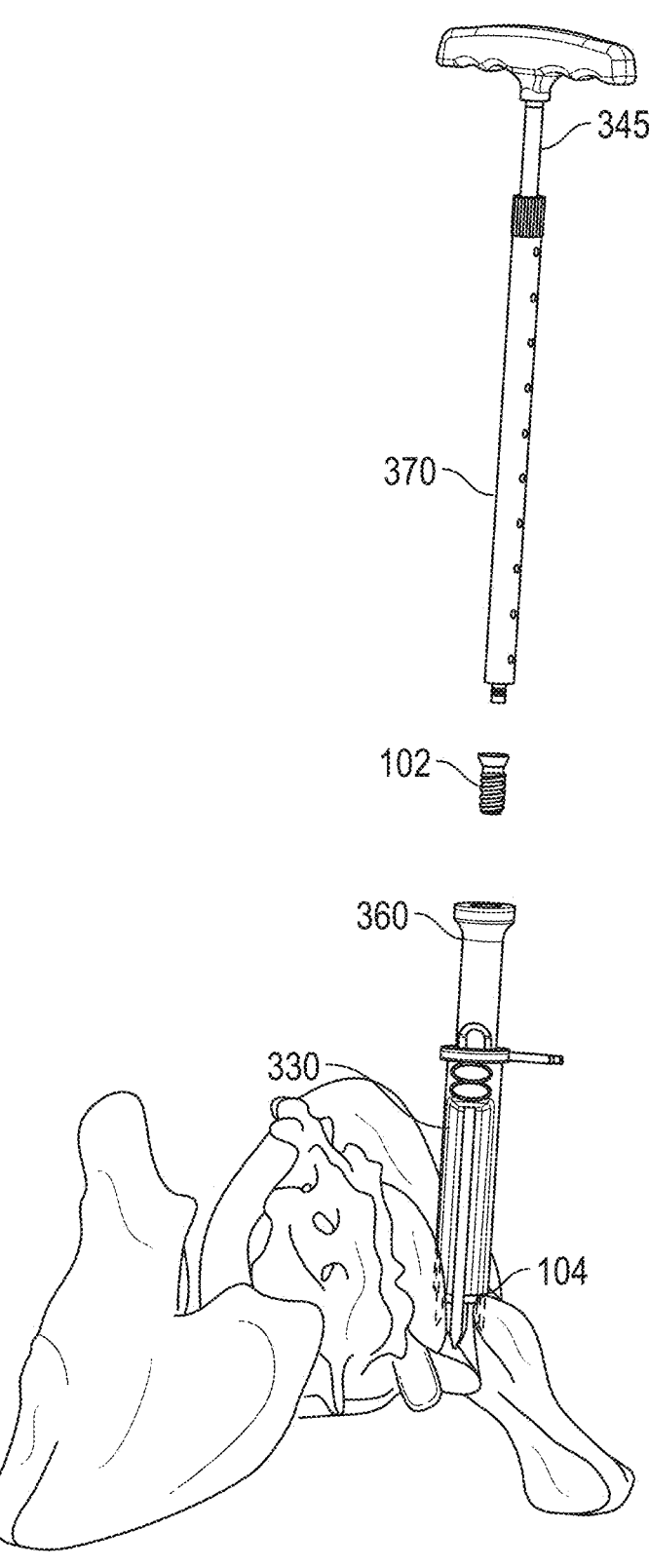

FIG. 48 illustrates a perspective view of a handle, guide, and inserter of an embodiment of an implant system.

Figure 49:
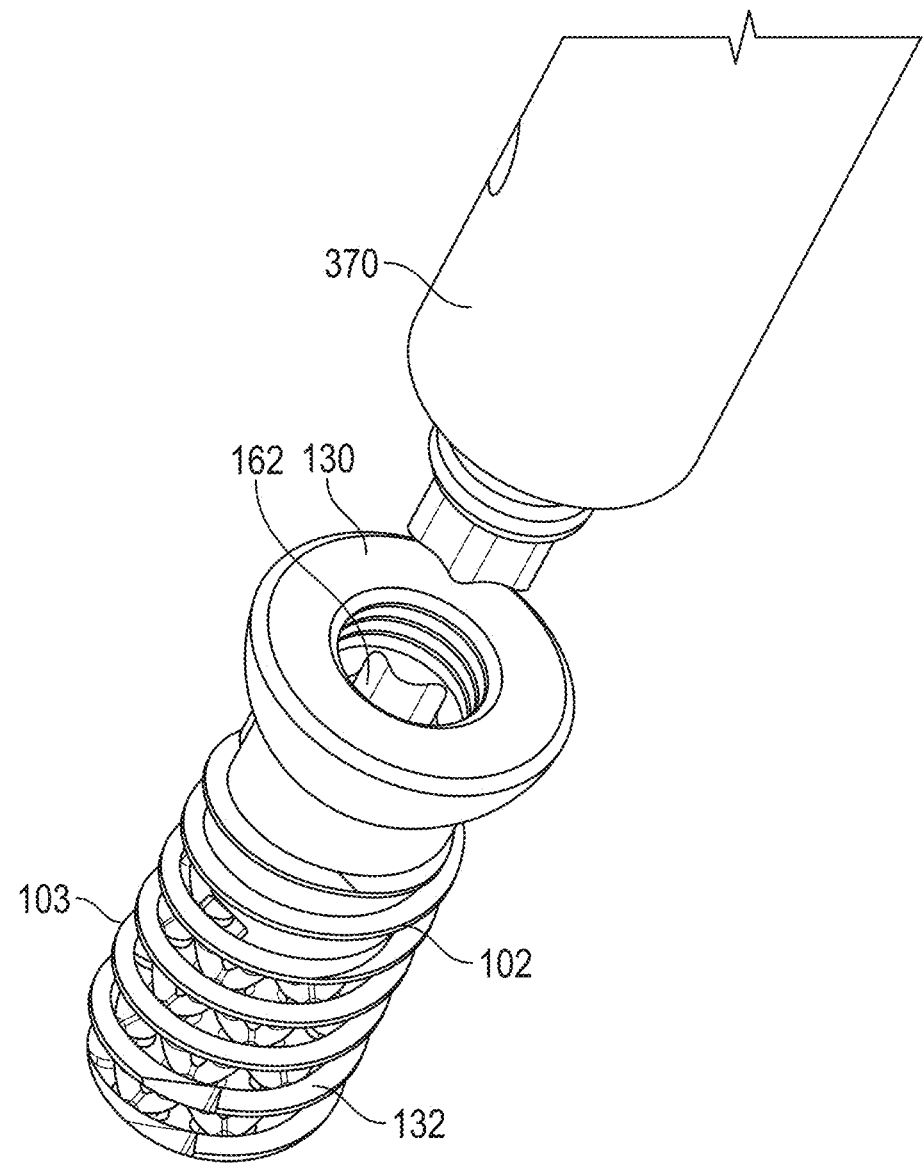

FIG. 49 illustrates an enlarged perspective view of an embodiment of the end of inserter next to an implant.

Figure 50:
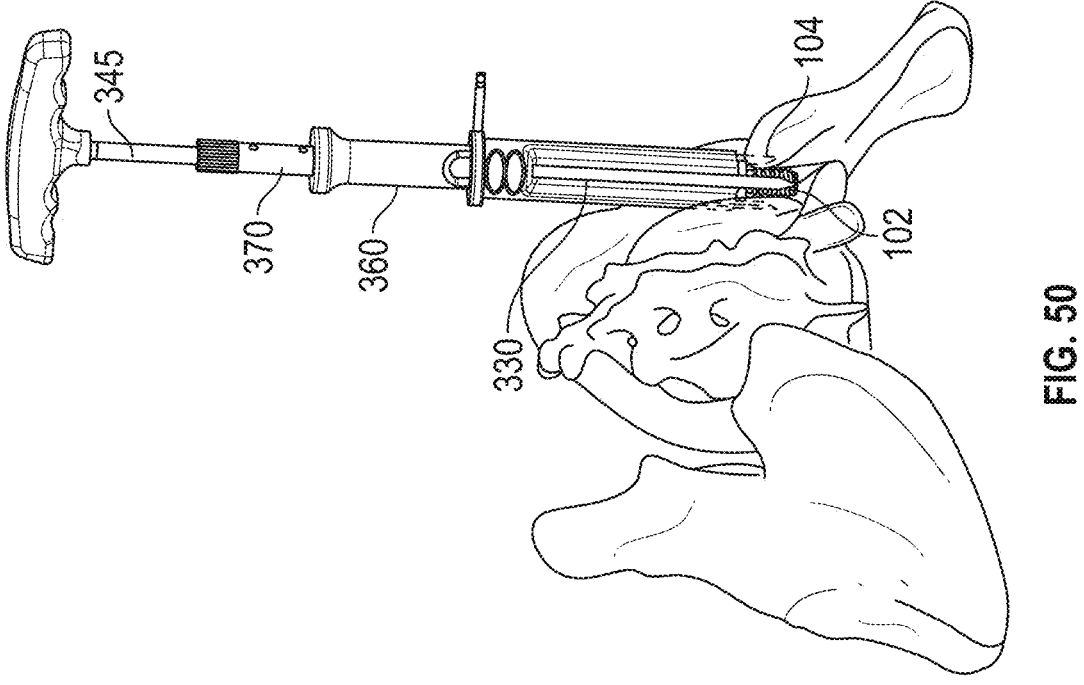

FIG. 50 illustrates a perspective view of one embodiment of an implant tool including a drill tool, implant inserter, dilator, and guide as part of an implant system.

Figure 51:
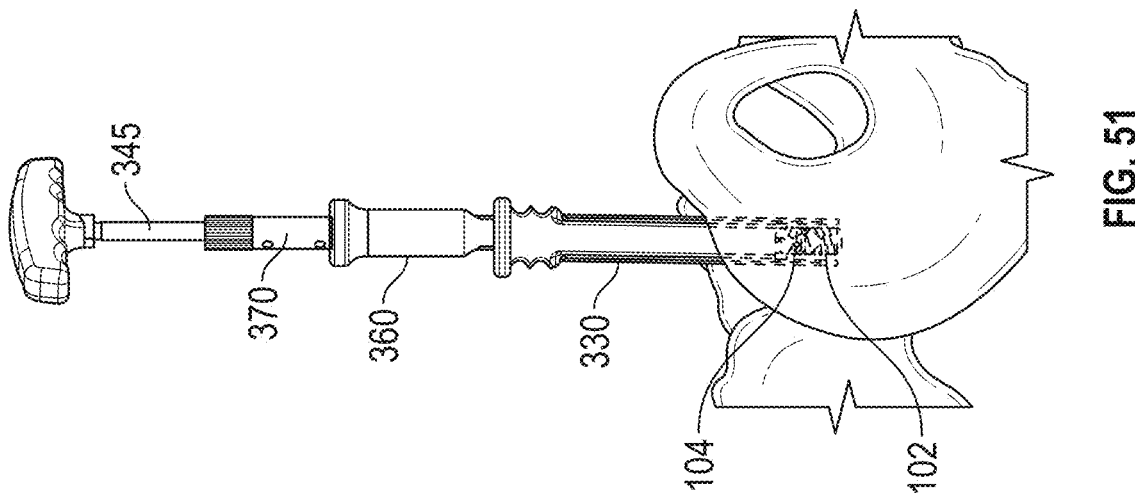

FIG. 51 illustrates an alternative perspective view of one embodiment of an implant tool including a drill tool, implant inserter, dilator, and guide as part of an implant system.

Figures 52, 53:
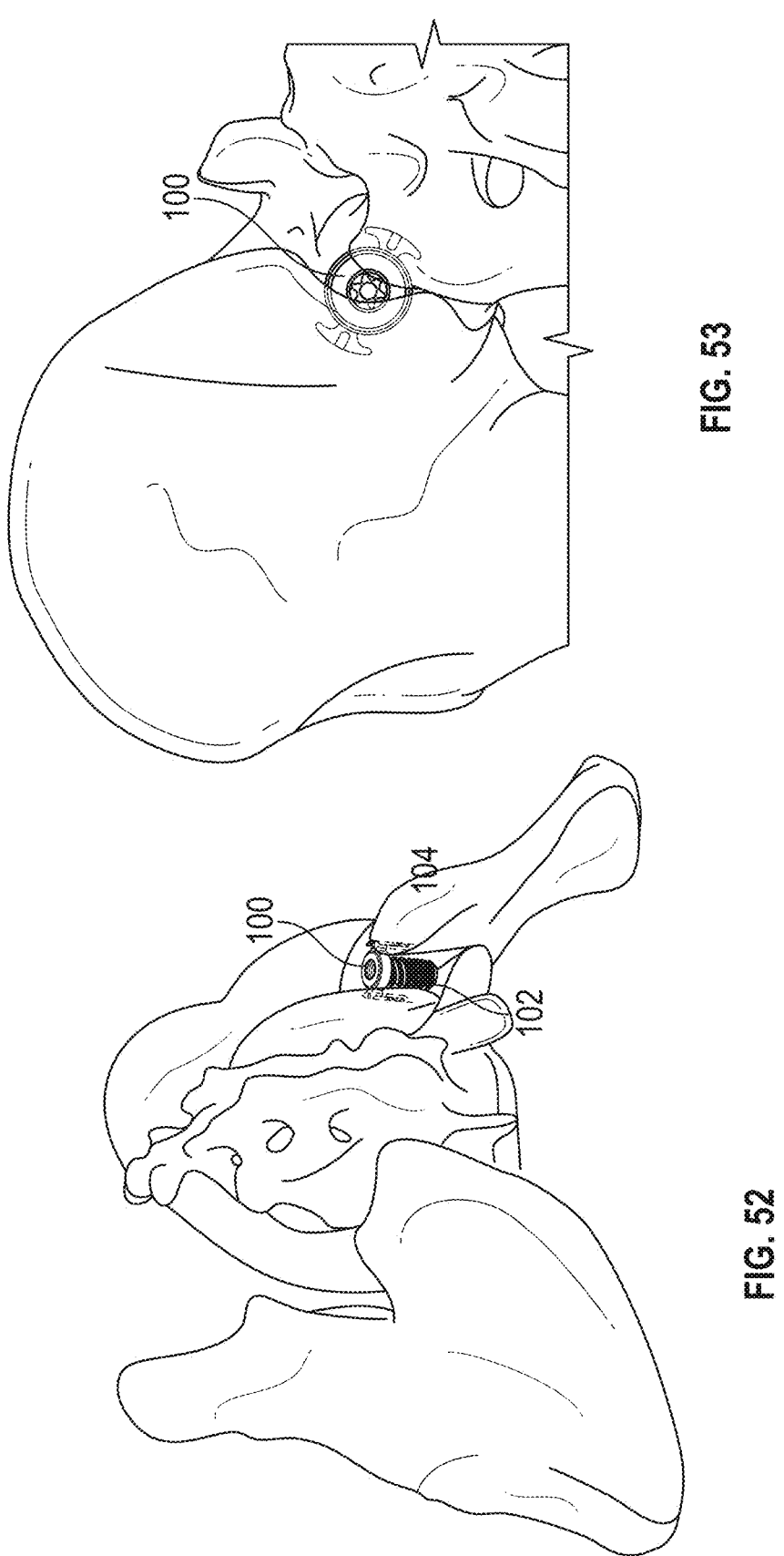

FIG. 52 illustrates a perspective view of an embodiment of the implant system within the SI joint.

FIG. 53 illustrates an alternative view of an embodiment of the implant system within the SI joint.

Figure 54B:
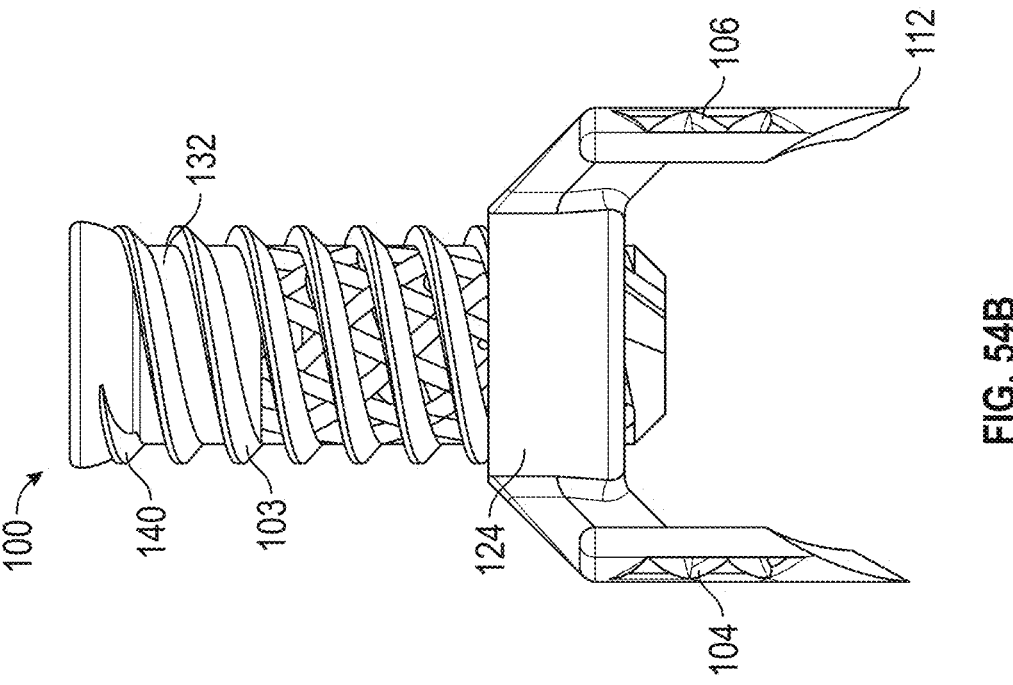
Figure 54A:
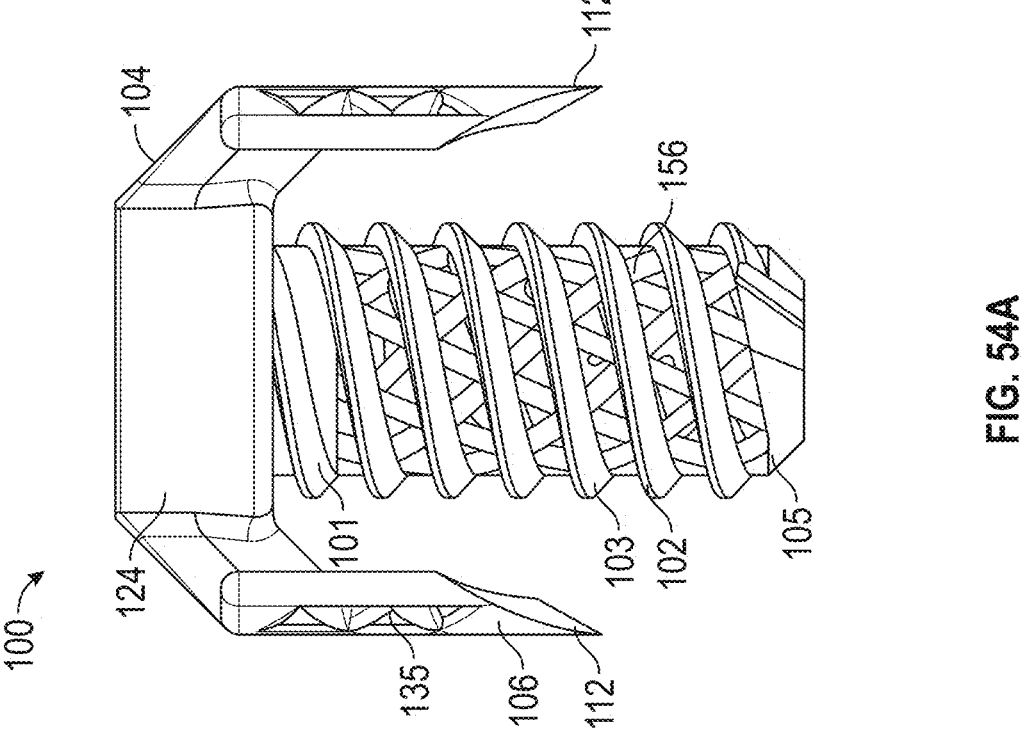

FIG. 54A illustrates a side view of an embodiment of a joint implant.

FIG. 54B illustrates a side view of an alternative configuration of the joint implant from FIG. 54A.

Figures 54C, 54D:
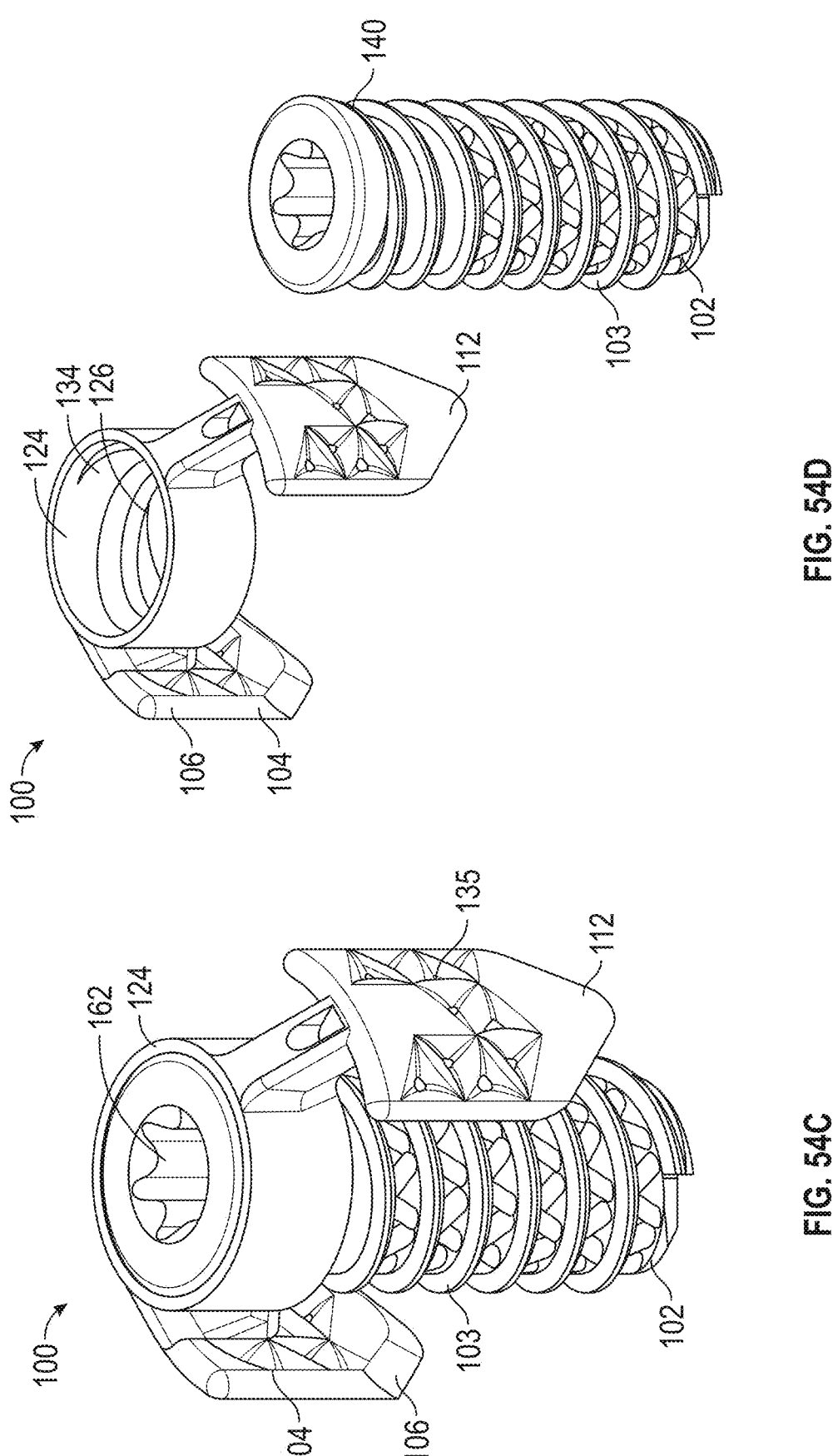

FIG. 54C illustrates a perspective view of the joint implant from FIG. 54A.

FIG. 54D illustrates an exploded view of the joint implant from FIG. 54D.

Figure 54E:
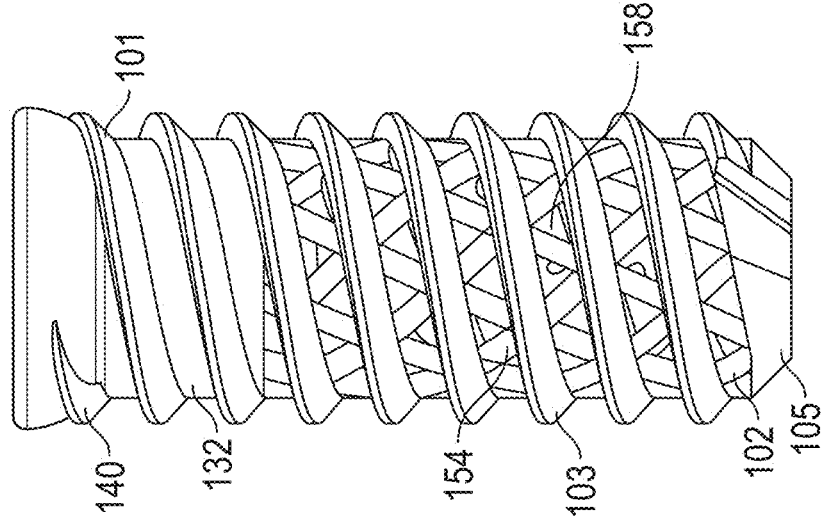
Figure 54E:
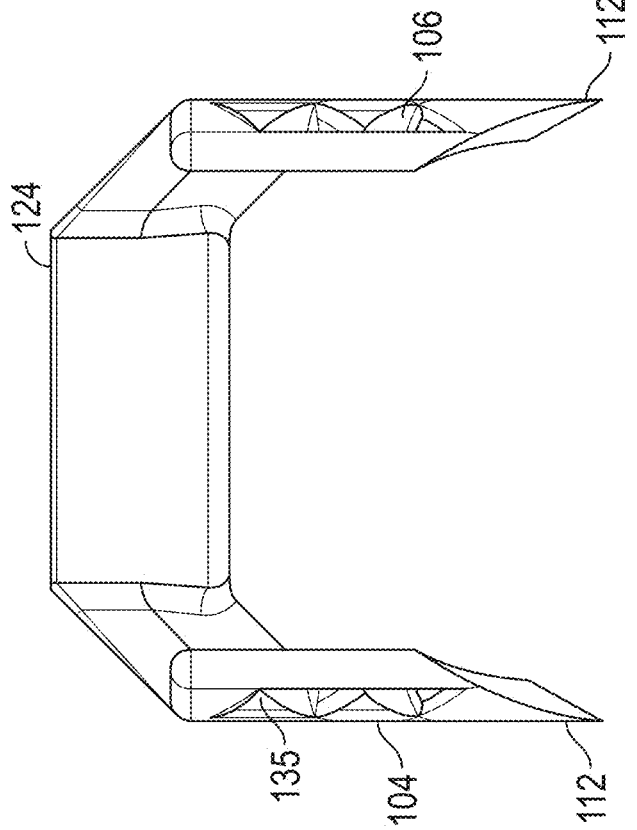

FIG. 54E illustrates a side view of the components of the joint implant from FIG. 54D.

Figure 54G:
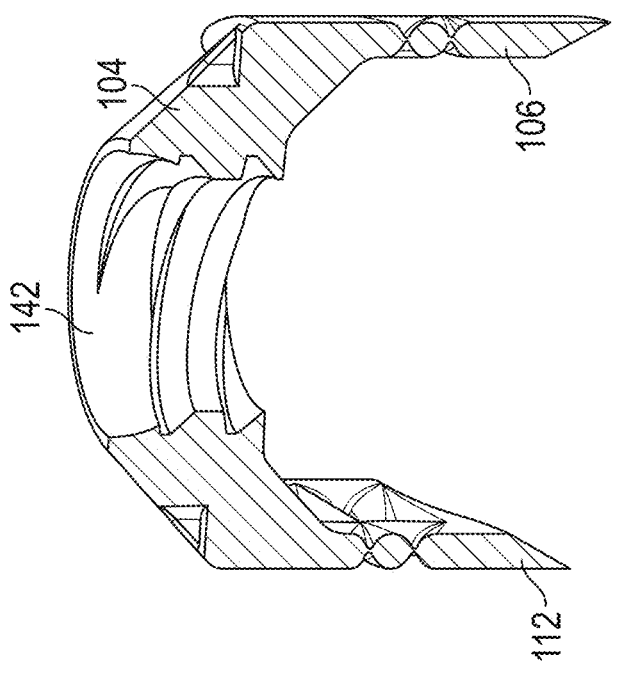
Figure 54G:
Figure 54F:
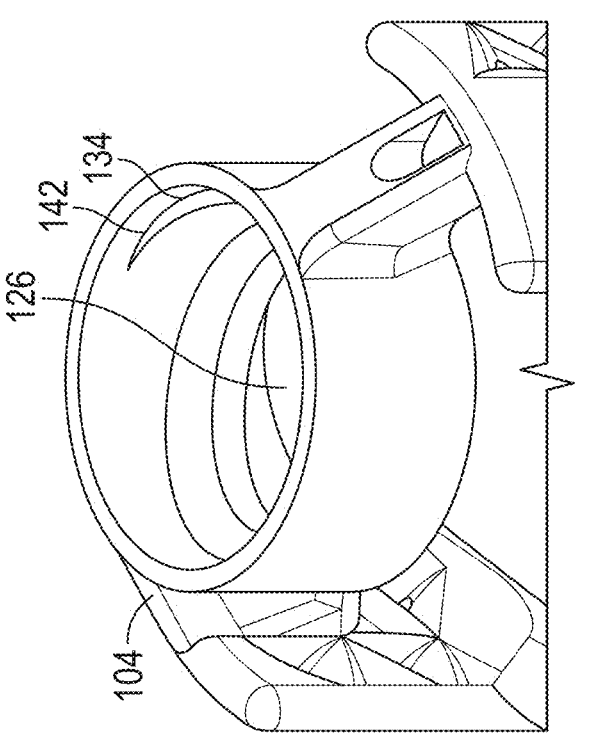

FIG. 54F illustrates an enlarged perspective view of the secondary implant from FIG. 54D.

FIG. 54G illustrates a cross sectional view of the secondary implant from FIG. 54D.

Figure 55:
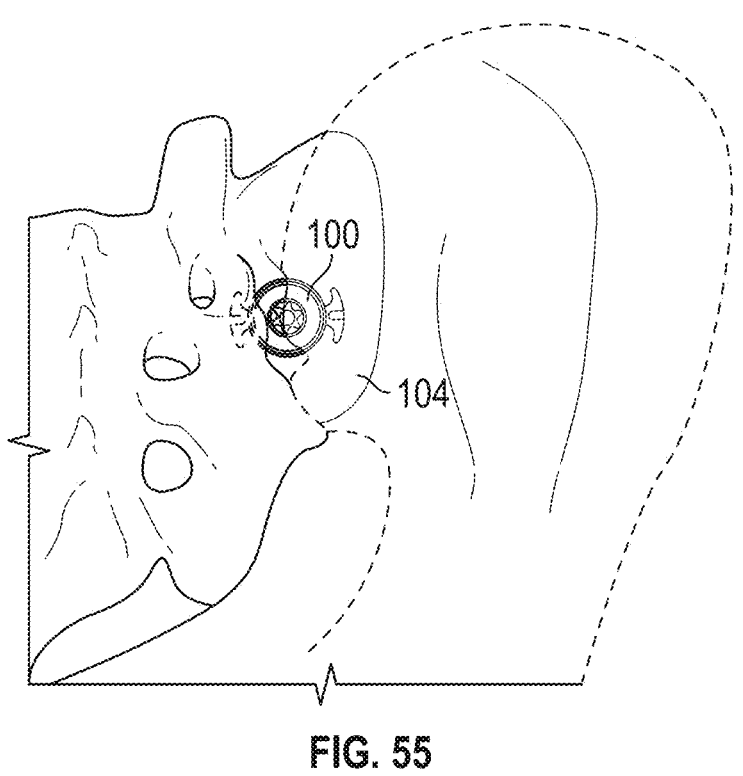

FIG. 55 illustrates a top view of an embodiment of the implant within the SI joint.

Figure 56:
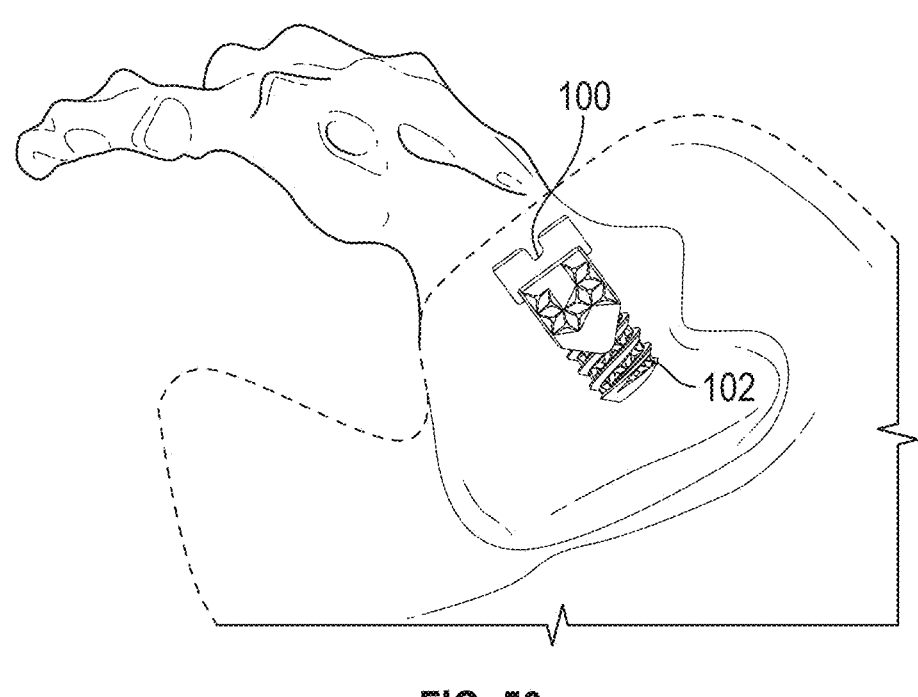

FIG. 56 illustrates a side view of an embodiment of the implant within the SI joint.

Figure 57:
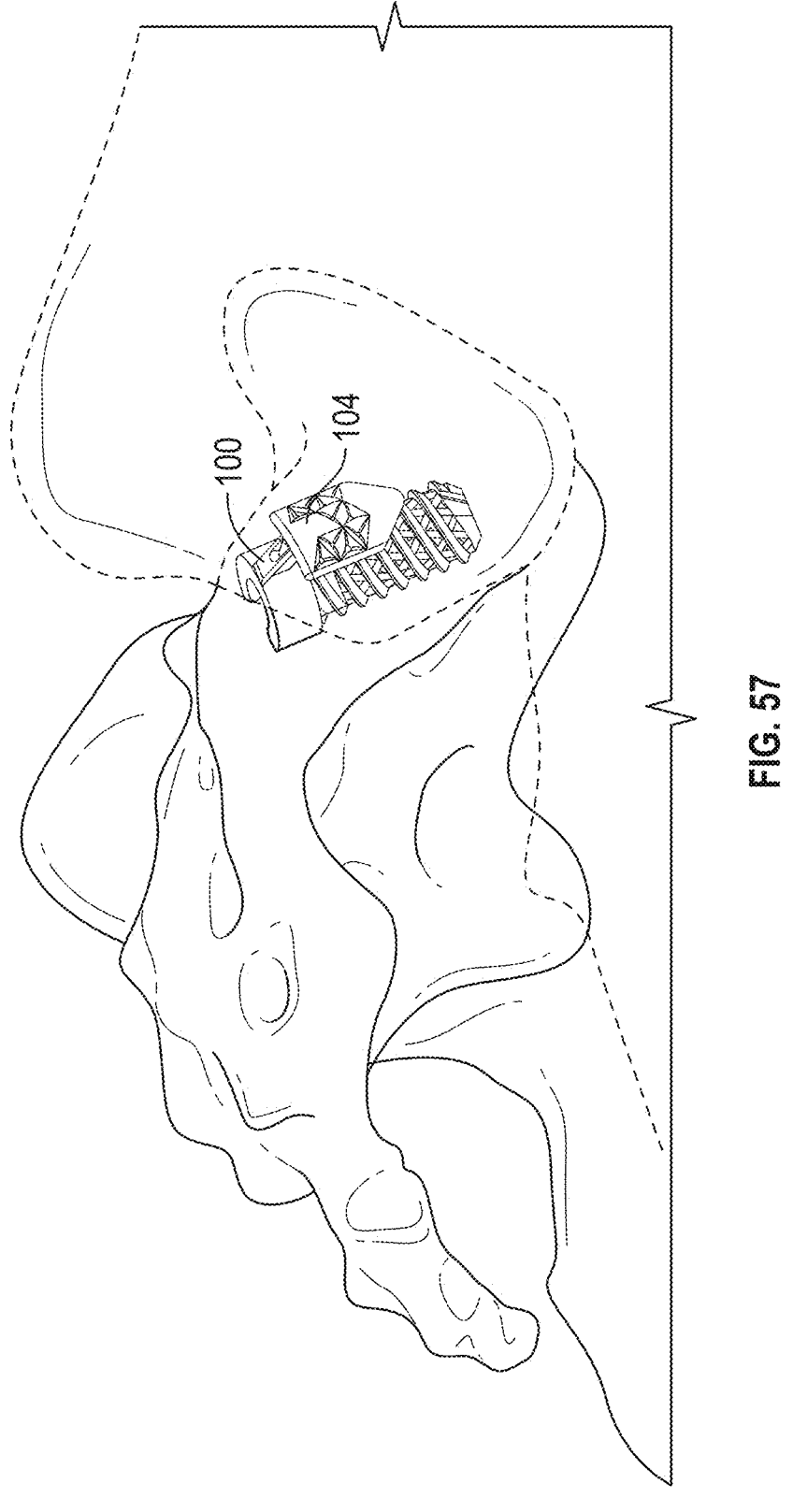

FIG. 57 illustrates an alternative perspective view of an embodiment of the implant within the SI joint.

Figure 58A:
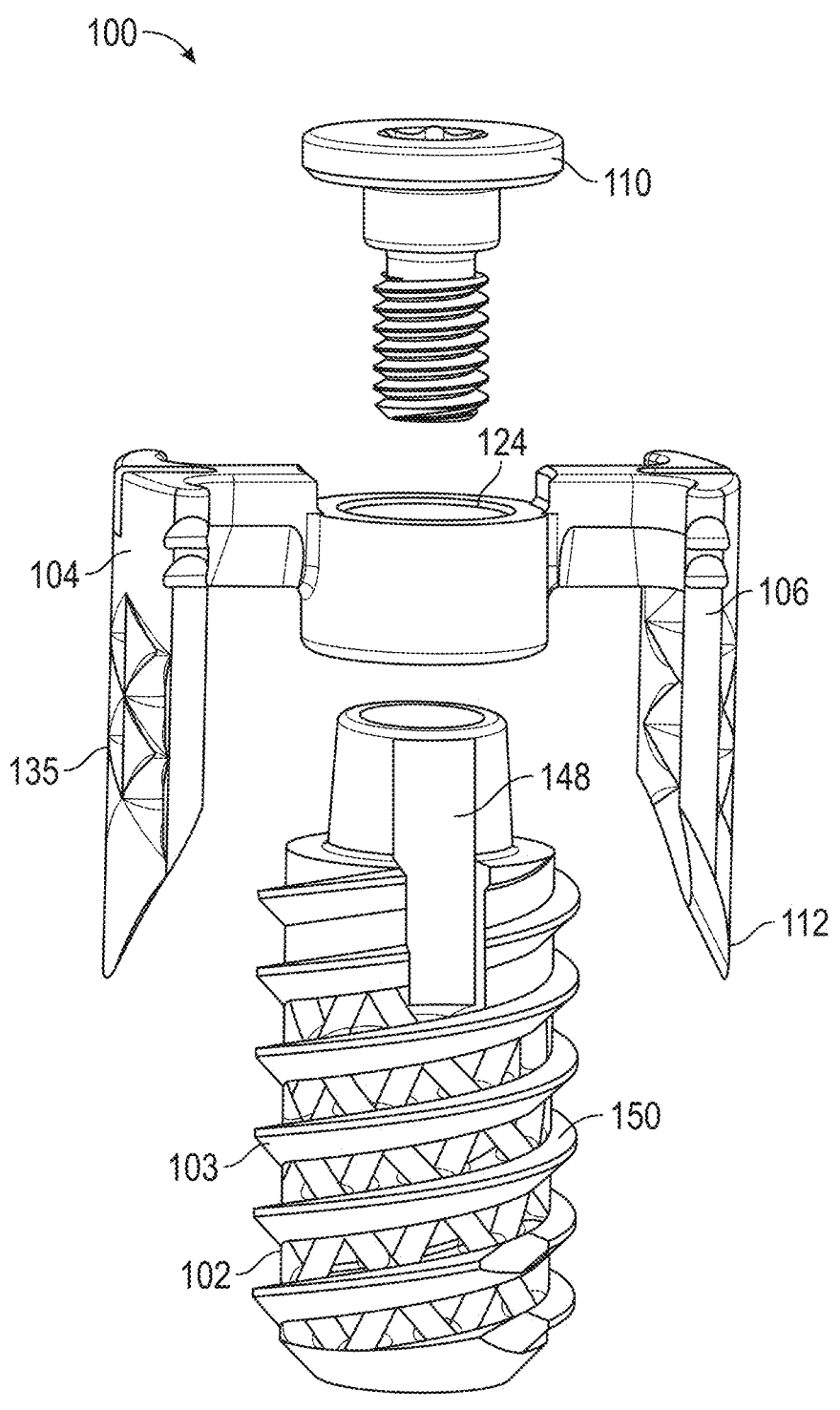

FIG. 58A illustrates an exploded view of an embodiment of the joint implant.

Figure 58B:
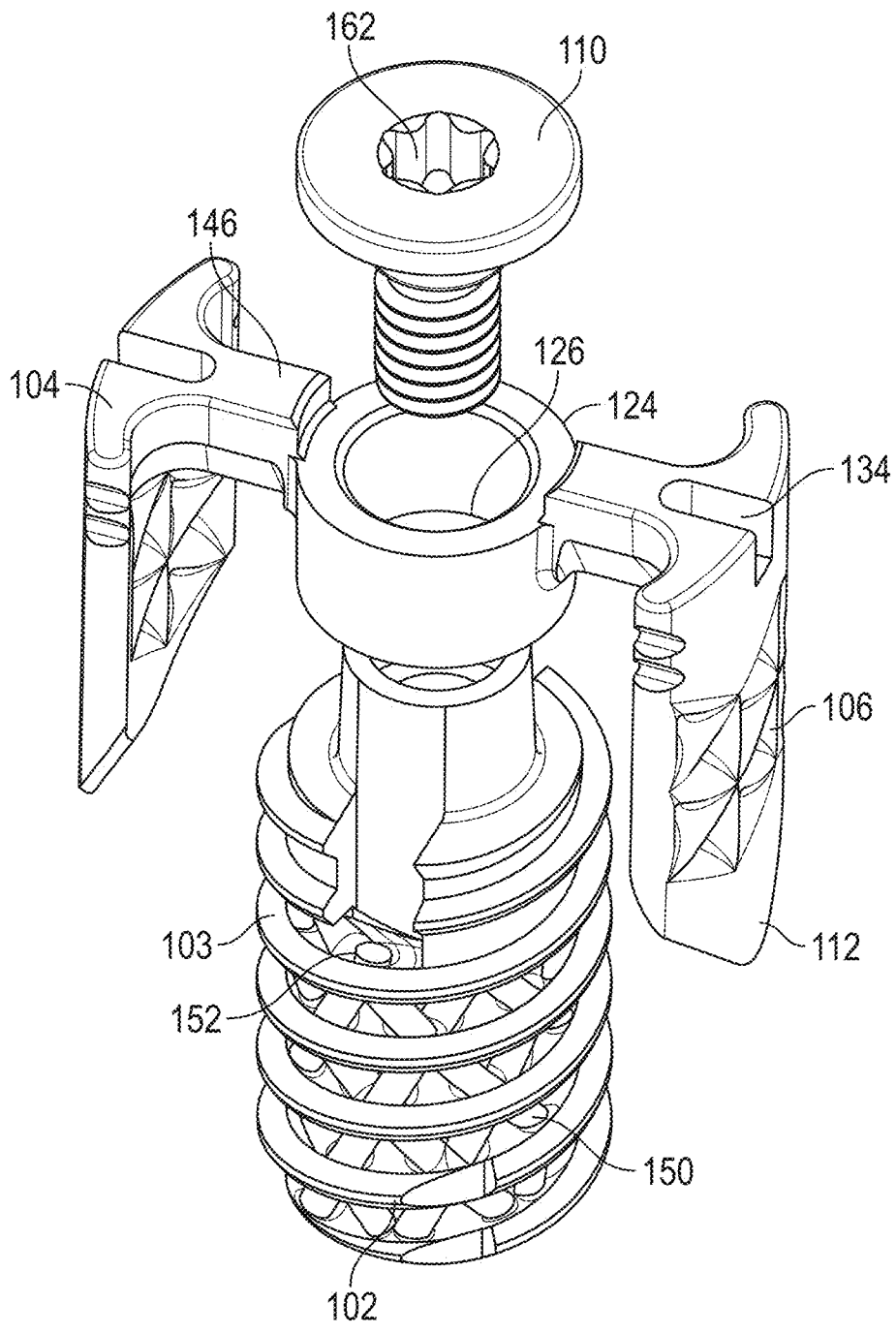

FIG. 58B illustrates an alternative exploded view of the joint implant from FIG. 58A.

Figure 58D:
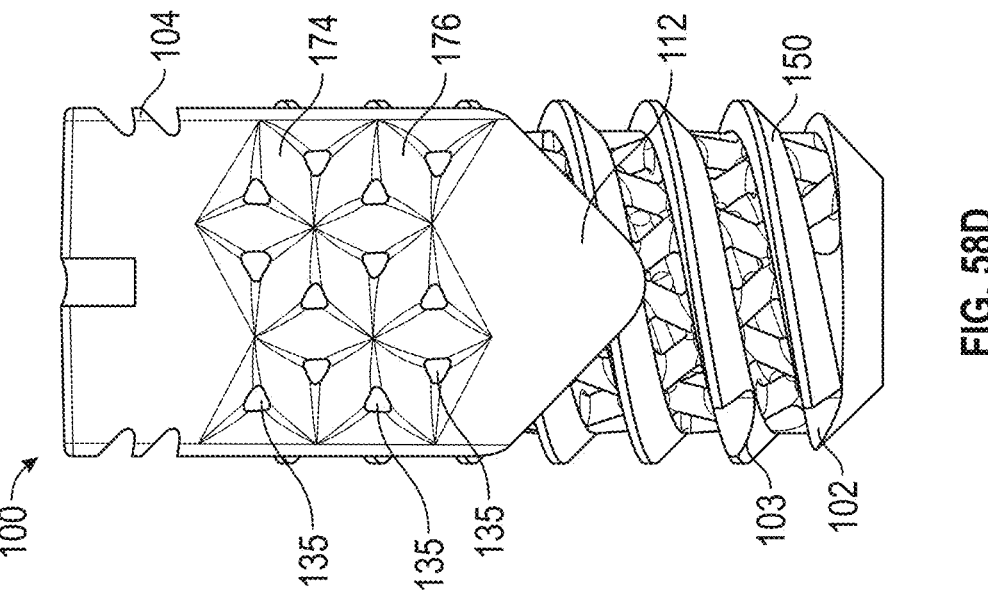
Figure 58C:
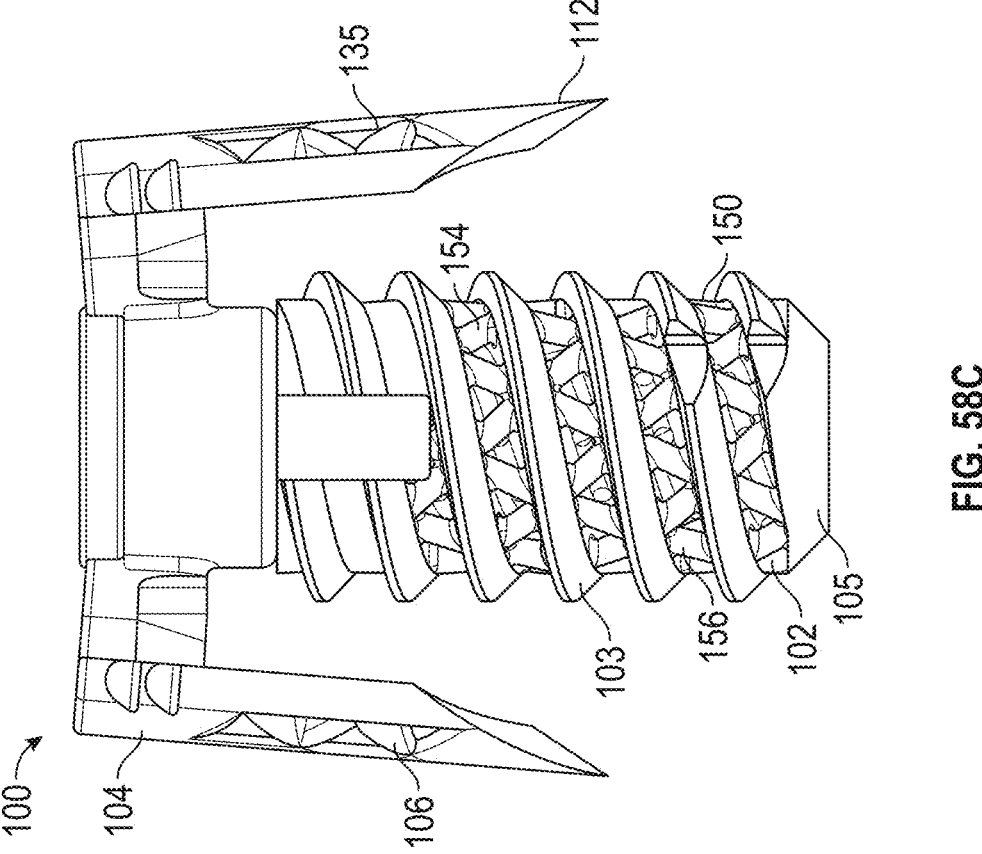

FIG. 58C illustrates a side view of an embodiment of the joint implant from FIG. 58A.

FIG. 58D illustrates an alternative side view of an embodiment of the joint implant from FIG. 58C.

Figure 58F:
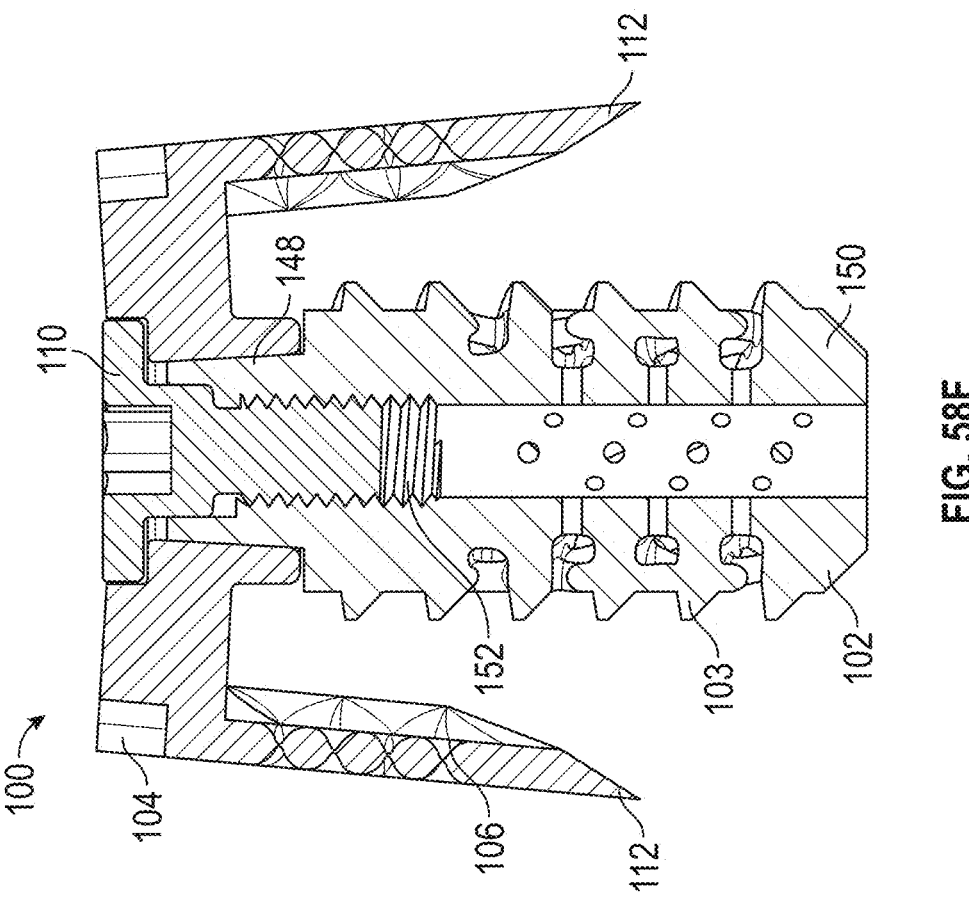
Figure 58E:
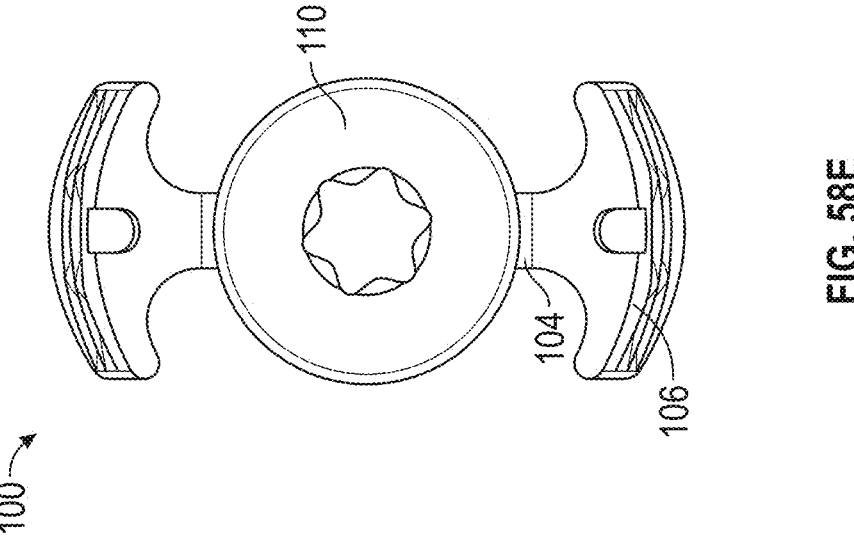

FIG. 58E illustrates a top view of an embodiment of the joint implant from FIG. 58C.

FIG. 58F illustrates a cross sectional side view of an embodiment of the joint implant from FIG. 58C.

Figure 59B:
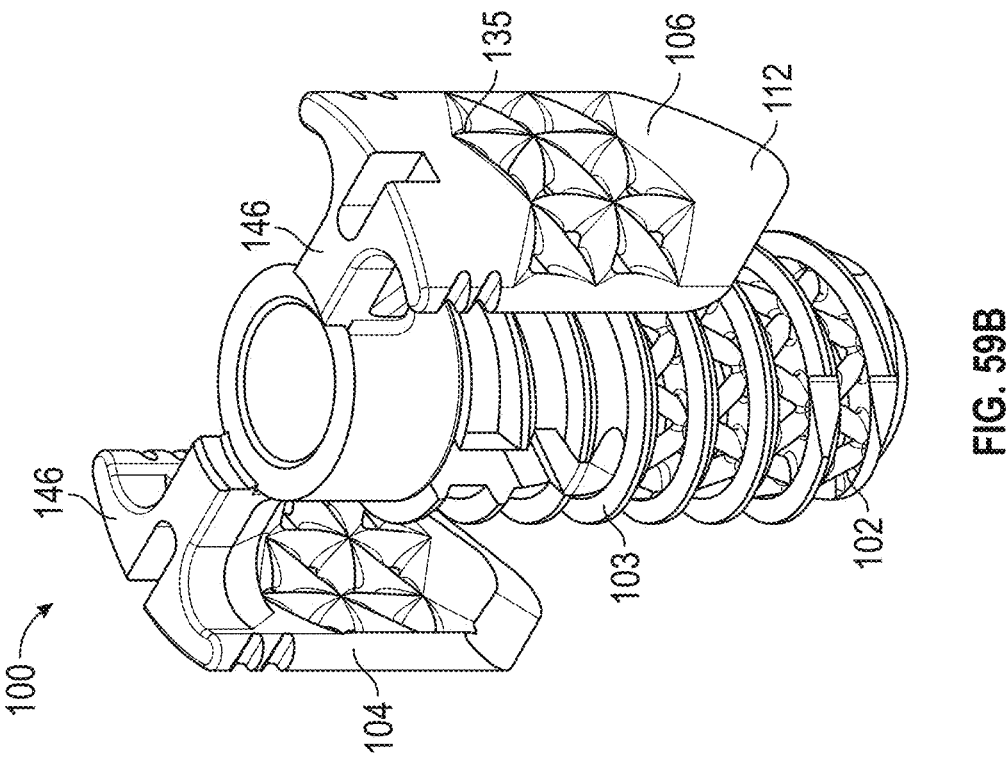
Figure 59A:
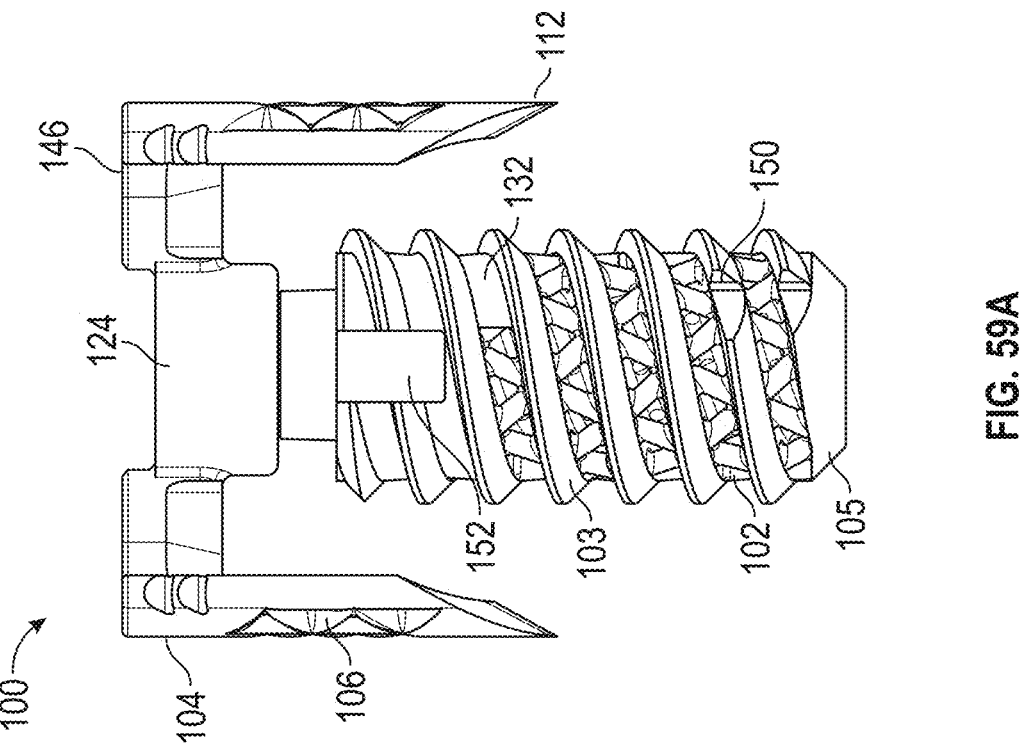

FIG. 59A illustrates a side view of an embodiment of the joint implant.

FIG. 59B illustrates a perspective view of an embodiment of the joint implant from FIG. 59A.

Figure 59D:
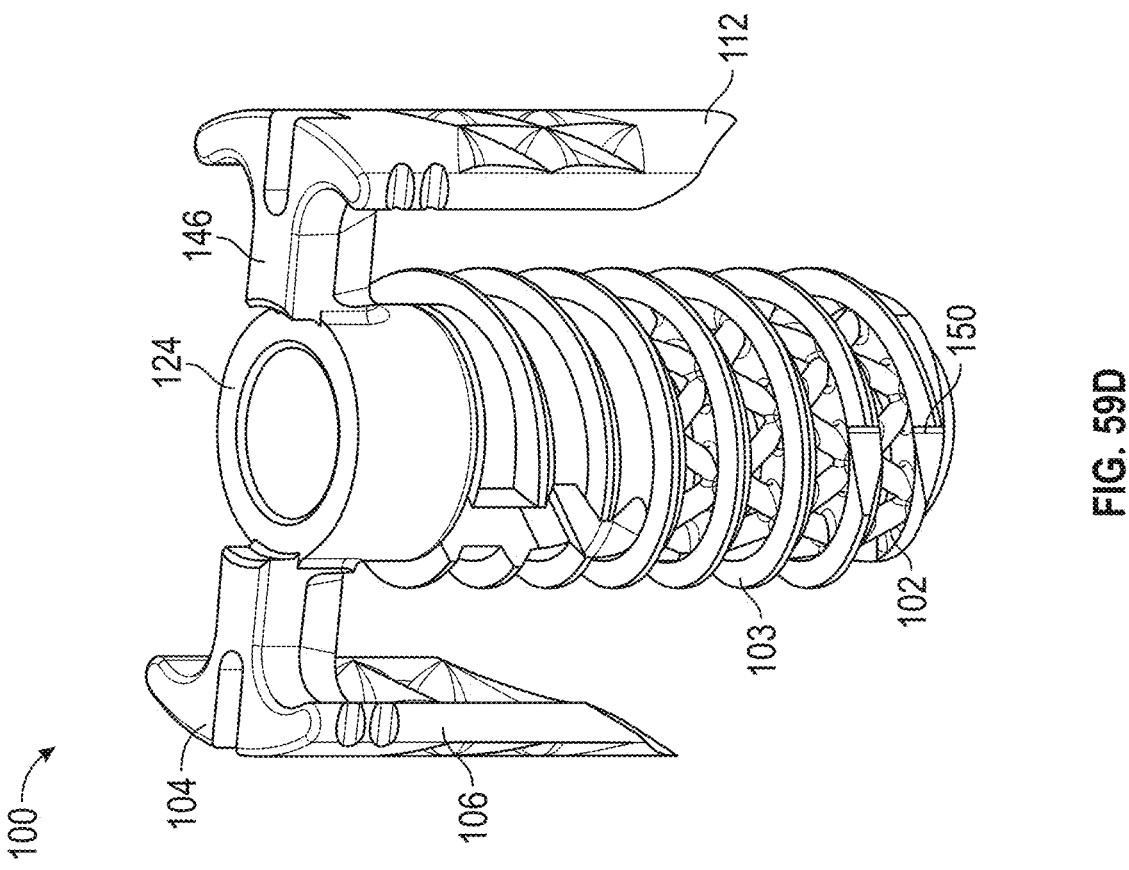
Figure 59C:
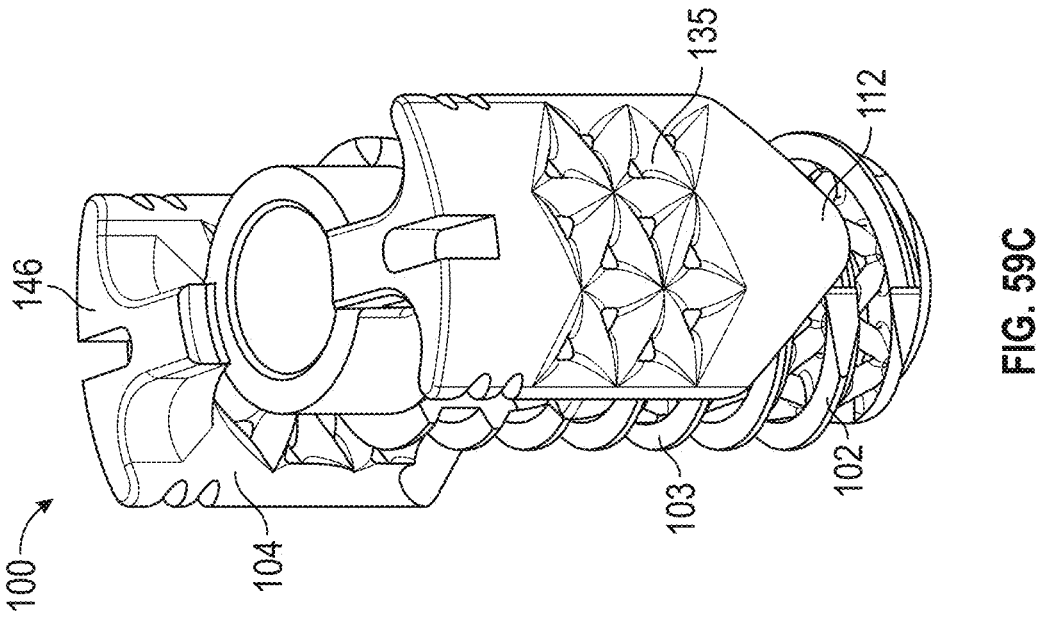

FIG. 59C illustrates a perspective view of an embodiment of the joint implant from FIG. 59A.

FIG. 59D illustrates a perspective view of an embodiment of the joint implant from FIG. 59A.

Figure 60:
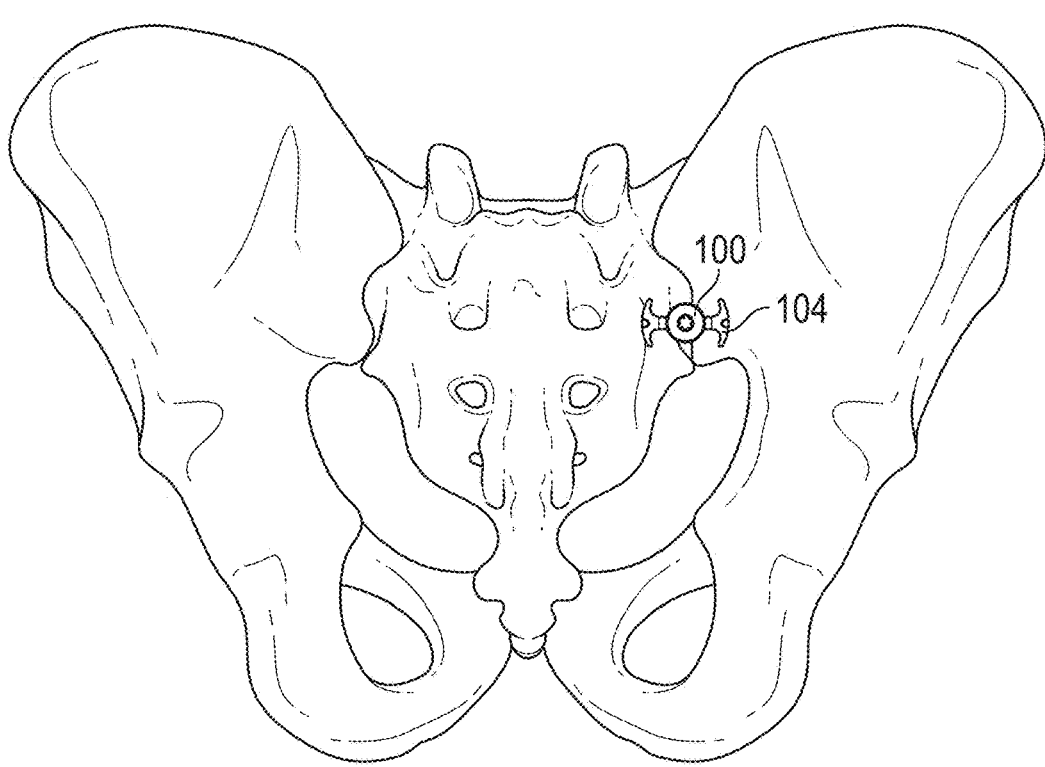

FIG. 60 illustrates a top view of an embodiment of the implant within the SI joint.

Figure 61:
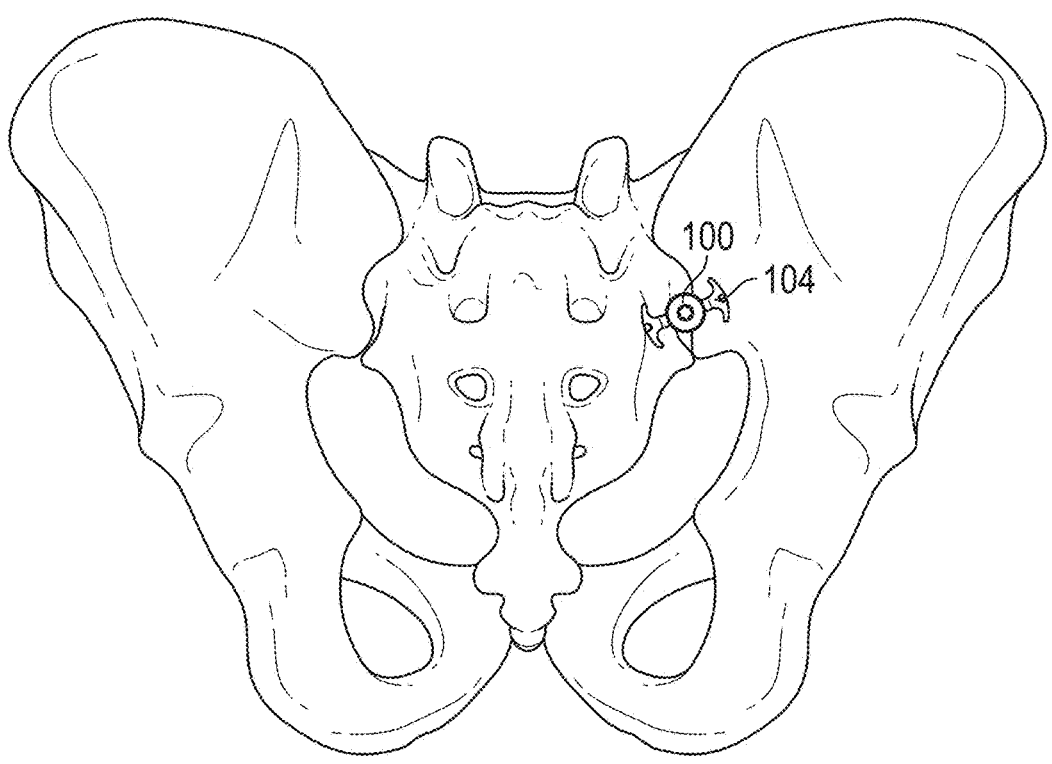

FIG. 61 illustrates a top view of a rotated embodiment of the implant within the SI joint.

Figure 62:
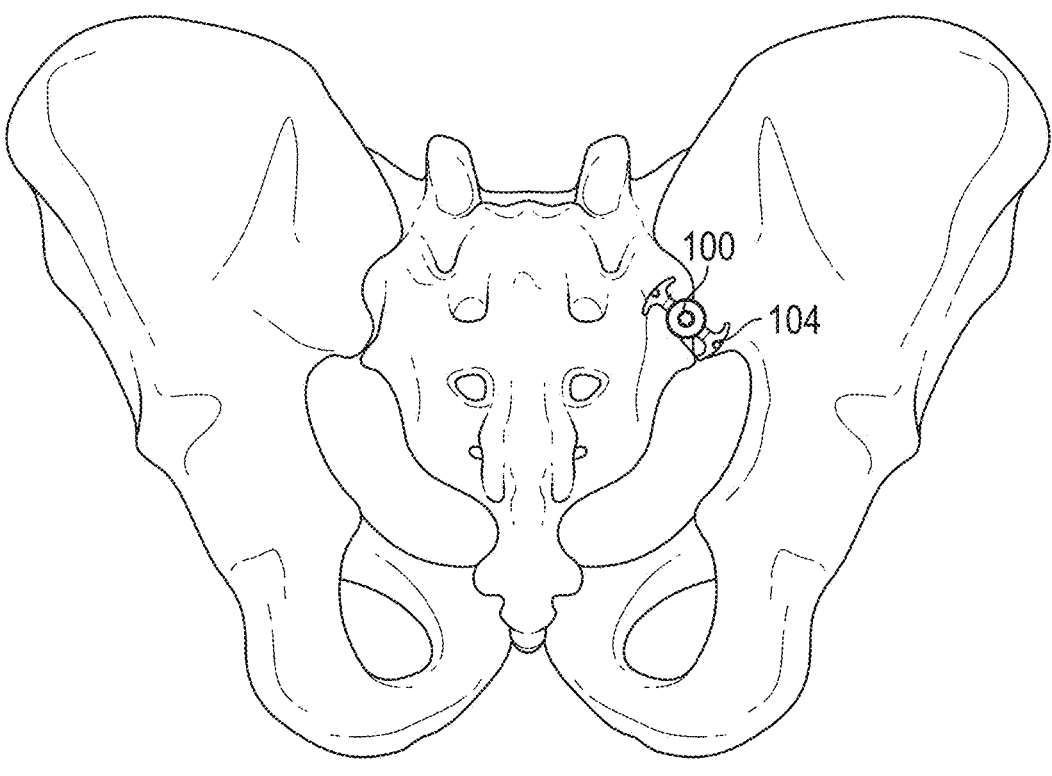

FIG. 62 illustrates a top view of a rotated embodiment of the implant within the SI joint.

Figure 63B:
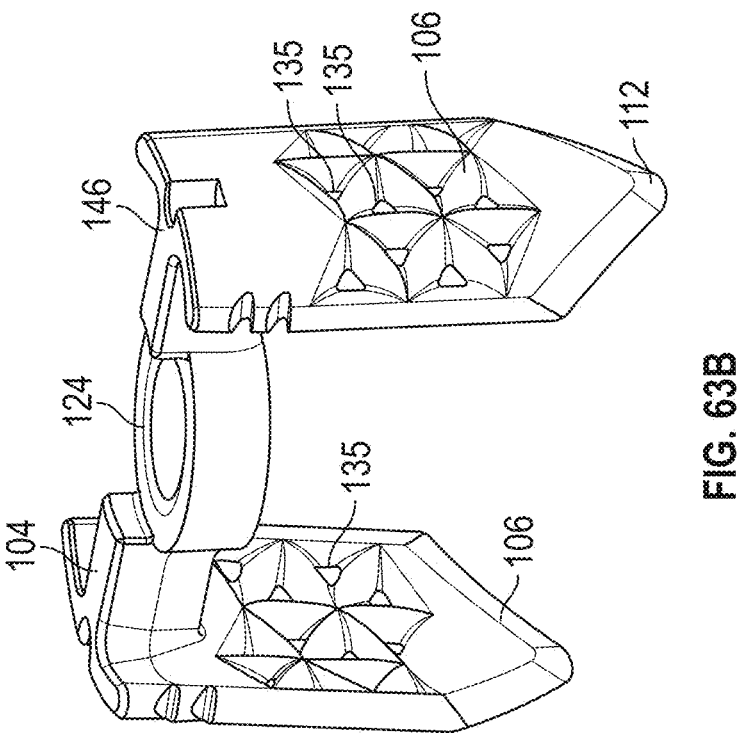
Figure 63A:
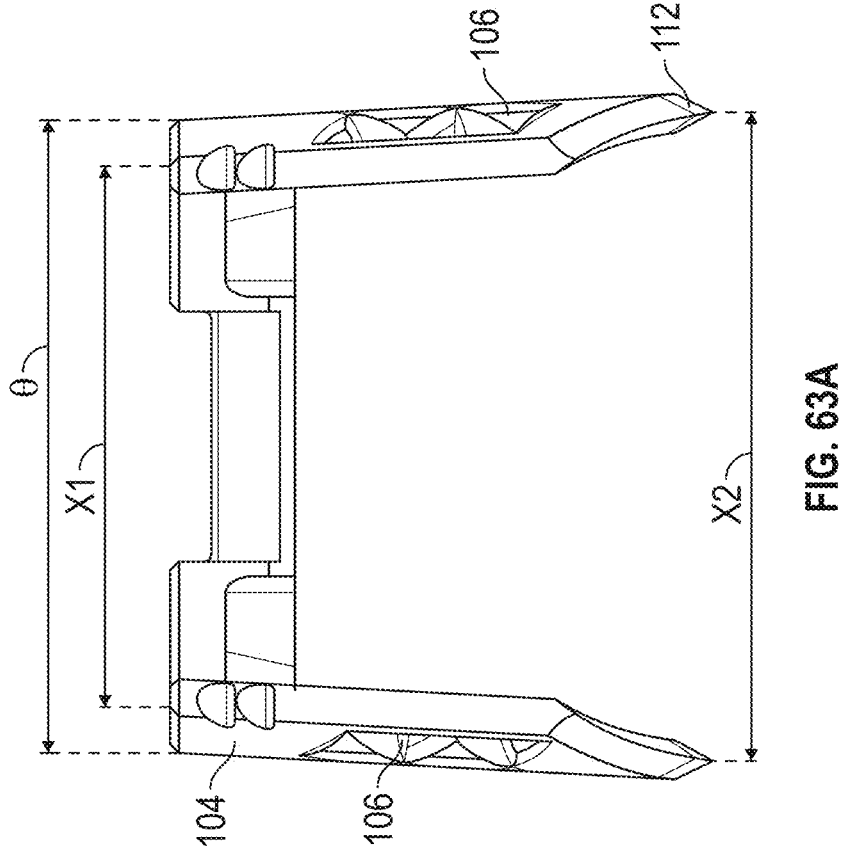

FIG. 63A illustrates a side view of an embodiment of the secondary implant.

6

FIG. 63B illustrates a perspective view of an embodiment of the secondary implant from FIG. 63A.

Figure 64B:
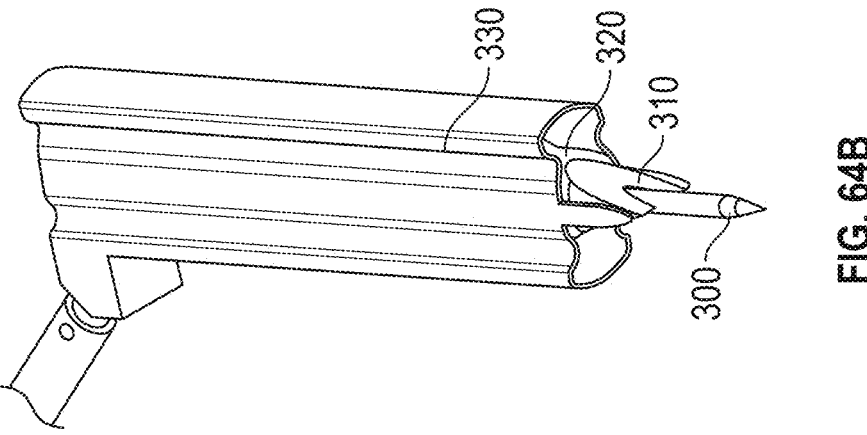
Figure 64A:
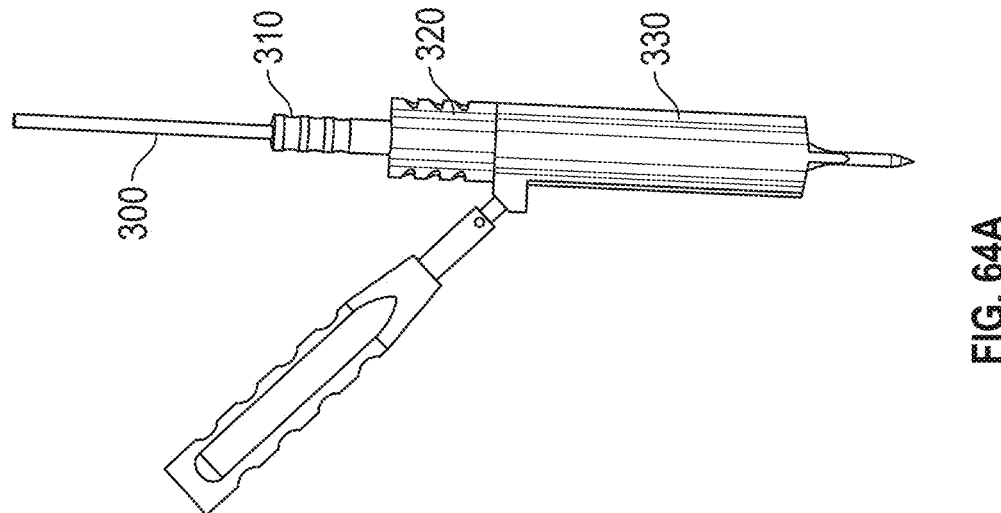

FIG. 64A illustrates a side view of the guide, dilator, and joint locator of an embodiment of the implant system.

FIG. 64B illustrates an enlarged perspective view of the end of the implant system from FIG. 64A.

Figure 65B:
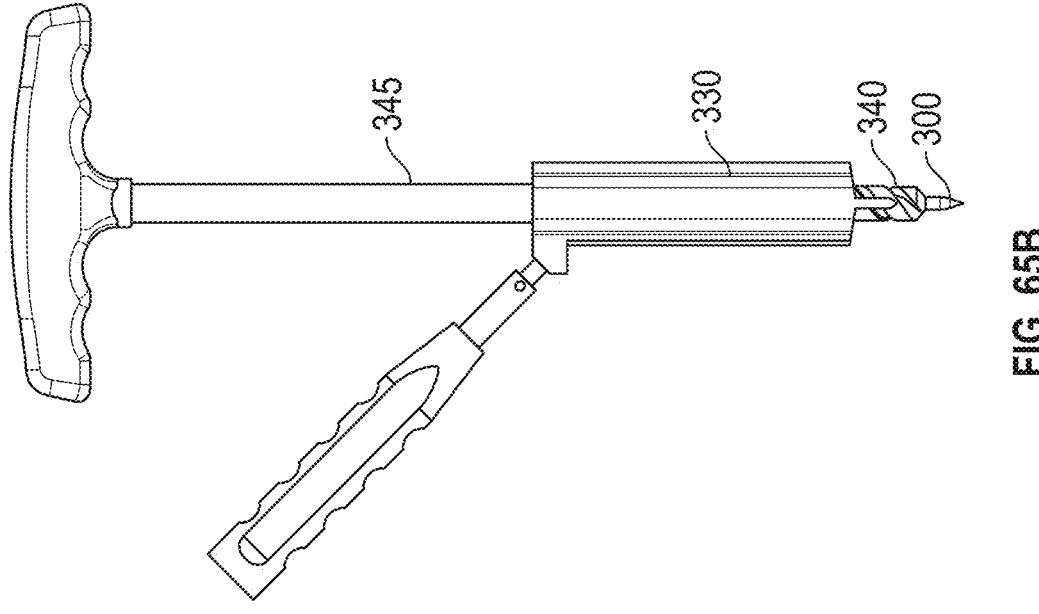
Figure 65A:
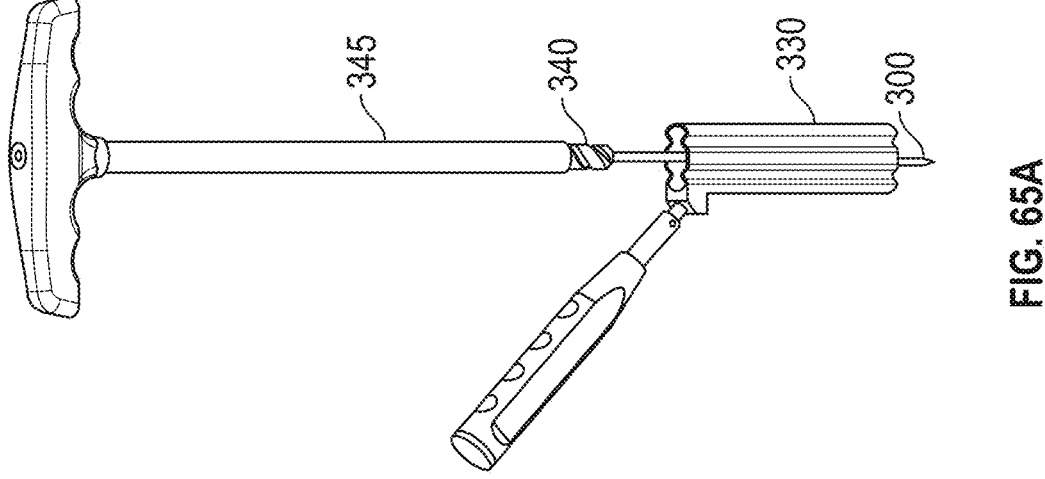

FIG. 65A illustrates a perspective view of the drill, drill bit, guide, and guidewire of an embodiment of the implant system.

FIG. 65B illustrates a side view of the drill, drill bit, guide, and guidewire of an embodiment of the implant system from FIG. 65A.

FIG. 66A illustrates a shaft, threaded rod, and implant of an embodiment of the implant system.

FIG. 66B illustrates a side view of the shaft, threaded rod, and implant as an embodiment of a system.

FIG. 66C illustrates an enlarged perspective view of the end of the implant system from FIG. 66B.

FIG. 66D illustrates an alternative enlarged perspective view of the end of the implant system from FIG. 66B.

Figures 67A, 67B, 67C:
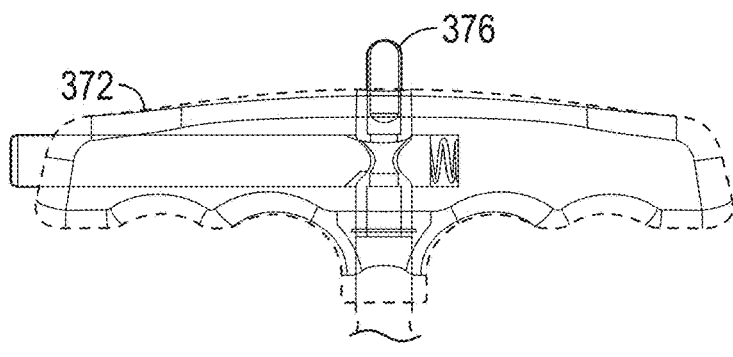

FIG. 67A illustrates a side view of an implant inserter, guide, and implant of an embodiment of the implant system.

FIG. 67B illustrates an exploded side view of an implant inserter, guide, and implant of an embodiment of the implant system from FIG. 67A.

FIG. 67C illustrates an enlarged side view of the threaded rod and handle of an embodiment of the implant system from FIG. 67A.

Figures 68A, 68B, 68C:
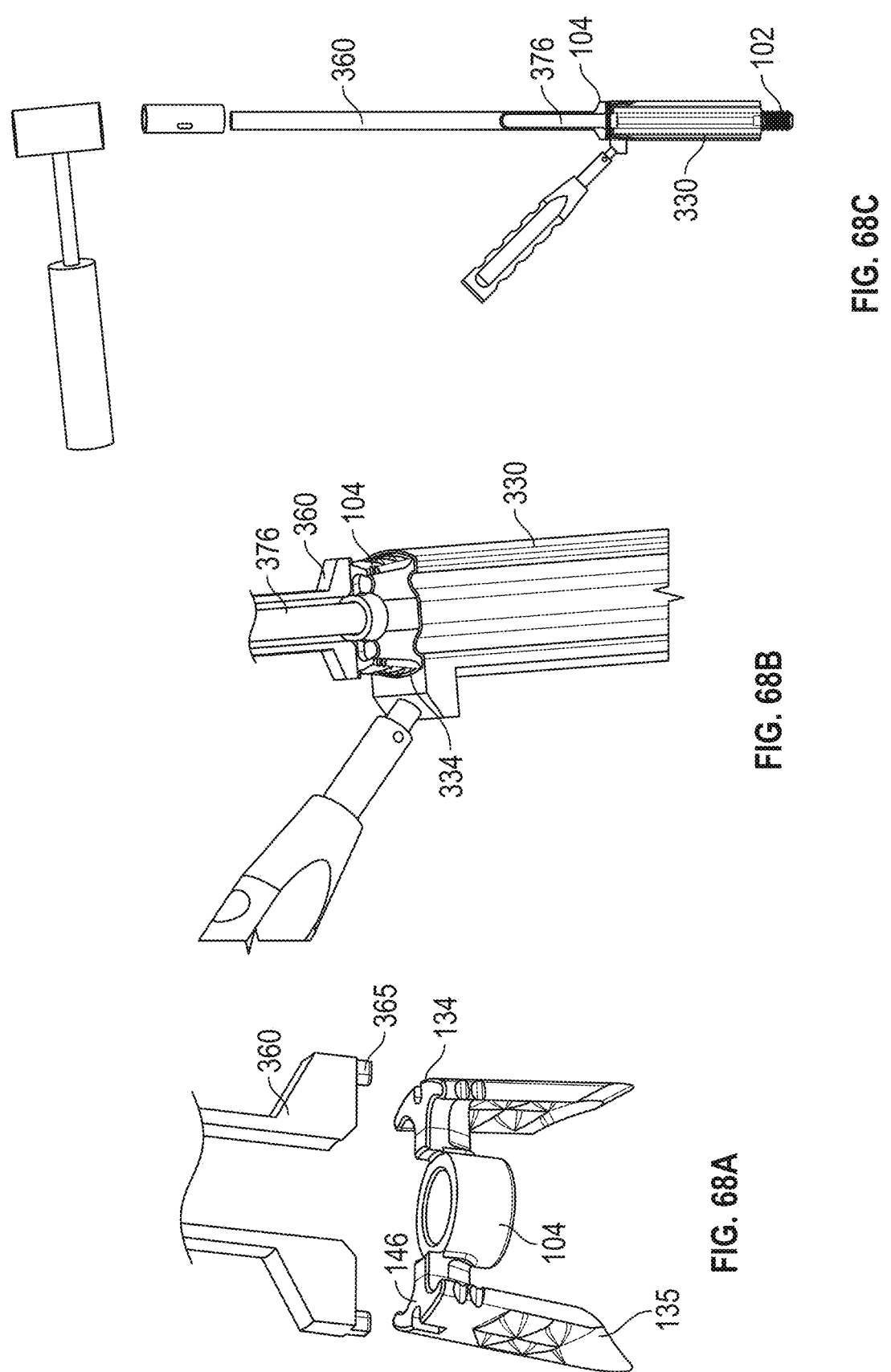

FIG. 68A illustrates an enlarged perspective view of the end of an inserter and a secondary implant of an embodiment of the implant system.

FIG. 68B illustrates an enlarged perspective view of a threaded rod, inserter, and guide of an embodiment of the implant system.

FIG. 68C illustrates a perspective view of an inserter, threaded rod, guide, and implant of an embodiment of the implant system.

Figure 69C:
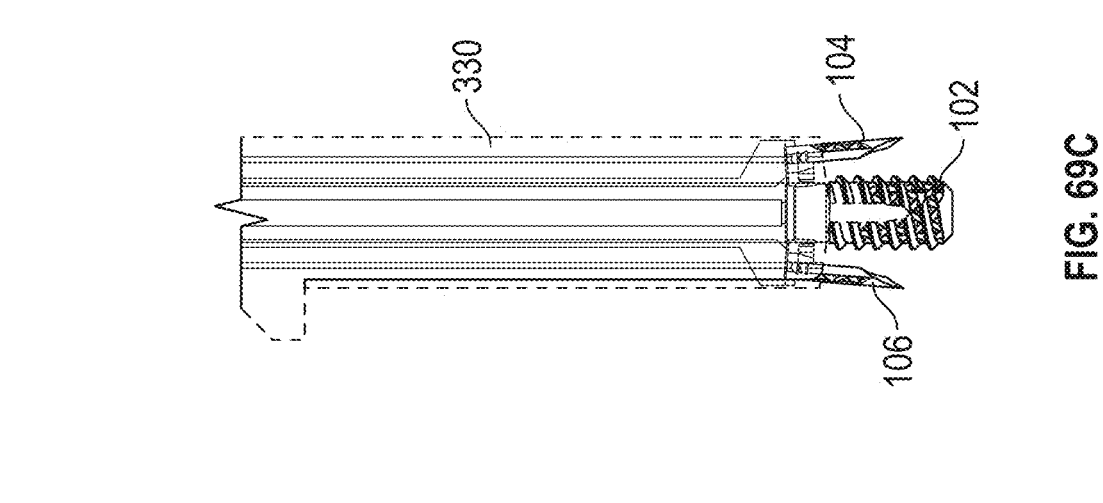
Figure 69B:
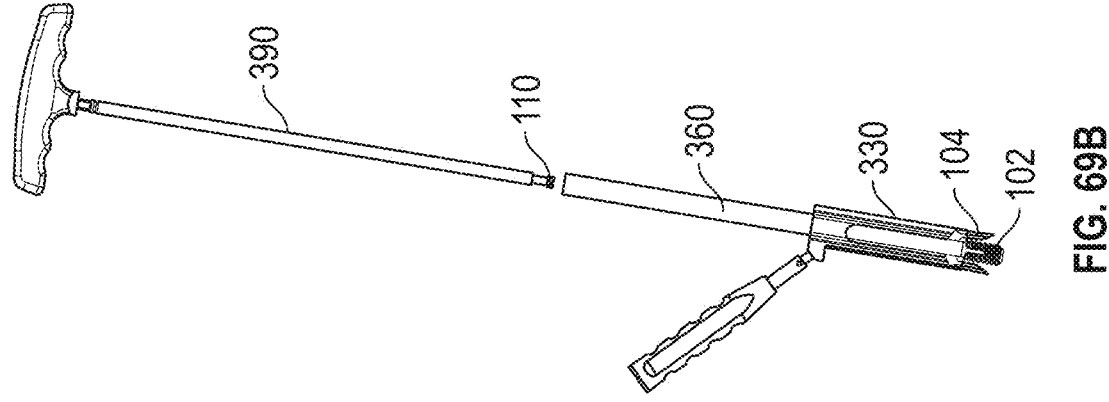
Figure 69A:
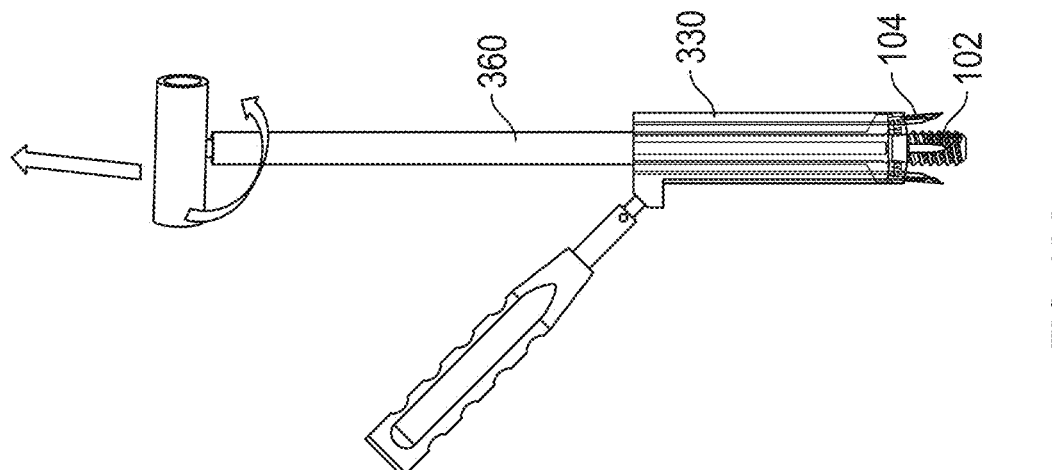

FIG. 69A illustrates a perspective view of an alternative embodiment of the implant system.

FIG. 69B illustrates a perspective view of an alternative embodiment of the implant system.

FIG. 69C illustrates an enlarged side view of the end of an embodiment of the implant system.

Figure 70B:
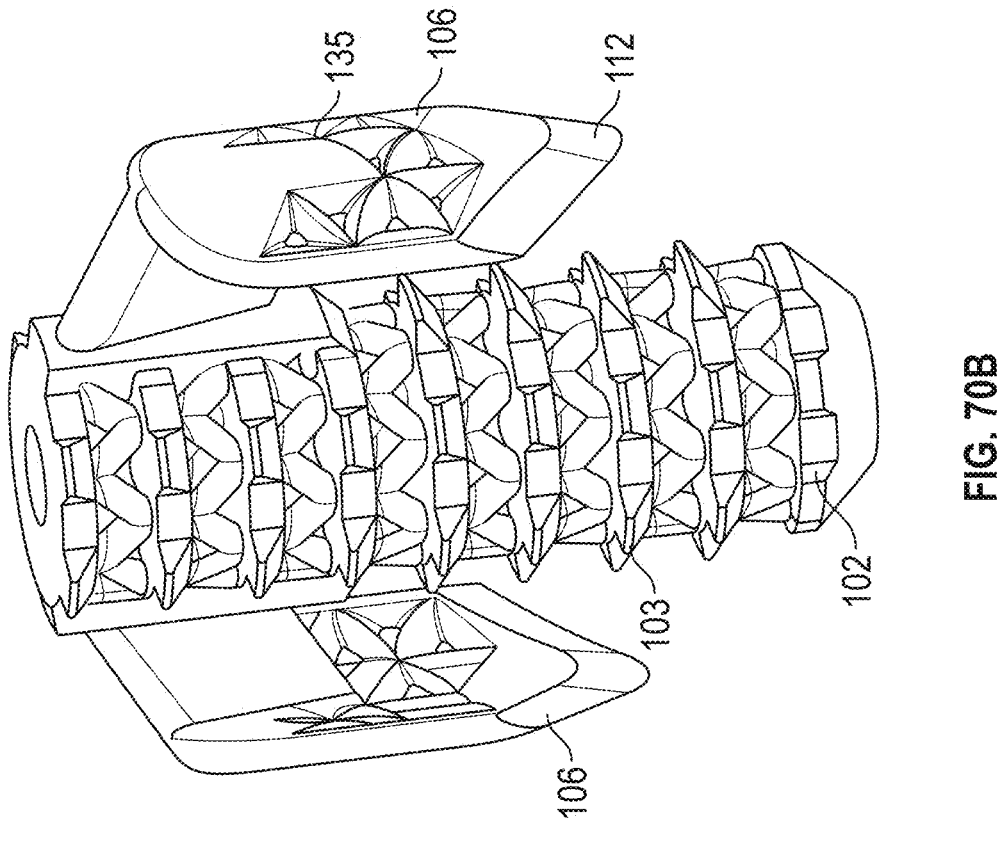
Figure 70A:
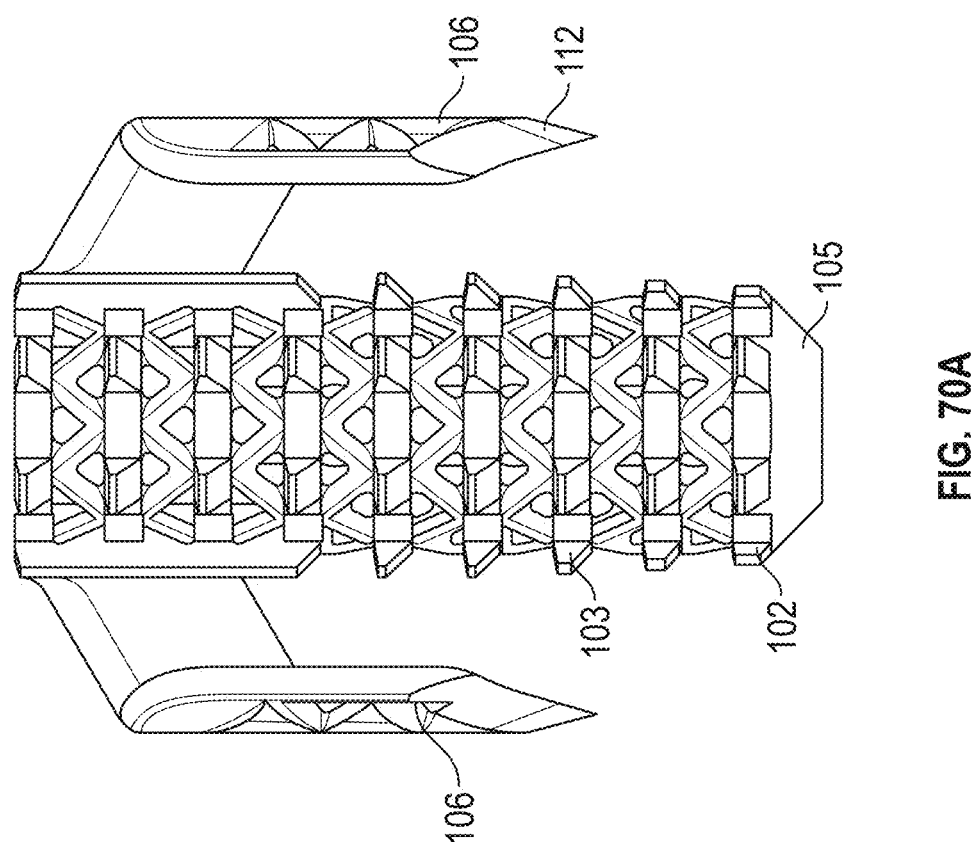

FIG. 70A illustrates a side view of an embodiment of a joint implant.

FIG. 70B illustrates a perspective view of an embodiment of the joint implant from FIG. 70A.

Figure 70C:
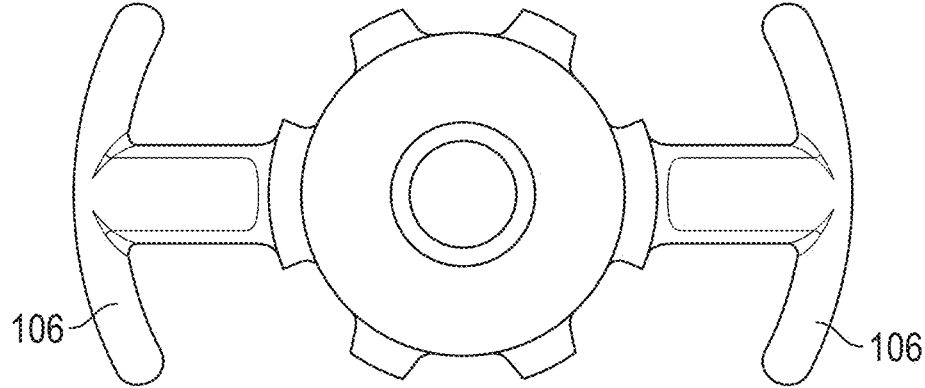

FIG. 70C illustrates a top view of an embodiment of the joint implant from FIG. 70A.

Figure 71B:
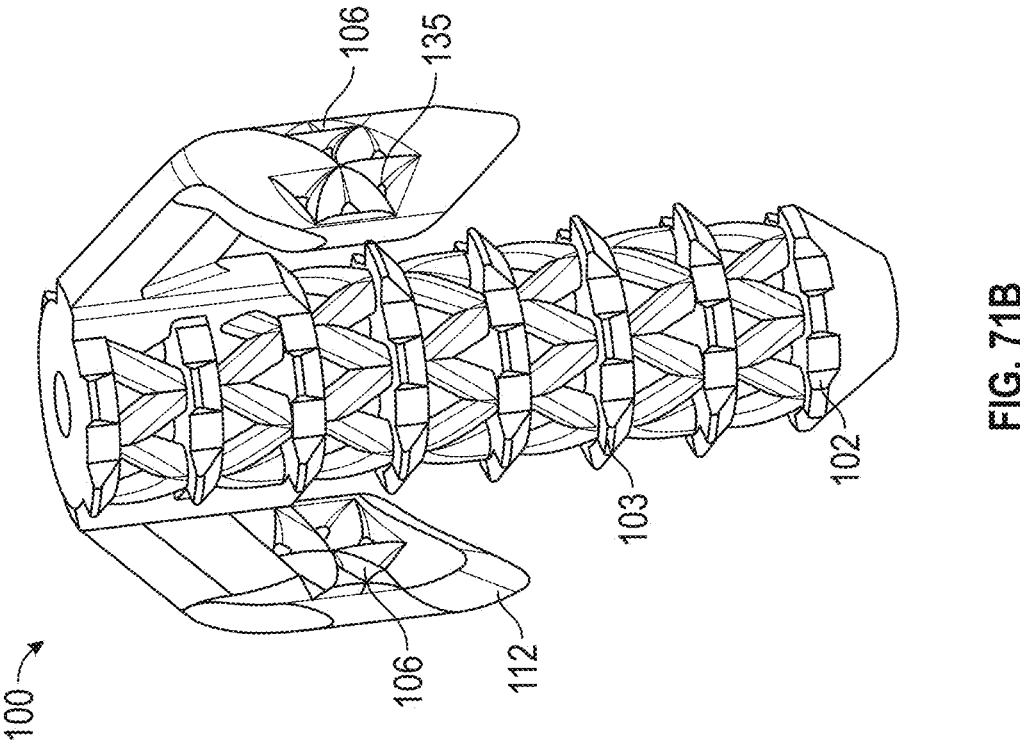
Figure 71A:
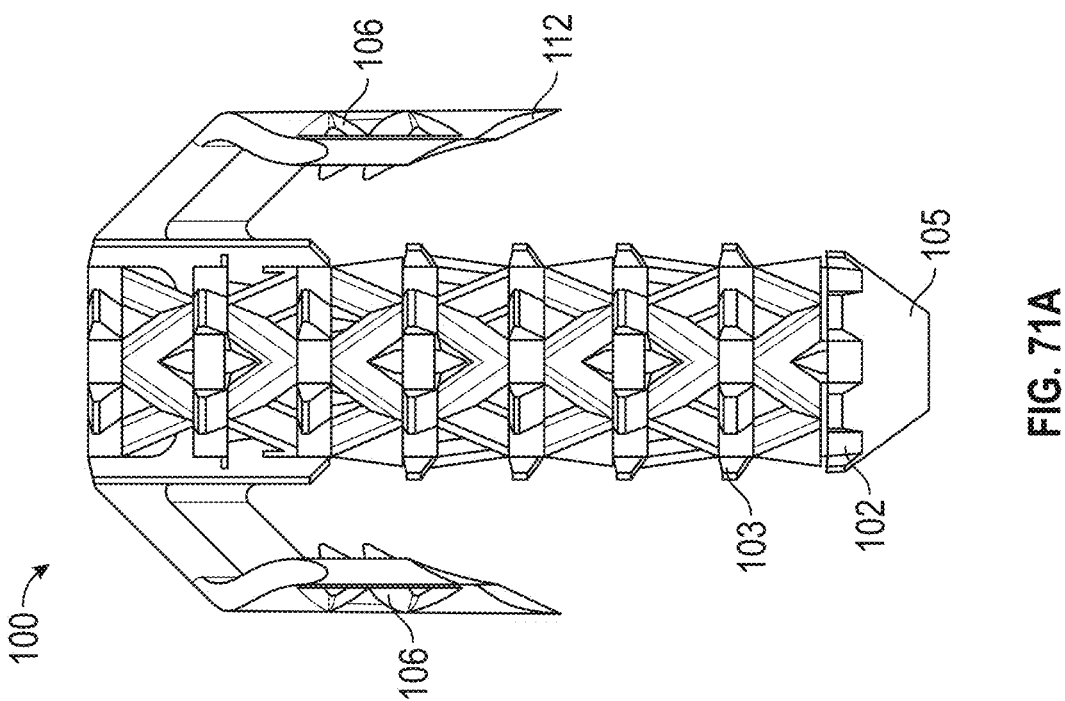

FIG. 71A illustrates a side view of an embodiment of a joint implant.

FIG. 71B illustrates a perspective view of an embodiment of the joint implant from FIG. 71A.

Figures 72A, 72B:
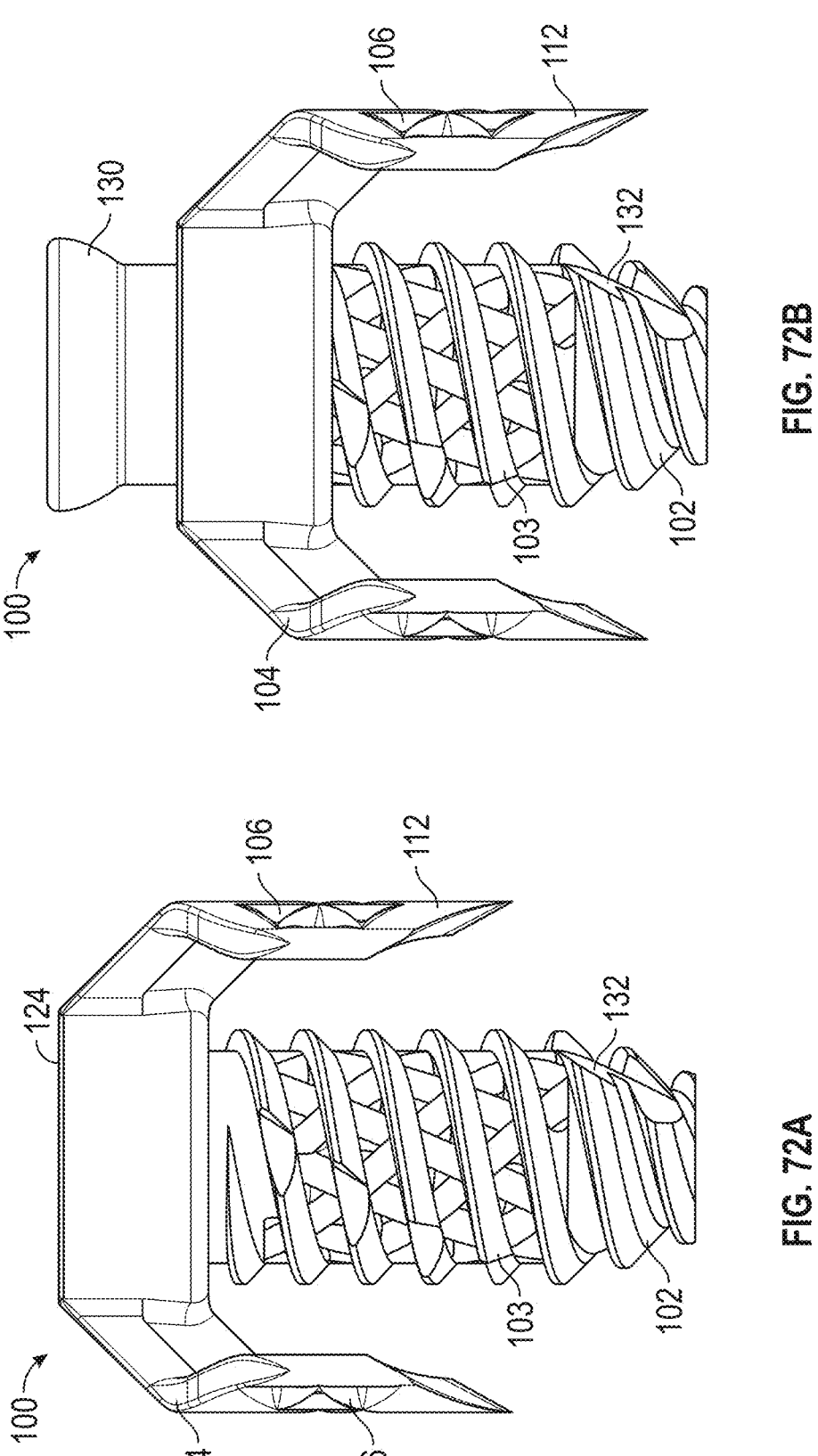

FIG. 72A illustrates a side view of an embodiment of a joint implant.

FIG. 72B illustrates an altered side view of an embodiment of the joint implant from FIG. 72A.

Figure 72D:
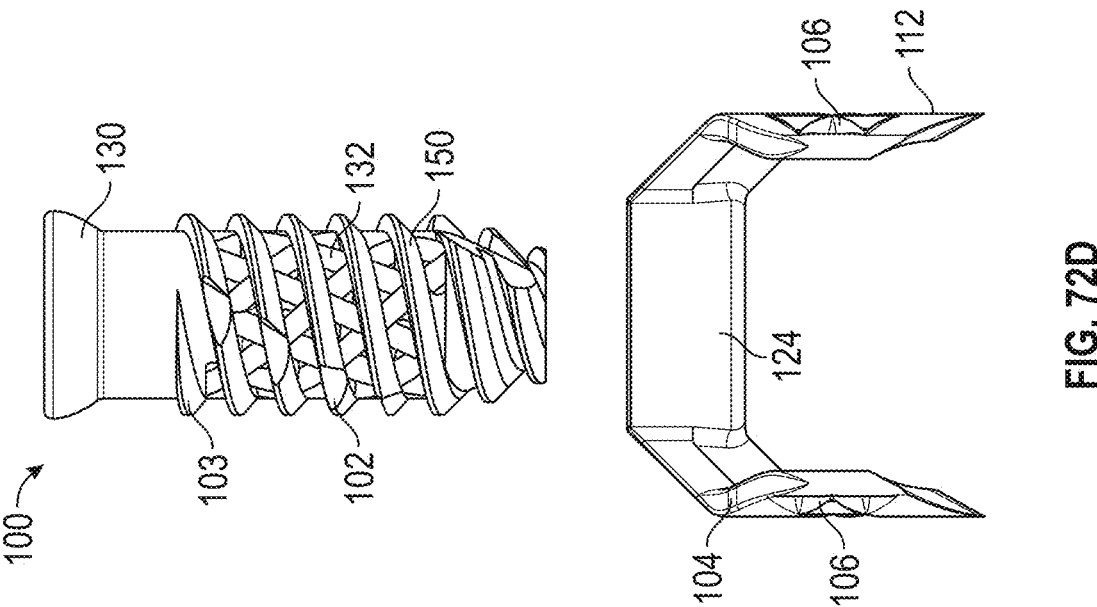
Figure 72C:
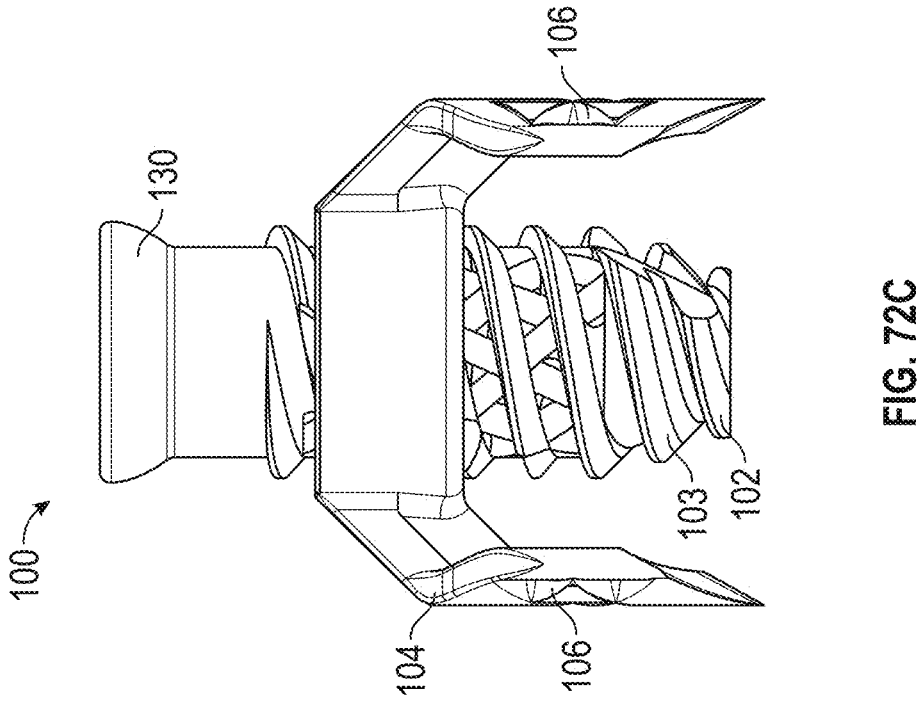

FIG. 72C illustrates an altered side view of an embodiment of the joint implant from FIG. 72A.

FIG. 72D illustrates an exploded side view of an embodiment of the joint implant from FIG. 72A.

Figure 72E:
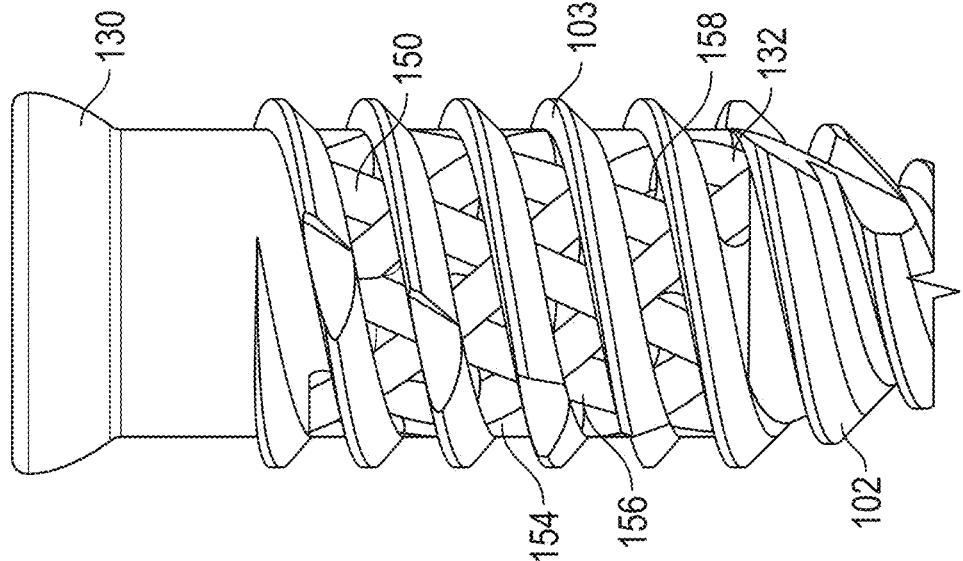
Figure 72E:
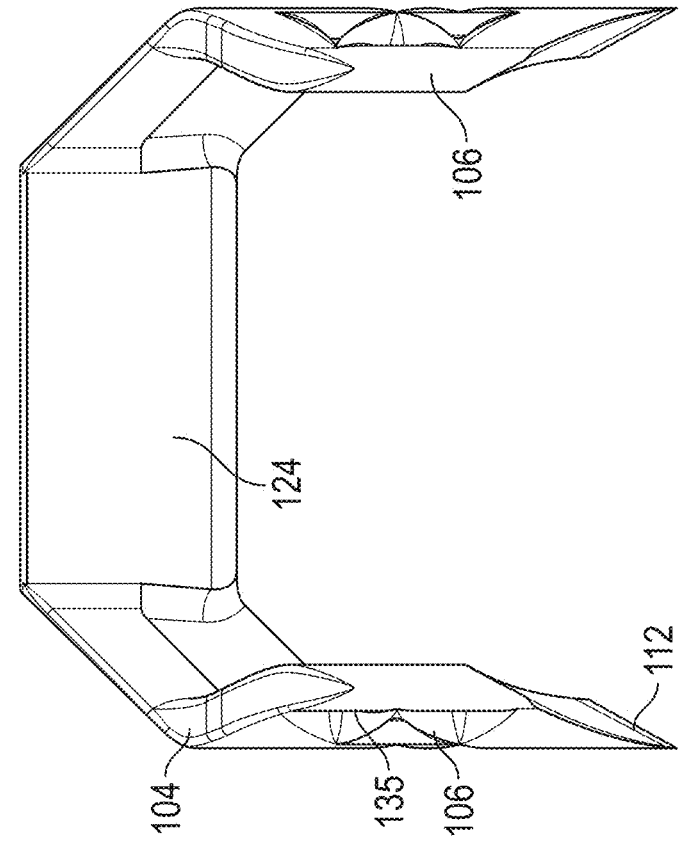

FIG. 72E illustrates an alternative exploded side view of an embodiment of the joint implant from FIG. 72A.

Figure 72F:
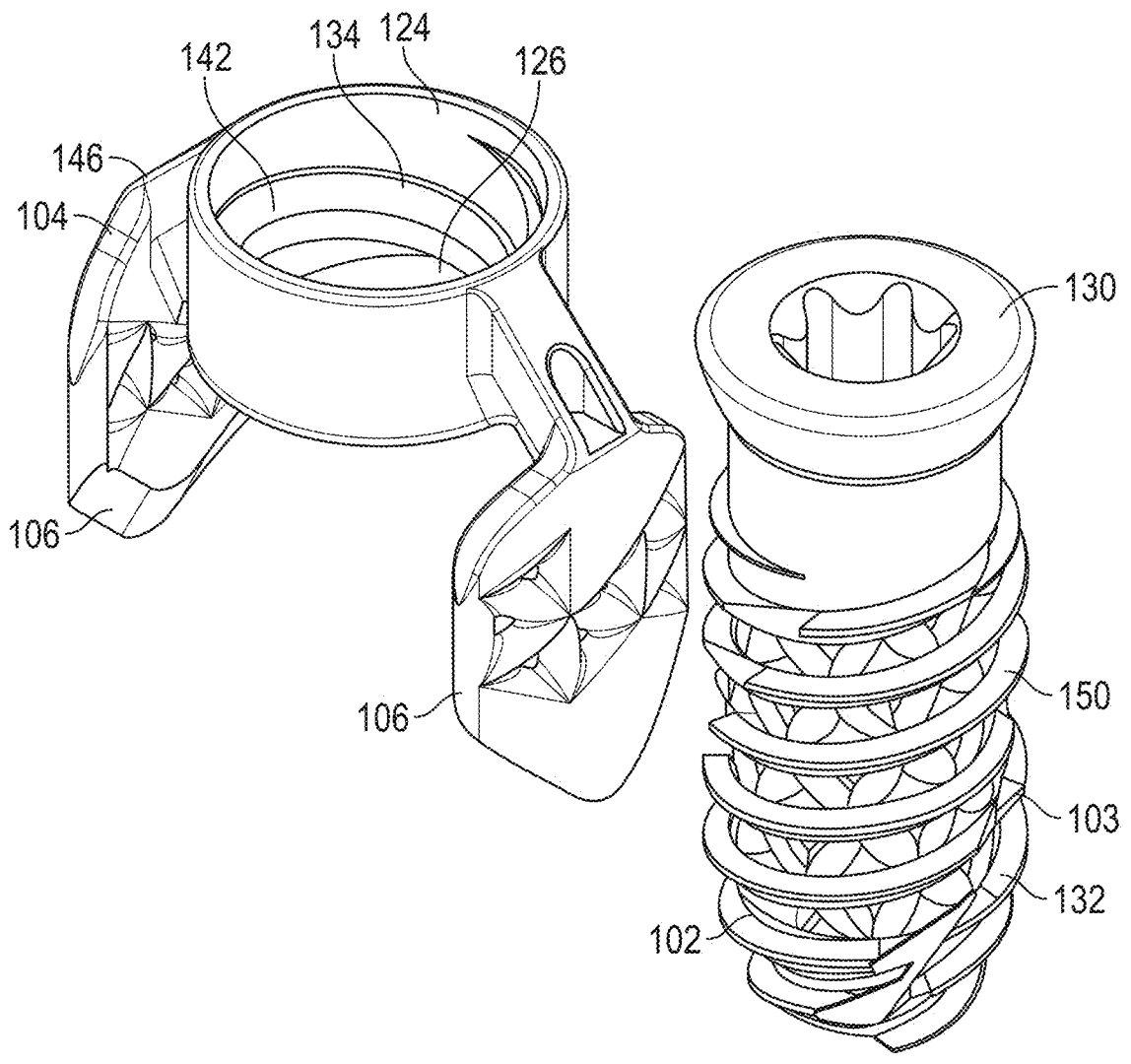

FIG. 72F illustrates an exploded perspective view of an embodiment of the joint implant from FIG. 72A.

Figure 73A:
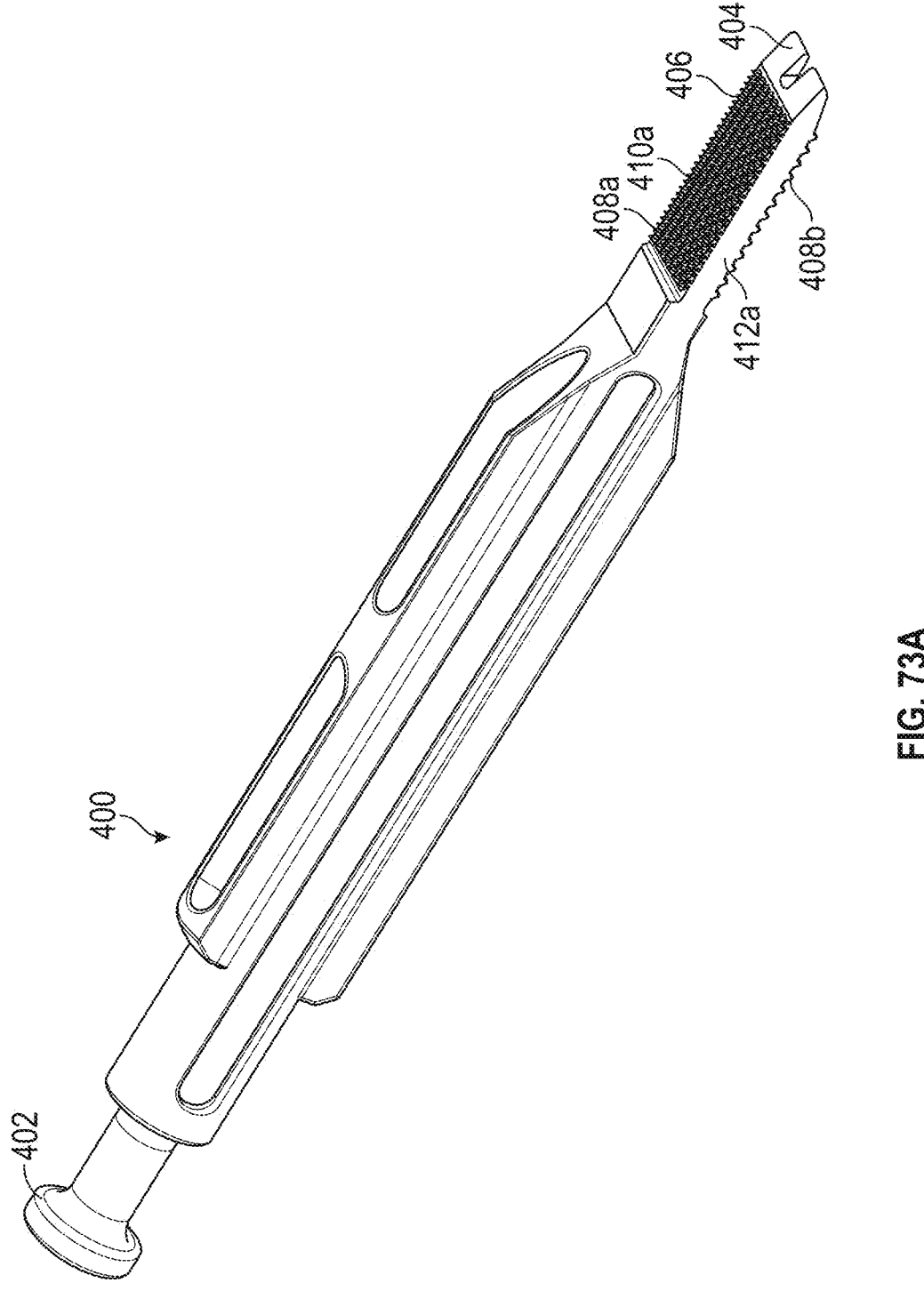

FIG. 73A illustrates a perspective view of a rasp as an embodiment of the implant system.

Figure 73B:
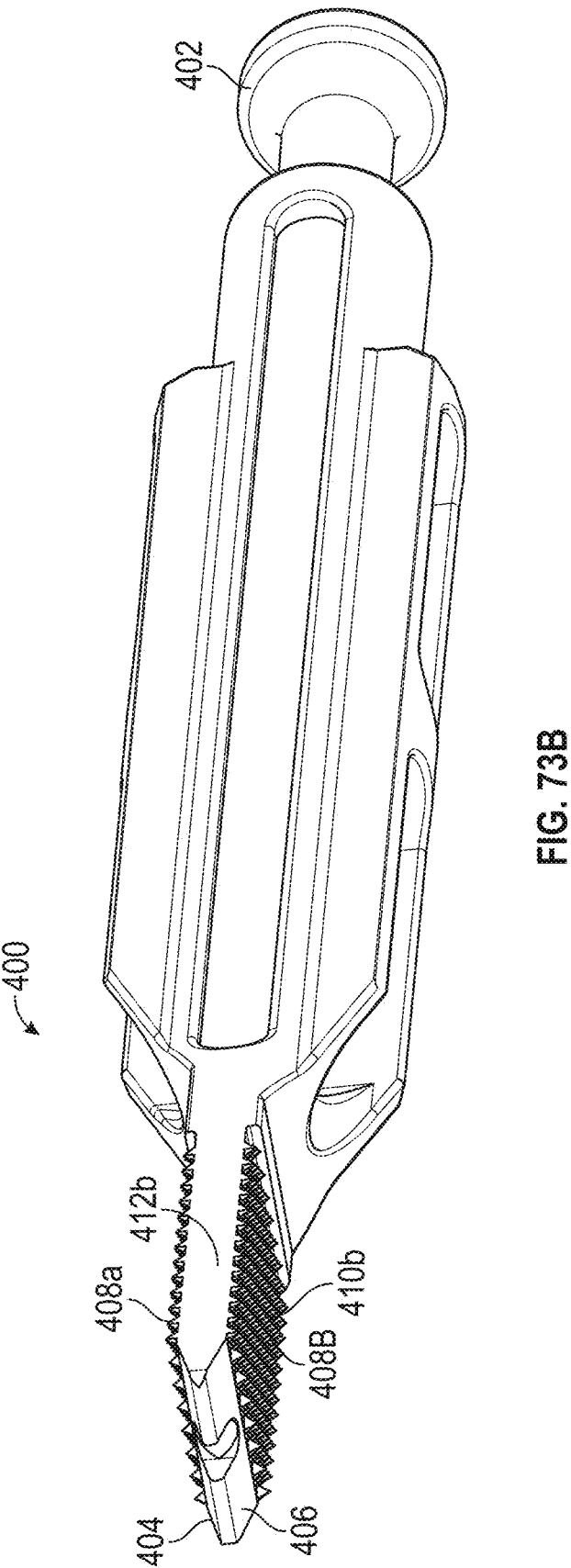

FIG. 73B illustrates an alternative perspective view of a rasp as an embodiment of the implant system from FIG. 73A.

Figures 73C, 73D:
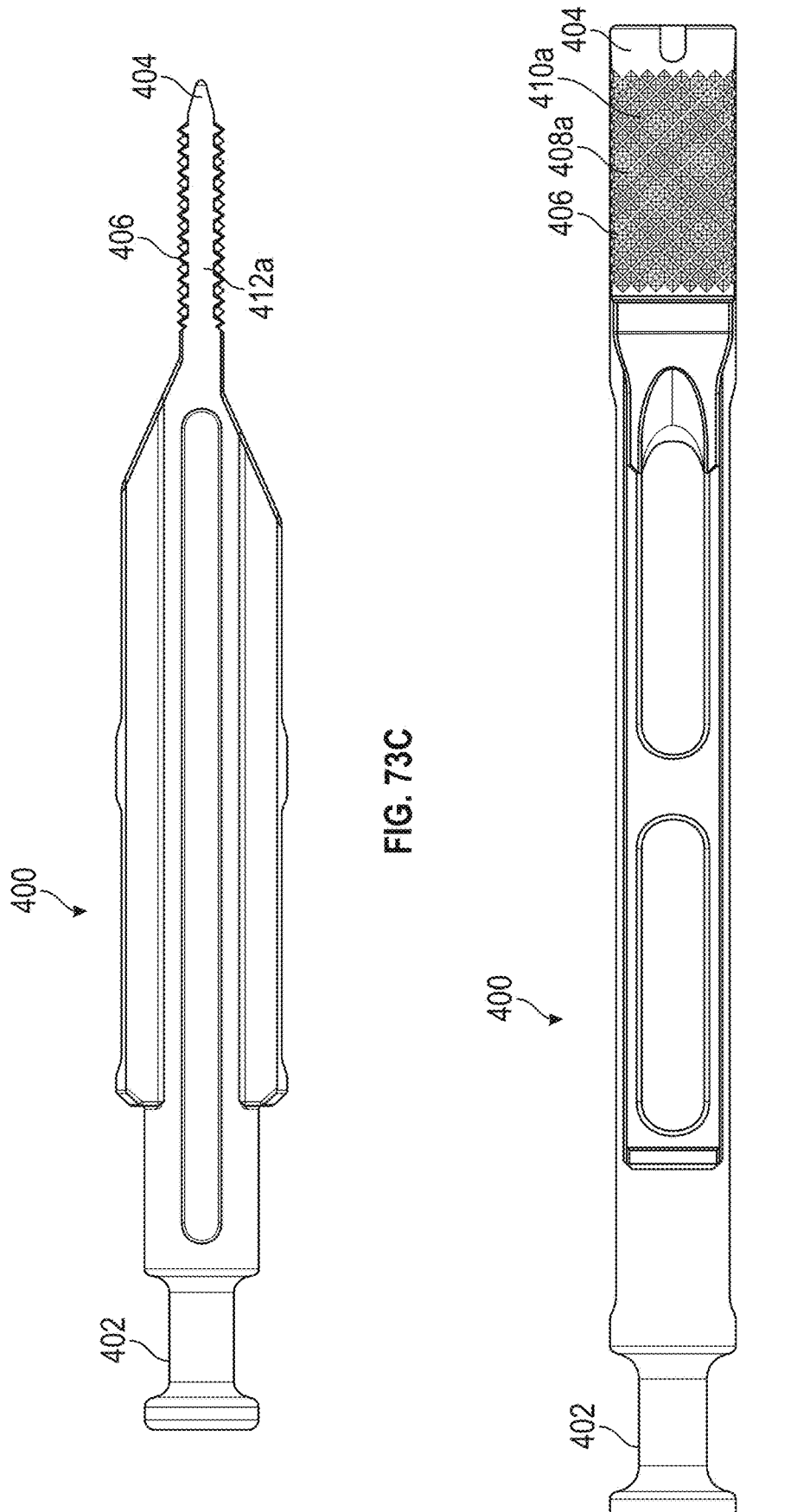

FIG. 73C illustrates a side view of the rasp from FIG. 73A.

FIG. 73D illustrates an alternative side view of the rasp from FIG. 73A.

Figure 73E:
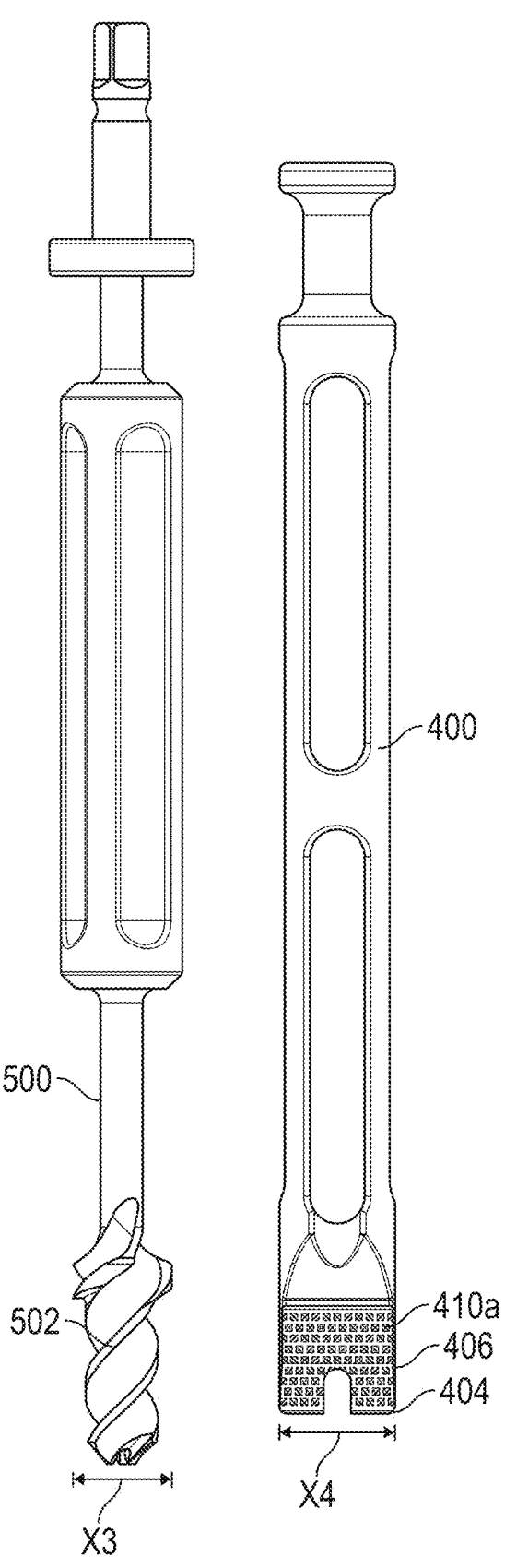

FIG. 73E illustrates the side view of some alternative embodiments of the implant system.

Figure 74B:
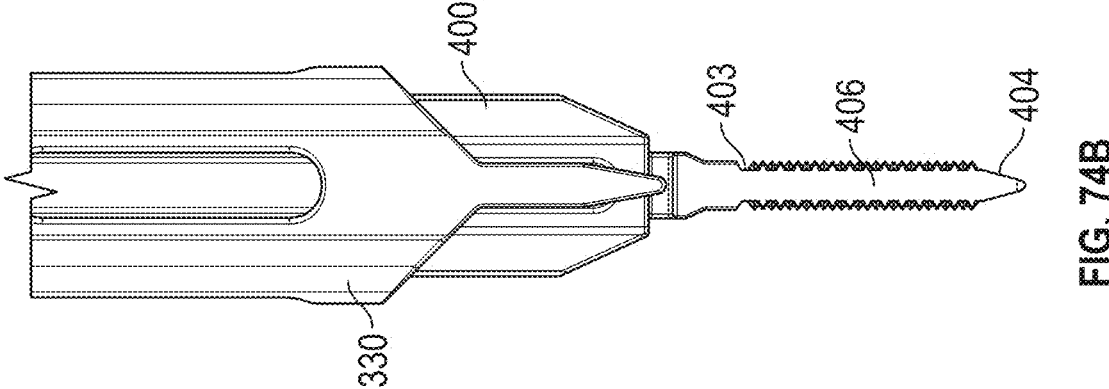
Figure 74A:
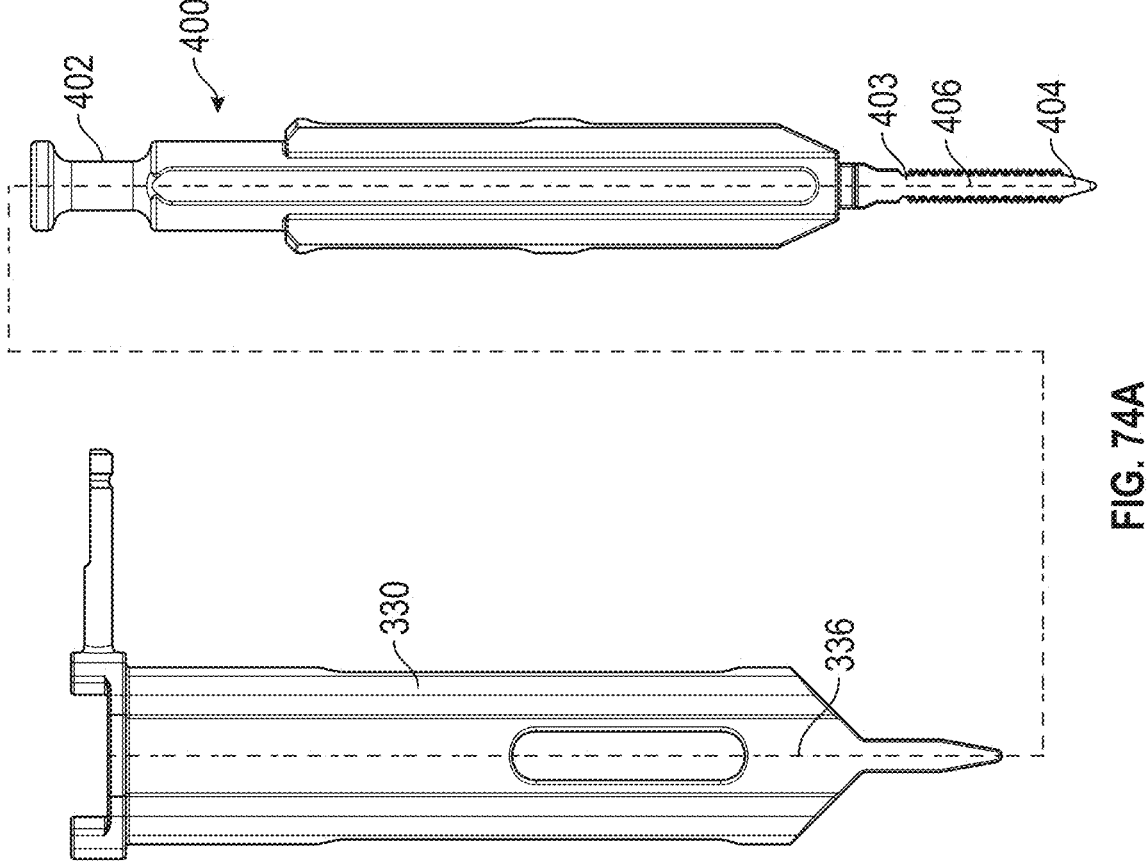

FIG. 74A illustrates a side view of a drill guide with a rasp in an embodiment of the implant system.

FIG. 74B illustrates a side view of a rasp and drill guide coupled in an embodiment.

Figure 74D:
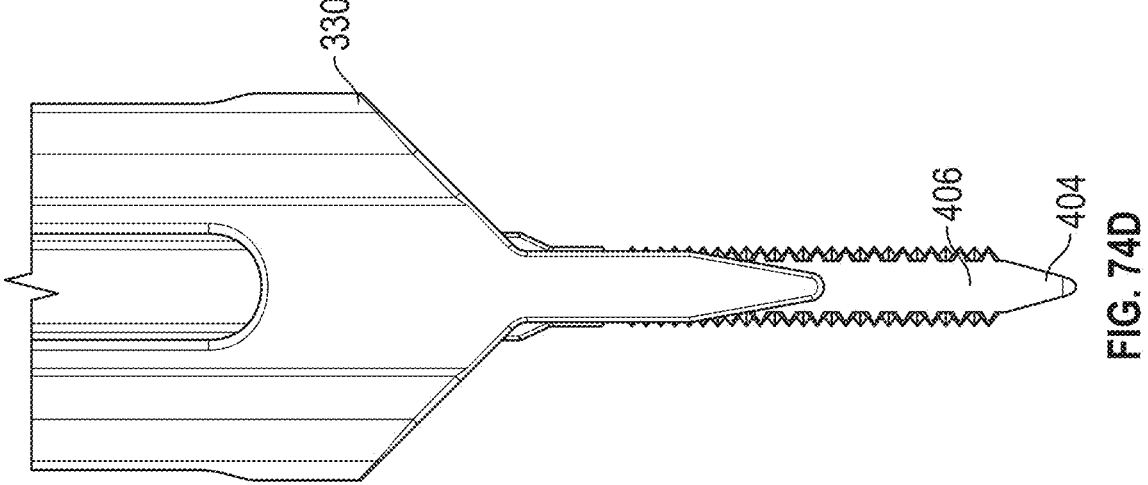
Figure 74C:
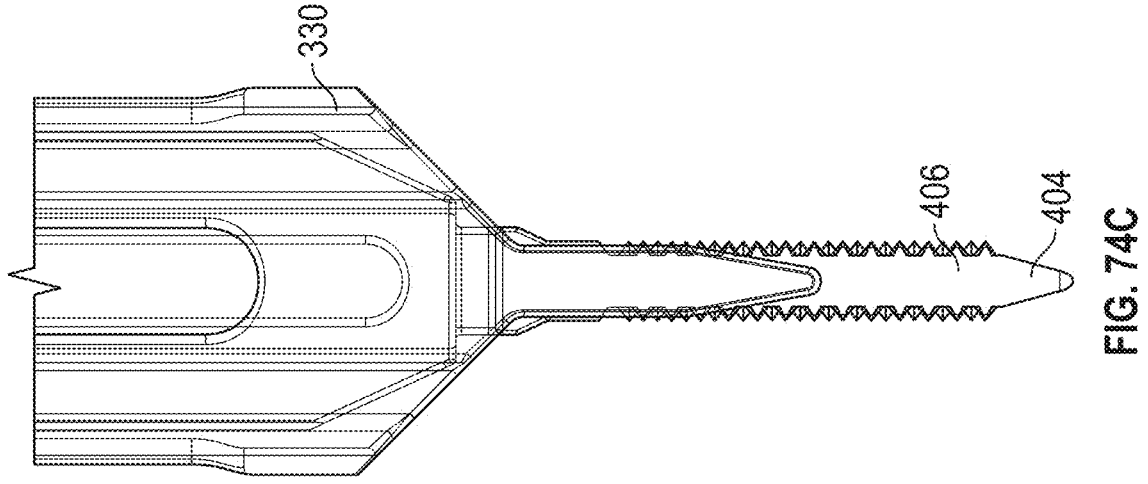

FIG. 74C illustrates a side view of a rasp placed through a drill guide in an embodiment.

FIG. 74D illustrates a side view of a rasp placed through a drill guide in an embodiment.

Figures 75A, 75B:
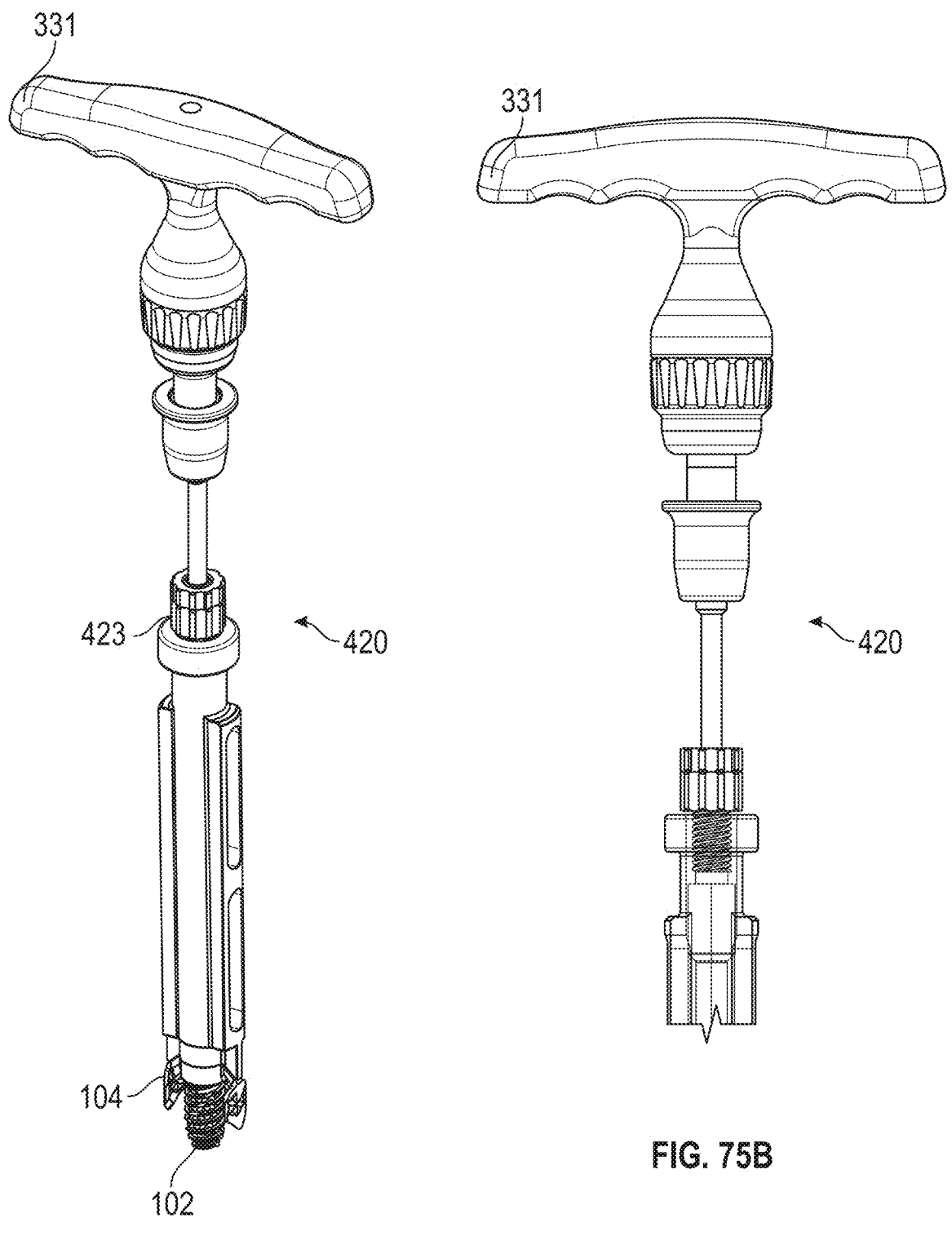

FIG. 75A illustrates a perspective view of an inserter in an embodiment.

FIG. 75B illustrates a side view of an inserter with a handle in an embodiment.

FIG. 75C illustrates a perspective view of an inserter with an engaged implant in an embodiment.

FIG. 75D illustrates a perspective view of an inserter engaging with an implant in an embodiment.

Figure 76A:
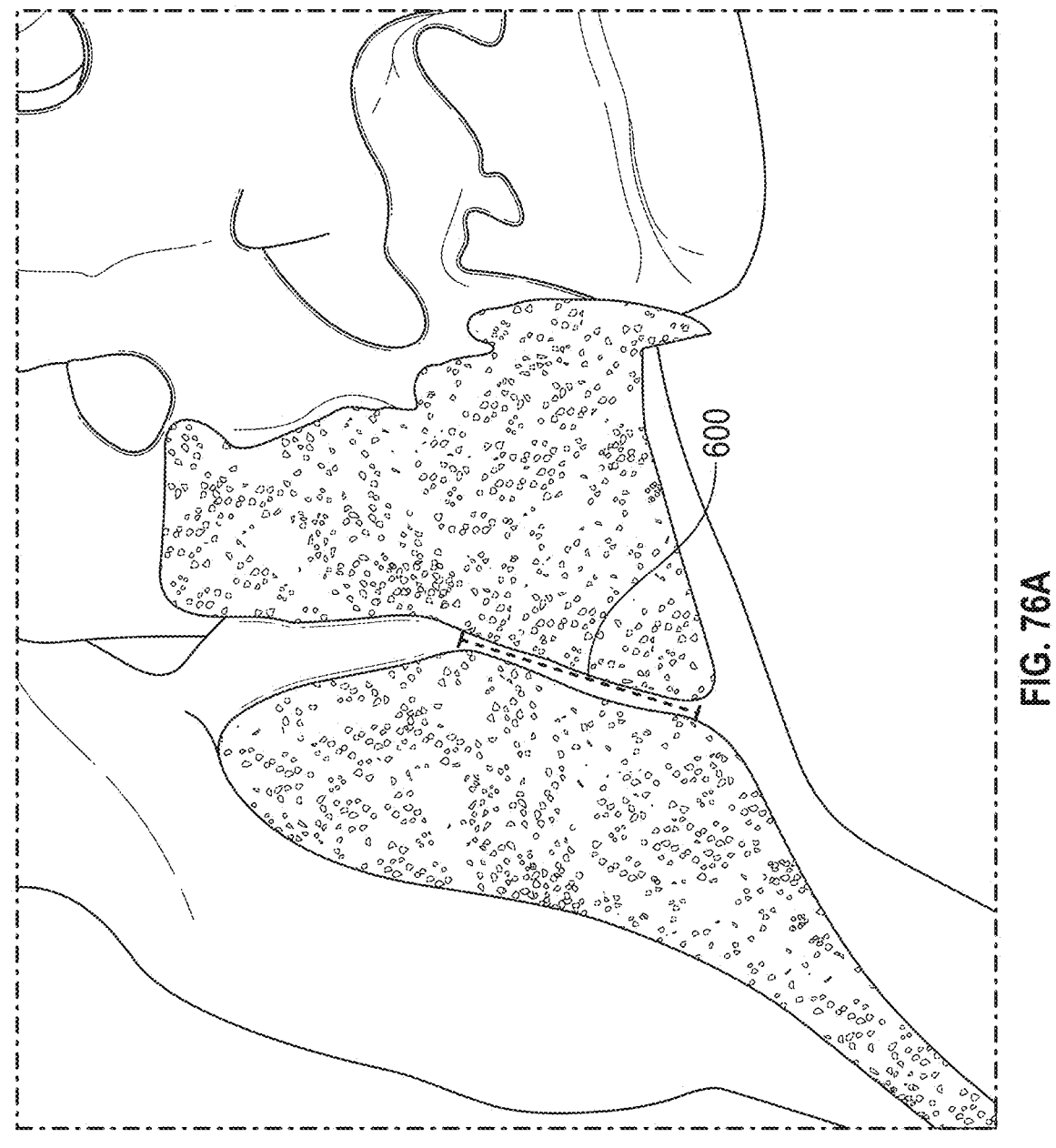

FIG. 76A illustrates an example of an SI joint.

Figure 76B:
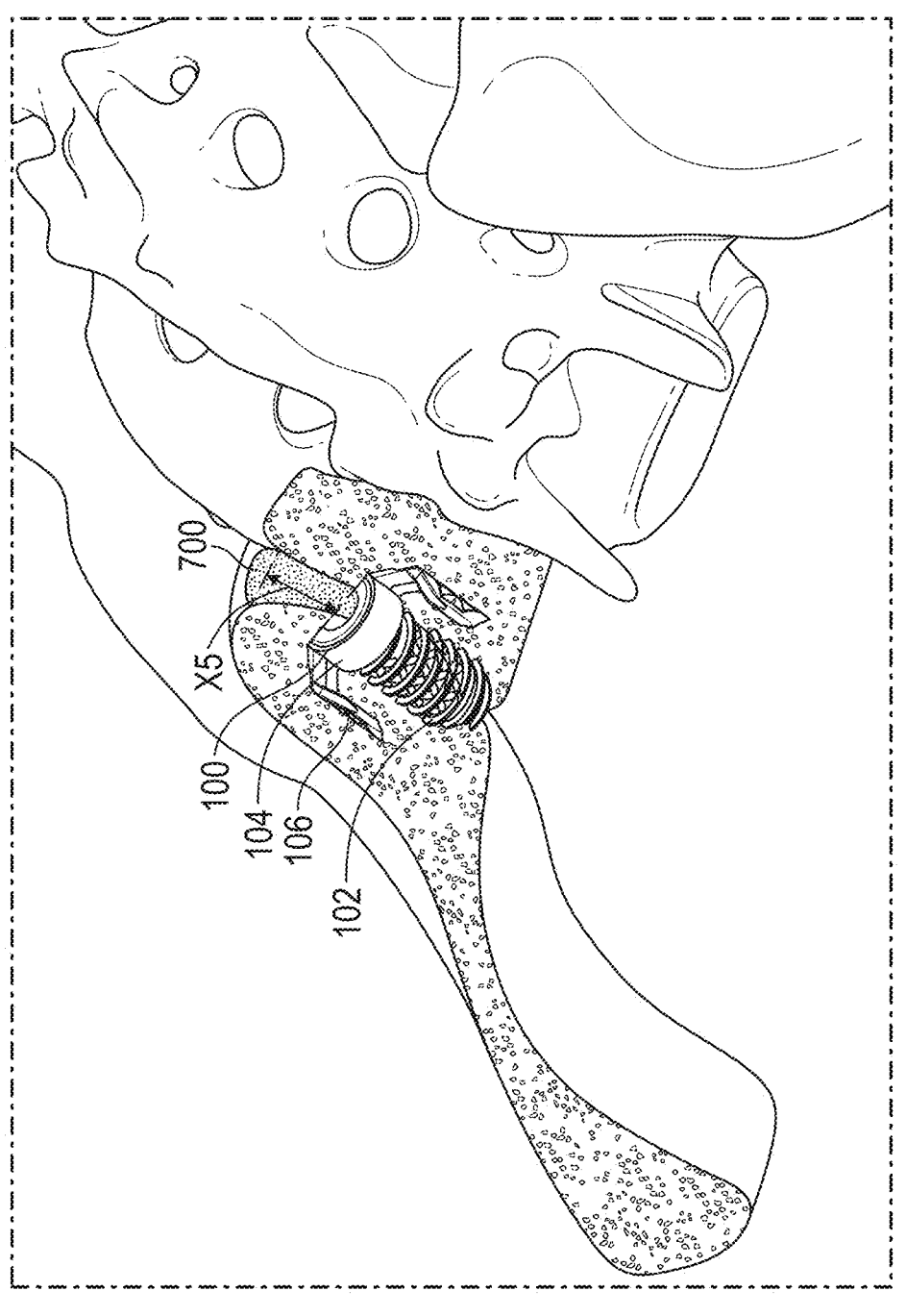

FIG. 76B illustrates an embodiment of an implant system positioned with an SI joint showing a portion of the bone cut away.

Figure 77A:
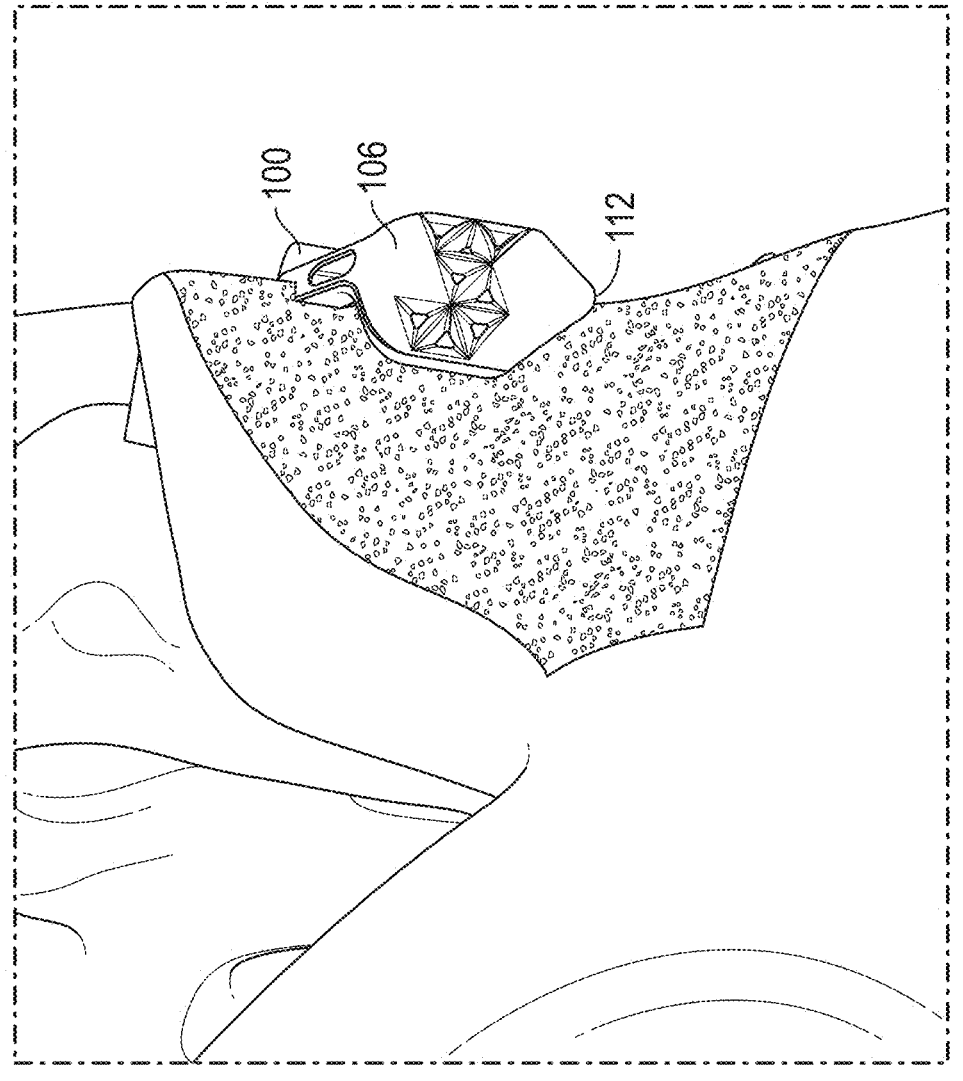

FIG. 77A illustrates an embodiment of an implant system positioned within an SI joint.

Figure 77B:
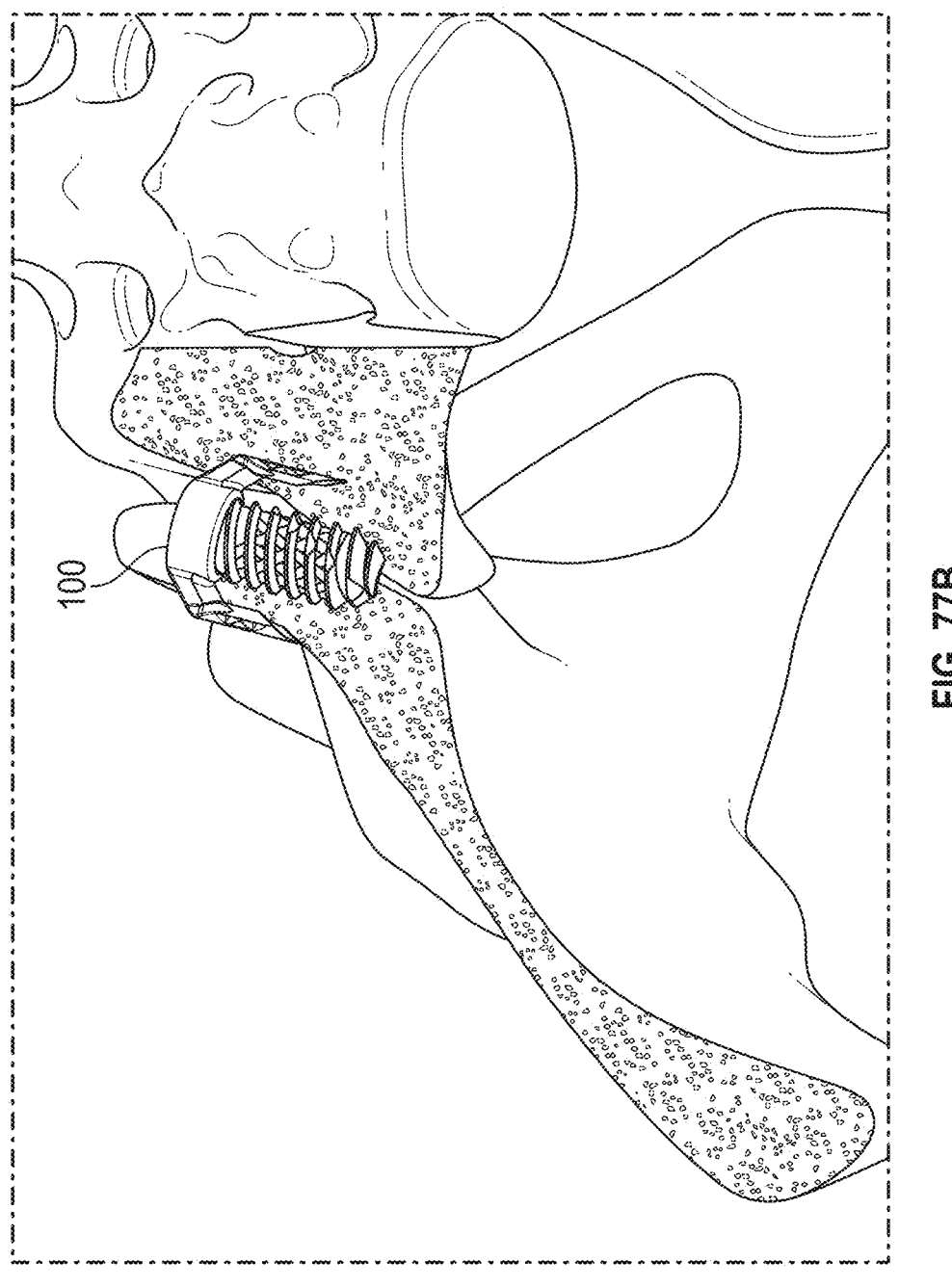

FIG. 77B illustrates an embodiment of an implant system positioned with an SI joint showing a portion of the bone cut away.

Figure 78:
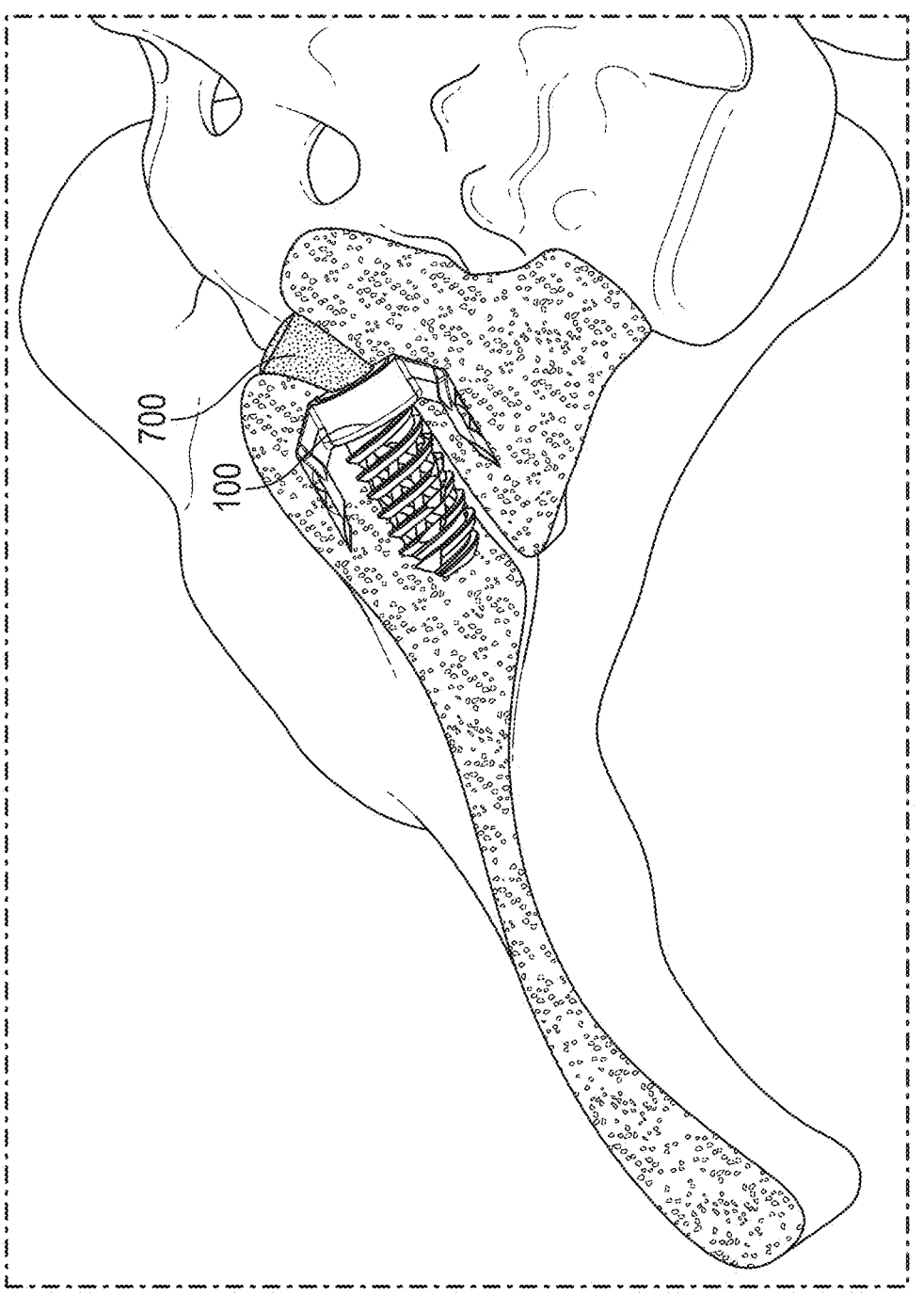

FIG. 78 illustrates an embodiment of an implant system positioned with an SI joint showing a portion of the bone cut away.

Figure 79:
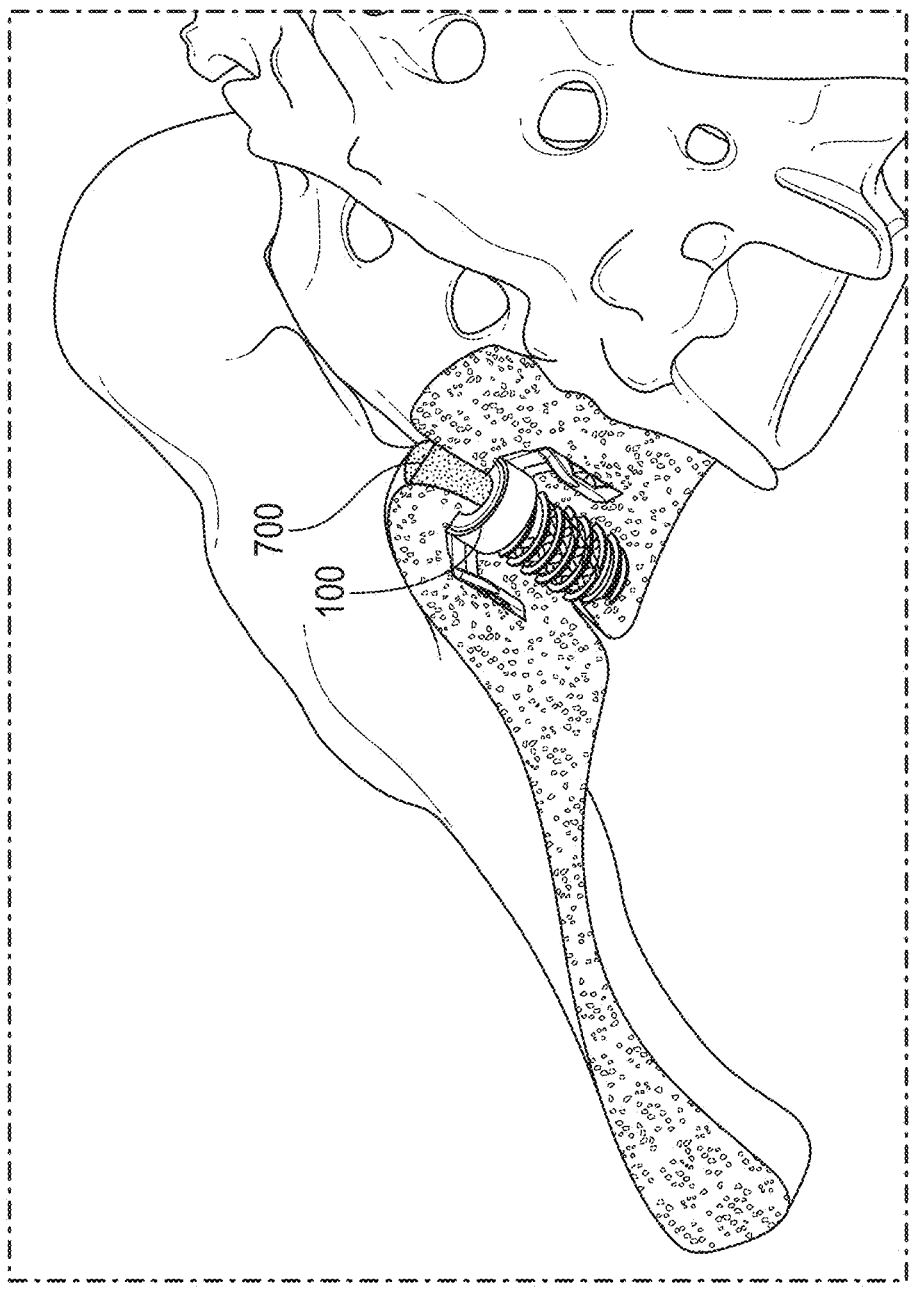

FIG. 79 illustrates an embodiment of an implant system positioned with an SI joint showing a portion of the bone cut away.

Figure 80A:
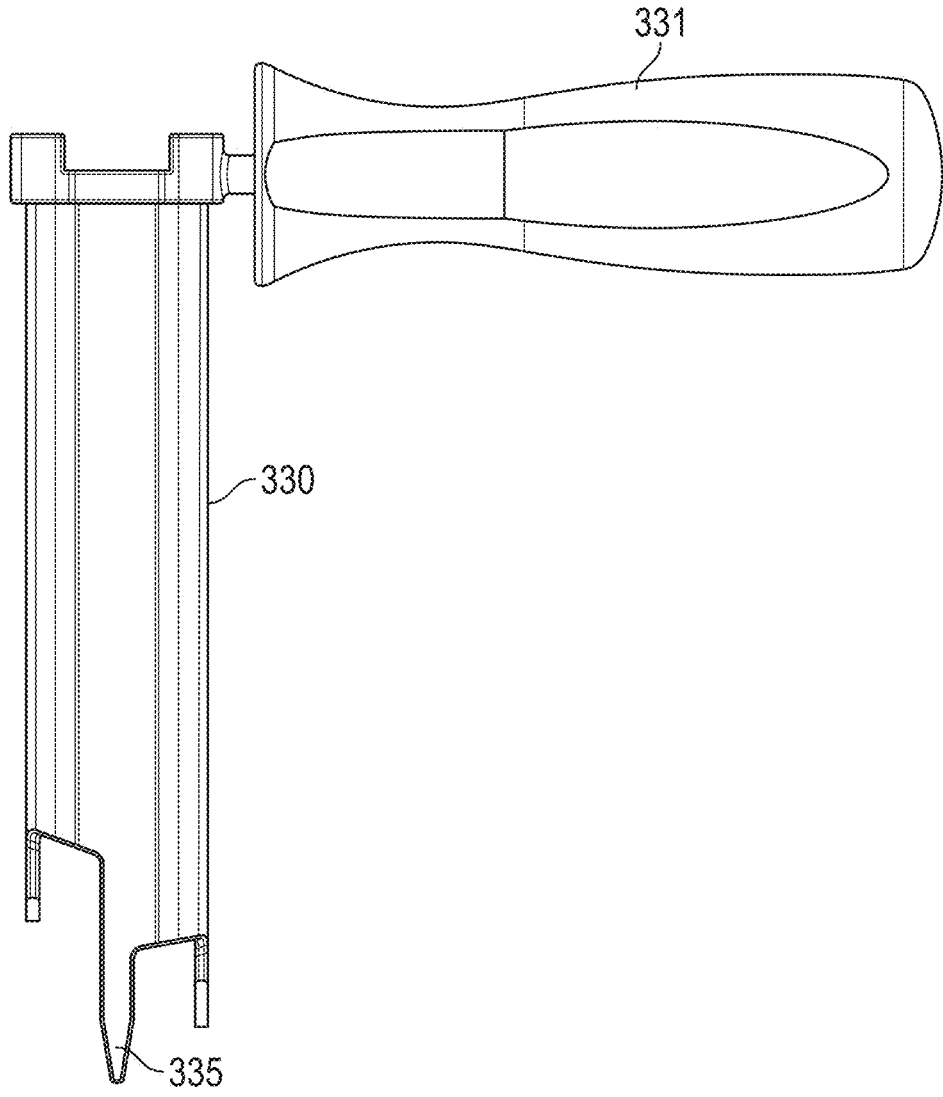

FIG. 80A illustrates an embodiment of a drill guide.

Figure 80B:
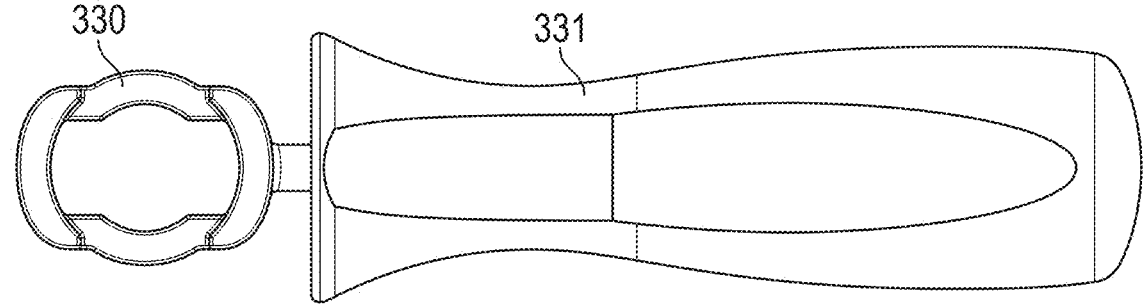

FIG. 80B illustrates an embodiment of a drill guide.

Figure 80C:
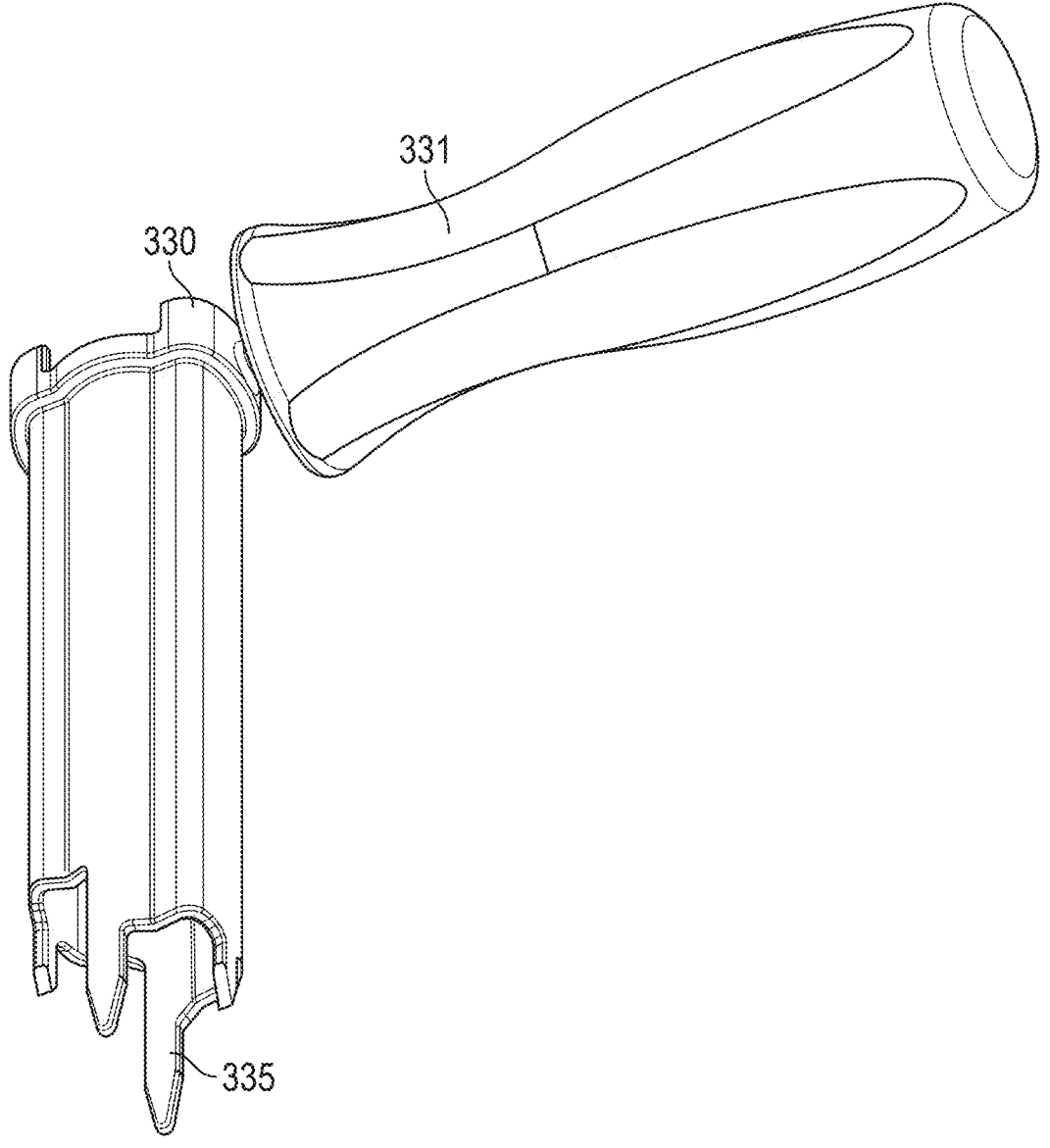

FIG. 80C illustrates an embodiment of a drill guide.

Figure 81A:
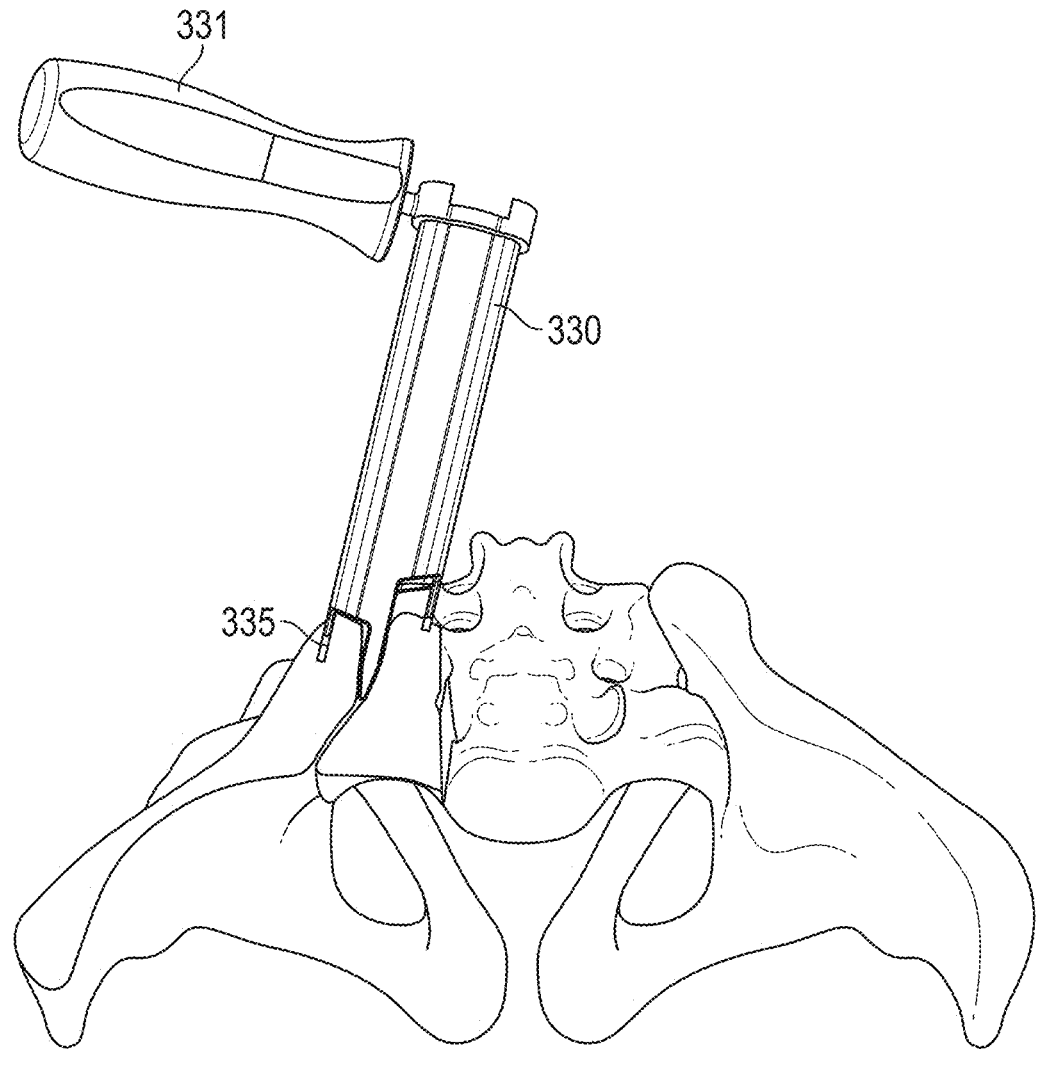

FIG. 81A illustrates an embodiment of a drill guide positioned at an SI joint.

Figure 81B:
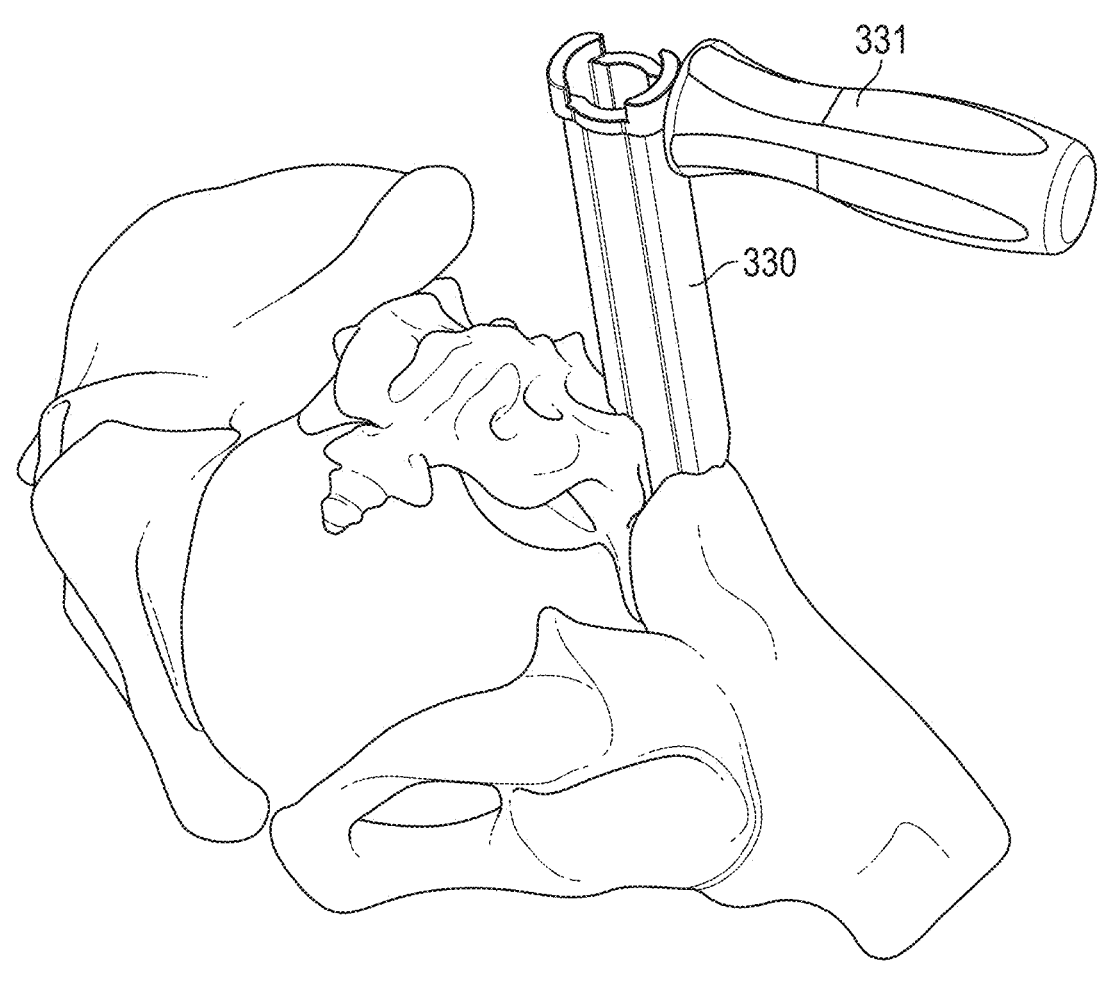

FIG. 81B illustrates an embodiment of a drill guide positioned at an SI joint.

Figure 81C:

FIG. 81C illustrates an embodiment of a drill guide positioned at an SI joint.

Figure 82A:
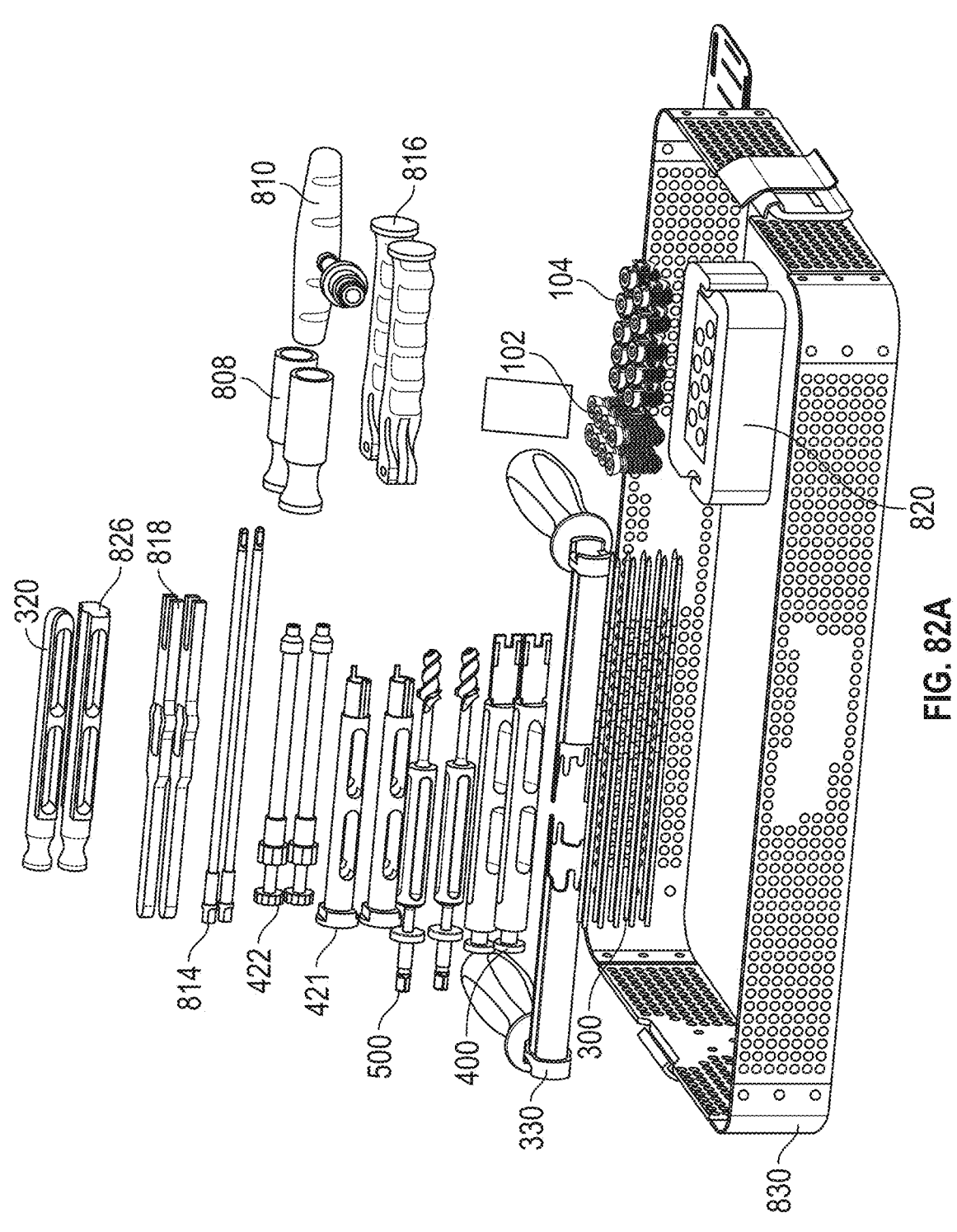

FIG. 82A illustrates an embodiment of an SI joint implant system kit.

Figure 82B:
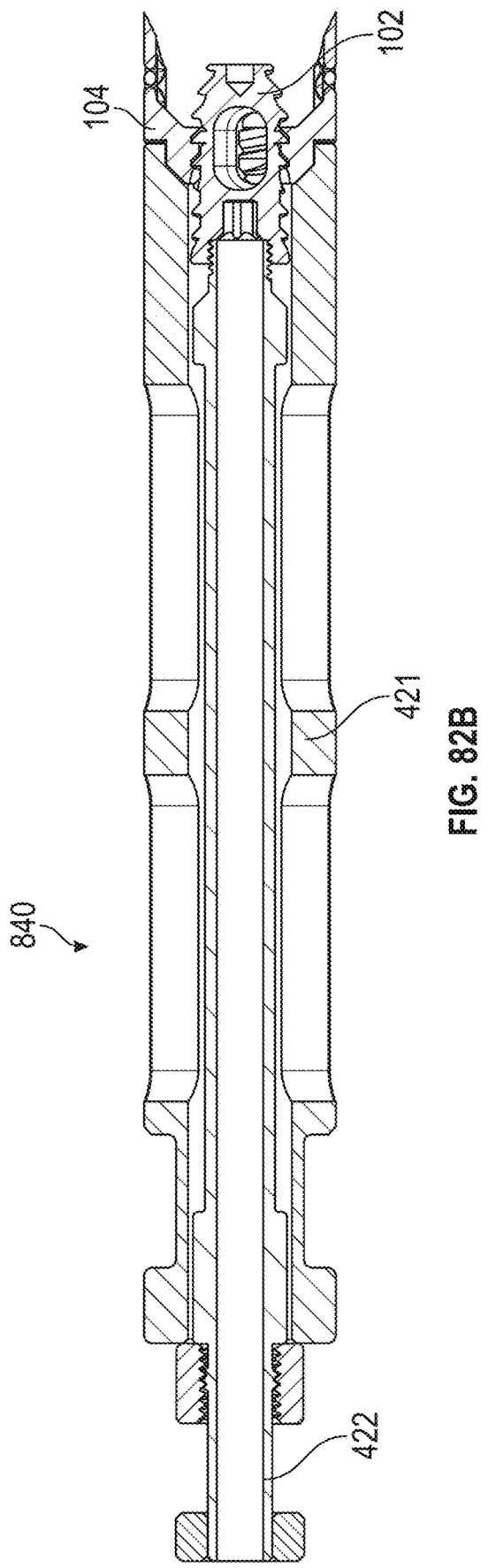

FIG. 82B illustrates an embodiment of an inserter including components of the SI joint implant system kit of FIG. 82A.

Figure 83A:
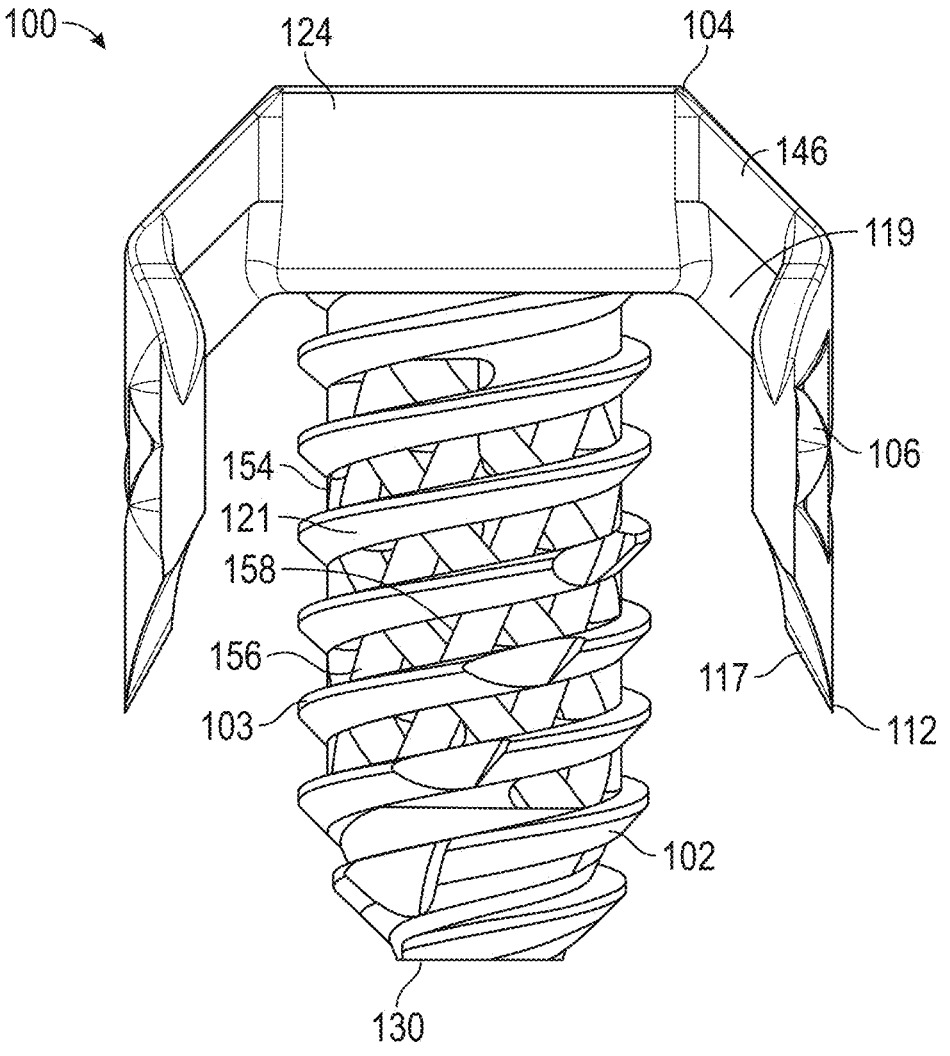
Figure 83B:
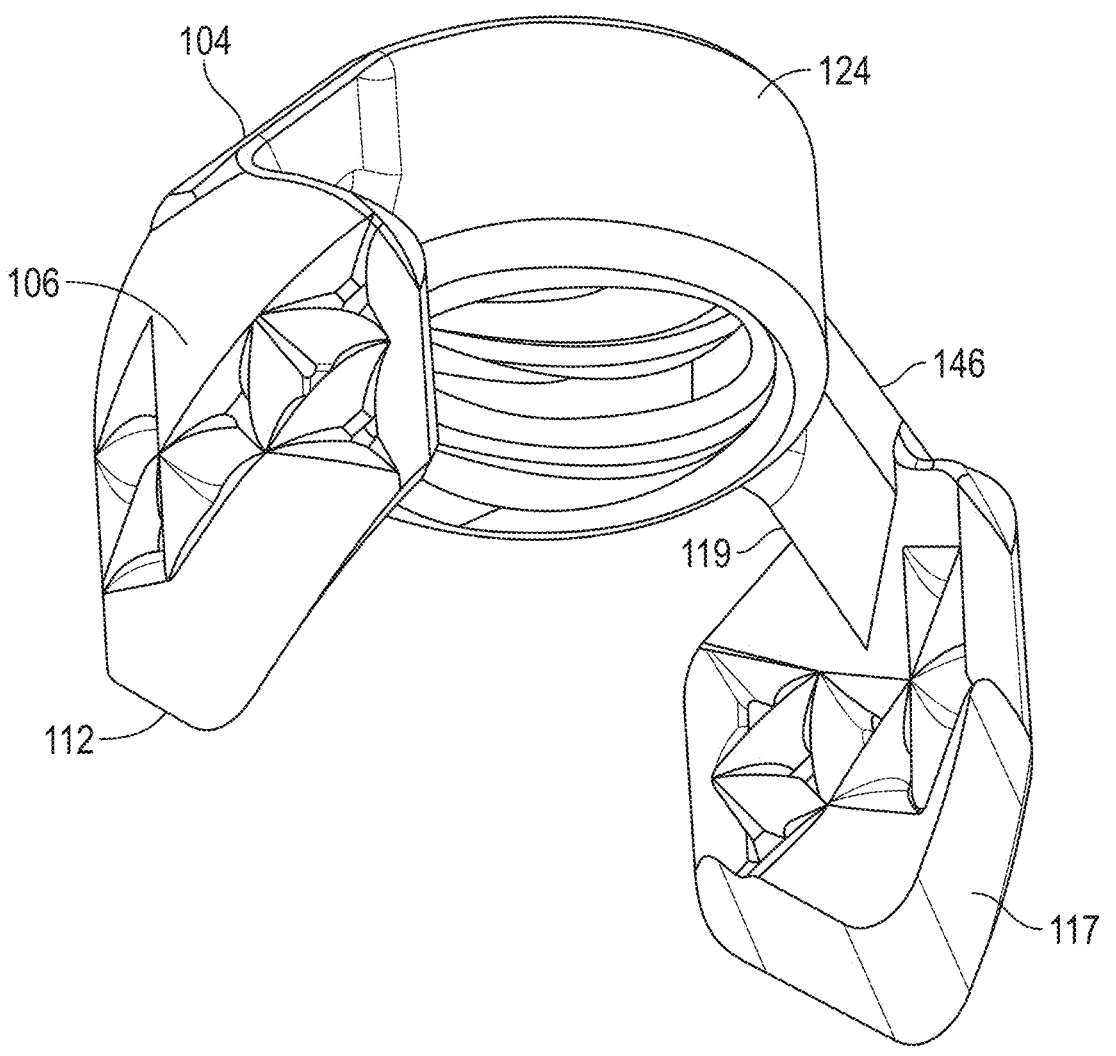
Figure 83C:
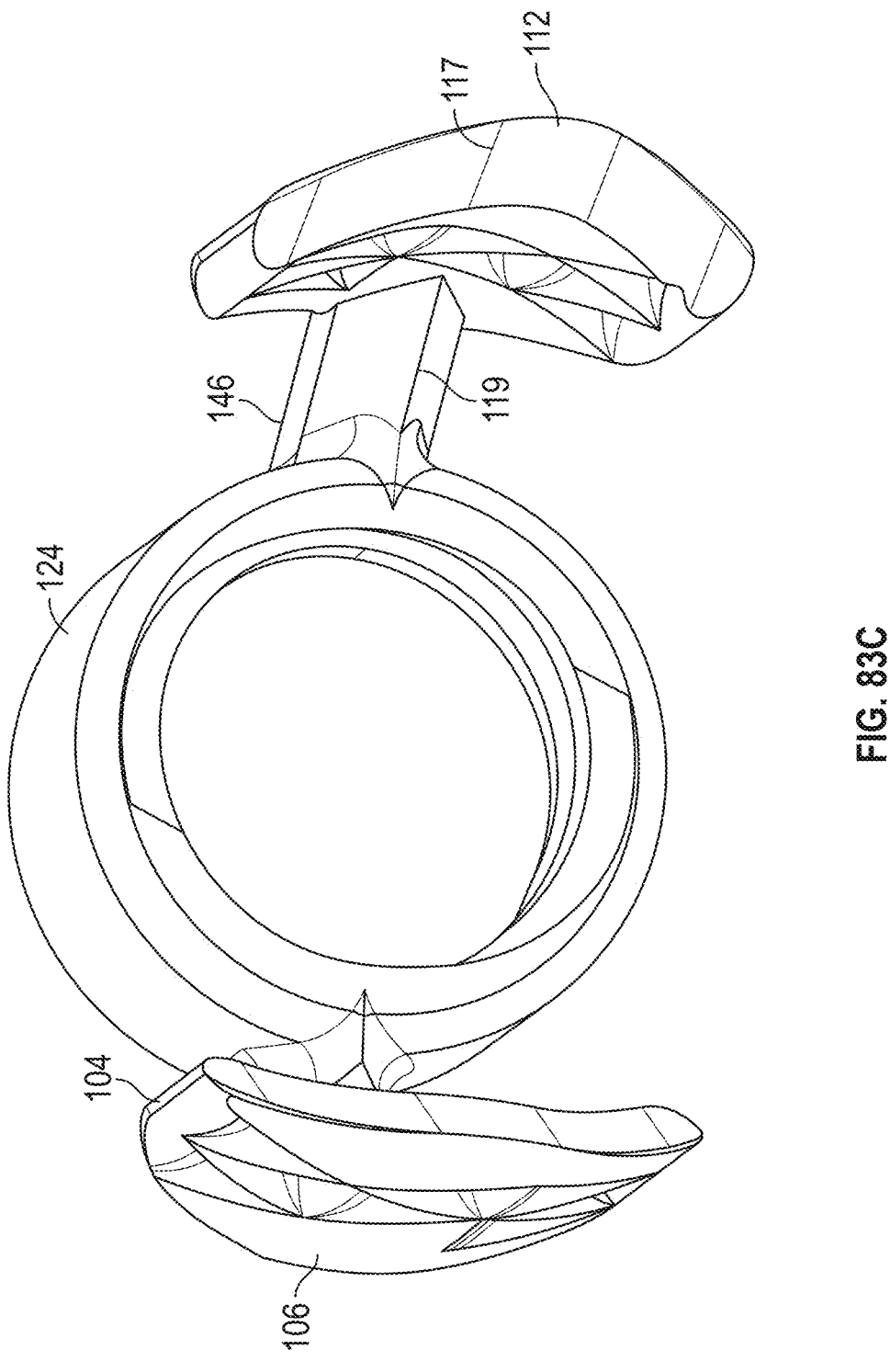

FIGS. 83A-83C illustrate an embodiment of a joint implant system.

FIGS. 84A-84G illustrate an embodiment of a joint implant system.

Figure 85A:
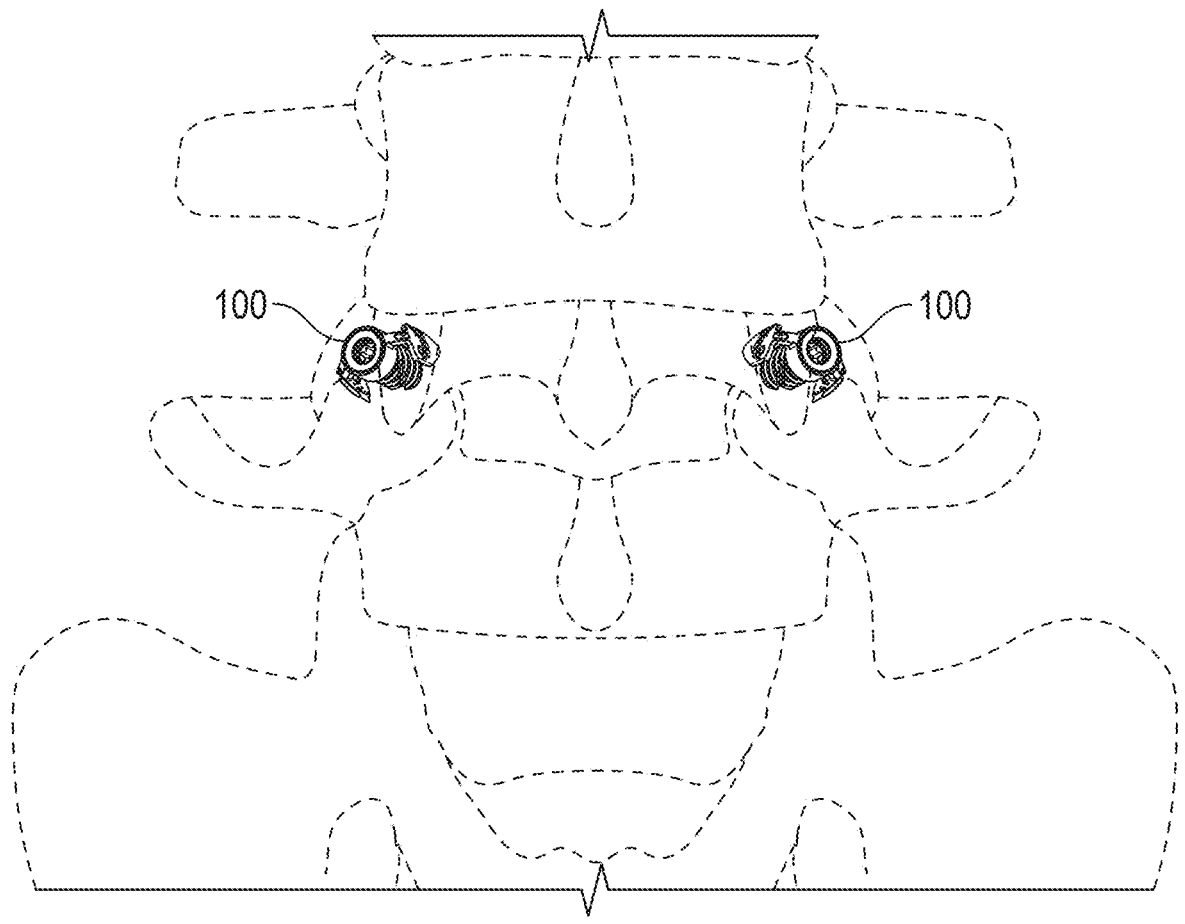
Figure 85B:
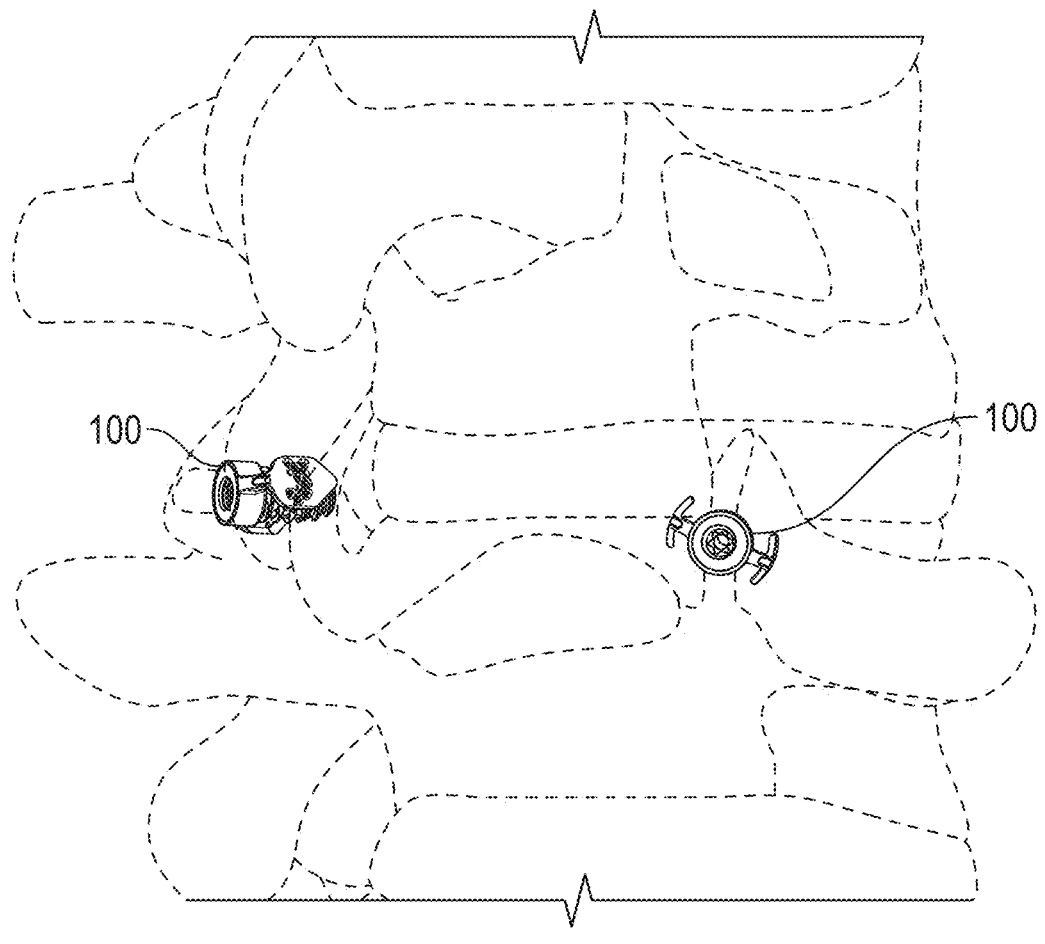

FIGS. 85A-85B illustrate an embodiment of implant systems positioned within facet joints.

Figure 86B:
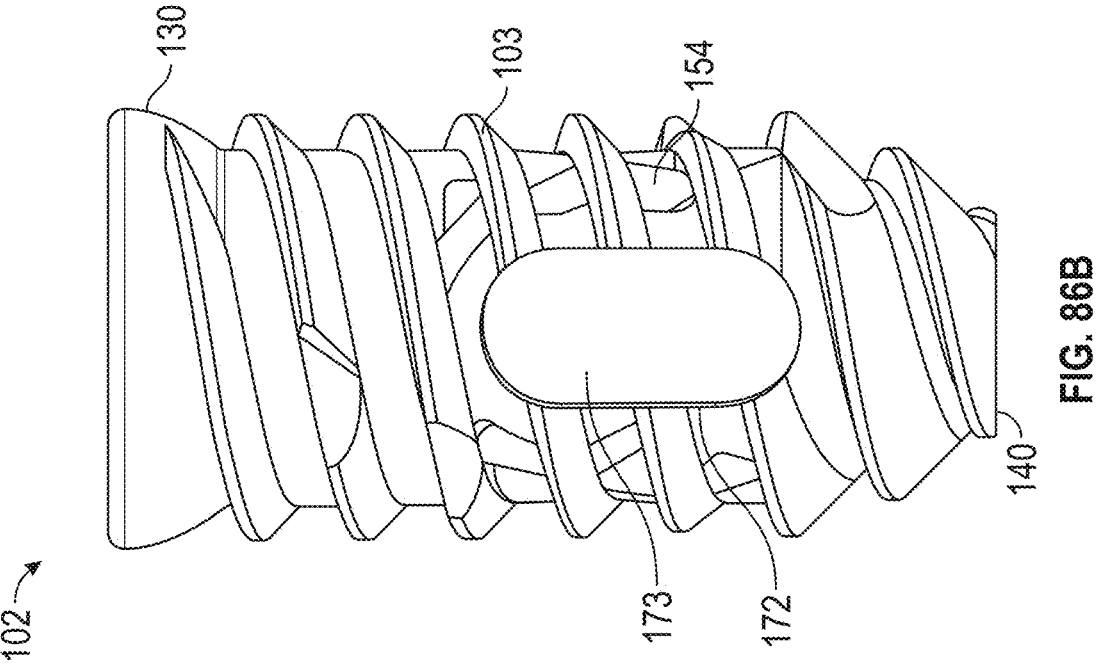
Figure 86A:
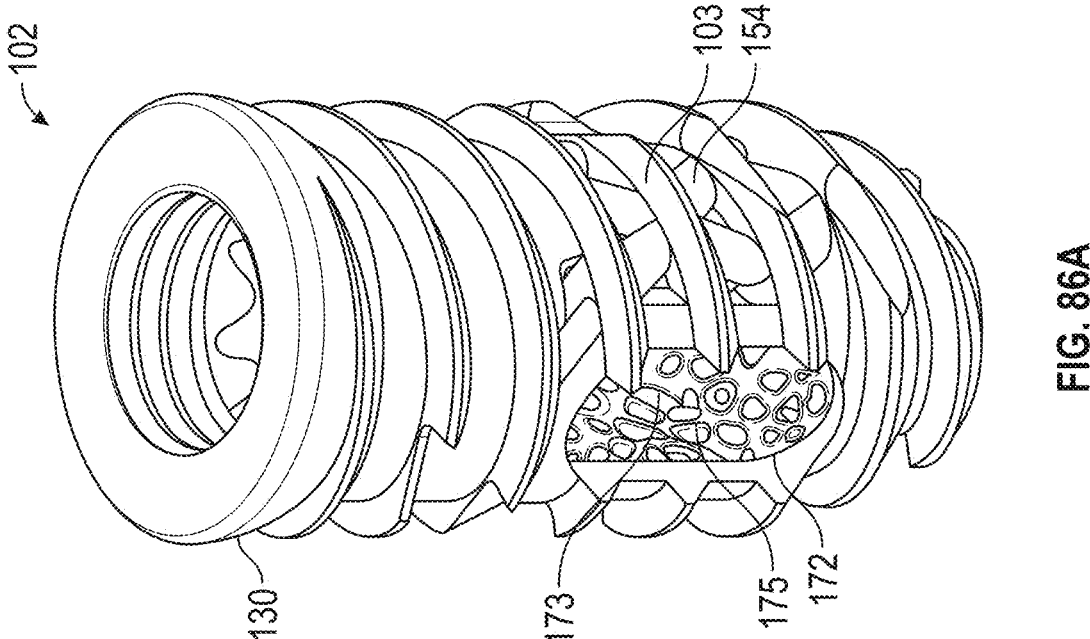
Figure 86C:
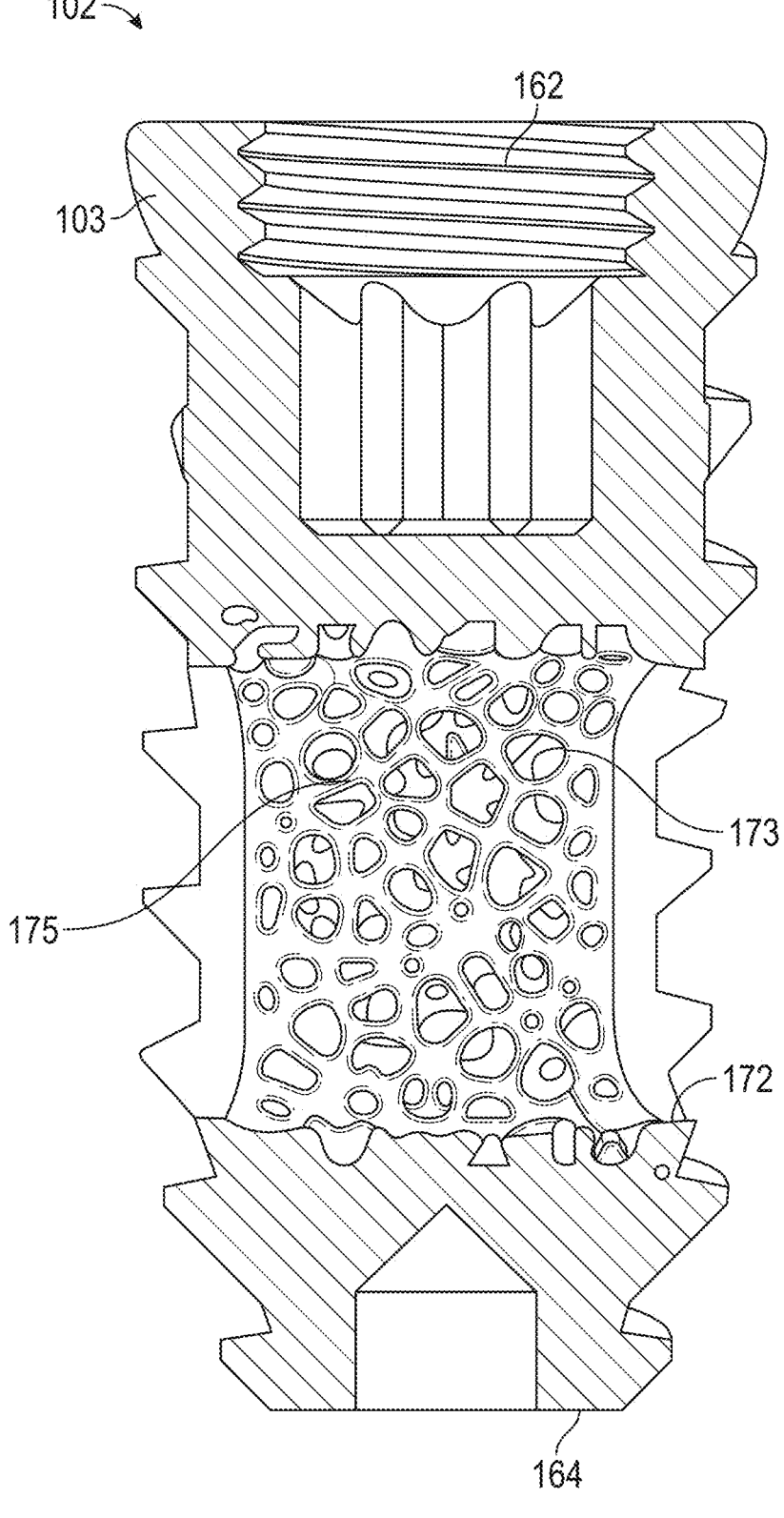

FIGS. 86A-86C illustrate an embodiment of a primary implant.

Figure 86D:
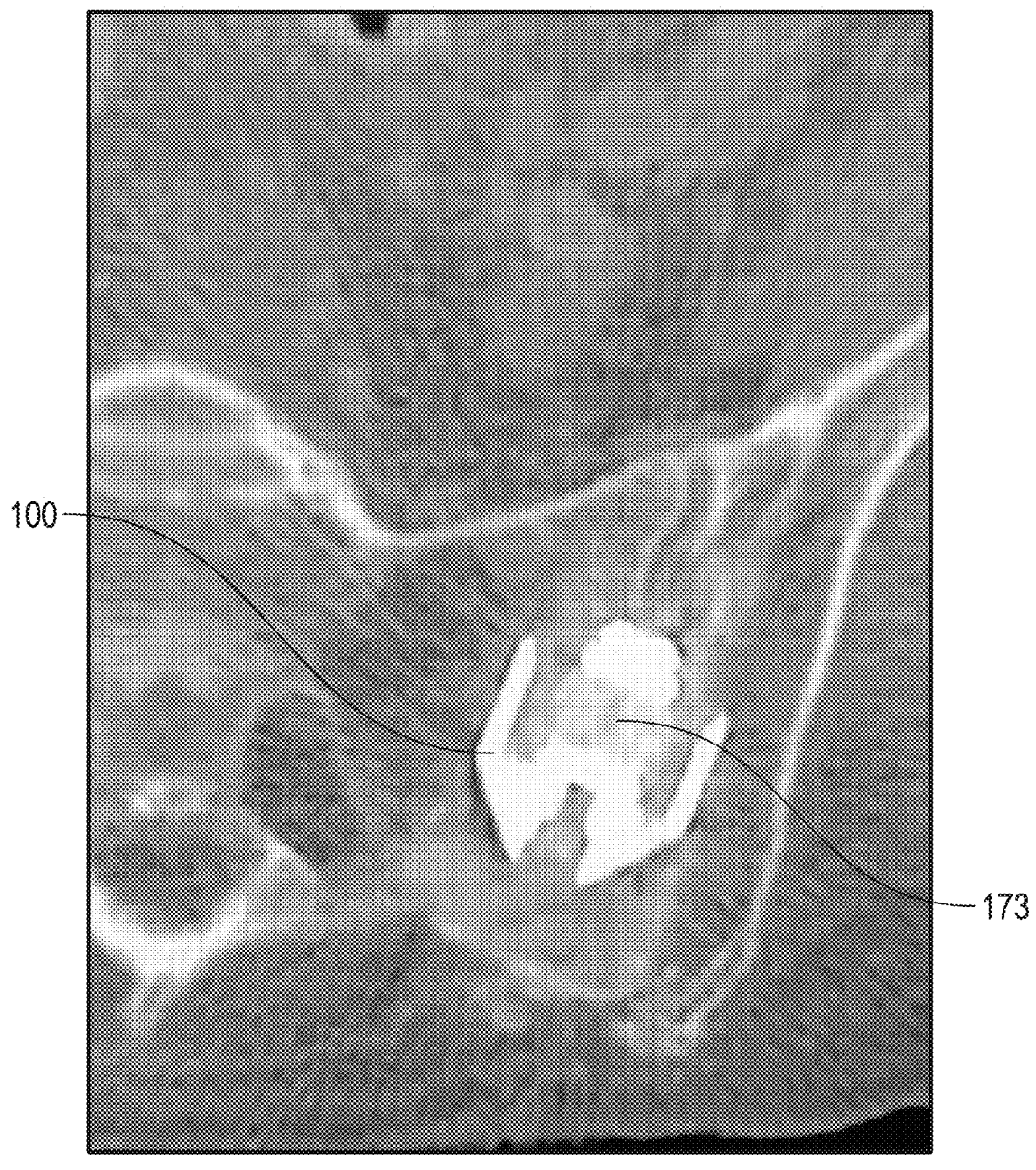

FIG. 86D illustrates an implant system positioned within an SI joint showing bone growth through the primary implant.

Figures 87A, 87B:
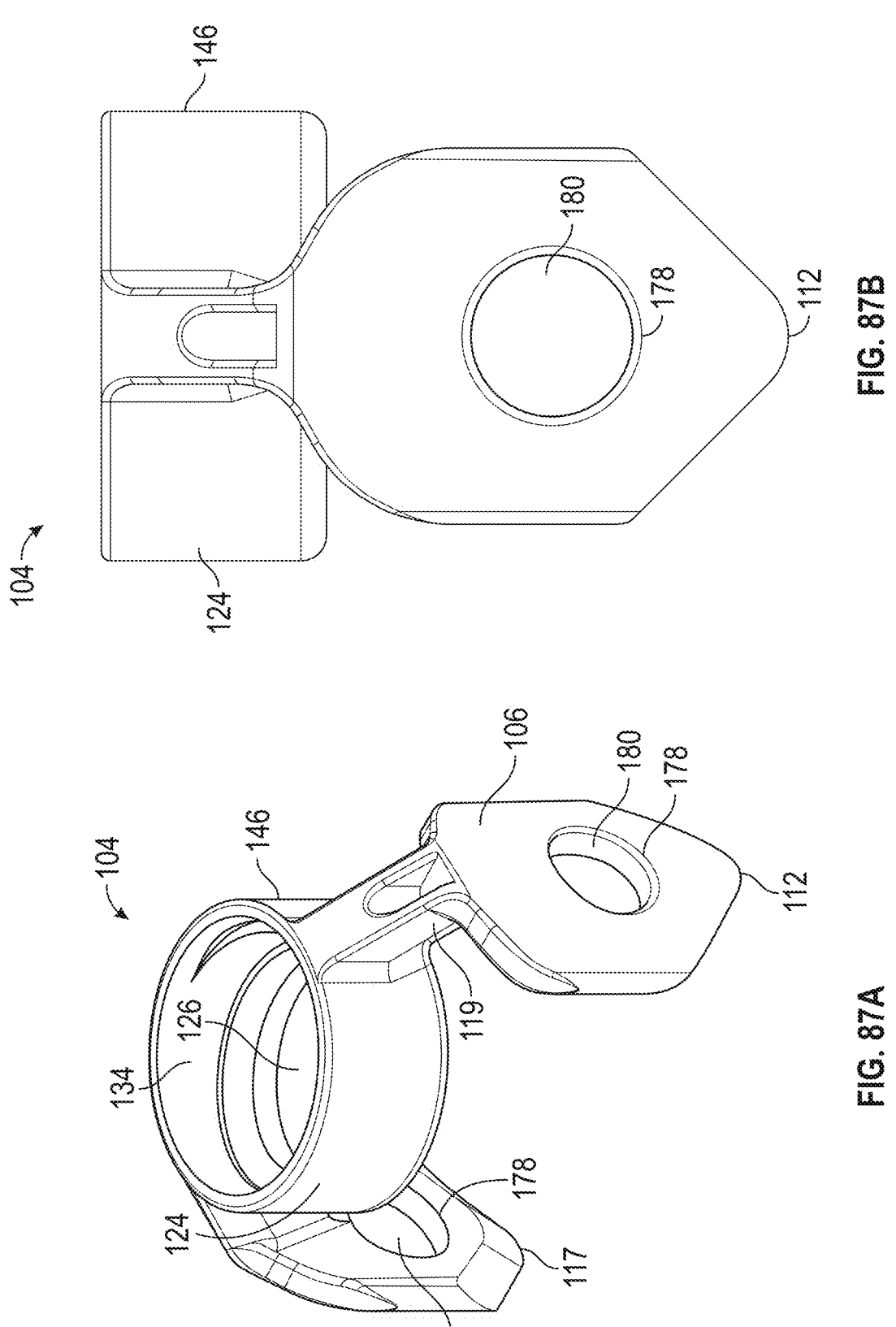
Figure 87C:
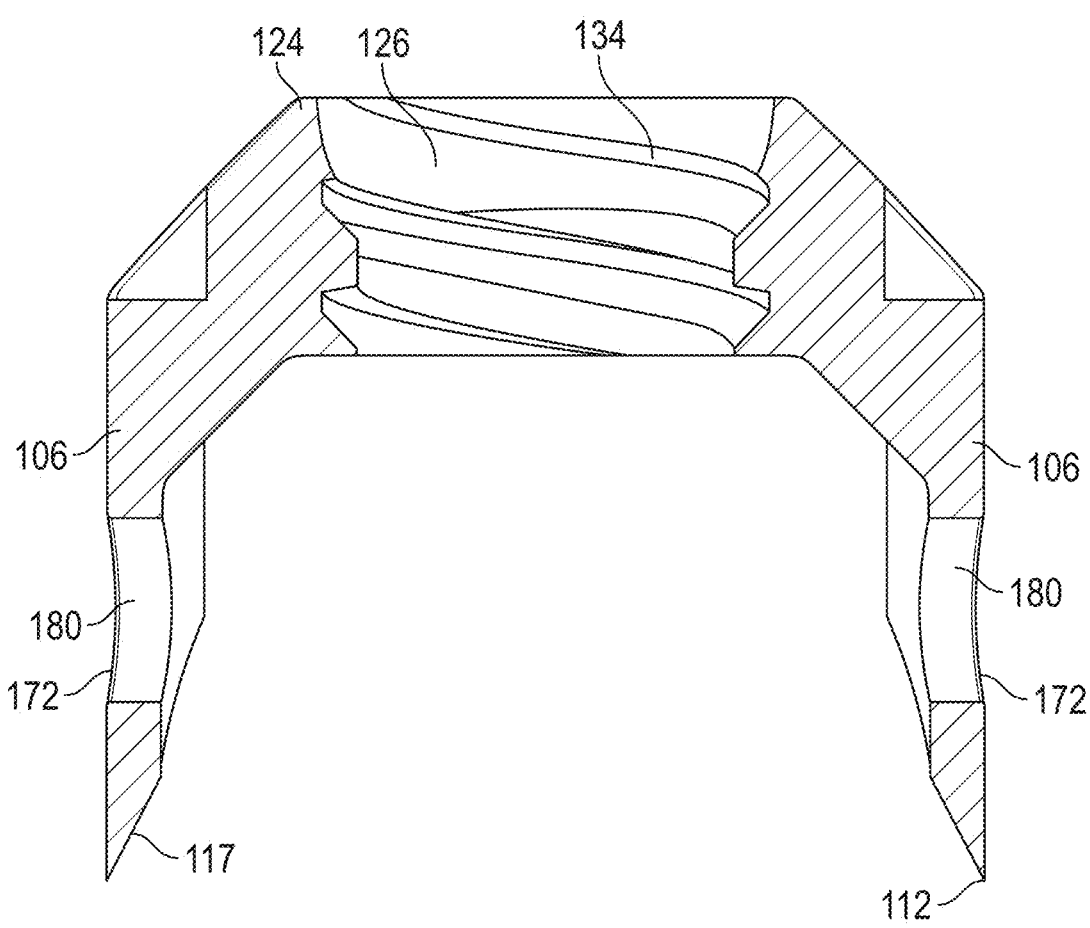

FIGS. 87A-87C illustrate an embodiment of a secondary implant.

FIGS. 88A-88J illustrate an embodiment of a two-part joint implant system with diagonally protruding blades.

FIGS. 89A-89J illustrate an embodiment of a two-part joint implant system with vertically protruding blades.

FIGS. 90A-90D illustrate an embodiment of an implant.

Figure 90A:
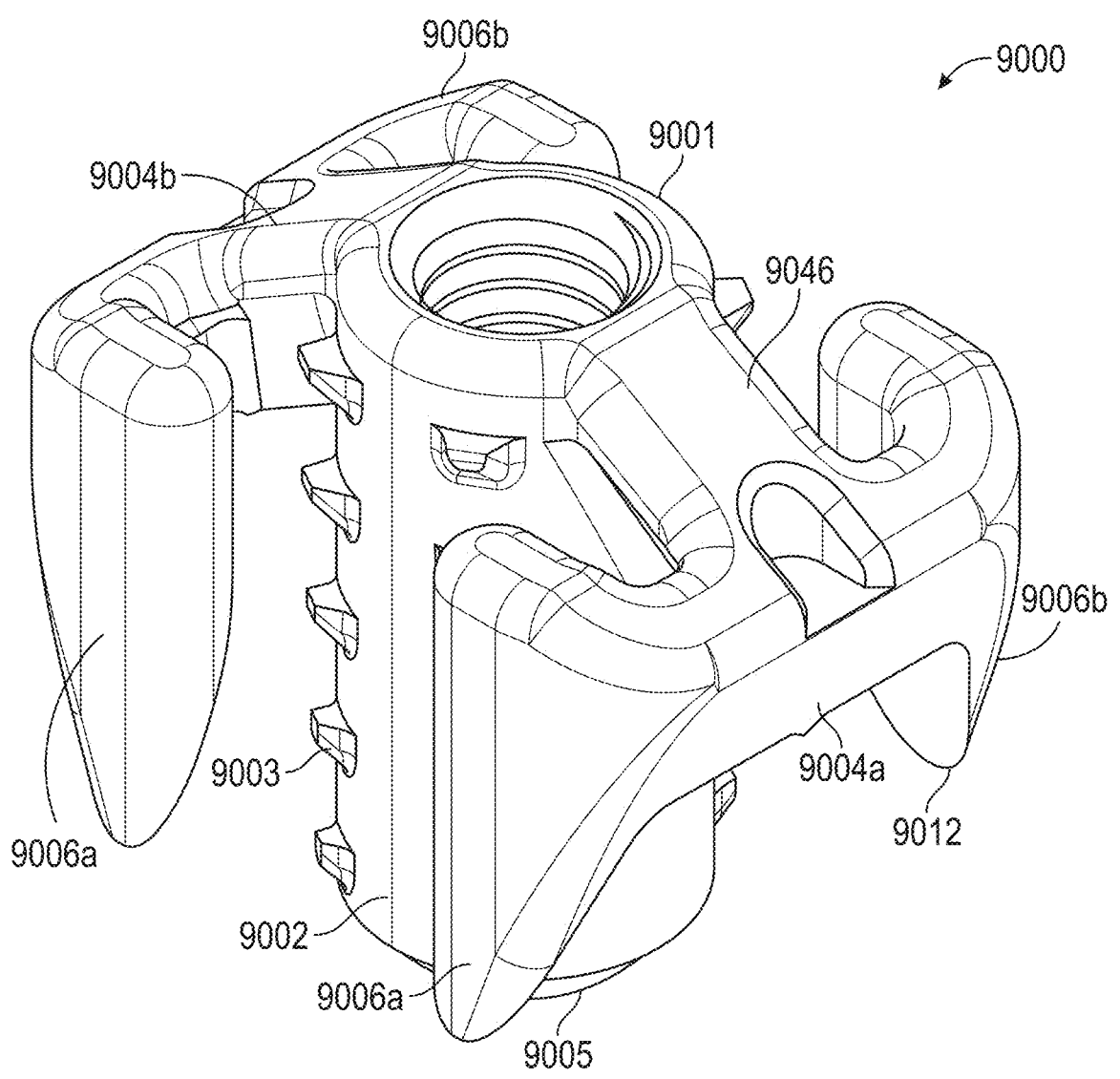
Figure 90B:
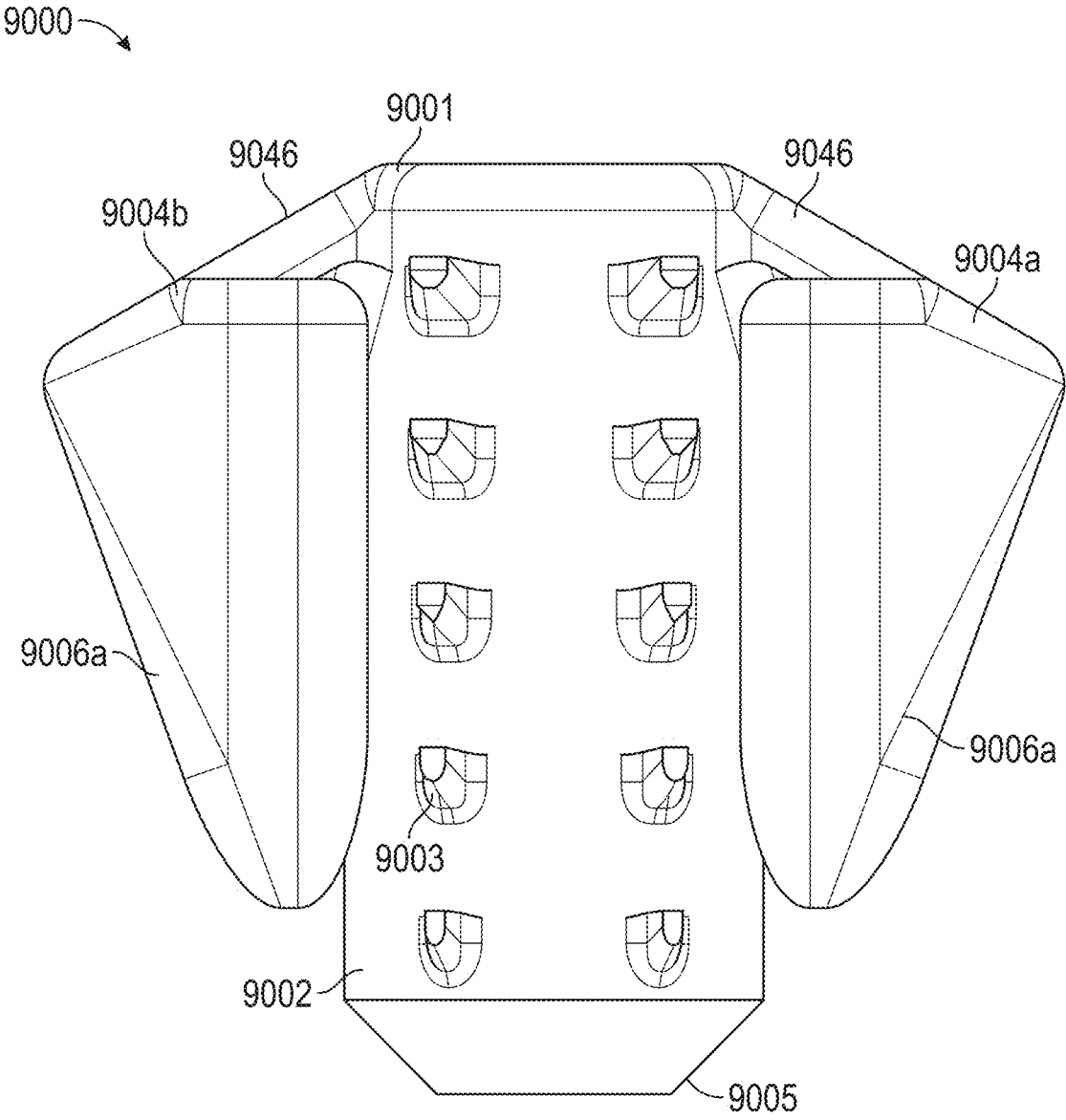
Figure 90C:
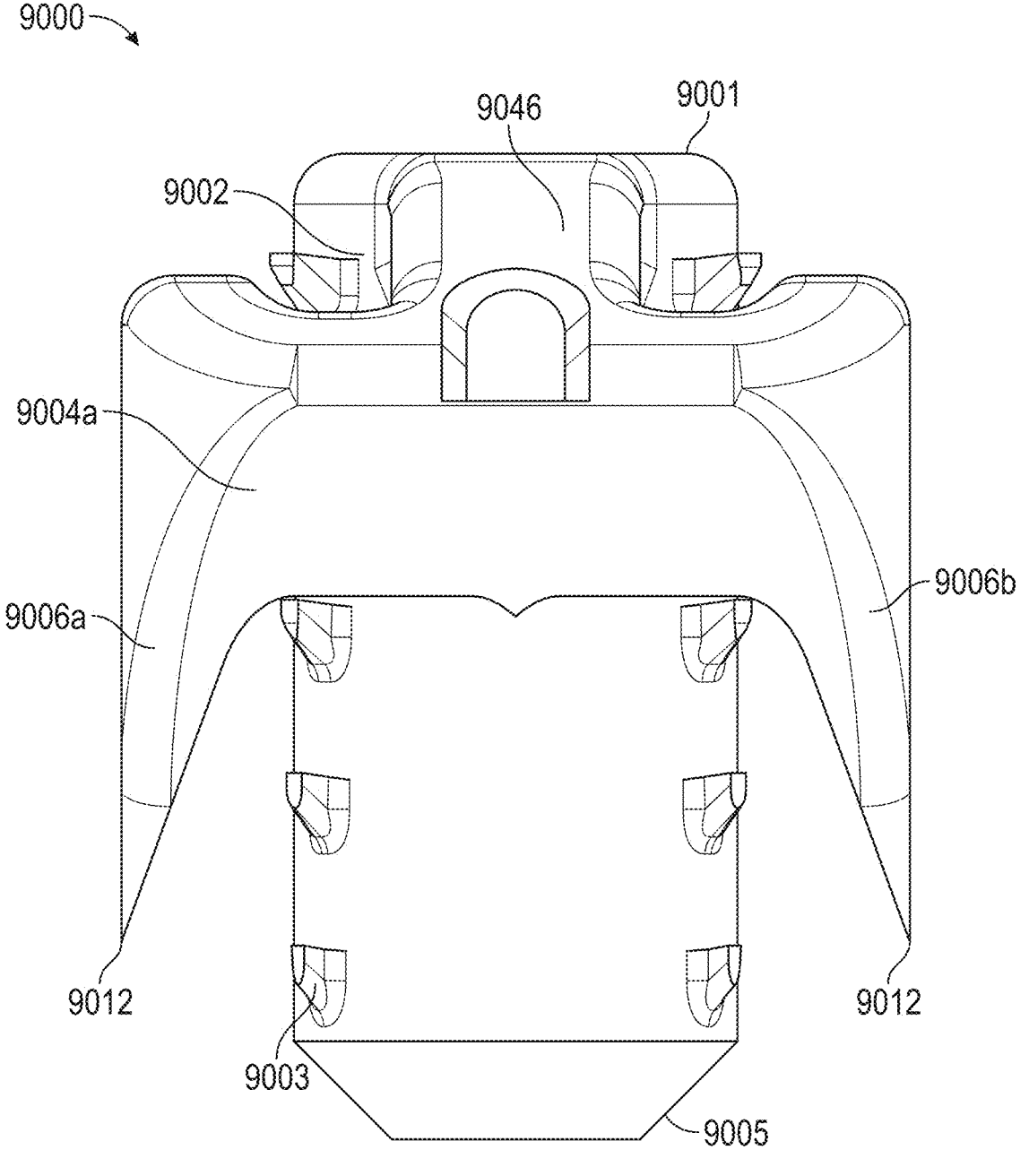
Figure 90D:
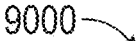
Figure 90E:
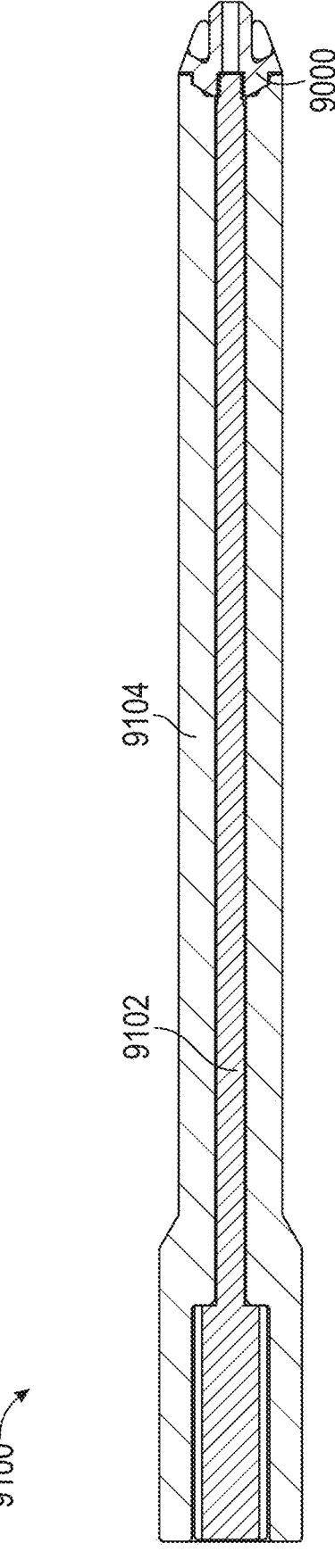

FIG. 90E illustrates an embodiment of an implant coupled to an inserter.

Figure 90F:
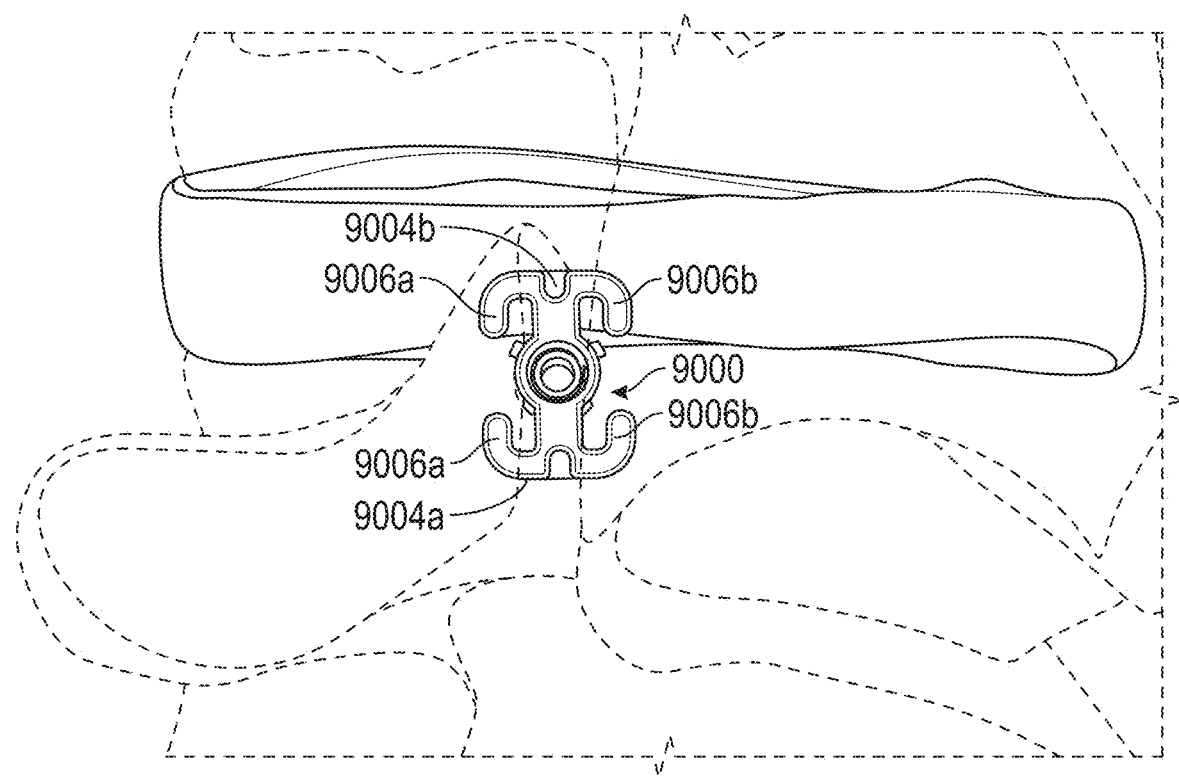

FIG. 90F illustrates an embodiment of an implant positioned within a facet joint.

Figure 91A:
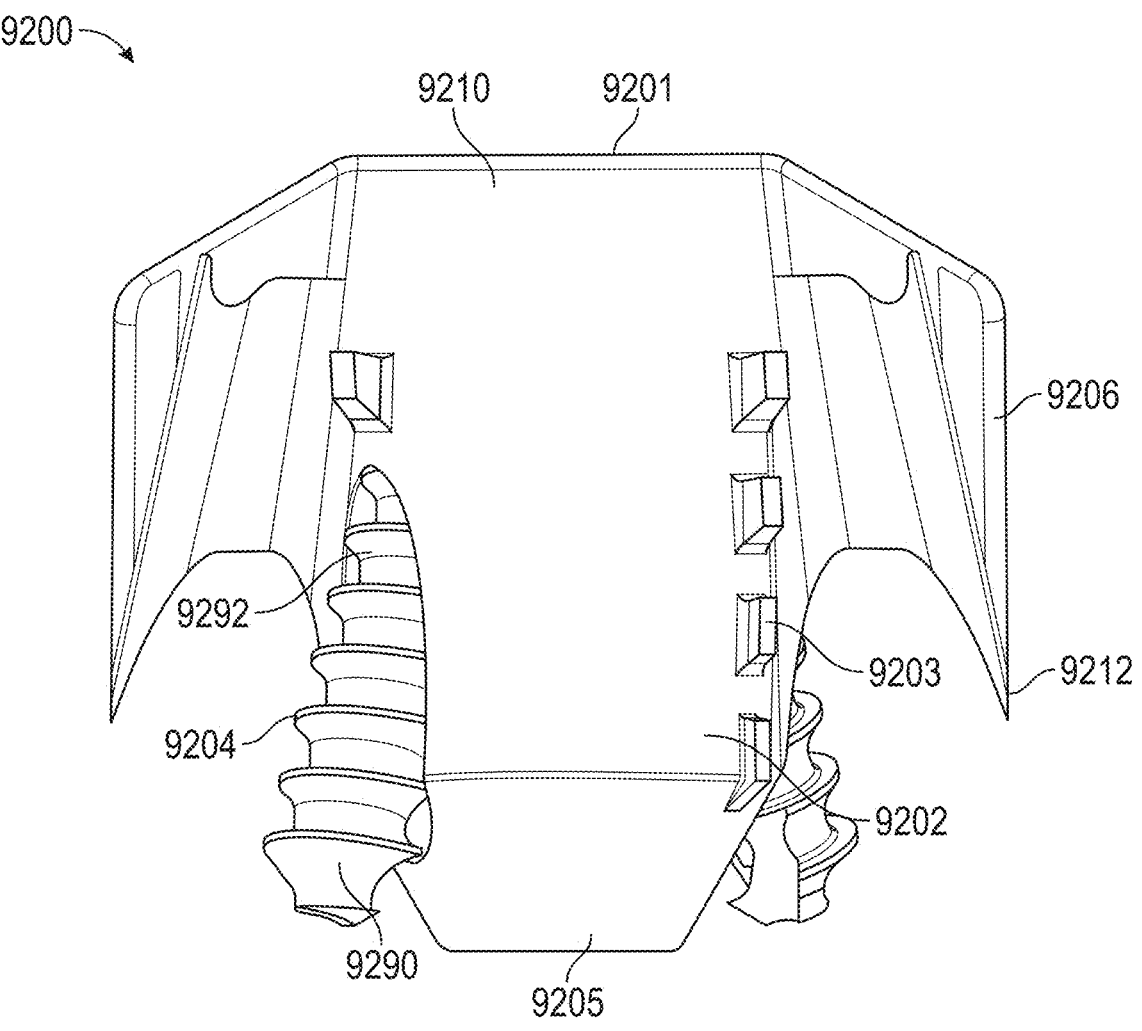

FIG. 91A illustrates a front view of an embodiment of a joint implant system.

Figure 91B:
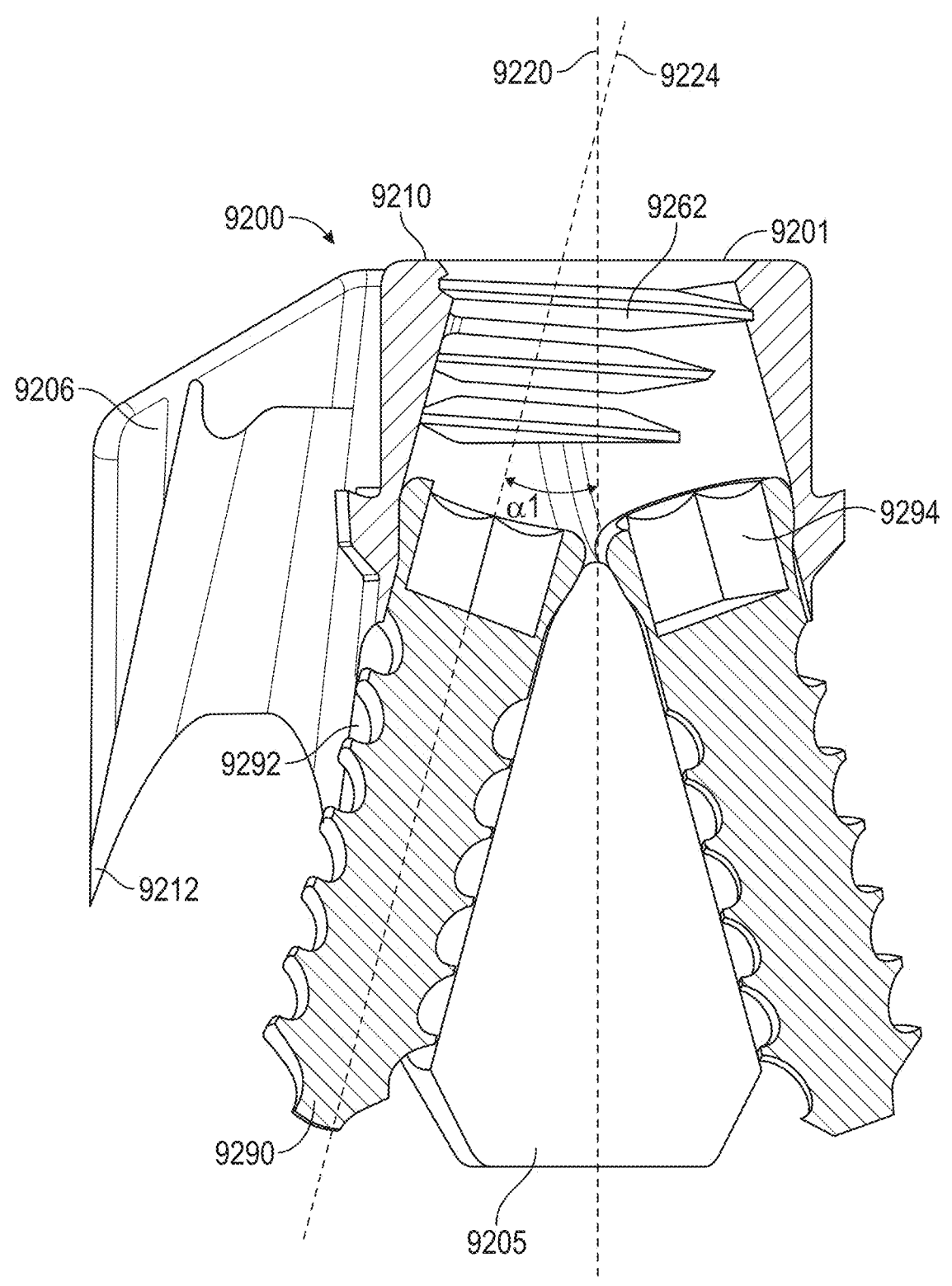

FIG. 91B illustrates a front, cross-sectional view of the embodiment of the joint implant system of FIG. 91A.

Figure 91C:
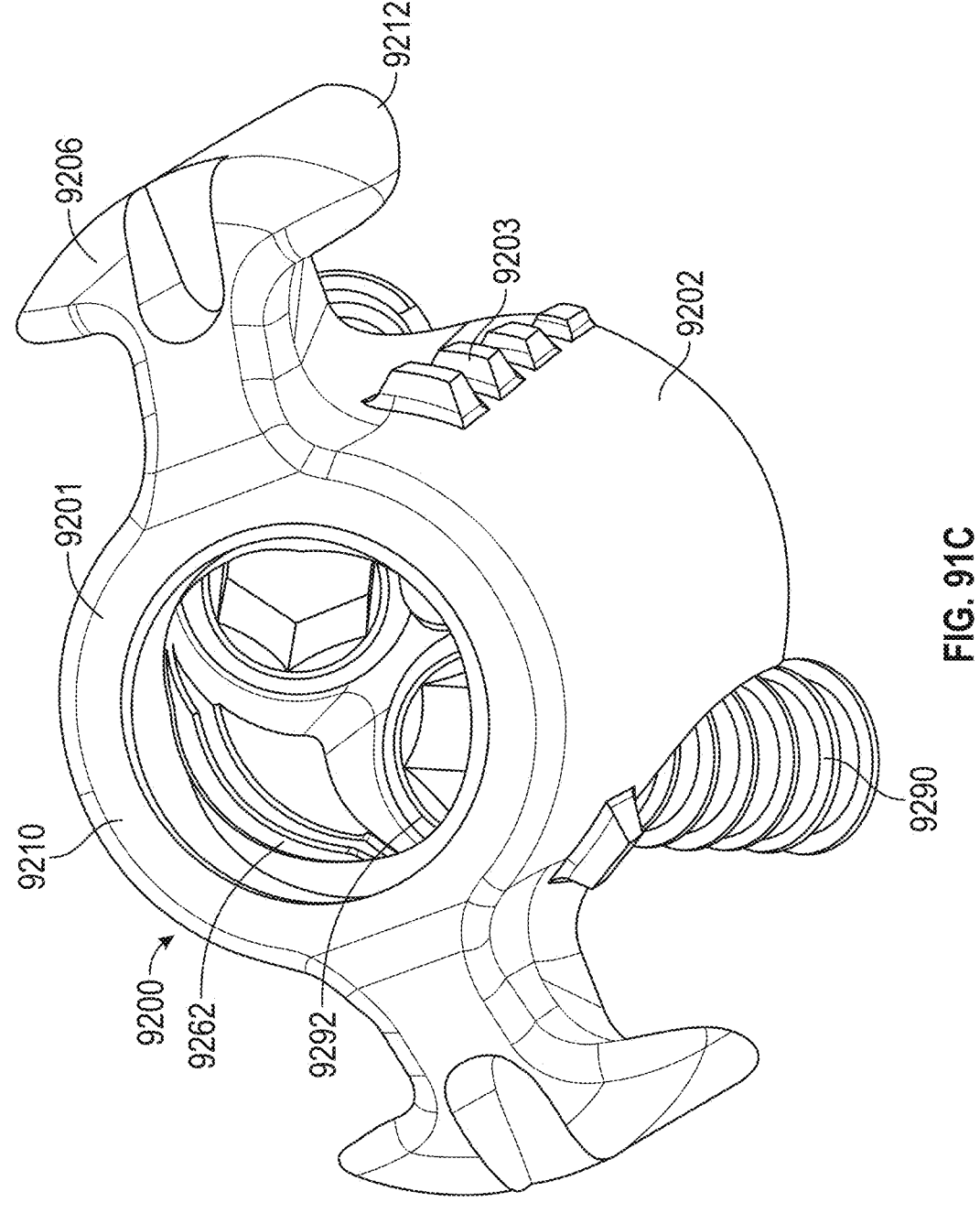

FIG. 91C illustrates a top perspective view of the embodiment of the joint implant system of FIG. 91A.

Figures 92, 93A:
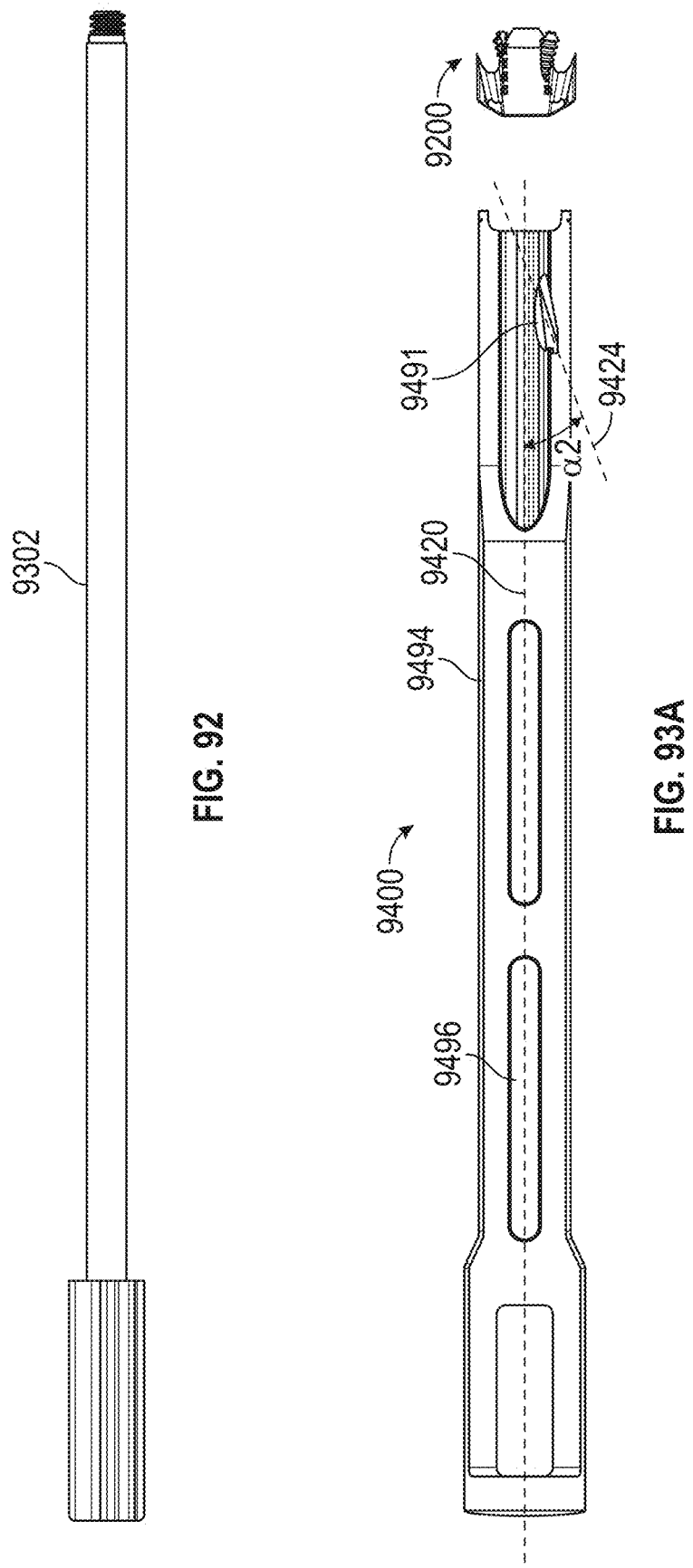

FIG. 92 illustrates an embodiment of a driver.

FIG. 93A illustrates an embodiment of an inserter and a joint implant system.

Figures 93B, 93C:
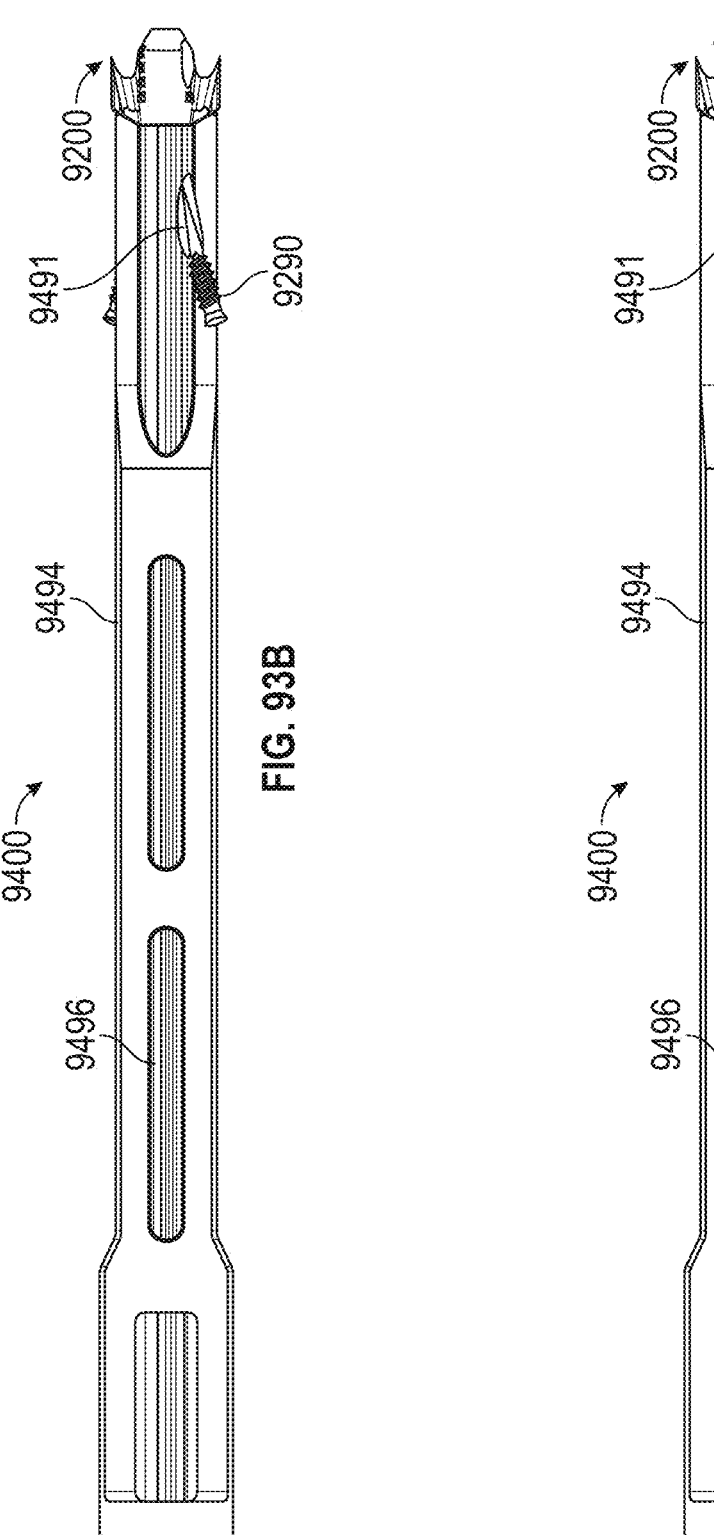

FIG. 93B illustrates the embodiment of the inserter engaging the joint implant system of FIG. 93A.

FIG. 93C illustrates the embodiment of the inserter engaging the joint implant system of FIG. 93A.

SUMMARY

Embodiments of the present application are directed to intrasacroiliac implants, implant components, implant inserters, rasps, drill bits, and related systems, devices, and methods.

In some embodiments, a sacroiliac joint implant system is provided, the sacroiliac joint implant system comprises a primary implant configured to be received in a sacroiliac joint of a patient. The primary implant comprising a body extending from a proximal end to a distal end and a plurality of threads extending from the body. The secondary implant configured to couple with the primary implant wherein the secondary implant comprises a plurality of anchors. The plurality of anchors comprises a first anchor configured to anchor within a sacrum of the patient and a second anchor configured to anchor within an ilium of the patient. The primary implant of the joint implant system may comprise a plurality of tabs defining a plurality of recesses, wherein the plurality of recesses are configured to receive the secondary implant. The secondary implant comprises a ring configured to receive a head of the primary implant. In some embodiments, the ring is configured to couple with the head of the primary implant to facilitate polyaxial movement of the primary implant relative to the secondary implant. The secondary implant comprises a plurality of arms extending laterally from the ring, wherein each of the plurality of anchors is coupled to one of the plurality of arms.

In some embodiments, the joint implant system may further comprise a fastener configured to couple the primary implant and the secondary implant. The primary implant comprises a channel configured to receive bone graft material. The primary implant comprises a plurality of openings between the channel and an exterior of the primary implant. Each of the plurality of anchors comprises a plurality of openings configured to facilitate bony ingrowth. Each of the plurality of anchors comprises a leading edge configured to cut bone.

In some embodiments, a method for implanting a sacroiliac joint implant system is provided. The method includes making an incision, advancing a primary implant through the incision and into a sacroiliac joint of a patient, the primary implant including a body extending from a proximal end to a distal end a plurality of threads extending from the body, advancing a secondary implant through the incision towards the sacroiliac joint, the secondary implant comprising a plurality of anchors, anchoring a first anchor of the plurality of anchors into a sacrum of the patient; and anchoring a second anchor of the plurality of anchors in the ilium of the patient.

The method can further include advancing the secondary implant through the incision towards the sacroiliac joint after advancing the primary implant through the incision and into the sacroiliac joint of the patient. Advancing the secondary implant through the incision towards the sacroiliac joint can be performed after advancing the primary implant through the incision and into the sacroiliac joint of the patient. The primary implant and the secondary implant may be coupled to one another. The primary implant and the second implant may be coupled to one another within the patient. The instrument assembly may comprise a guide with a plurality of slots extending therethrough, wherein advancing a secondary implant through the incision towards the sacroiliac joint comprises advancing each of the plurality of anchors along one of the plurality of slots of the guide. The primary implant may be advanced through a central lumen of the guide. The central lumen can be in communication with the plurality of slots. The method can include advancing a bone punch along the plurality of slots prior to advancing each of the plurality of anchors along one of the plurality of slots of the guide. The method can further include coupling the primary implant to an inserter and advancing the secondary implant along channels of the inserter to couple the secondary implant with the primary implant.

DETAILED DESCRIPTION

Embodiments of the present application are directed to a posterior SI joint implant system for SI joint fusion. Fusion of the SI joint can fix the sacrum and ilium relative to one another, which may reduce pain due to instability or inflammation. The embodiments described herein provide fixation of the SI joint in different planes by combining fixation points using a single implant system.

FIGS. 1A-1D depict an embodiment of an SI joint implant system 100. The SI joint implant system 100 can provide fixation of the SI joint (e.g., for SI joint fusion). In certain embodiments, the SI joint implant system 100 can prevent or resist shearing forces at the SI joint. Alternatively or additionally, in certain embodiments, the SI joint implant system 100 can prevent or resist rotational movement at the SI joint. Alternatively or additionally, in certain embodiments, the SI joint implant system 100 can prevent or resist forces that compress and/or distract the SI joint.

In certain embodiments, the SI joint implant system 100 can include a primary implant 102. As described in further detail herein, in certain embodiments, the primary implant can be positioned within the SI joint to engage both the ilium and the sacrum. In certain embodiments, the primary implant can resist shearing forces, such as for example, shearing forces of the sacrum, when positioned within the SI joint. In certain embodiments, the primary implant can resist rotational movement.

In certain embodiments, the SI joint implant system 100 can include a secondary implant 104. As described in further detail herein, in certain embodiments, the secondary implant 104 may anchor within both the ilium and the sacrum on opposing sides of the SI joint. In certain embodiments, the secondary implant 104 may extend across the SI joint.

In certain embodiments, the primary implant 102 and secondary implant 104 can be used in combination to provide fixation to an SI joint. In other embodiments, only one of the primary implant 102 and secondary implant 104 may be used. In combination, the primary implant 102 and secondary implant 104 can act as one system to achieve multiple points of fixation and resist multiple forces. For example, in certain embodiments, the primary implant 102 and second implant 104 can act as one system to resist all of the forces acting on the SI joint. As described herein, in certain embodiments, the primary implant 102 and the secondary implant 104 may be coupled together when implanted. In other embodiments, the primary implant 102 and the secondary implant 104 may be uncoupled when implanted.

As described herein, the primary implant 102 can be configured to be inserted into the SI joint. For example, in some embodiments, the primary implant 102 can be inserted into a defect created in the SI joint as described herein. The primary implant 102 can have a proximal end 101 and a distal end 105. In certain embodiments, the primary implant 102 is configured so that the distal end 105 can be inserted within the SI joint without creating joint distraction.

In some embodiments, the primary implant can be configured to engage the ilium and the sacrum to secure the SI joint with the implant. For example, in certain embodiments, the primary implant 102 can include one or more engagement features 103. As shown in FIGS. 1A-1D, the engagement features 103 may bite into each side of the ilium and sacrum for fixation and to prevent back out. The engagement features 103 may be in the form of threads (e.g., helical threads). For example, in certain embodiments, the primary implant 102 can be in the form of a screw.

In certain embodiments, the threads of the primary implant 102 may extend from the proximal end 101 to the distal end 105 of the primary implant or may extend over any portion thereof. In certain embodiments, the threads do not extend from the proximal end to distal end, for example, to provide a space for anchoring of the secondary implant 104 (as shown for example, in the embodiments of FIGS. 7A-8D and 10A-11D). In certain embodiments, the threads may be placed with different pitches and widths depending the size of the primary implant 102 and the amount of bone needed to capture to prevent back out.

In certain embodiments, the primary implant can be configured to facilitate bony ingrowth. Bony ingrowth can help for a rigid fusion and prevent implant migration. For example, in certain embodiments, the material of primary implant 102 can be porous to allow for bony ingrowth. In certain embodiments, the design of the primary implant 102 may include lattices, planar trusses, non-planar trusses, cancellous or trabecular bone patterns, webs, pin holes, circles, and/or any other design that suitable to allow for bone to permeate and grow into the material. For example, as shown in FIGS. 1A-1D, the primary implant 102 can include a truss or beam system 154. The truss or beam system 154 can act as a scaffolding to provide increased biomechanical strength to the implant 102 and to facilitate bone growth. The truss or beam system 154 can facilitate fusion with surrounding bone. The truss or beam system 154 can also provide stability as the implant 102 fuses with the surrounding bone.

The truss or beam system 154 can be formed of a plurality of truss elements or beams 156. In some embodiments, the plurality of truss elements or beams 156 can extend between at least some of the engagement features 103. A number of windows or openings 158 can be formed between the truss elements of beams 156 of the truss or beam system 154 to facilitate fusion of the implant with surrounding bone. The openings 158 can be positioned so that at least some of the openings 158 will contact the bone of the sacrum and the ilium regardless of the orientation of the primary implant 102 when fully seated within the SI joint to promote bony ingrowth.

In certain embodiments, the primary implant 102 can be cannulated from the proximal end 101 to the distal end 105, having a channel 160 extending between the proximal end 101 and the distal end 105. In some embodiments, as described in further detail herein, the channel 160 can allow for a guidewire or guide rod to extend through the implant 102.

In some embodiments, the primary implant 102 can be loaded with demineralized bone matrix (DBM), cortical fibers, synthetic bone matrix, BMP2 or BMP7, peptide graft, autograft or any combination thereof. In some embodiments, the channel 160 can be packed and/or filled with bone graft material. In some embodiments, the openings 158 and/or alternative openings may be in communication with the channel 160. When the channel 160 is packed and/or filled with bone graft material, the bone graft material can flow through the openings 158 for introduction of bone graft material within the channel 160 to the SI joint.

The truss or beam system 154 can allow for larger volumes of bone graft material to be packed into the implant 102 while maintaining the biomechanical strength of the implant in comparison to implants without a truss or beam system 154.

The openings 158 can be positioned so that at least some of the bone graft flowing through the openings 158 will contact the bone of the sacrum and the ilium regardless of the orientation of the primary implant 102 when fully seated within the SI joint.

In some embodiments, the primary implant 102 can include a plurality of openings 168 in communication with the channel 160. The openings 168 may be positioned along an interior surface of the primary implant 102 that defines the channel 160. The openings 168 may be in communication with the openings 158 of the truss or beam system 154.

In some embodiments it may be desirable for the channel 160 to have a diameter large enough to receive bone graft, but small enough to avoid or inhibit deformation of breakage due to fragility. The diameter can also be sufficiently small for the implant to fit in a desired anatomic location, such as the SI joint.

In certain embodiments, acid etching, bead blasting, surface coating such as HA (Hydroxyapatite), or any other suitable surface technology may be utilized to enhance the surface finish to create an optimal area for bone to grow to in the primary implant 102. In certain embodiments, 3D printing may be utilized to create surfaces structures and features for bone to grow to. In certain embodiments, the surface structures may be on the nanometer or micrometer scale which can be optimal or desirable for bone to grow to.

In certain embodiments, the primary implant 102 may be CNC machined, 3D printed, or manufactured by any other suitable means. In certain embodiments, the primary implant 102 can be made of stainless steel, titanium, poly-ether-ether-ketone (PEEK), ceramic, human allograft or any other suitable implantable material strong enough to resist the forces described herein and pass biomechanical testing. In certain embodiments, the implant material can be important to achieve bony ingrowth.

Figure 5A:
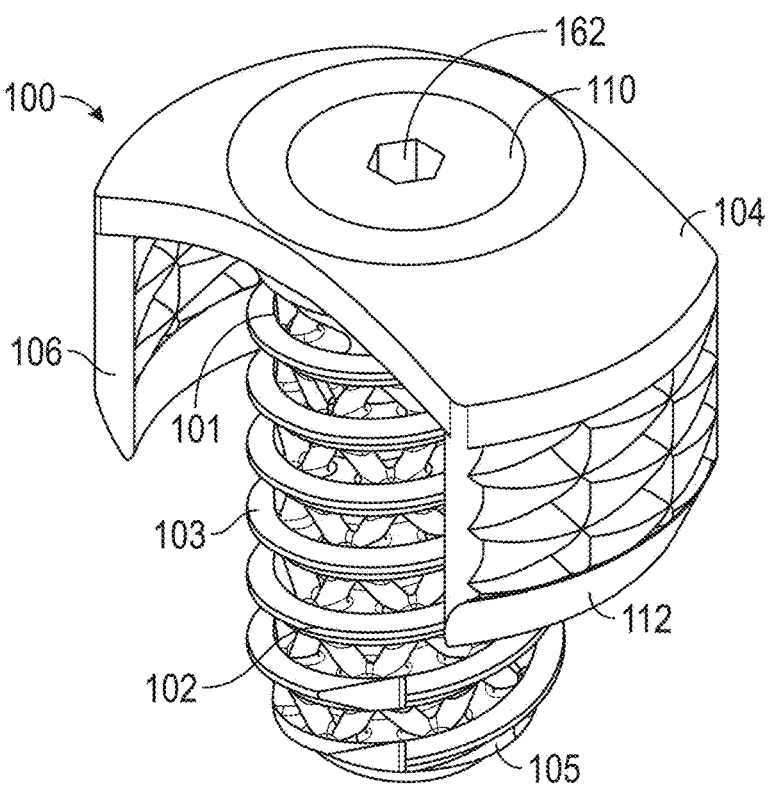
FIG. 5A illustrates a perspective view of an embodiment of a joint implant.
Figure 5B:
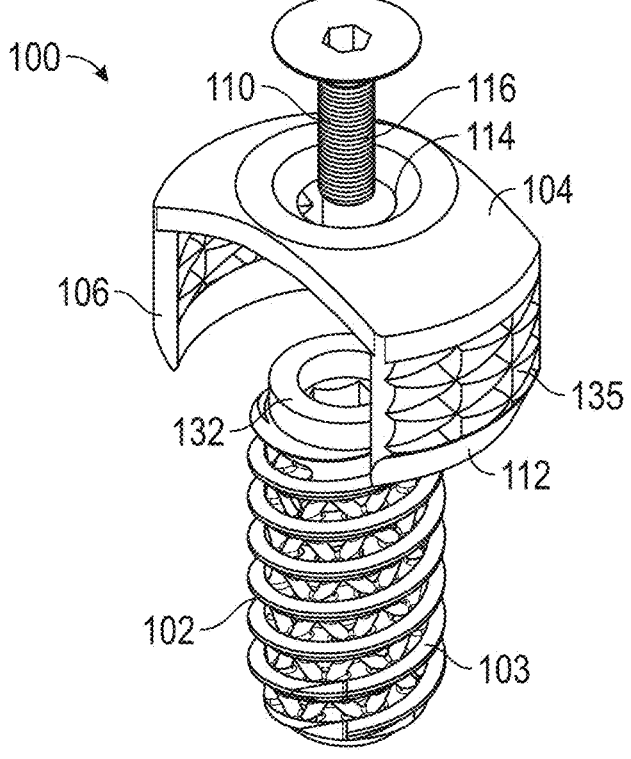
FIG. 5B illustrates an exploded view of the embodiment of the joint implant of FIG. 5A.
Figures 5C, 5D:
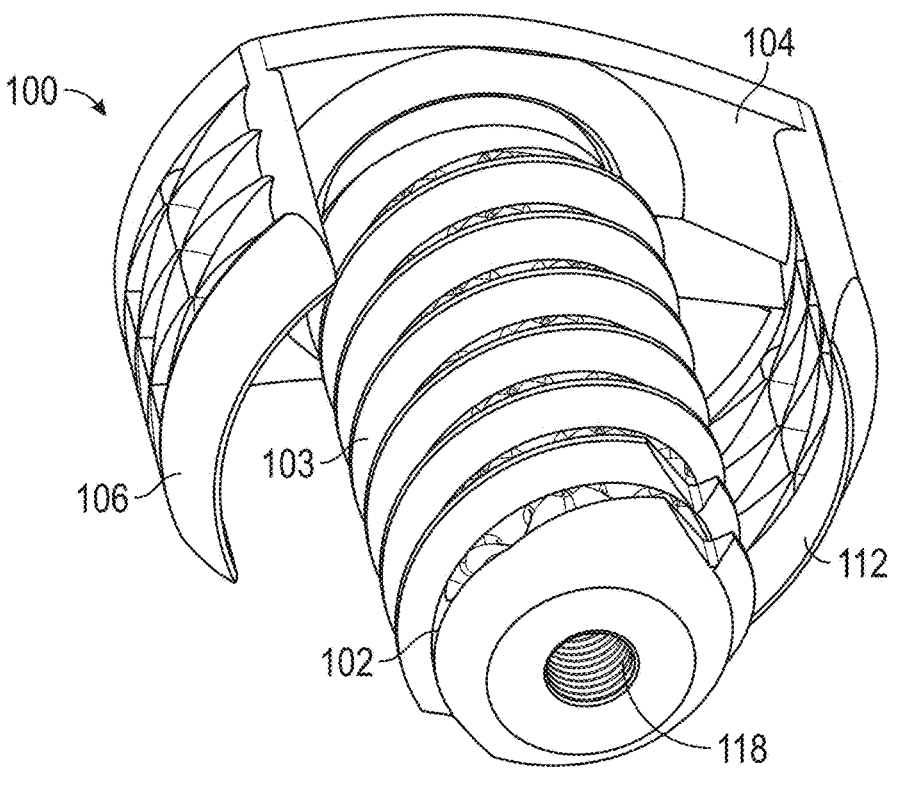
FIG. 5C illustrates a perspective view of the embodiment of the joint implant of FIG. 5A.
FIG. 5D illustrates a side vide of the embodiment of the joint implant of FIG. 5A.
Figure 6A:
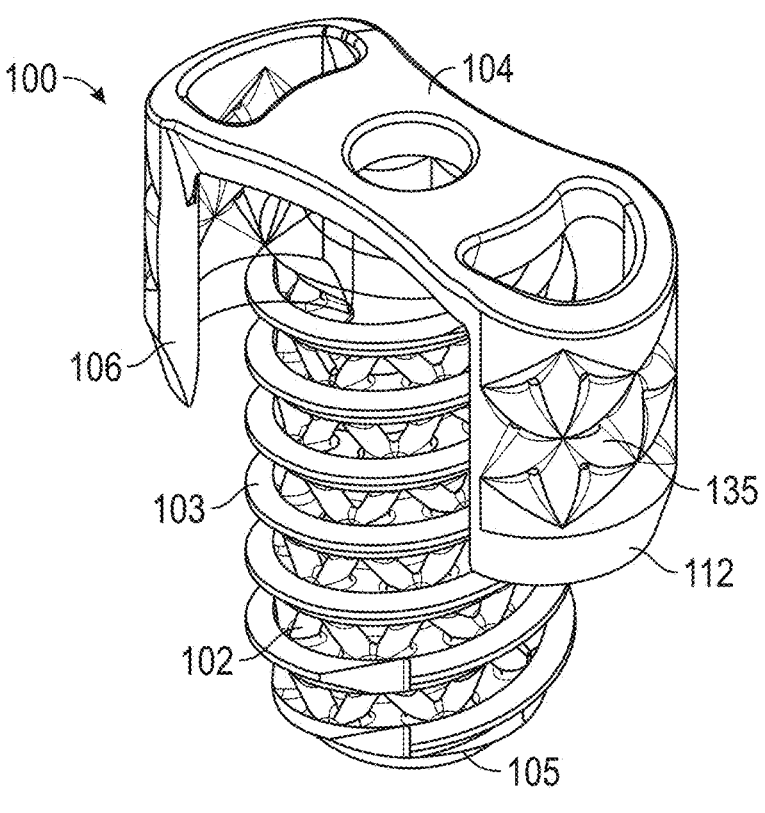
FIG. 6A illustrates a perspective view of an embodiment of a joint implant.
Figure 6B:
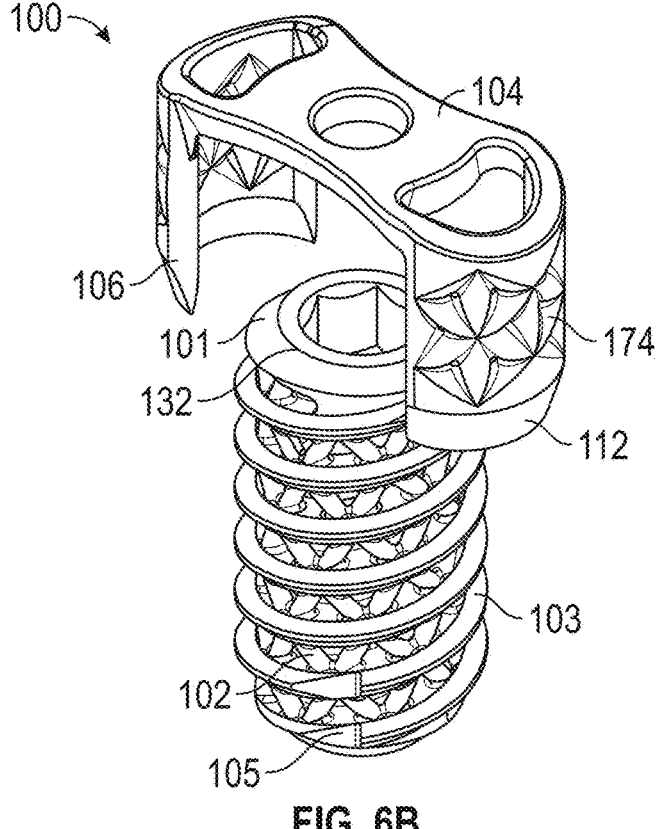
FIG. 6B illustrates an exploded view of the embodiment of the joint implant of FIG. 6A.
Figures 6C, 6D:
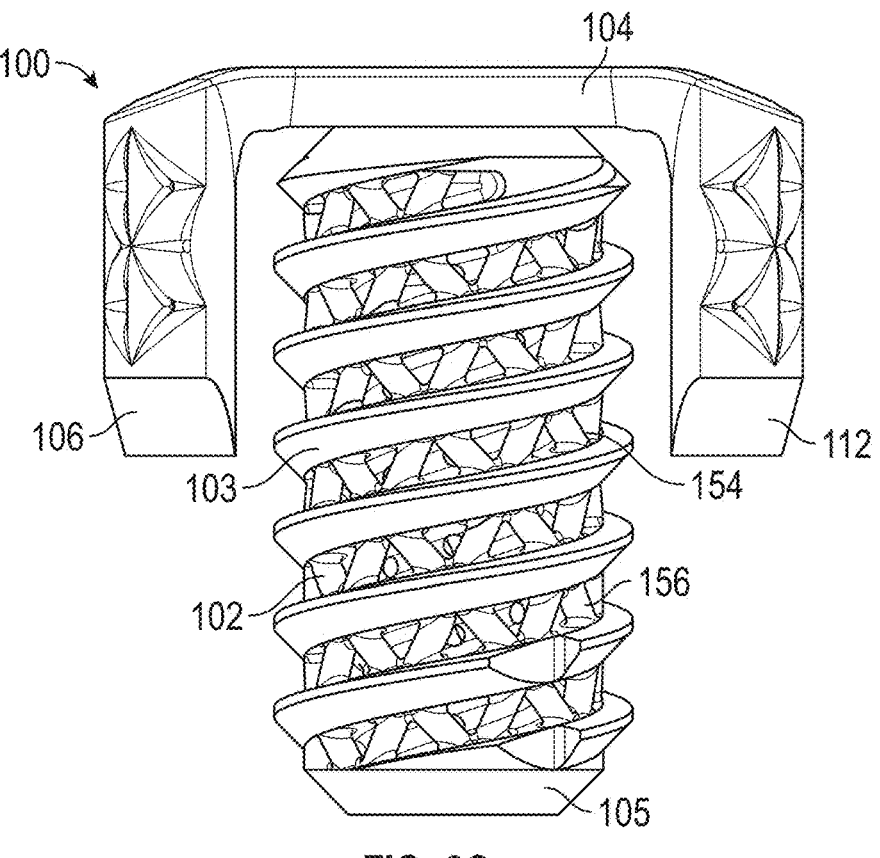
FIG. 6C illustrates a perspective view of the embodiment of the joint implant of FIG. 6A.
FIG. 6D illustrates a side vide of the embodiment of the joint implant of FIG. 6A.
Figure 7B:
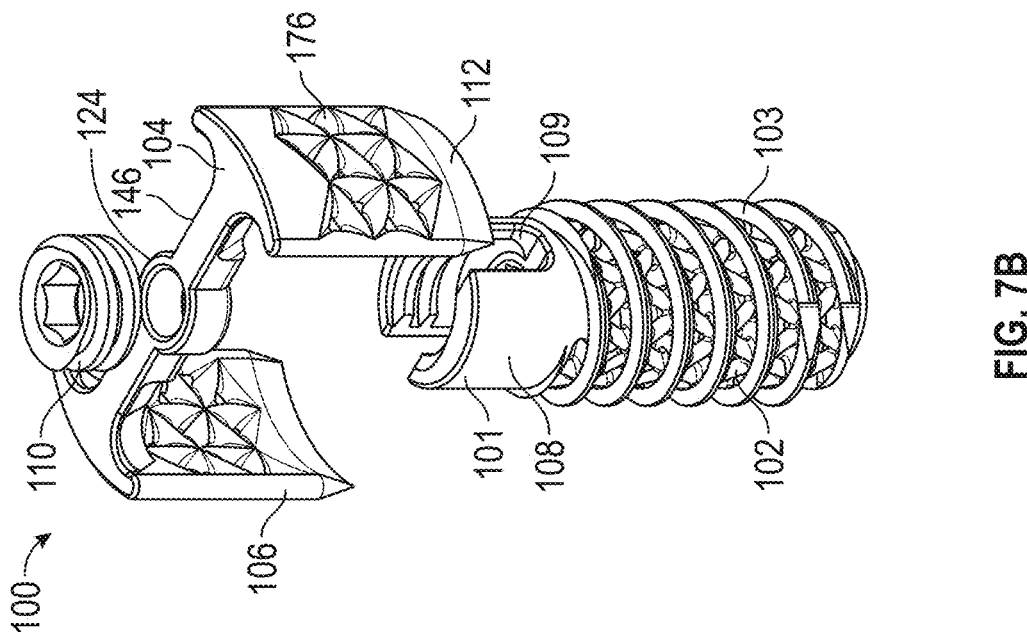
FIG. 7B illustrates an exploded view of the embodiment of the joint implant of FIG. 7A.
Figure 7A:
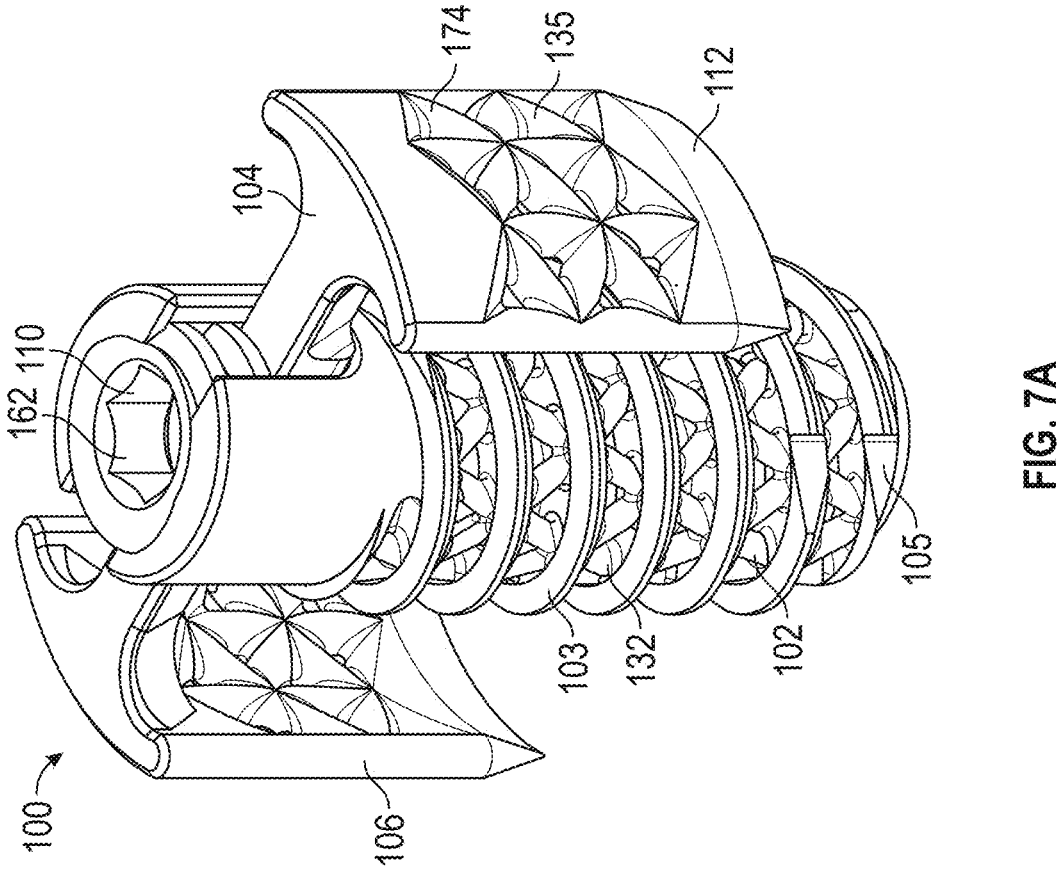
FIG. 7A illustrates a perspective view of an embodiment of a joint implant.
Figure 7D:
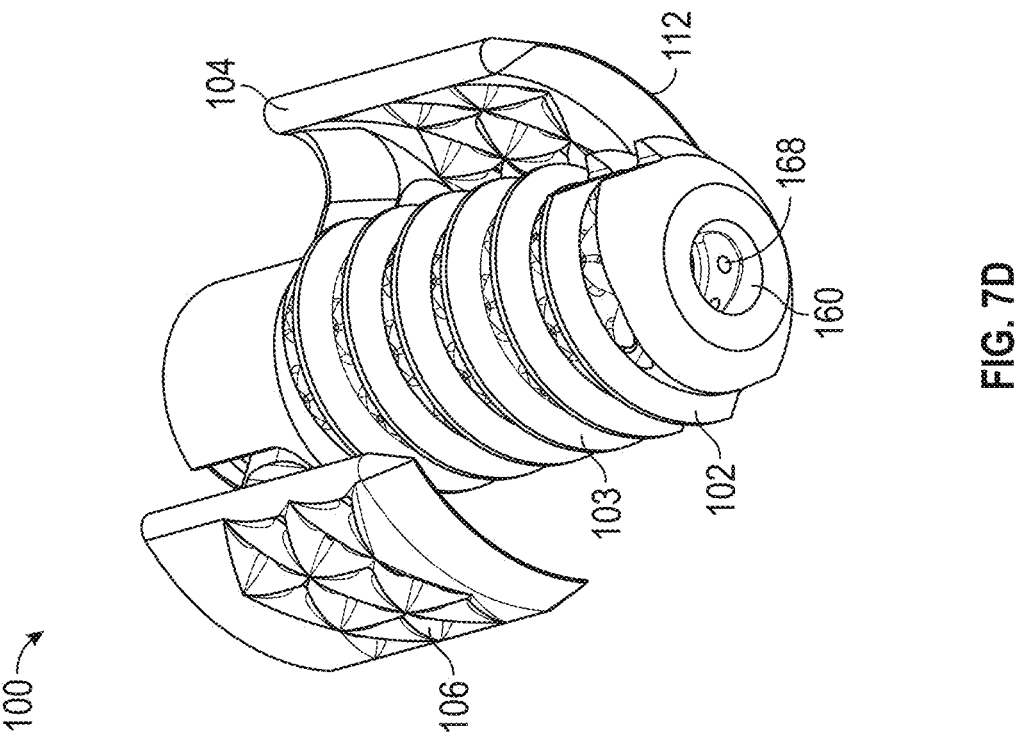
FIG. 7D illustrates a side vide of the embodiment of the joint implant of FIG. 7A.
Figure 7C:
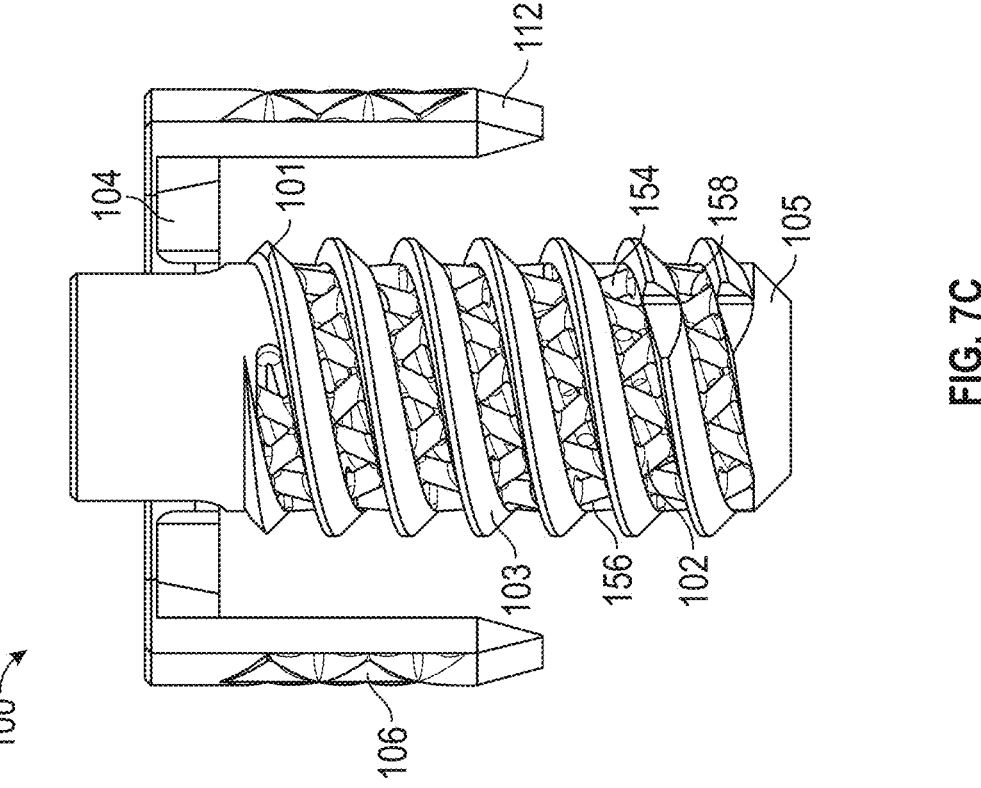
FIG. 7C illustrates a perspective view of the embodiment of the joint implant of FIG. 7A.
Figure 8A:
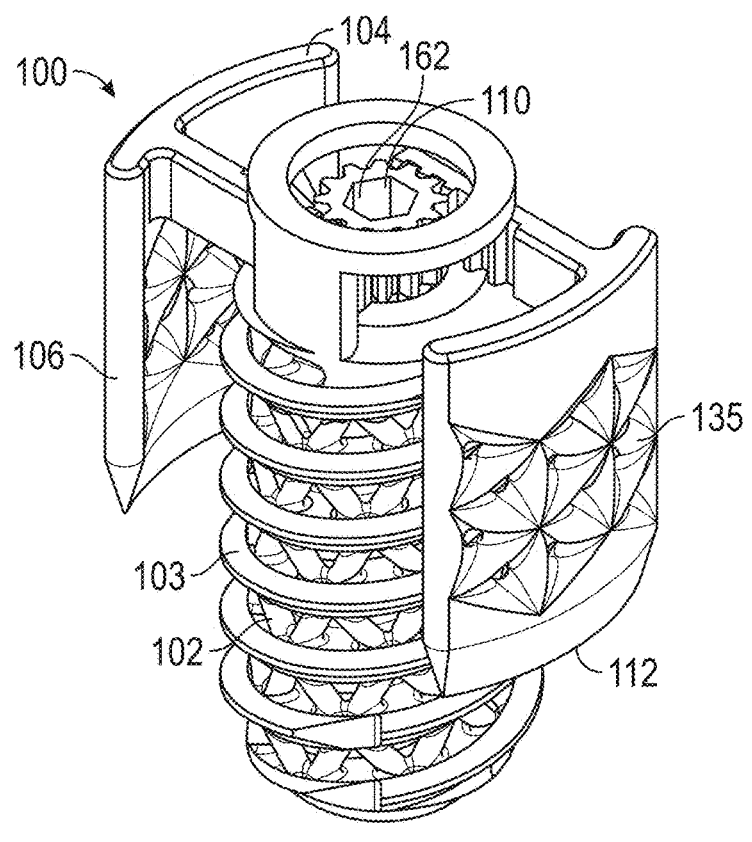
FIG. 8A illustrates a perspective view of an embodiment of a joint implant.
Figure 8B:
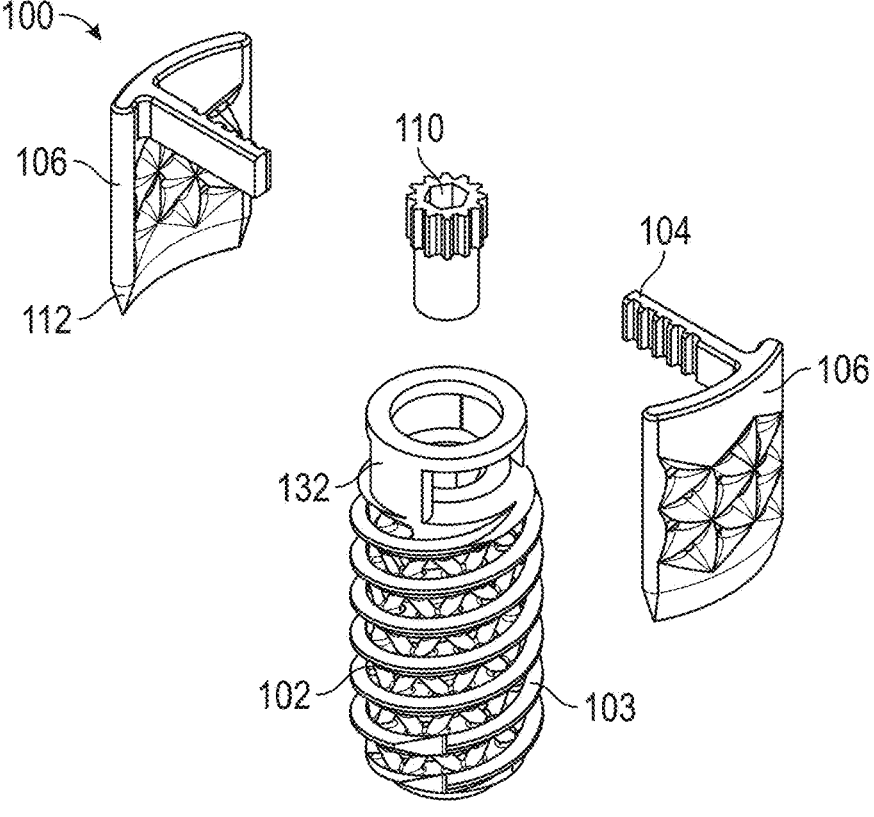
FIG. 8B illustrates an exploded view of the embodiment of the joint implant of FIG. 8A.
Figure 8D:
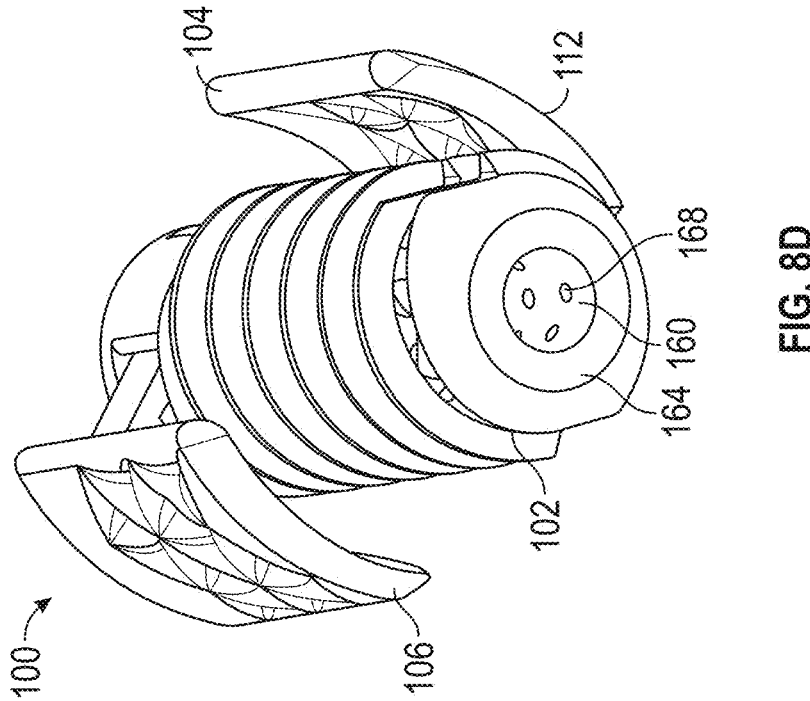
FIG. 8D illustrates a side vide of the embodiment of the joint implant of FIG. 8A.
Figure 8C:
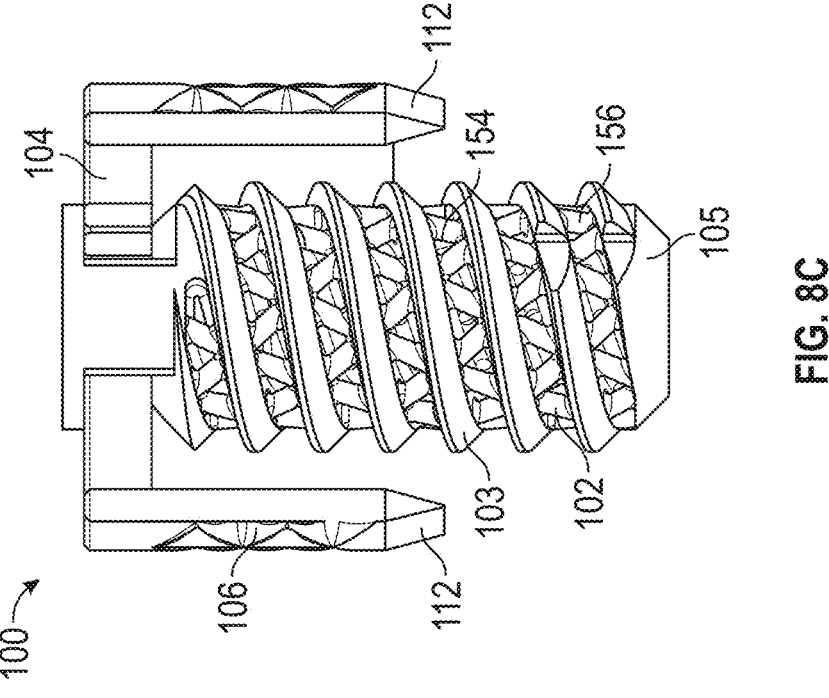
FIG. 8C illustrates a perspective view of the embodiment of the joint implant of FIG. 8A.
Figure 9B:
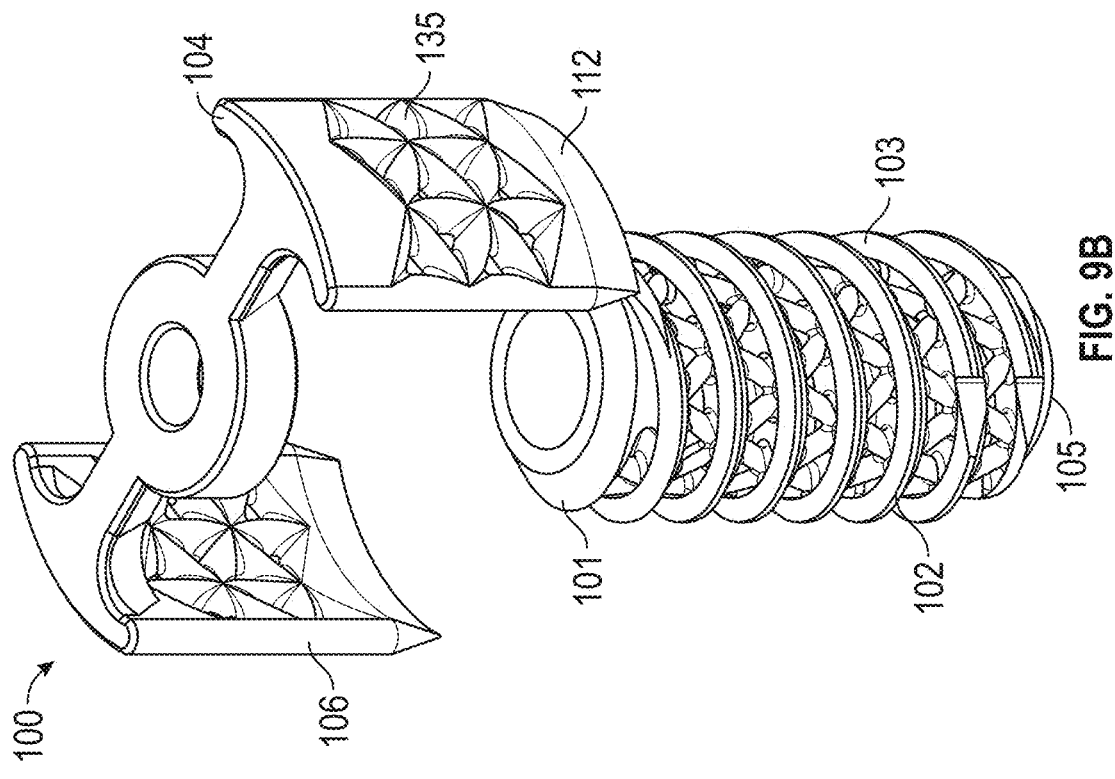
FIG. 9B illustrates an exploded view of the embodiment of the joint implant of FIG. 9A.
Figure 9A:
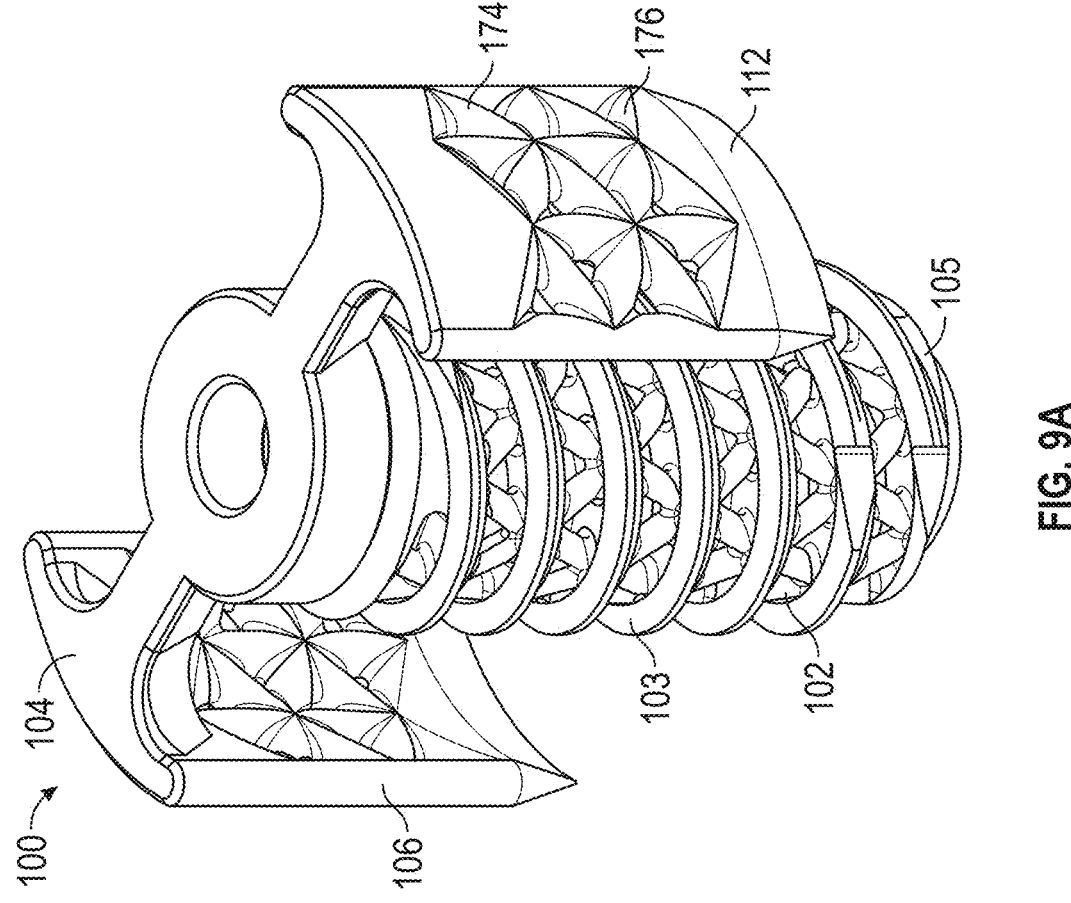
FIG. 9A illustrates a perspective view of an embodiment of a joint implant.
Figure 9D:
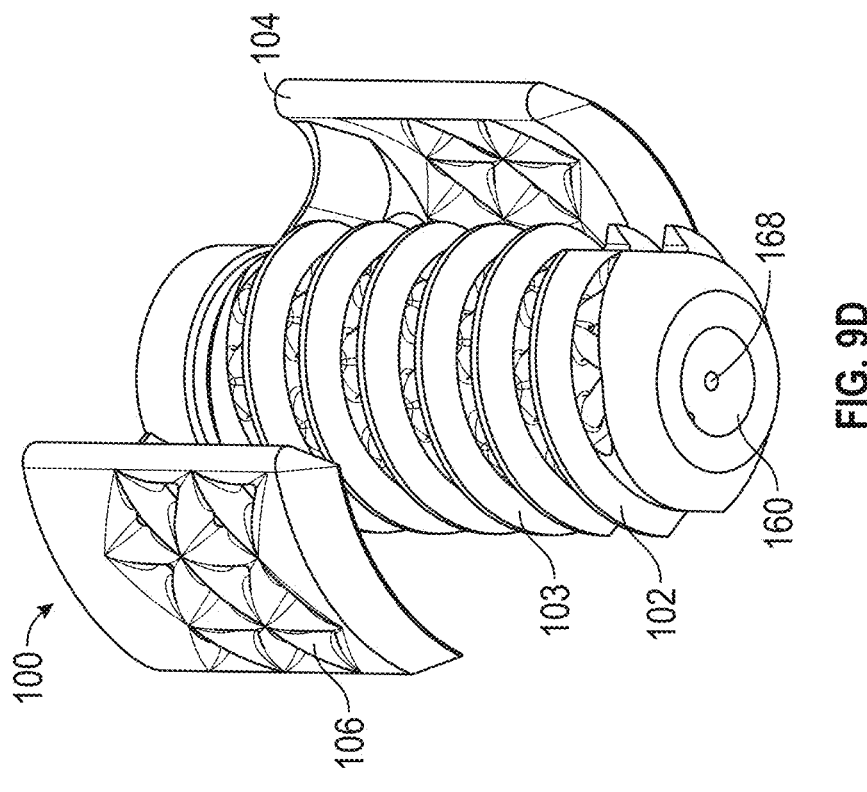
FIG. 9D illustrates a side vide of the embodiment of the joint implant of FIG. 9A.
Figure 9C:
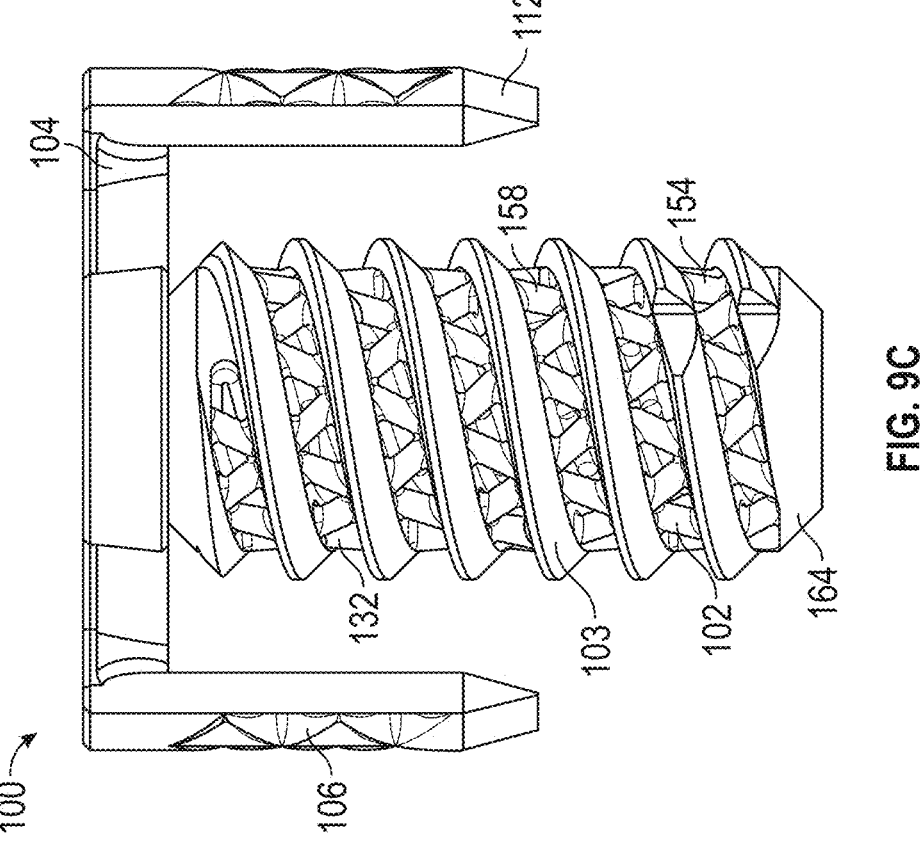
FIG. 9C illustrates a perspective view of the embodiment of the joint implant of FIG. 9A.
Figure 10B:
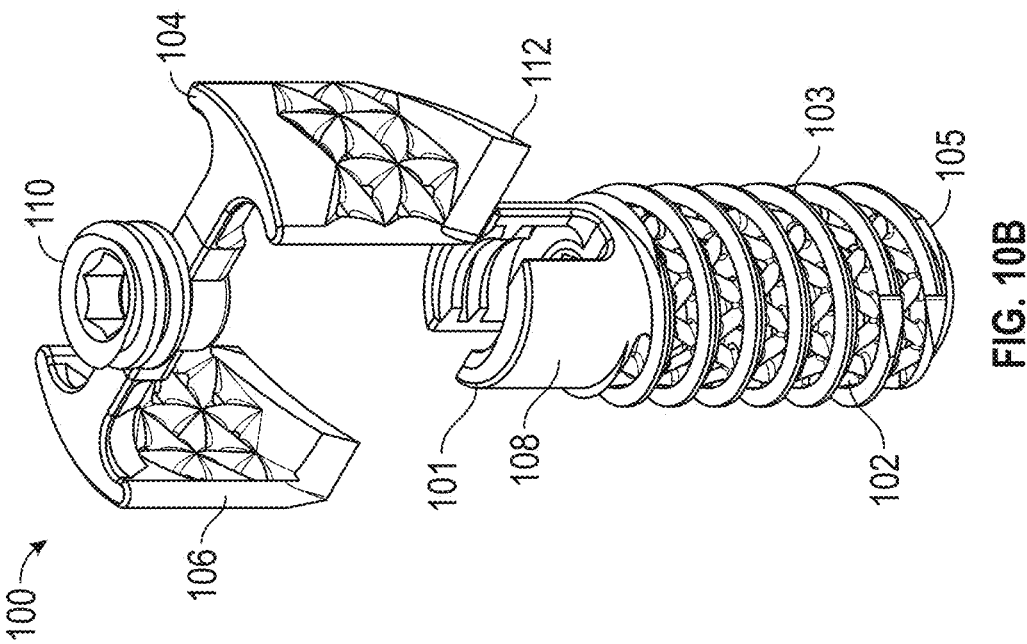
FIG. 10B illustrates an exploded view of the embodiment of the joint implant of FIG. 10A.
Figure 10A:
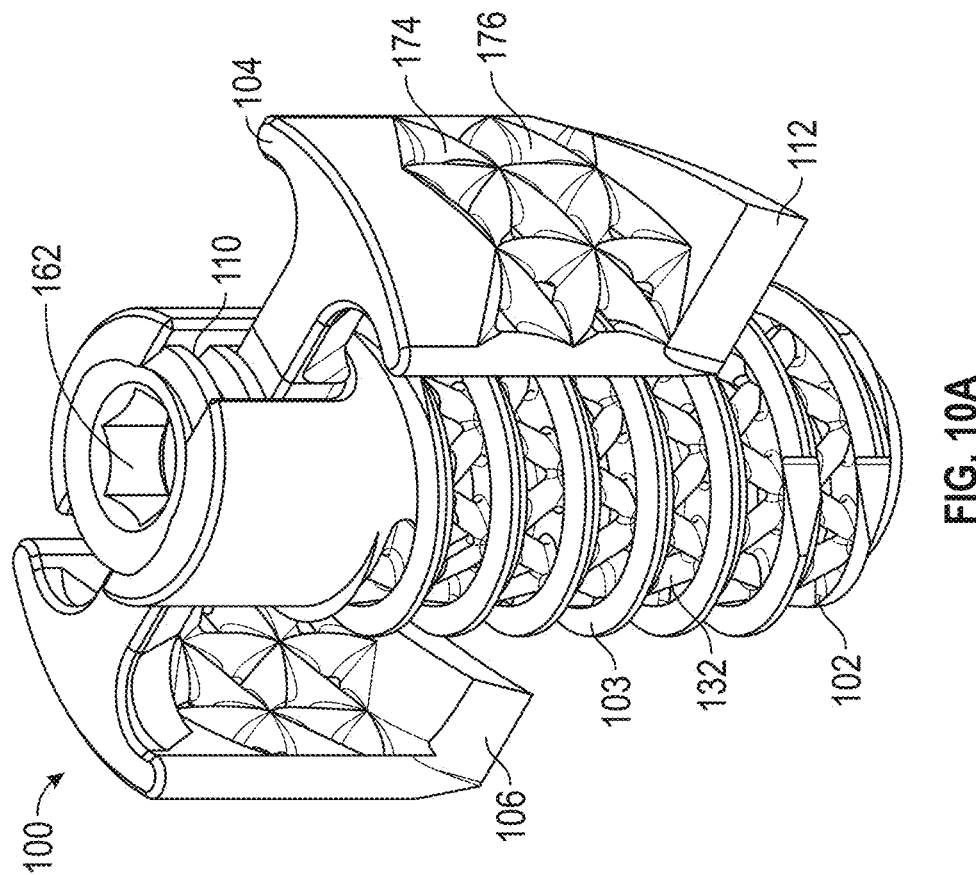
FIG. 10A illustrates a perspective view of an embodiment of a joint implant.
Figures 10C, 10D:
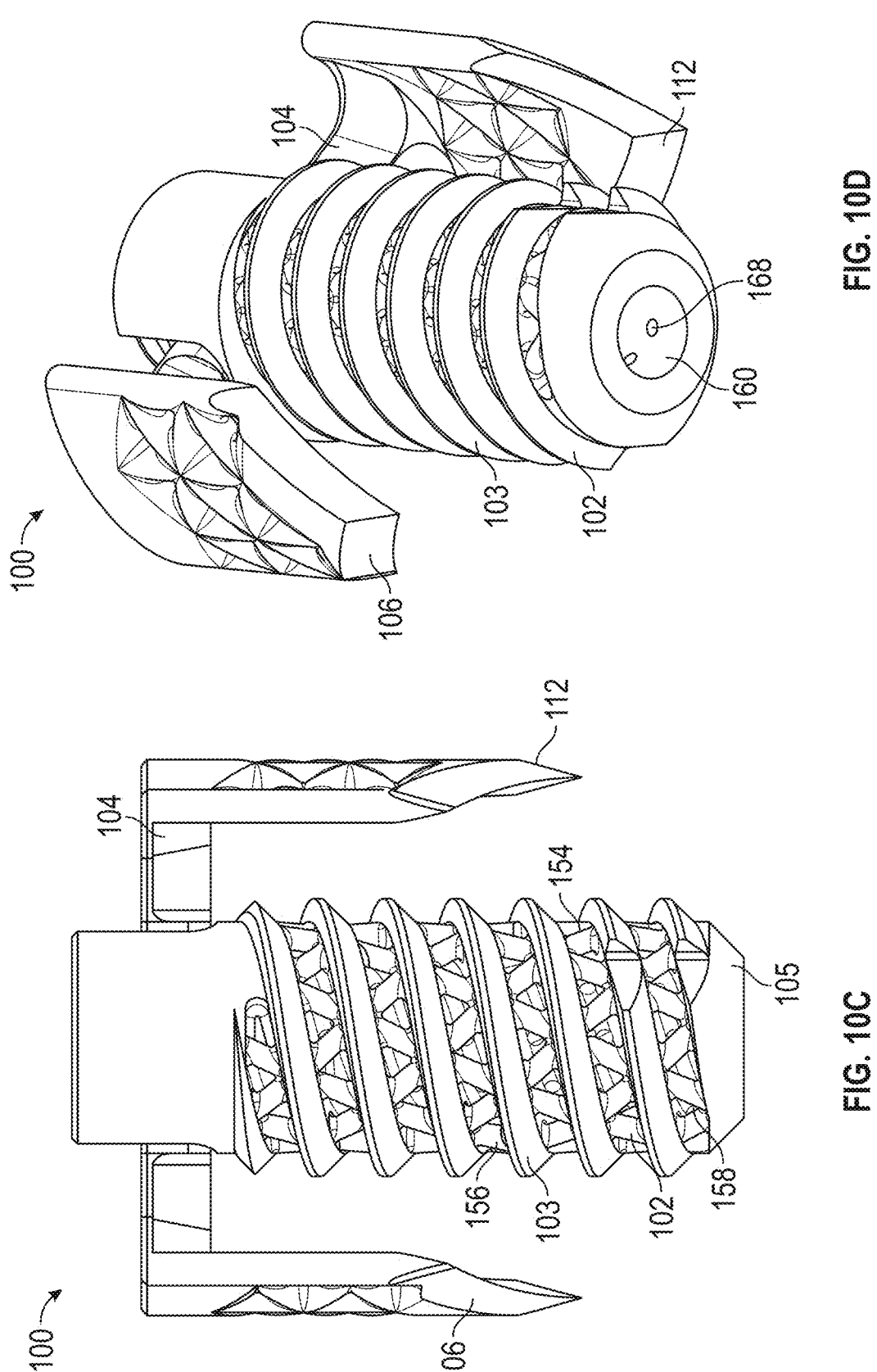
FIG. 10C illustrates a perspective view of the embodiment of the joint implant of FIG. 10A.
FIG. 10D illustrates a side vide of the embodiment of the joint implant of FIG. 10A.
Figure 11B:
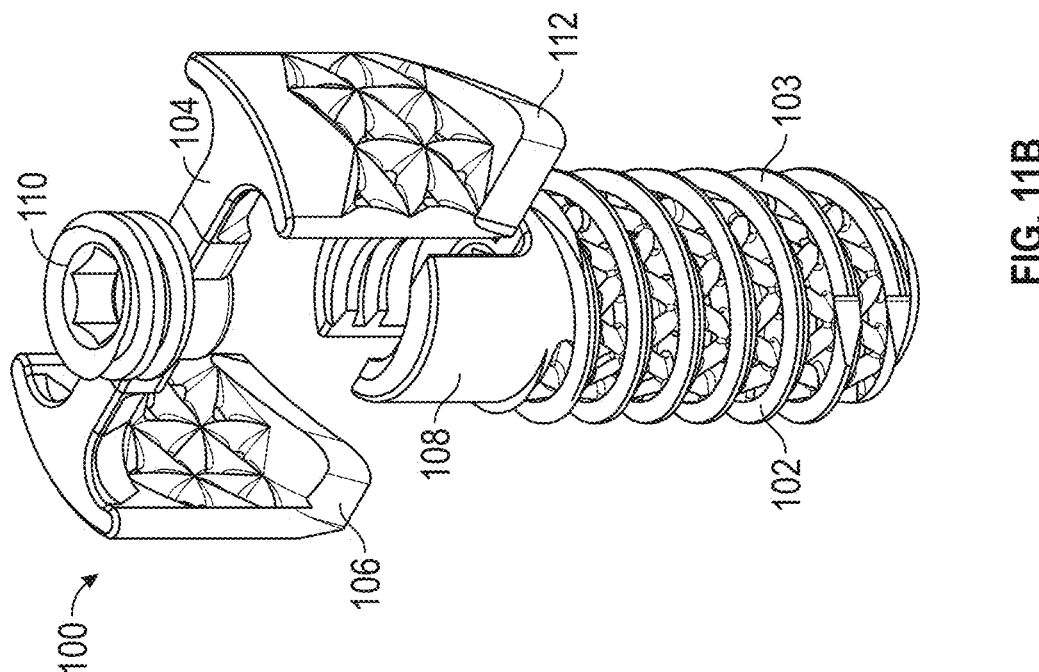
FIG. 11B illustrates an exploded view of the embodiment of the joint implant of FIG. 11A.
Figure 11A:
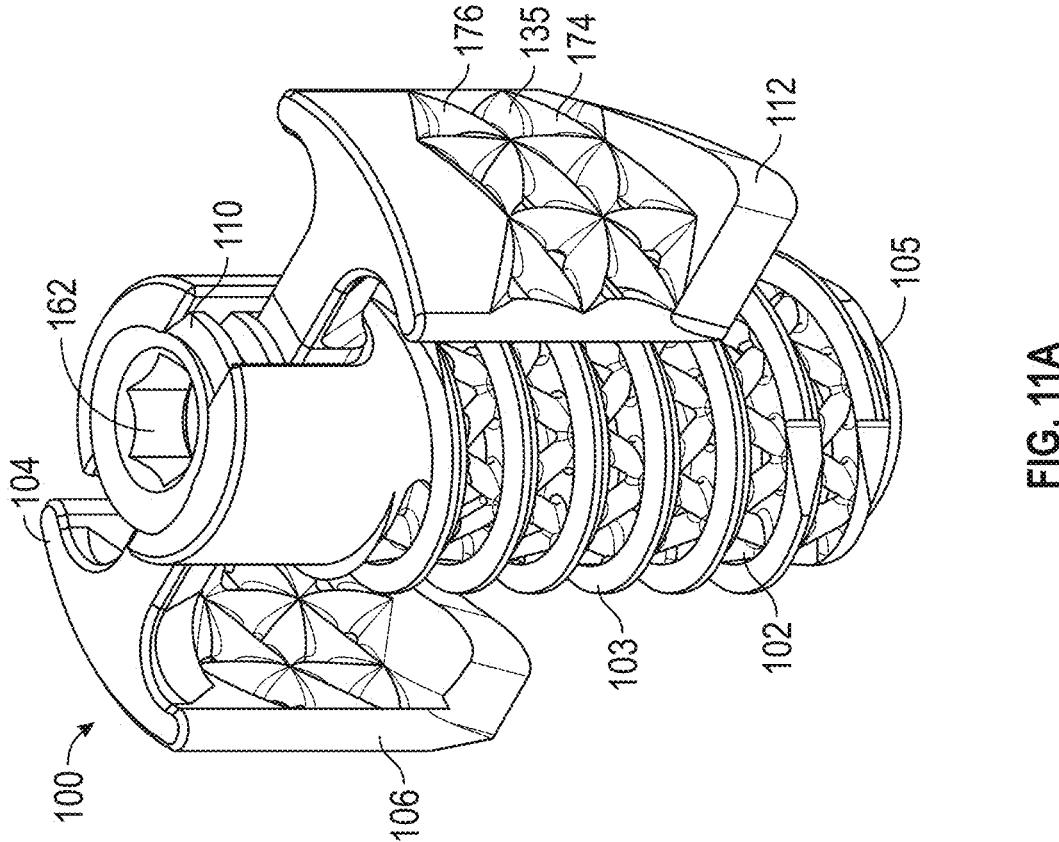
FIG. 11A illustrates a perspective view of an embodiment of a joint implant.
Figure 11D:
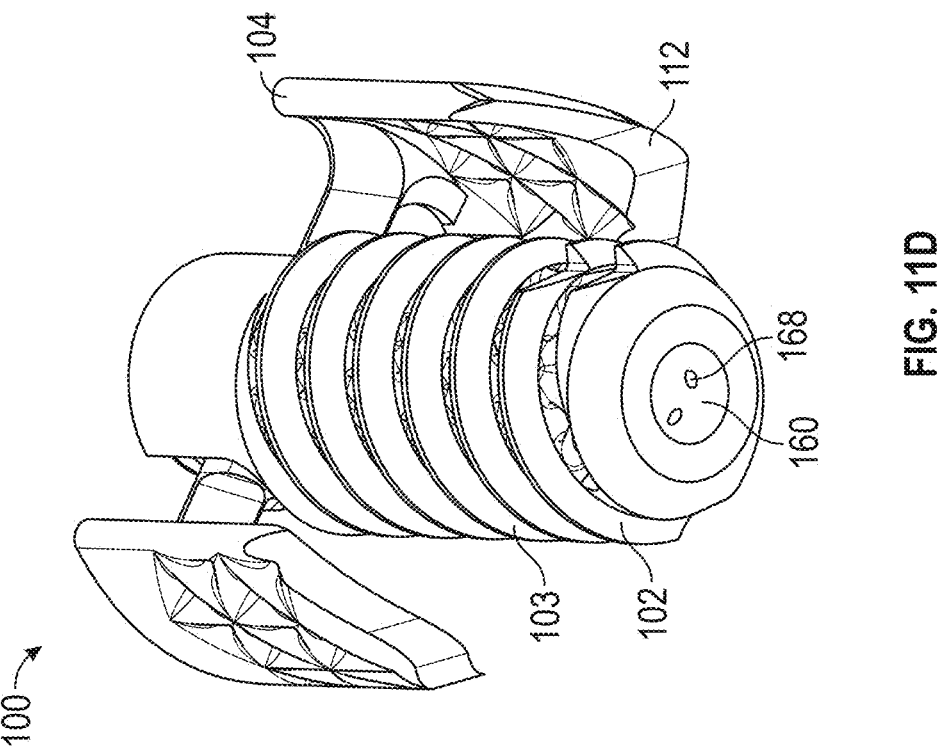
FIG. 11D illustrates a side vide of the embodiment of the joint implant of FIG. 11A.
Figure 11C:
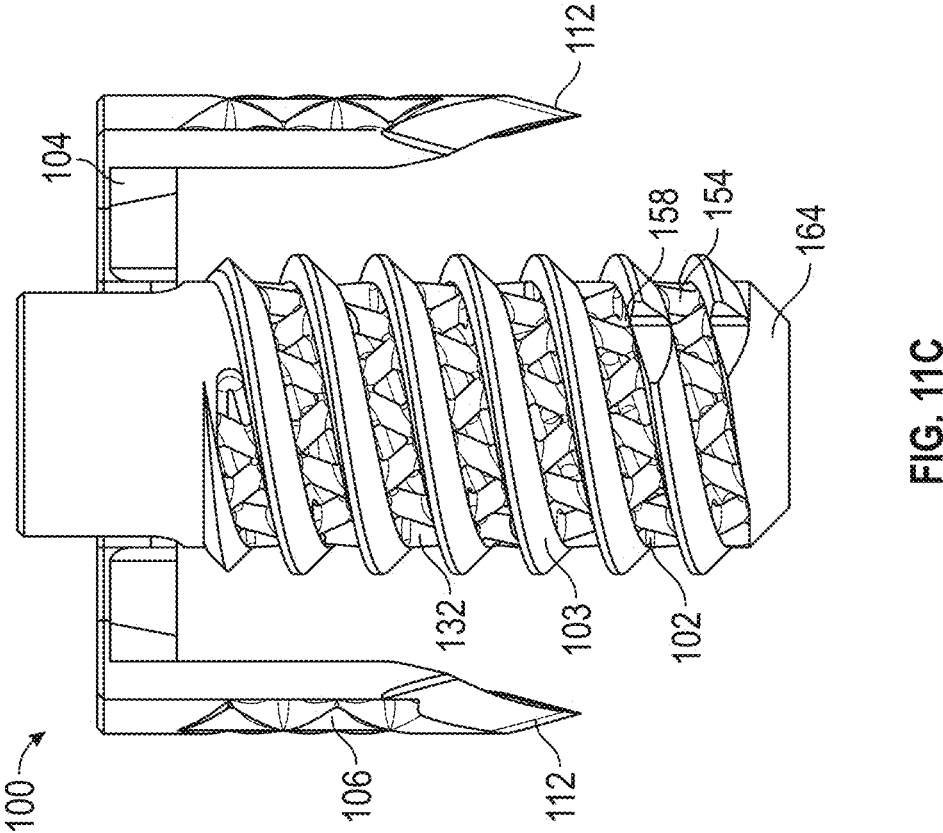
FIG. 11C illustrates a perspective view of the embodiment of the joint implant of FIG. 11A.

In certain embodiments, the implant can be configured to be inserted with a driver, such as a hex driver, a star driver, a square driver, a torx driver, or any other suitable driver for driving the implant into bone. The proximal end 101 of the implant 102 can include an engagement feature 162 for coupling with an inserter such as in FIG. 5A, as described herein. The engagement feature 162 may be a recess configured to couple with an inserter. The engagement feature 162 can be shaped to couple with a hex driver, a star driver, a square driver, a torx driver, or any other suitable driver for driving the implant 102 into bone.

Figures 1A, 1B:
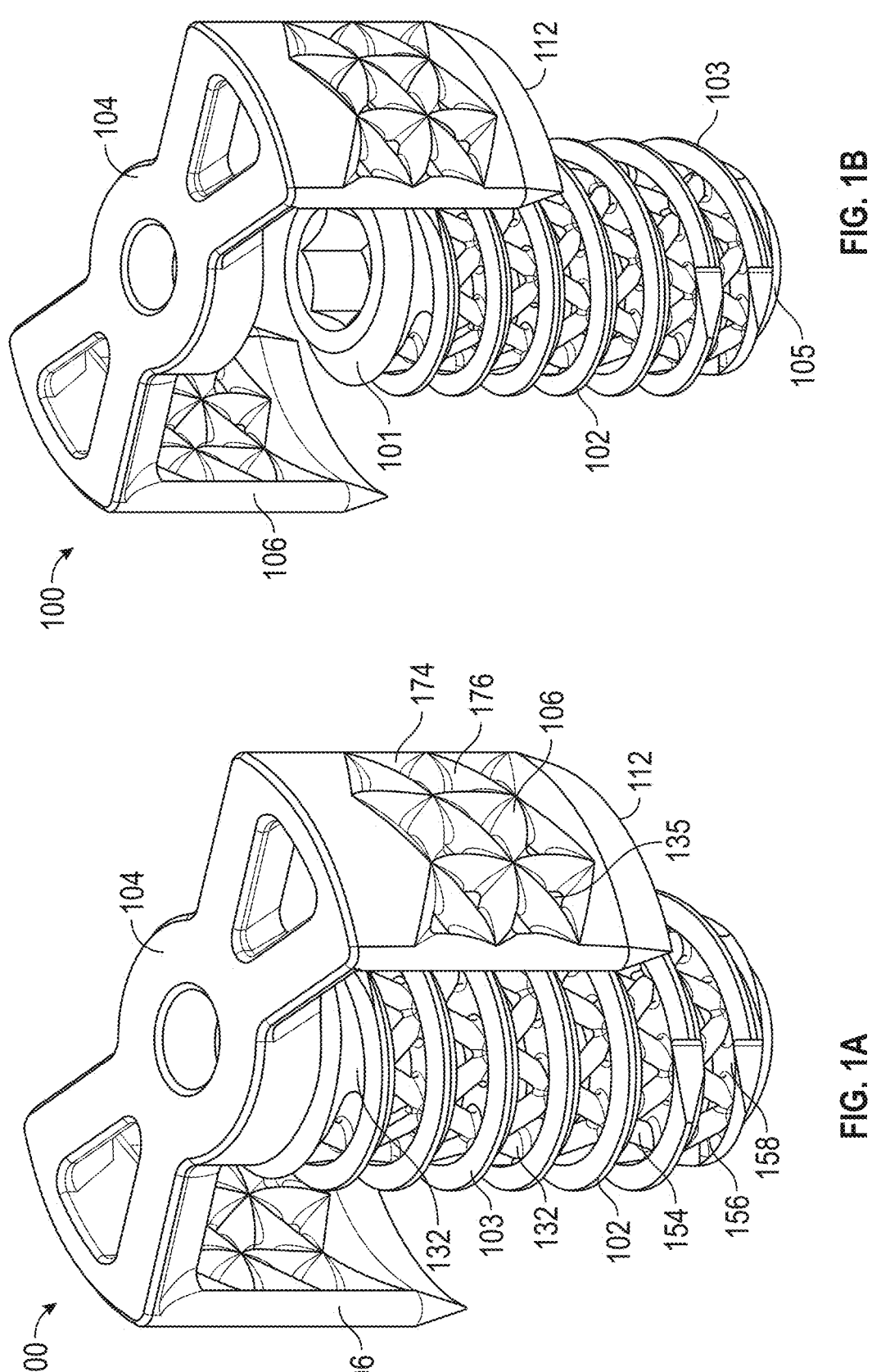
FIG. 1A illustrates a perspective view of an embodiment of a joint implant.
FIG. 1B illustrates an exploded view of the embodiment of the joint implant of FIG. 1A.
Figure 1D:
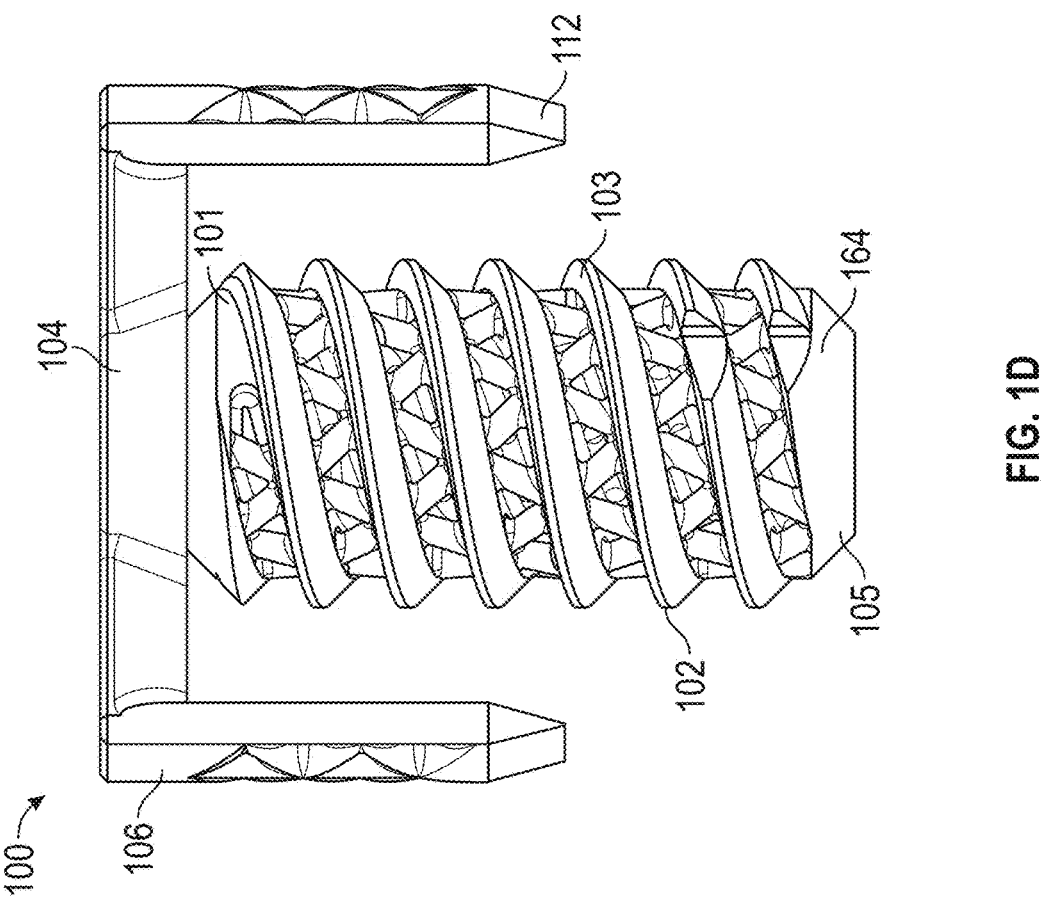
FIG. 1D illustrates a side vide of the embodiment of the joint implant of FIG. 1A.
Figure 1C:
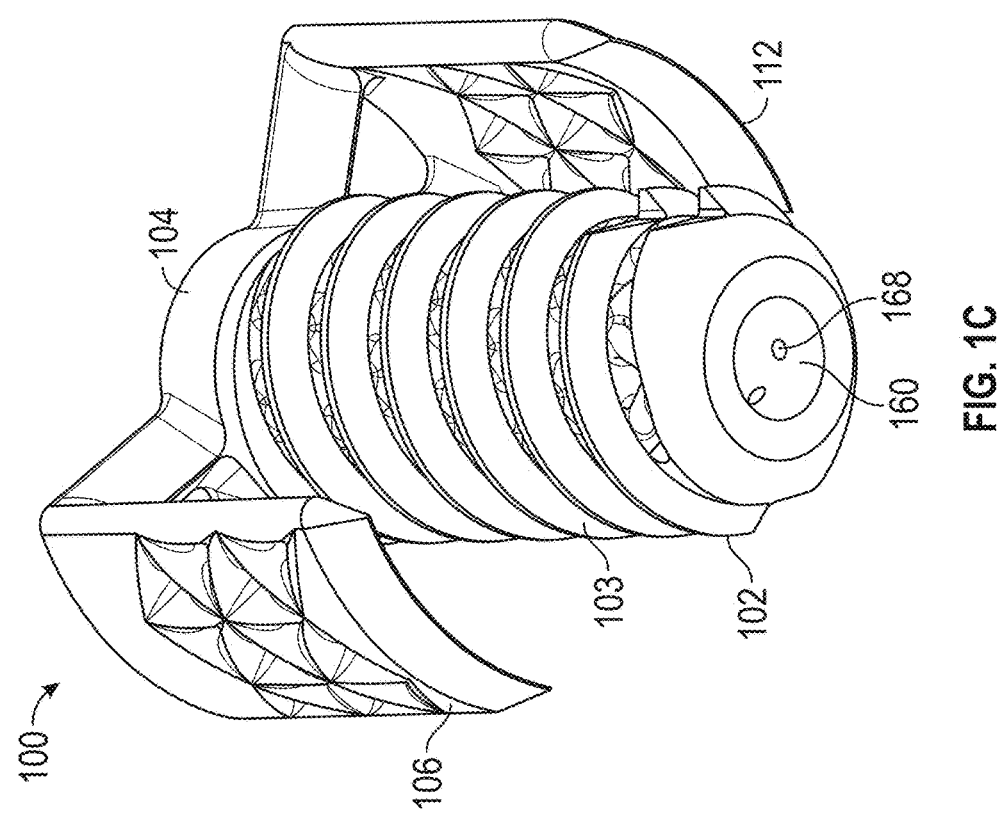
FIG. 1C illustrates a perspective view of the embodiment of the joint implant of FIG. 1A.
Figure 2B:
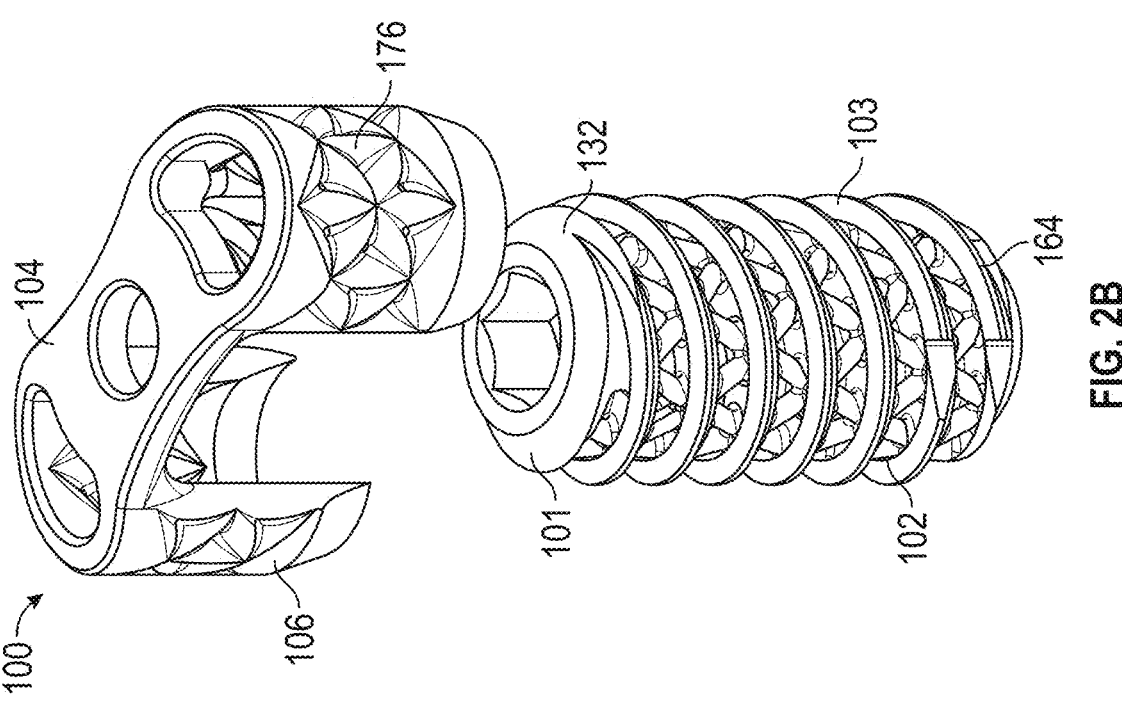
FIG. 2B illustrates an exploded view of the embodiment of the joint implant of FIG. 2A.
Figure 2A:
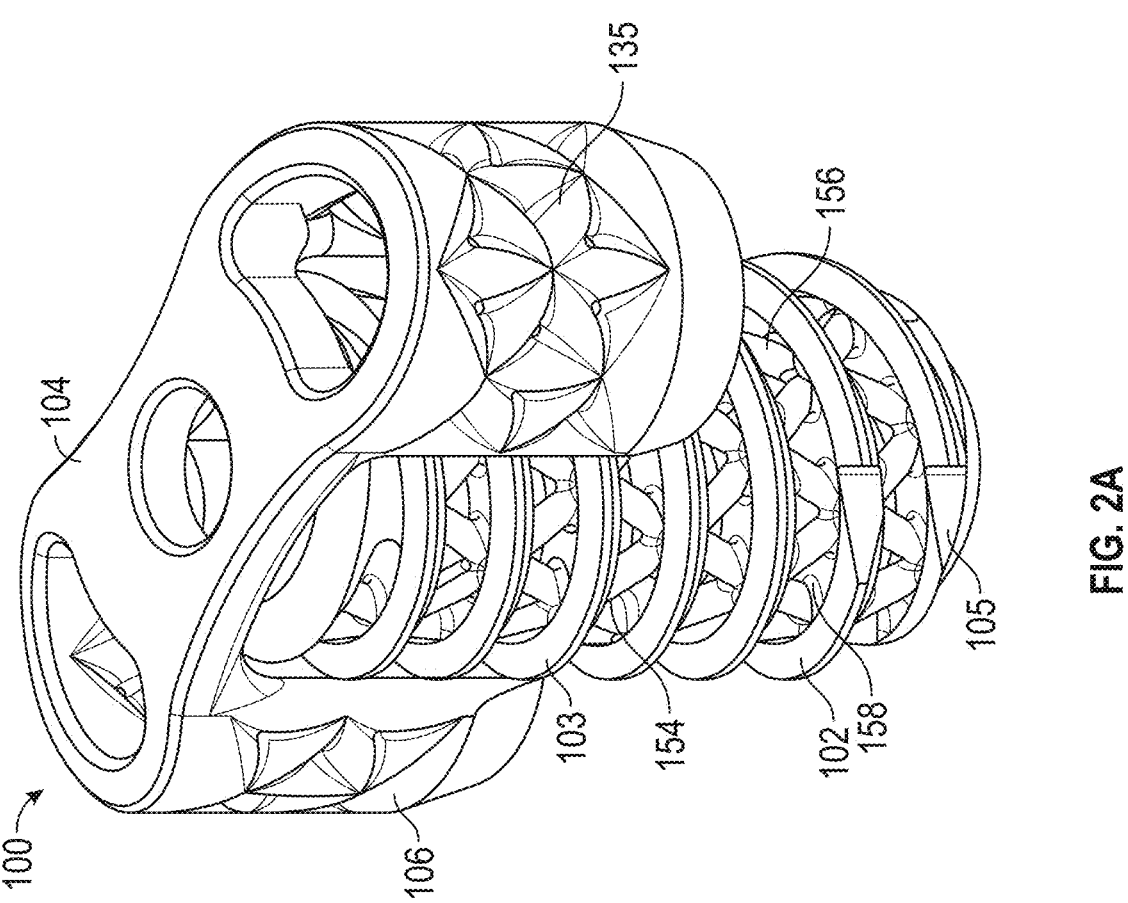
FIG. 2A illustrates a perspective view of an embodiment of a joint implant.
Figure 2C:
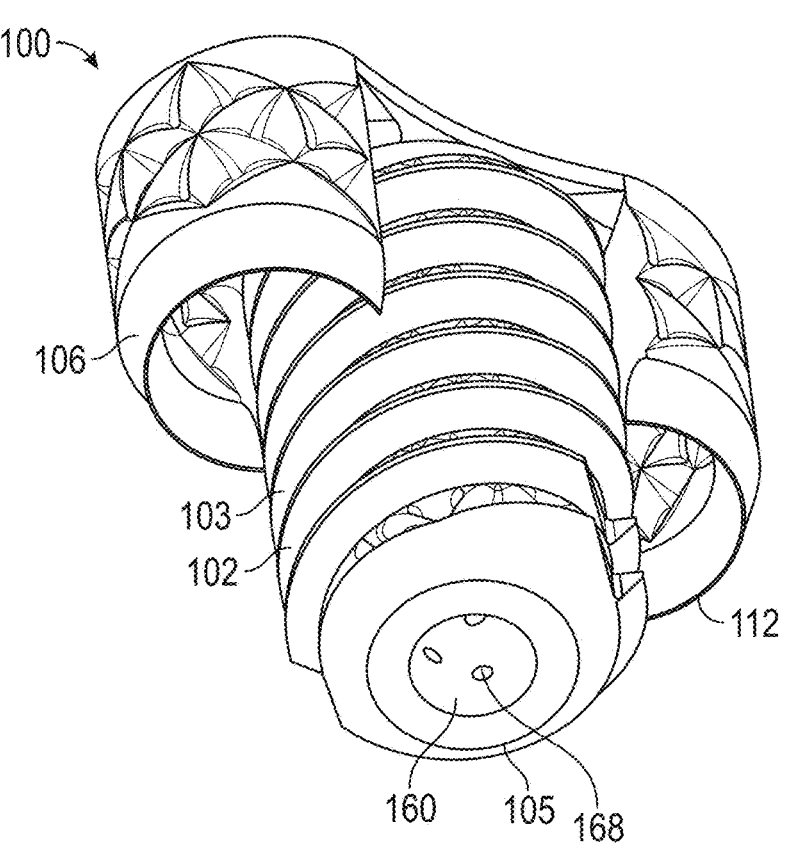
FIG. 2C illustrates a perspective view of the embodiment of the joint implant of FIG. 2A.
Figure 2D:
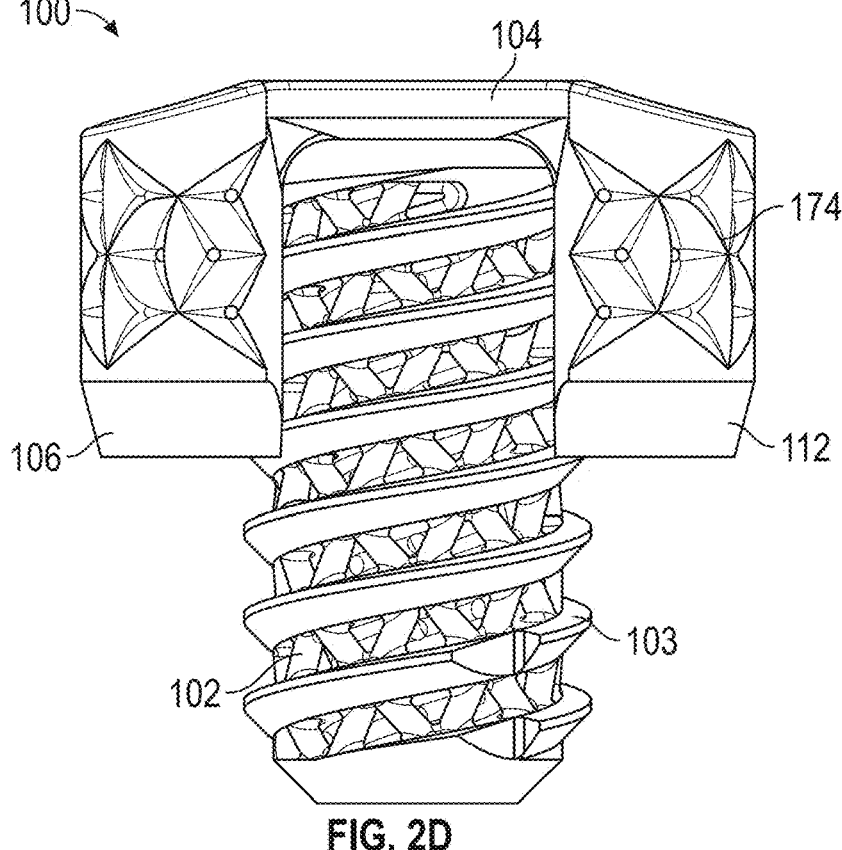
FIG. 2D illustrates a side vide of the embodiment of the joint implant of FIG. 2A.
Figure 3A:
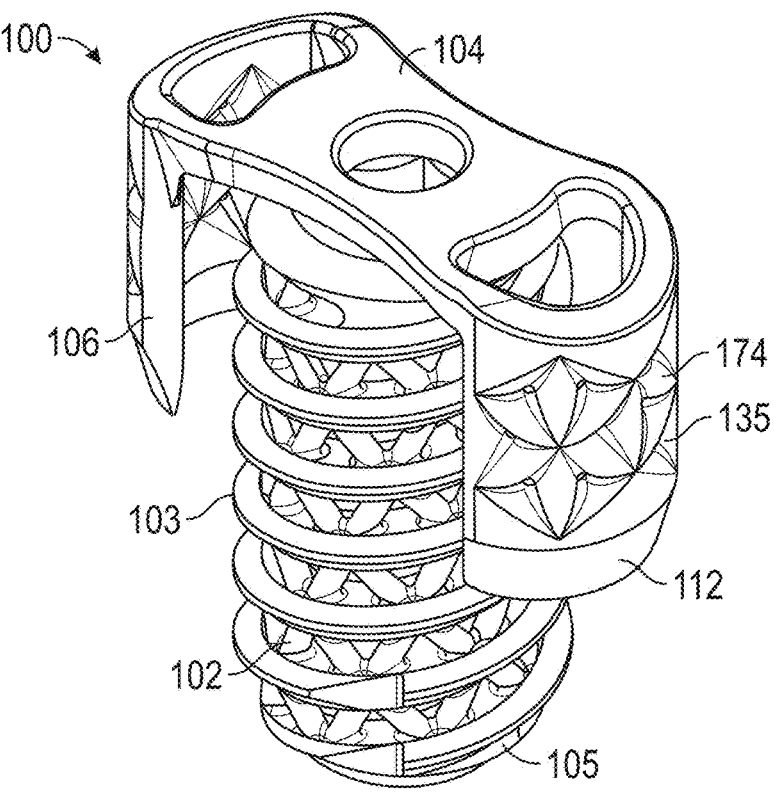
FIG. 3A illustrates a perspective view of an embodiment of a joint implant.
Figure 3B:
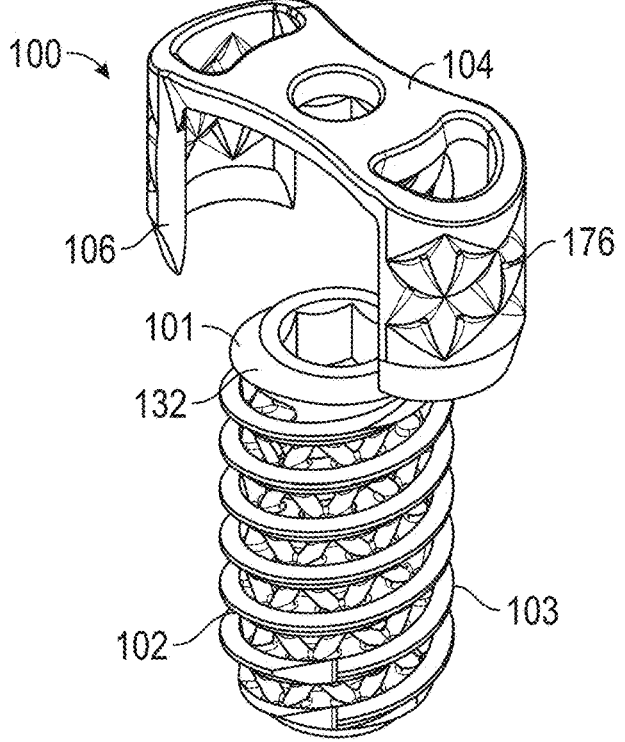
FIG. 3B illustrates an exploded view of the embodiment of the joint implant of FIG. 3A.
Figures 3C, 3D:
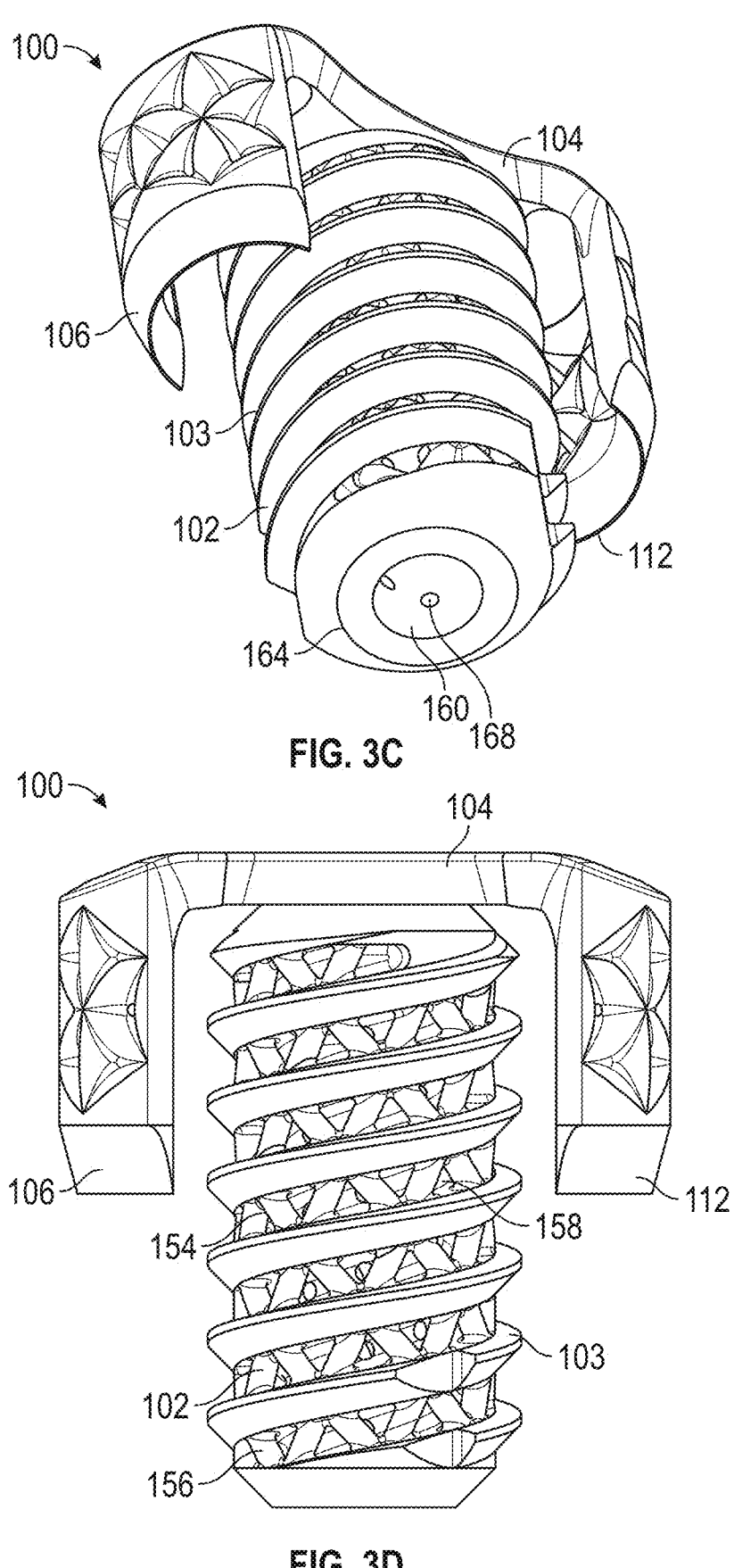
FIG. 3C illustrates a perspective view of the embodiment of the joint implant of FIG. 3A.
FIG. 3D illustrates a side vide of the embodiment of the joint implant of FIG. 3A.
Figure 4A:
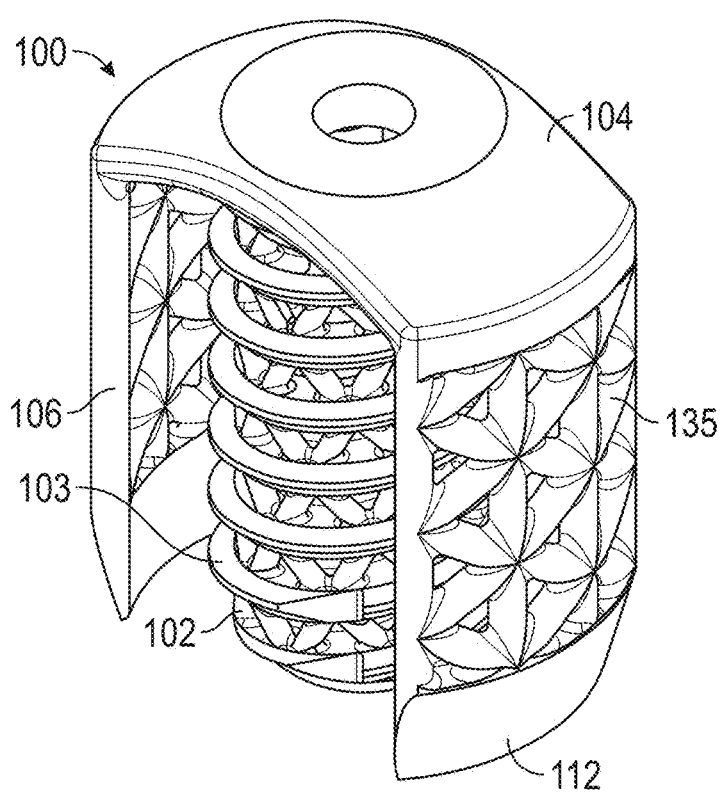
FIG. 4A illustrates a perspective view of an embodiment of a joint implant.
Figure 4B:
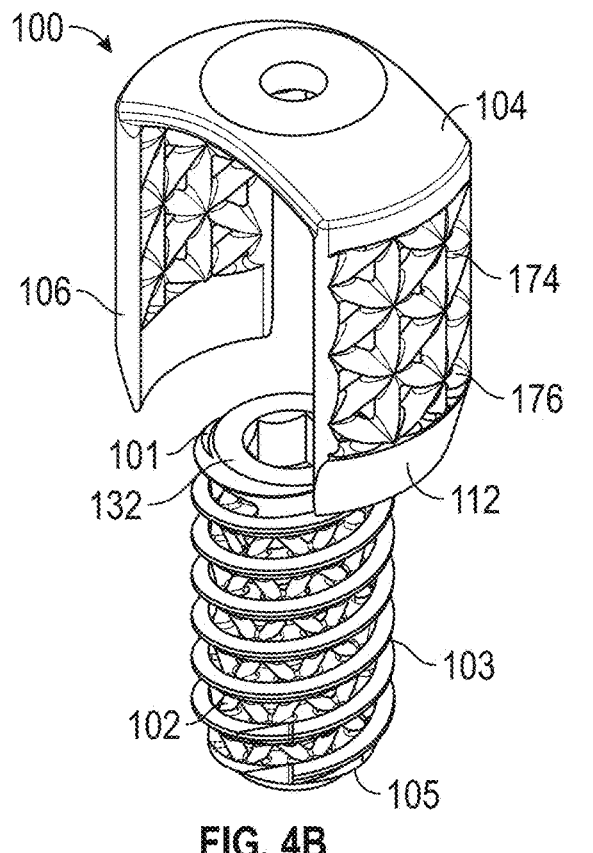
FIG. 4B illustrates an exploded view of the embodiment of the joint implant of FIG. 4A.
Figures 4C, 4D:
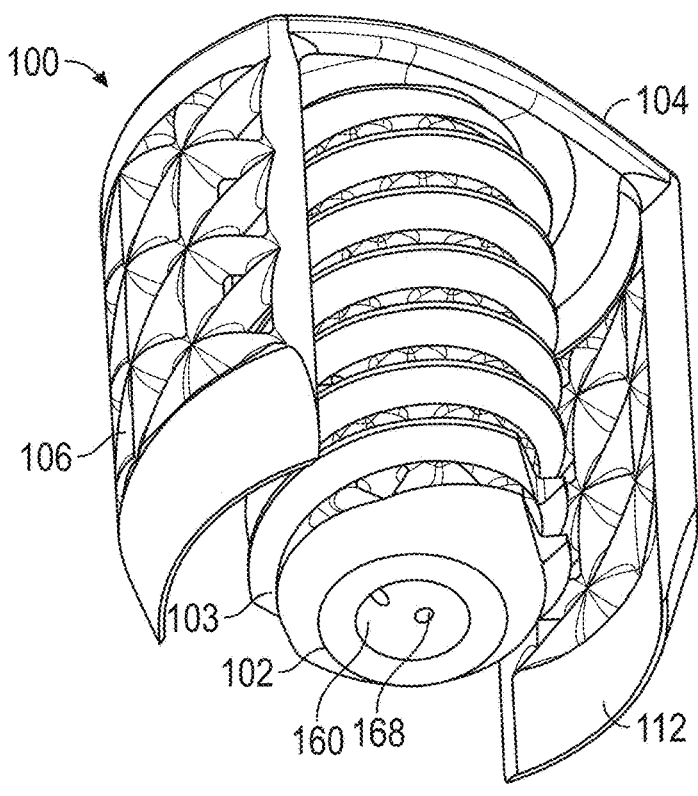
FIG. 4C illustrates a perspective view of the embodiment of the joint implant of FIG. 4A.
FIG. 4D illustrates a side vide of the embodiment of the joint implant of FIG. 4A.

As shown in FIG. 1D, a tip 164 of the implant can be flat. In certain embodiments, the primary implant 102, or a shank 132 of the primary implant 102, may be conical. In certain embodiments, the primary implant 102 or the shank 132 can be tapered. In certain embodiments, the primary implant 102 or shank 132 can be symmetrical about a central axis with no taper. In some embodiments, the primary implant 102 or the shank 132 can be untapered throughout the entire length of the implant or a portion of the length. For example, the shank 132 can have a uniform cross-section or a generally uniform cross-section. In some embodiments, the engagement features 103 (e.g., threads) can extend a uniform distance or generally uniform distance from the shank 132 throughout the length of the primary implant 102. Such untapered embodiments may further prevent or reduce migration or back out of the primary implant 102 from the SI joint in comparison to tapered implants. In some embodiments, the primary implant 102 can be self tapping or self drilling.

In some embodiments, the primary implant 102 may be only partially cannulated. For example, the channel 160 may extend from the proximal end 101 only partially along the length of the primary implant 102 towards the distal end 105. In other embodiments, the primary implant 102 may not be cannulated. In other words, the implant 102 may have a solid core. A primary implant 102 that is only partially cannulated may have a higher biomechanical strength than an implant that is cannulated through its entire length. An implant that is not cannulated may have a higher biomechanical strength than a partially or fully cannulated implant.

As described herein, in certain embodiments, the secondary implant 104 can be configured to anchor within both the ilium and the sacrum on opposing sides of the SI joint. In certain embodiments, the secondary implant 104 can include a plurality of anchors 106. The anchors 106 can be a set of tangs, circles, half circles, wedges, triangles, squares, or other three-dimensional shaped anchors. The anchors 106 can have a curvature, for example in a half circle shape, to prevent or restrict movement of the anchors 106 in response to shear stresses (e.g., when the secondary implant is maleated into bone). In contrast, in some embodiments, a flat or planar anchor 106 may slide back and forth in response to shear stresses. Each of the anchors 106 of the secondary implant 104 may contain a blade or sharp edge 112 at the distal leading edge to cut bone during implantation of the secondary implant 104 (e.g., while the secondary implant is maleated into the bone). The edge 112 may converge or taper to a sharp distal point. For example, the edge may converge or taper laterally inwards (e.g., from one lateral direction inwards and the opposite lateral direction inwards, wherein the lateral directions refer to left and right directions of the page with respect to FIG. 1D).

At least one of the anchors 106 can be implanted in the ilium and at least one of the anchors 106 can be implanted into sacrum. For example, as shown in FIGS. 1A-1D, the secondary implant 104 can include two anchors 106. A first anchor 106 can be configured to be implanted in the ilium and a second anchor 106 can be configured to be implanted in the sacrum.

When the anchors 106 are positioned within the ilium and the sacrum, the secondary implant 104 can act as a tension band. The secondary implant 104 can resist forces that compress/distract and forces that rotate the SI joint.

The secondary implant 104 may come in different shapes and patterns. In certain embodiments, different options for secondary implants 104 having different shapes and patterns can be made available at surgeon preference, for example, for different patient anatomies.

In certain embodiments, the secondary implant 104 can be configured to facilitate bony ingrowth. Bony ingrowth can help for a rigid fusion and prevent implant migration. For example, in certain embodiments, the material of secondary implant 104 can be porous to allow for bony ingrowth. In certain embodiments, the design of the secondary implant 104 may include lattices, planar trusses, non-planar trusses, cancellous or trabecular bone patters, webs, pin holes, circles, and/or any other design that suitable to allow for bone to permeate and grow into the material. For example, as shown in FIGS. 1A-1D, the secondary implant 104 can include a truss or beam system 174. The truss or beam system 174 can act as a scaffolding to provide increased biomechanical strength to the implant 104 and to facilitate bone growth. The truss or beam system 174 can facilitate fusion with surrounding bone. The truss or beam system 174 can also provide stability as the implant 104 fuses with the surrounding bone.

The truss or beam system 174 can be formed of a plurality of truss elements or beams 176. In some embodiments, the plurality of truss elements or beams 176 can extend between at least some of the engagement features 103. A number of windows or openings 135 can be formed between the truss elements of beams 176 of the truss or beam system 174 to facilitate fusion of the implant with surrounding bone. The openings 135 can be positioned so that at least some of the openings 135 will contact the bone of the sacrum and the ilium regardless of the orientation of the secondary implant 104 when fully seated within the SI joint to promote bony ingrowth.

In certain embodiments, acid etching, bead blasting, surface coating such as HA (Hydroxyapatite), or any other suitable surface technology may be utilized to enhance the surface finish to create an optimal area for bone to grow to in the secondary implant 104. In certain embodiments, 3D printing may be utilized to create surfaces structures and features for bone to grow to. In certain embodiments, the surface structures may be on the nanometer or micrometer scale which can be optimal or desirable for bone to grow to.

In certain embodiments, the secondary implant 104 may be CNC machined, 3D printed, or manufactured by any other suitable means. In certain embodiments, the secondary implant 104 can be made of stainless steel, titanium, polyether-ether-ketone (PEEK), ceramic, human allograft or any other suitable implantable material strong enough to resist the forces described herein and pass biomechanical testing. In certain embodiments, the implant material can be important to achieve bony ingrowth.

In certain embodiments, the secondary implant 104 can couple to the primary implant 102 (or otherwise be in contact with or align with the primary implant 102 when implanted). For example, the secondary implant 104 can be coupled to a proximal end 101 of the primary implant 102. In certain embodiments, interconnected porosity can be attainable within both implants.

In combination, the primary implant 102 and secondary implant 104 can act as one system to achieve multiple points of fixation and resist multiple forces. For example, in certain embodiments, the primary implant 102 and second implant 104 can act as one system to resist all of the forces acting on the SI joint.

In certain embodiments, the secondary implant 104 can extend superiorly from the center of the primary implant 102. In certain embodiments, the secondary implant 104 can extend laterally beyond an outer edge of the primary implant 102 so that the anchors 106 are positioned laterally to the outer edge of the primary implant 102. In certain embodiments, the secondary implant 104 can extends laterally outwards from the primary implant 102 to a distance sufficient for capturing enough bone from both the sacrum and ilium to prevent compression and distraction. In certain embodiments, the length of the secondary implant 104 may match the length of the primary implant 102, may be half or three quarters of the length of the primary implant 102, or may be any other suitable length relative to the primary implant 102. Each anchor 106 may extend the full length of the primary implant 102, may be half or three quarters of the length of the primary implant 102, or may be any other suitable length relative to the primary implant 102. In certain embodiments, a distal end of each anchor 106 can be coplanar with the distal end 105 of the primary implant 102. The length the secondary implant 104 and/or the length of the anchors 106 may be determined by the amount of fixation needed and can be patient dependent.

FIGS. 2A-2D depict another embodiment of the SI joint implant system 100. The embodiment of FIGS. 2A-2D may include any of the same or similar features or functions as any of the other embodiments described herein and vice versa. In comparison to the embodiment of FIGS. 1A-1D, each of the anchors 106 of the embodiment of FIGS. 2A-2D may have a greater degree of curvature.

FIGS. 3A-3D depict another embodiment of the SI joint implant system 100. The embodiment of FIGS. 3A-3D may include any of the same or similar features or functions as any of the other embodiments described herein and vice versa. In comparison to the embodiment of FIGS. 1A-1D, each of the anchors 106 of the embodiment of FIGS. 3A-3D may have a greater degree of curvature. In comparison to the embodiment of FIGS. 2A-2D, each of the anchors 106 of the embodiment of FIGS. 3A-3D may have a smaller degree of curvature.

In some embodiments, a degree of curvature of each anchor 106 can be between 15 degrees and 270 degrees, between 15 degrees and 210 degrees, between 15 degrees and 180 degrees, between 15 degrees and 150 degrees, between 15 degrees and 120 degrees, between 15 and 90 degrees, between 15 degrees and 60 degrees, between 15 degrees and 45 degrees, between 30 degrees and 90 degrees, between 90 degrees and 180 degrees, or any other suitable range. In some embodiments, the degree of curvature of each anchor 106 can be about 15 degrees, about 30 degrees, about 45 degrees, about 60 degrees, about 90 degrees, about 120 degrees, about 150 degrees, about 180 degrees, or any other suitable degree.

FIGS. 4A-4D depict another embodiment of the SI joint implant system 100. The embodiment of FIGS. 4A-4D may include any of the same or similar features or functions as any of the other embodiments described herein and vice versa. As shown in FIGS. 4A-4D, in certain embodiments, the anchors 106 can extend distally to the distal end 105 of the primary implant 102. For example, the distal end of the anchors 106 can be coplanar with the distal end 105 of the primary implant 102.

FIGS. 5A-5D depict another embodiment of the SI joint implant system 100. The embodiment of FIGS. 5A-5D may include any of the same or similar features or functions as any of the other embodiments described herein and vice versa. In certain embodiments, the implant system 100 can include a fastener or attachment mechanism 110. The fastener or attachment mechanism 110 can couple the primary implant 102 and the secondary implant 104. This can be important when performing minimally invasive surgery and working through dense tissue. The secondary implant 104 can include an opening 114 configured to receive the fastener or attachment mechanism 110. The primary implant 102 can receive the fastener or attachment mechanism 110, for example, within the channel 160. As shown in FIGS. 5A-5D, the fastener or attachment mechanism 110 can be threaded fastener having a plurality of external threads 116. The primary implant 102 and/or the secondary implant 104 can include plurality of internal threads 118. For example, the internal threads 118 may extend at least partially or entirely along the length of the channel 160.

FIGS. 6A-6D depict another embodiment of the SI joint implant system 100. The embodiment of FIGS. 6A-6D may include any of the same or similar features or functions as any of the other embodiments described herein and vice versa.

FIGS. 7A-7D depict another embodiment of the SI joint implant system 100. The embodiment of FIGS. 7A-7D may include any of the same or similar features or functions as any of the other embodiments described herein and vice versa.

As shown in FIGS. 7A-7D, in certain embodiments, the secondary implant 104 can include a body or anchor ring 124. One or more anchors 106 can extend from the anchor ring 124. In certain embodiments, the one or more anchors 106 can be coupled to the anchor ring 124 by one or more arms 146.

As shown in FIGS. 7A-7D, in certain embodiments, the primary implant 102 may include tabs 108 that act as a guide for the secondary implant 104. The tabs 108 are attached to the primary implant 102 and may be broken off where the tabs 108 connect to the primary implant 102 (for example, at a frangible joint). In some embodiments, the tabs 108 may form a tulip configuration. The tabs 108 can act as a guide for the secondary implant 104. For example, the tabs 108 may define carve-outs or recesses 109 between the tabs 108 configured to receive the arms 146 of the secondary implant 104.

The tabs 108 can also allow for a fastener or attachment mechanism (such as a screw, for example a set screw (e.g., a grub screw), or a threaded nut) to connect the primary implant 102 and secondary implant 104. As described herein, this can be important when performing minimally invasive surgery and working through dense tissue.

In certain embodiments, after the secondary implant 104 is positioned within the recesses 109, the attachment mechanism 110 can engage the tabs 108 above the secondary implant 104 to secure the secondary implant 104 within the tabs 108 and to the primary implant 102.

In certain embodiments, the tabs 108 can provide for alignment to prevent or reduce cross-threading or failure to engage the threads when trying to connect the primary implant 102 and secondary implant 104. The tabs 108 may have internal threads 122 that capture threads 123 of the attachment mechanism 110 and allow the secondary implant 104 to be pulled into the primary implant 102. This may be useful if the secondary implant 104 doesn't sit perfectly into the primary implant 102. The recesses 109 can be positioned on one side or both sides of the threads 122 to allow the secondary implant 104 to slide down without hitting the threads 122.

The tabs 108 may be attached to the primary implant 102 permanently and can be configured to break or snap off due to forces applied by a user when desired. In other embodiments, the tabs may be assembled to primary implant 102 prior to insertion into the SI joint and then removed once the attachment mechanism 110 is properly inserted to anchor the primary implant 102 to the secondary implant 104. Breaking off or removal of the tabs 108 may provide a lower profile of the implant system 100 above the SI joint. In some embodiments, the implant system 100 can be flush or countersunk with the SI joint.

FIGS. 8A-8D depict another embodiment of the SI joint implant system 100. The embodiment of FIGS. 8A-8D may include any of the same or similar features or functions as any of the other embodiments described herein and vice versa.

As shown in FIGS. 8A-8D, in some embodiments, the secondary implant 104 may be adjustable so that the anchors 106 can be positioned at different lateral distances from primary implant 102. The anchors 106 can open to a position in which the lateral distance is greater and close to a distance where the lateral distance is smaller. In some embodiments, an implant 104 with adjustable anchor distances can be used, for example, to pull the ilium and sacrum together for compression (e.g., by drawing the anchors 106 towards the primary implant and/or towards one another). This force can prevent joint distraction and allow for compression on the primary implant 102. Pulling the ilium and sacrum together for compression can permit bone to implant contact if the SI joint is wide or hypermobile.

The secondary implant 104 may be comprised of one or multiple parts. The adjustable (for example, opening and/or closing) mechanism may be ratcheting, worm gear, spindle or any other mechanism that can open or close allowing for compression and distraction. An example of an adjustable secondary implant 10 is shown in FIGS. 8A-8D. As shown in FIGS. 8A-8D, the implant 10 includes two anchors 106 as separate pieces. The attachment mechanism 110 can be in the form of a gear wheel having teeth 125 configured to engage complementary teeth 127 on each of the anchors 106. The teeth 127 may be positioned along the arms 146 of the secondary implant 104. The attachment mechanism 110 can be adjusted (e.g., via rotation of the attachment mechanism) to pull the ilium and sacrum together.

In some embodiments, the primary implant 102 can include carve-outs or channels 113 on one or both sides to receive the arms 146 of the secondary implant 104 therethrough. The channels 113 may extend radially about the primary implant 102 and allow for rotation of portions of the secondary implant 104 relative to the implant 102. In certain embodiments, the channels 113 may restrict axial movement (e.g., proximal and distal movement) of the implant 104. When the arms 146 extend through the channels 113 and couple with the attachment mechanism 110, the secondary implant 104 may be secured to the primary implant 102.

In some alternative embodiments, the mechanism 110 of FIGS. 8A-8D does not attach the primary implant 102 to the secondary implant 104, but is only used to adjust the positioning of the two anchors 106, for example, to pull the ilium and sacrum together.

12,648,855 B2

17

FIGS. 9A-9D depict another embodiment of the SI joint implant system 100. The embodiment of FIGS. 9A-9D may include any of the same or similar features or functions as any of the other embodiments described herein and vice versa.

FIGS. 10A-10D depict another embodiment of the SI joint implant system 100. The embodiment of FIGS. 10A-10D may include any of the same or similar features or functions as any of the other embodiments described herein and vice versa. As shown in FIGS. 10A-D, the edge 112 may converge to a sharp distal point generally inwards from the anterior and posterior directions (e.g., into and out of the page with reference to FIG. 10C), which may facilitate driving of the anchors 106 into bone, alternatively or in addition to converging generally laterally inwards.

FIGS. 11A-11D depict another embodiment of the SI joint implant system 100. The embodiment of FIGS. 10A-10D may include any of the same or similar features or functions as any of the other embodiments described herein and vice versa. In some embodiments, the edge 112 may converge to a blunted or curved distal end generally inwards from the anterior and posterior direction, alternatively or in addition to converging generally laterally inwards to a sharp distal end.

Figure 32:
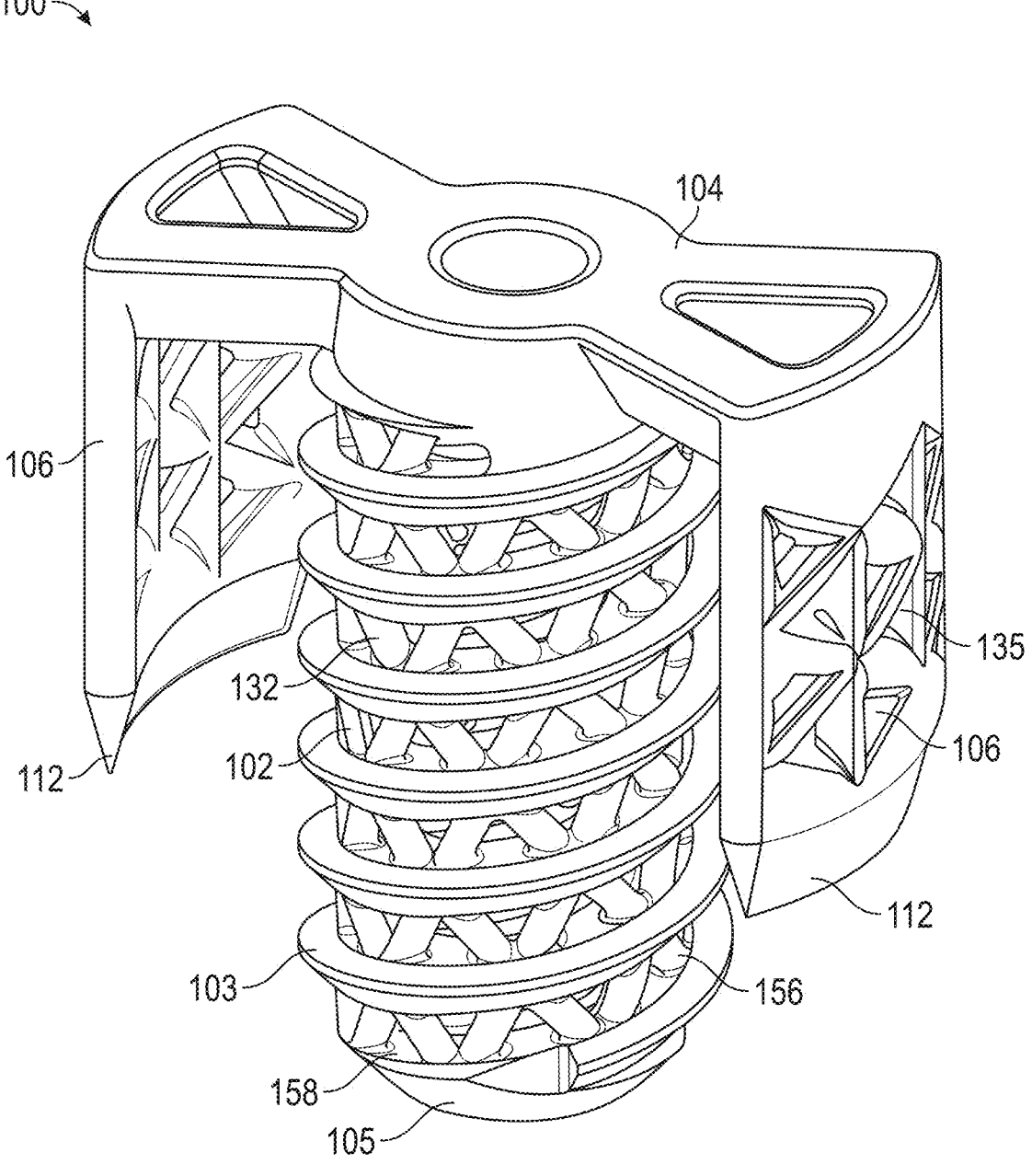
FIG. 32 illustrates a perspective view of an alternative embodiment of a joint implant.
Figures 33A, 33B:
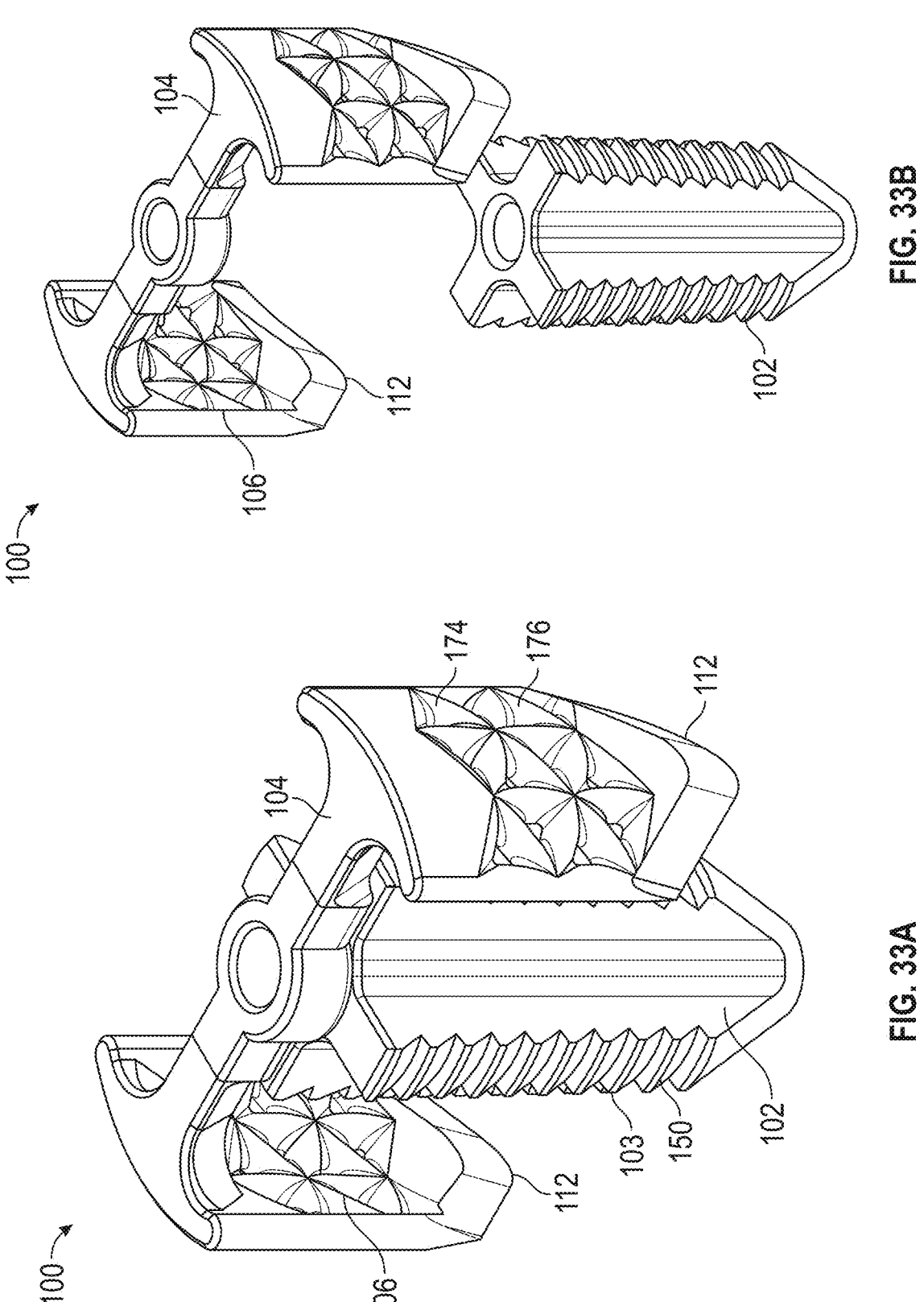
FIG. 33A illustrates a perspective view of an alternative embodiment of a joint implant.
FIG. 33B illustrates an exploded view of the embodiment of the joint implant of FIG. 33A.
Figures 33C, 33D:
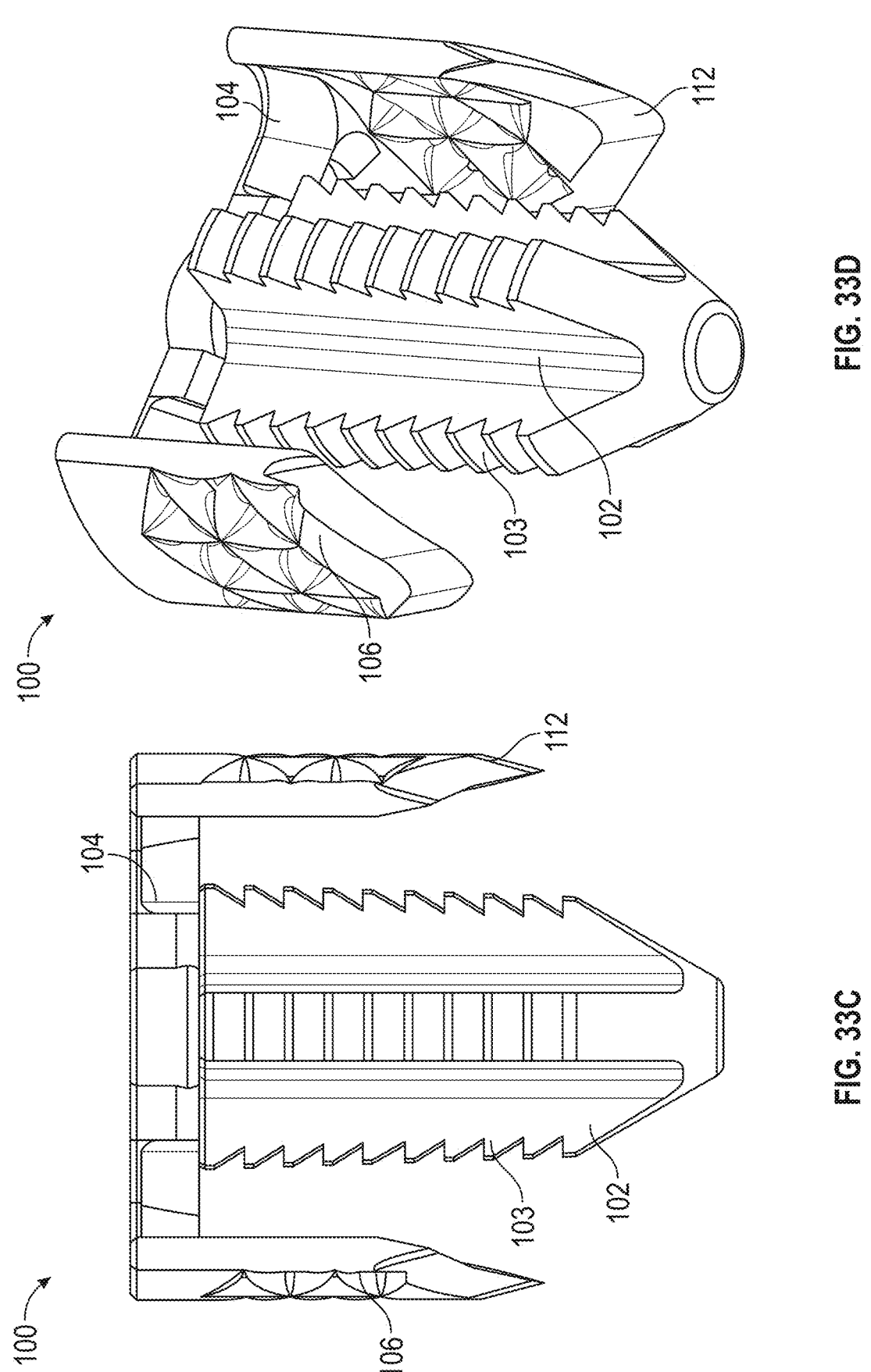
FIG. 33C illustrates a side view of the embodiment of the joint implant of FIG. 33A.
FIG. 33D illustrates a perspective view of the embodiment of the joint implant of FIG. 33A.

FIG. 32 depicts another embodiment of the SI joint implant system. The embodiment of FIG. 32 may include any of the same or similar features or functions as any of the other embodiments described herein and vice versa. As shown in FIG. 32, in some embodiments, the primary implant 102 and secondary implant 104 can be formed together as a single-piece.

FIGS. 33A-33D depict another embodiment of the SI joint implant system 100. The embodiment of FIGS. 33A-33D may include any of the same or similar features or functions as any of the other embodiments described herein and vice versa.

FIGS. 33A-33D show an embodiment of the implant system 100 in which the primary implant 102 includes engagement features 103 in the form of barbs instead of threads. In such embodiments, the primary implant 102 can be implanted by malleting a proximal end 101 of the primary implant 102. The secondary implant 104 can then be coupled to the primary implant 102. In some embodiments, the secondary implant 104 can be coupled to the primary implant 102 before placing the primary implant 102, and the implant system 100 can be placed in a single step by malleting a proximal end 101 of the secondary implant 104 while the secondary implant 104 is coupled to the primary implant.

As described herein, in certain embodiments, the secondary implant may contain a blade or sharp edge at the distal leading edge 112 to cut bone. In certain embodiments, the secondary implant 104 can be impacted directly into the bone without using a cutting tool such as a broach. Alternatively, for example, if the bone is too dense, a broach or other cutting device may be used prior to placement of the secondary implant 104. In certain embodiments, the secondary implant 104 may be inserted with an impactor or other device that creates enough blunt force to drive the secondary implant 104 into the bone.

Figure 34:
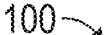
FIG. 34 illustrates a perspective view of an alternative embodiment of a joint implant.
Figure 34:
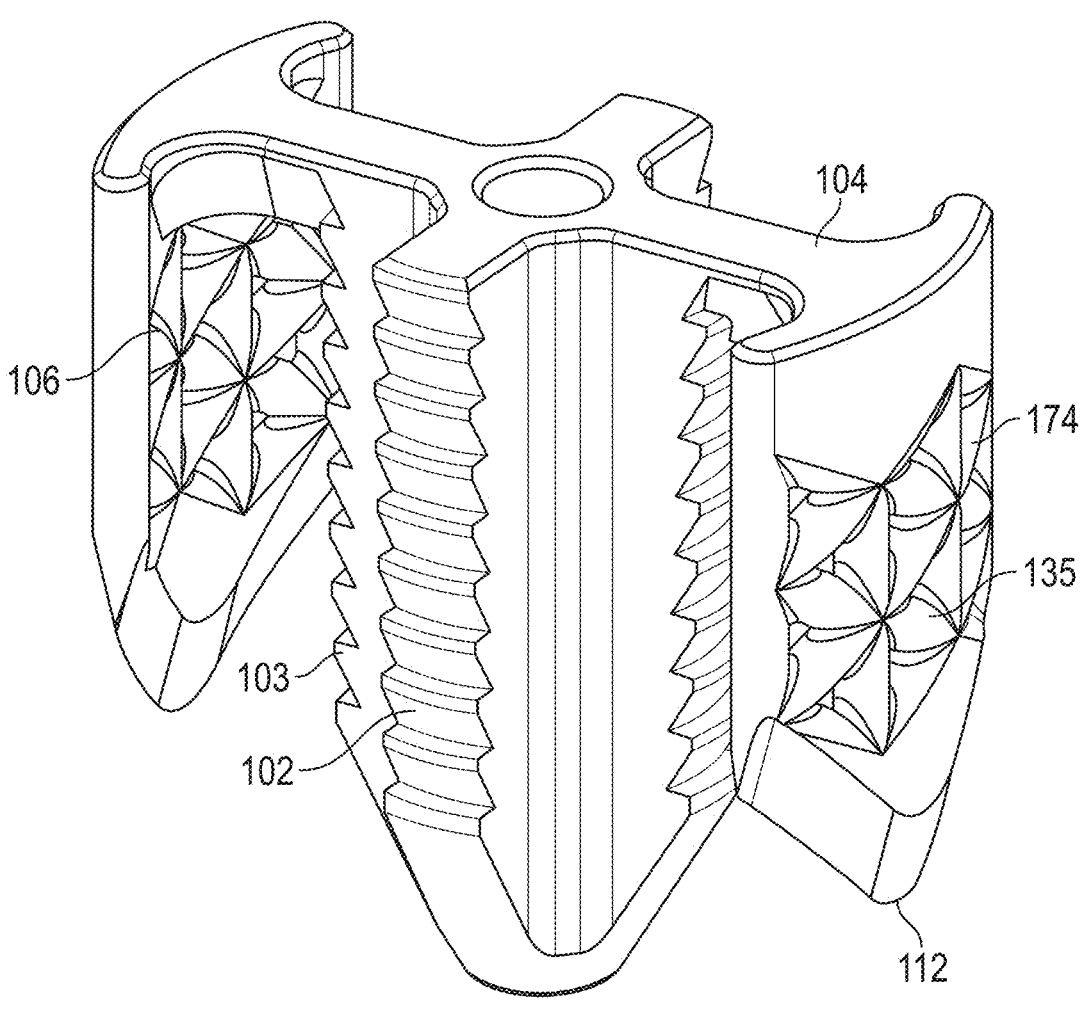
Figures 35A, 35B:
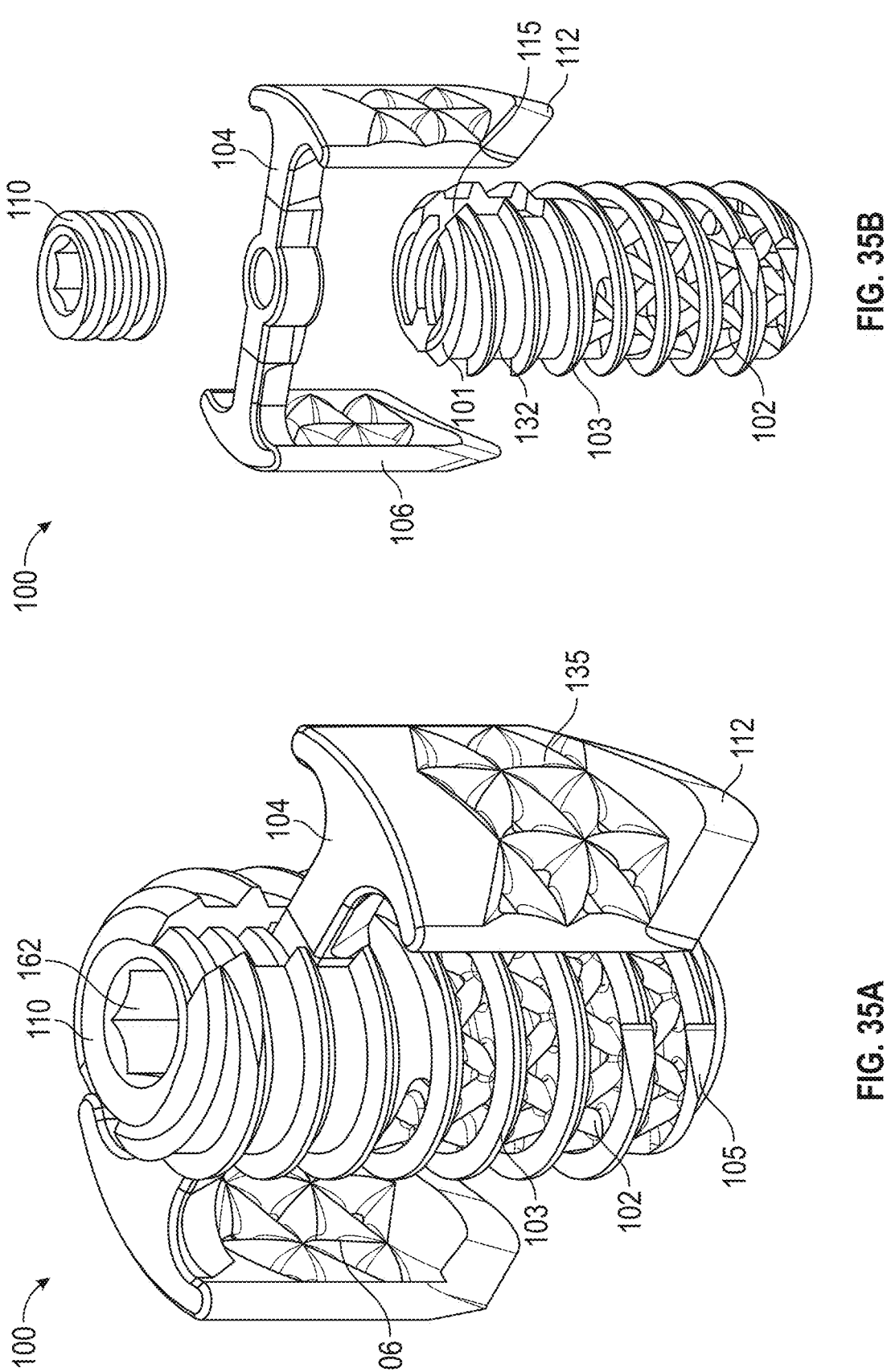
FIG. 35A illustrates a perspective view of an alternative embodiment of a joint implant.
FIG. 35B illustrates an exploded view of the embodiment of the joint implant of FIG. 35A.
Figures 35C, 35D:
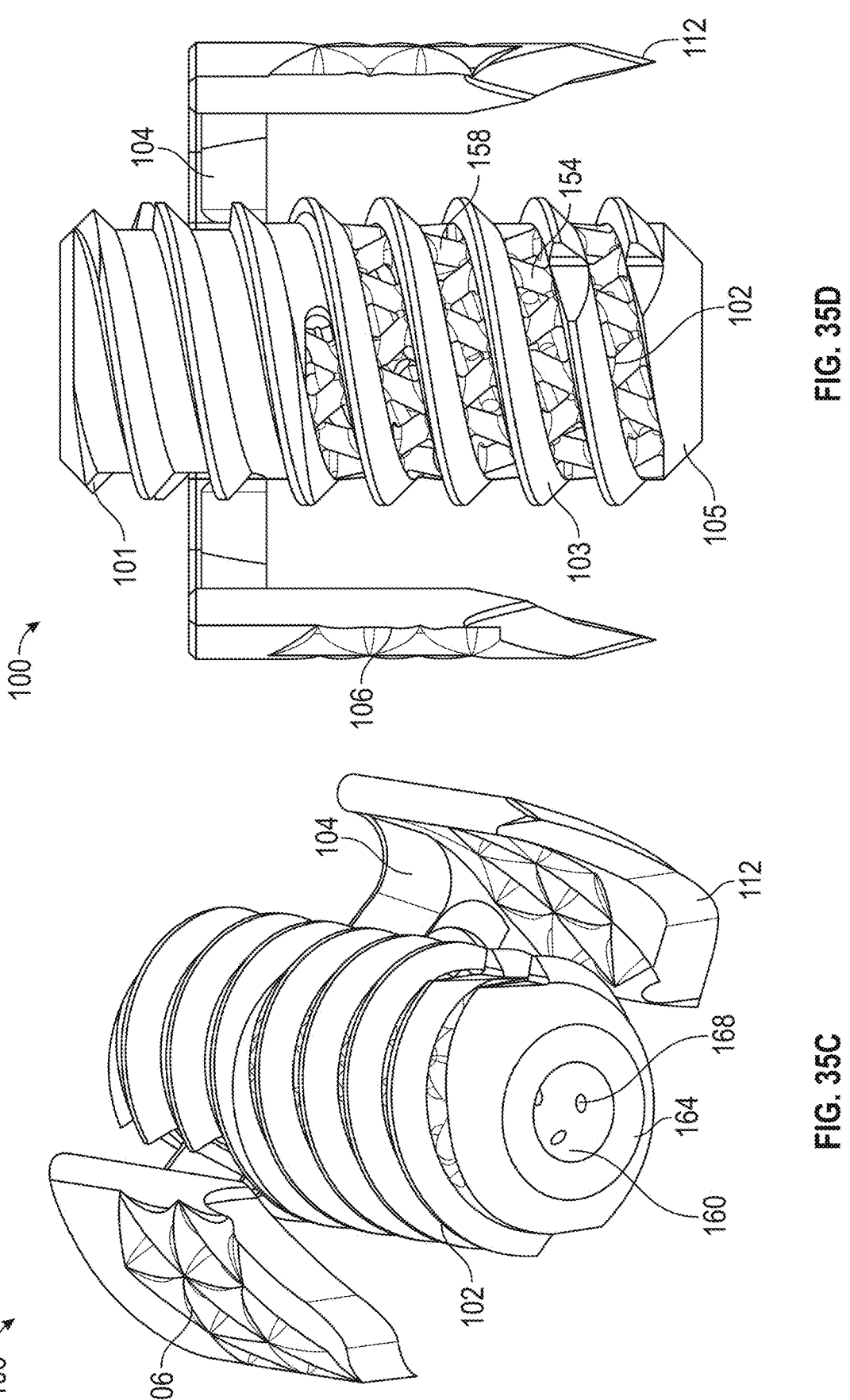
FIG. 35C illustrates a perspective view of the embodiment of the joint implant of FIG. 35A.
FIG. 35D illustrates a side view of the embodiment of the joint implant of FIG. 35A.
Figure 36A:
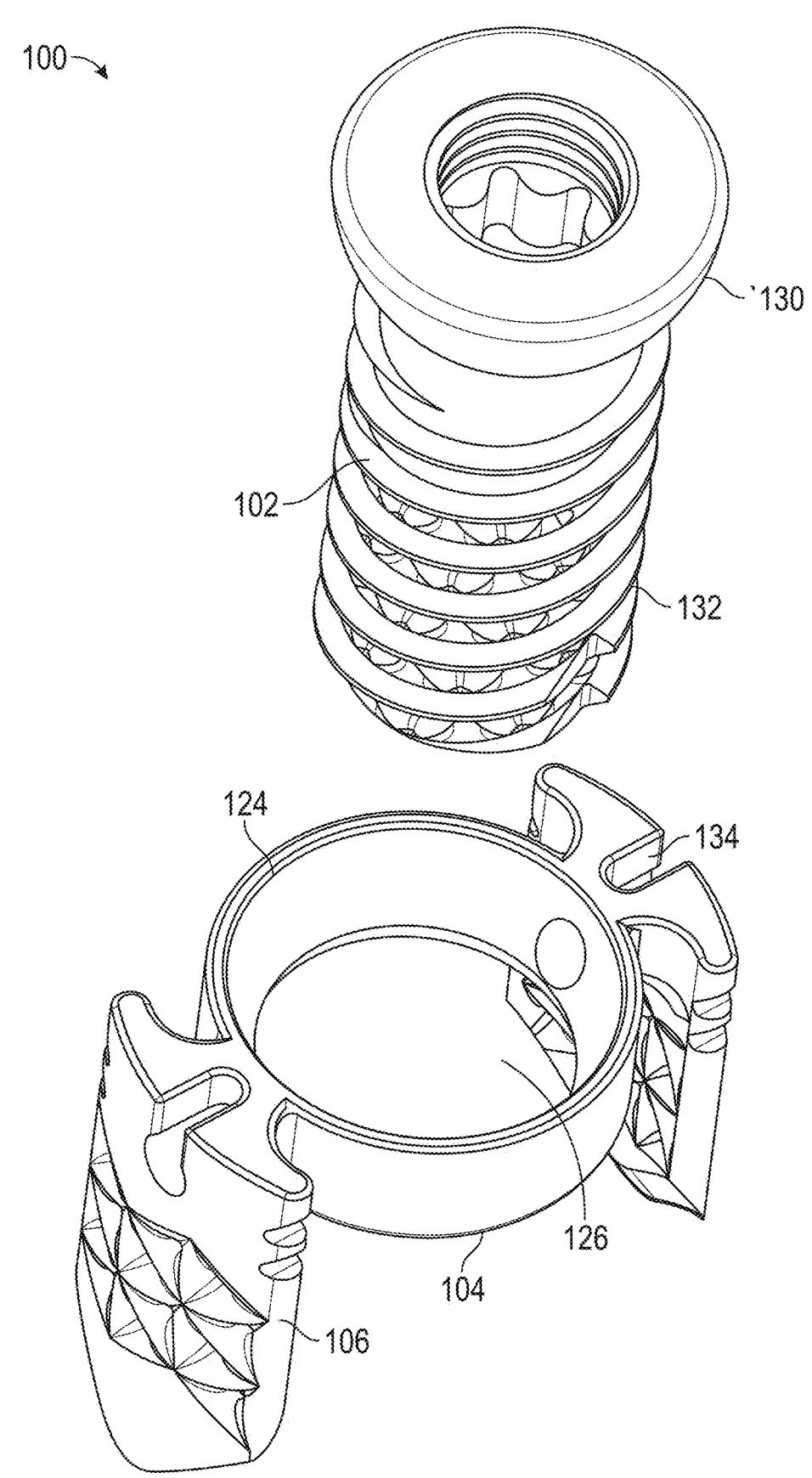
FIG. 36A illustrates a perspective view of an alternative embodiment of a joint implant.
Figure 36B:
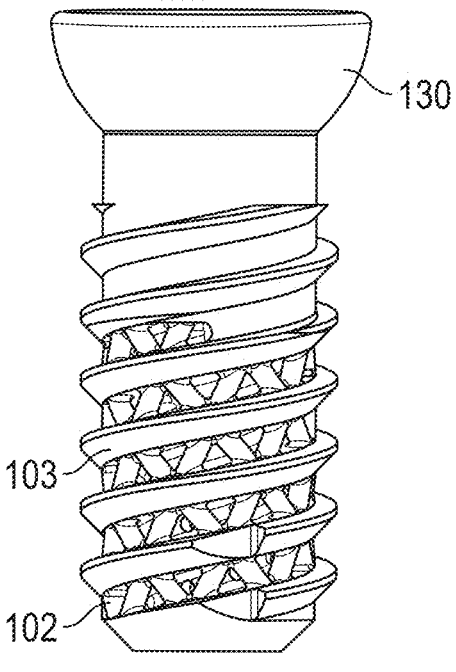
FIG. 36B illustrates a side view of an alternative embodiment of the joint implant of FIG. 36A.
Figure 36B:
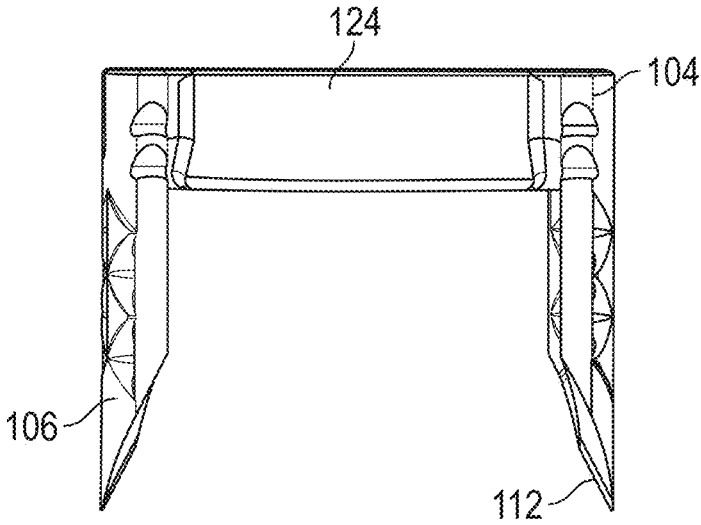
Figure 36C:
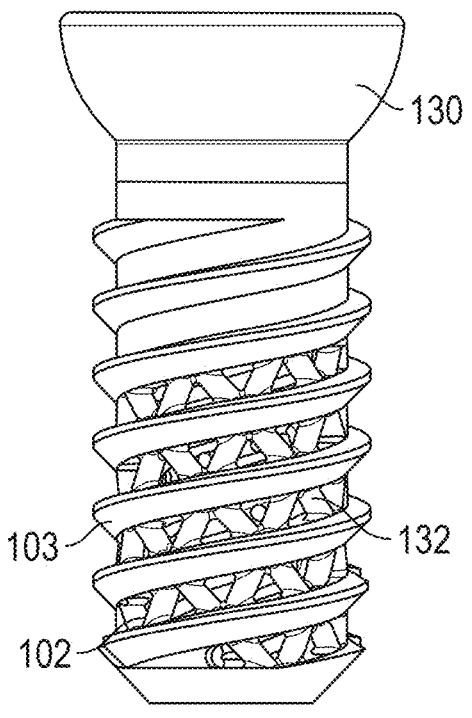
FIG. 36C illustrates a side view of an alternative embodiment of the joint implant of FIG. 36A.
Figure 36C:
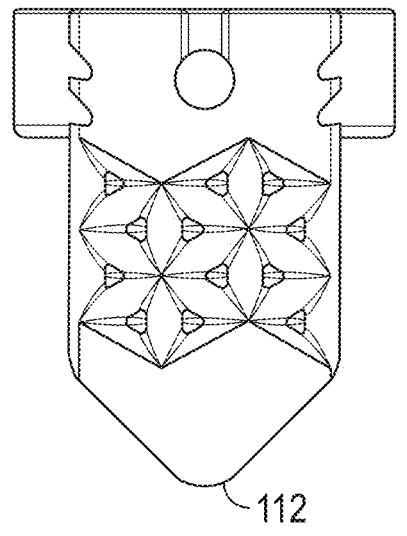
Figures 36D, 36E:
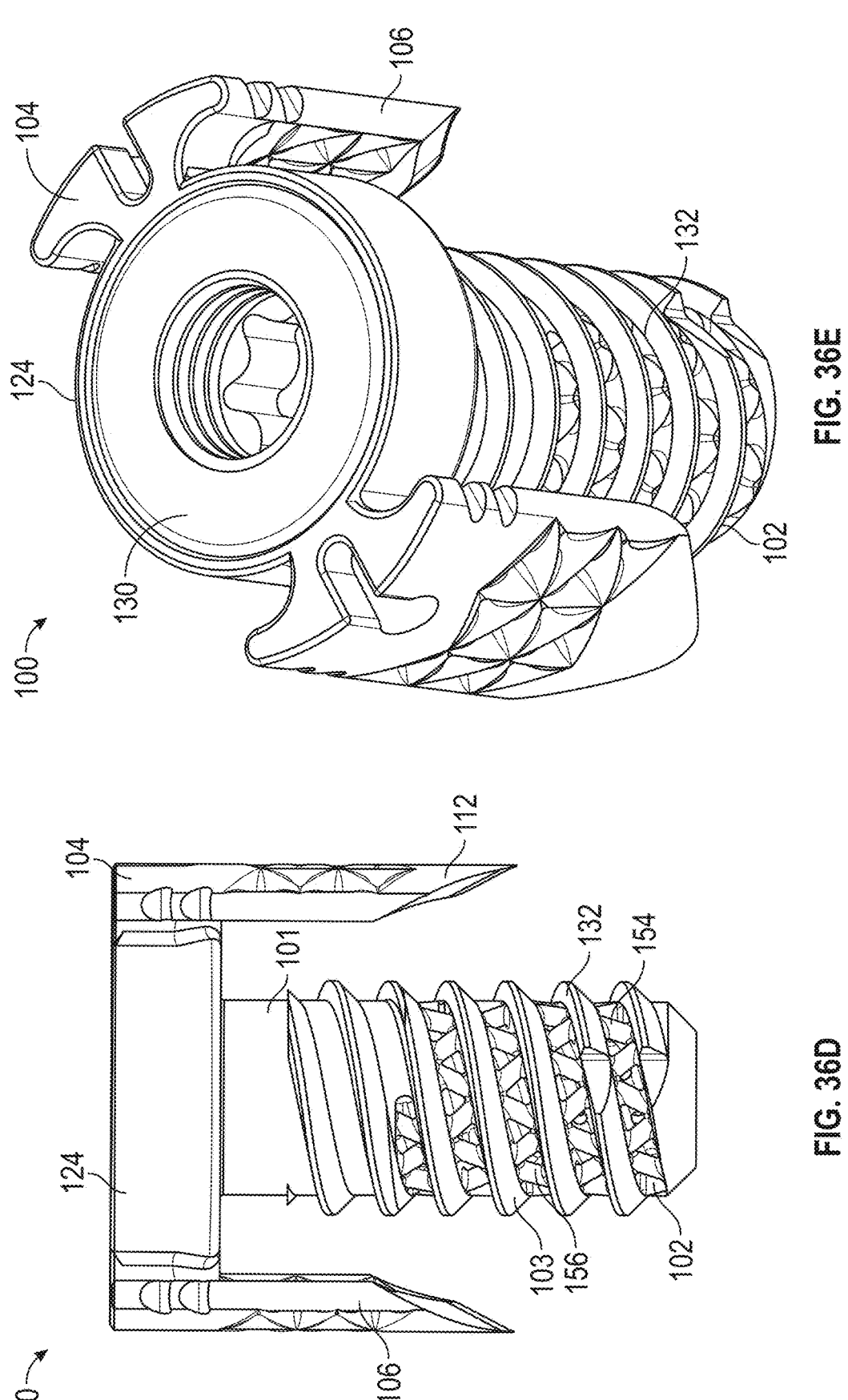
FIG. 36D illustrates a side view of an alternative embodiment of the joint implant of FIG. 36A.
FIG. 36E illustrates a perspective view of an alternative embodiment of the joint implant of FIG. 36A.
Figure 36G:
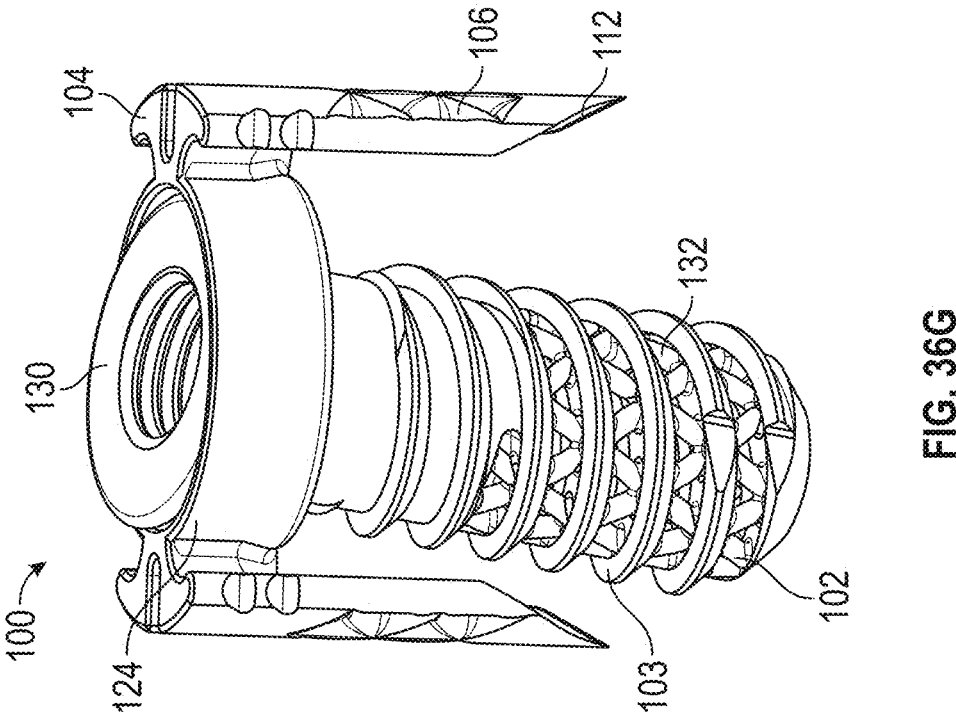
FIG. 36G illustrates a perspective view of an alternative embodiment of the joint implant of FIG. 36A.
Figure 36F:
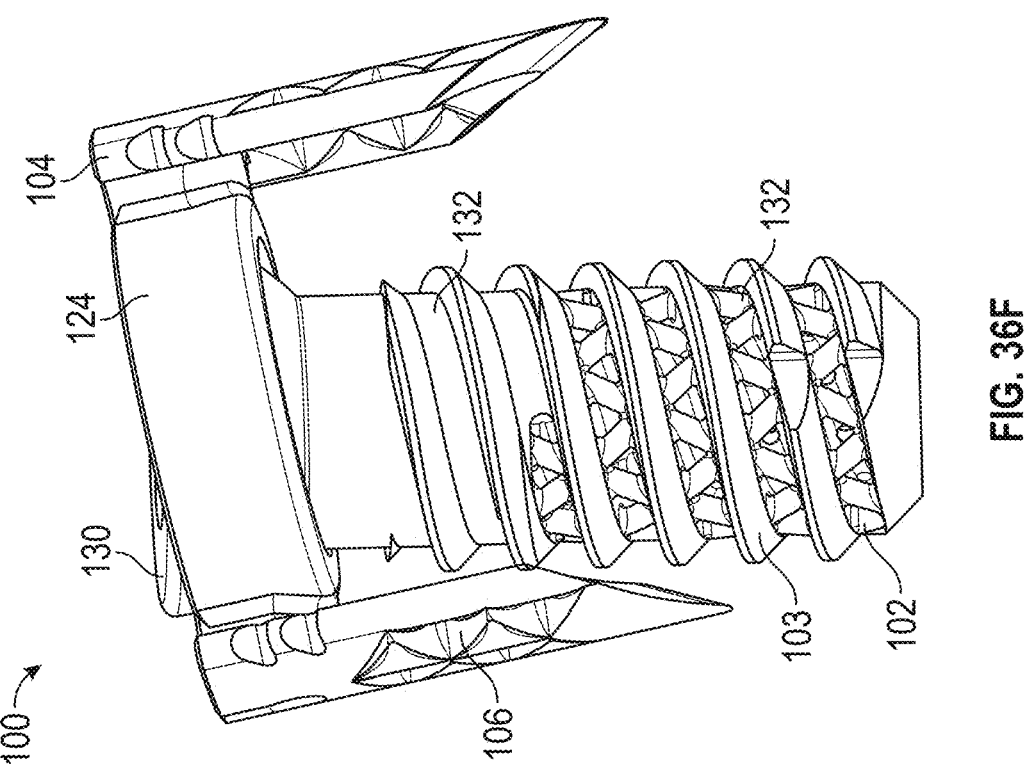
FIG. 36F illustrates a perspective view of an alternative embodiment of the joint implant of FIG. 36A.

FIG. 34 depicts another embodiment of the SI joint implant system. The embodiment of FIG. 34 may include any of the same or similar features or functions as any of the other embodiments described herein and vice versa. FIG. 34 depicts an embodiment of the implant system 100 in which the primary implant 102 and secondary implant 104 are formed as a single piece. The embodiment of FIG. 34 includes barbs 150.

FIGS. 35A-35D depict another embodiment of the SI joint implant system 100. The embodiment of FIGS. 35A-35D may include any of the same or similar features or functions as any of the other embodiments described herein and vice versa.

FIGS. 35A-35D depict an embodiment of the system 100 in which the primary implant 102 includes engagement features 103 in the form of threads extending along an entirety of the length of the shank 132. In other words, the threads can extend from a proximal end 101 of the primary implant 102 to the distal end 105. Threads extending along the entirety of the length of the shank 132 can promote countersinking of the entire primary implant 102 within the SI joint and can provide improved back out prevention in comparison to implants in which the threads only partially extend along the length of the implant, for example, by increasing bone purchase.

As shown in FIGS. 35A-35D, in some embodiments, the primary implant 102 can include recesses 115 extending distally form the proximal end 101. The recesses 115 may include any of the same or similar features or functions of the recesses 109 formed by the tabs 108, but may extend at least partially through the portion of the shank 132 having engagement features 103 thereon.

FIGS. 36A-36G depict another embodiment of the SI joint implant system 100. The embodiment of FIGS. 36A-36G may include any of the same or similar features or functions as any of the other embodiments described herein and vice versa.

As shown in FIGS. 36A-36G, the secondary implant 104 can include a plurality of anchors 106, as described herein, and an anchor body or anchor ring 124 defining a central opening 126. As shown, the anchors 106 can extend laterally form the ring 124. The ring 124 can be sized, shaped, and/or otherwise configured so that the central opening 126 is sized, shaped, and or otherwise configured to receive the primary implant 102 therethrough. In certain embodiments, the primary implant 102 can include a head 130 and a shank 132. The ring 124 can be sized, shaped, and/or otherwise configured so that an inner diameter thereof corresponds to an outer diameter of the head 130.

In certain embodiments, the head 130 and/or another portion of the primary implant 102 can be sized, shaped, and/or otherwise configured to prevent backout of the anchor after implantation through the central opening 126. For example, the head 130 can be sized, shaped, and/or otherwise configured to block, prevent, or restrict proximal movement of a portion of at least a portion of the ring 124 when positioned within the opening 126.

In other embodiments, the primary implant 102 may be headless. In other words, in some embodiments, the primary implant 102 does not include a separate head having a different diameter than the shank 132. Instead, the proximal end 101 of the primary implant can have the same diameter, a similar diameter, or a smaller diameter than the shank 132 of the primary implant 102 to facilitate countersinking of the implant 102.

FIGS. 54A-54G depict another embodiment of the SI joint implant system 100. The embodiment of FIGS. 54A-54G may include any of the same or similar features or functions as any of the other embodiments described herein and vice versa.

FIGS. 54A-54G depict an embodiment of the implant system 100 in which the primary implant 102 has threads 140 that can thread into complementary threads 142 of the secondary implant 104. The primary implant 102 can be advanced until it bottoms out in the secondary implant 104, preventing it from going further down into the SI joint. The complementary threads can allow for a positive stop and prevent over-inserting of the implant 102. This also prevents stripping of the implant 102 in the bone.

In the embodiment of FIGS. 54A-54G, a proximal end of the anchors 106 of the secondary implant are positioned below a proximal end of the primary implant 102. The positioning of the anchors 106 below the proximal end of the primary implant 102 can allow the anchors 106 to be countersunk within the bone of the ilium and sacrum and prevent the anchors 106 from being proud when implanted, for example, if the ilium and sacrum are uneven.

FIGS. 55, 56, and 57 show the implant of FIGS. 54A-54G implanted within the body.

FIGS. 38A-58F depict another embodiment of the SI joint implant system 100. The embodiment of FIGS. 58A-58F may include any of the same or similar features or functions as any of the other embodiments described herein and vice versa.

FIGS. 58A-58F depict another embodiment of an implant system 100 having a primary implant 102, a secondary implant 104, and a fastener or attachment mechanism 110. In certain embodiments, the primary implant 102 of FIGS. 58A-58F can be implanted prior to the secondary implant 104. In the embodiment of FIGS. 58A-58F, the secondary implant includes a body or anchor ring 124. One or more anchors 106 can extend from the anchor ring 124. In certain embodiments, the one or more anchors 106 can be coupled to the anchor ring 124 by one or more arms 146.

The primary implant 102 can include a proximal head or proximal end 148. As shown in FIGS. 58A-58F, in some embodiments, the proximal head or end 148 is an unthreaded portion of the primary implant 102. The ring 124 can define an opening 126 shaped, sized, or otherwise configured to receive the proximal end 148 of the primary implant 102. In certain embodiments, the ring 124 can be advanced over the proximal end 148 of the primary implant, for example, in a proximal to distal direction.

As shown in FIGS. 58A-58F, the primary implant 102 can include a threaded section 150, which may be below the proximal end 148 in some embodiments. In certain embodiments, the primary implant 102 can include a groove cut or recess 152 within the threaded section 150. The groove cut or recess 152 can be a mating feature configured to receive a complementary mating feature, such as a protrusion or tab, of an implant driver or inserter for advancing the primary implant 102 to a desired depth.

The fastener or attachment mechanism 110 can secure the secondary implant 104 to the primary implant 102. In certain embodiments, the attachment mechanism 110 can be in the form of a threaded fastener that can mate with corresponding interior threads within the primary implant 102. As shown in FIGS. 58A-58F, a head of the threaded fastener 110 can have a larger diameter than the opening 126 of the anchor ring 124. The fastener 110 can be coupled with the primary implant 102 after the anchor ring 124 of the secondary implant 104 is positioned over the proximal end 148 of the primary implant 102 to secure the secondary implant 104 to the primary implant 102. For example, the head of the threaded fastener 110 can prevent distal to proximal movement of the secondary implant 104 relative to the primary implant 102.

In the absence of the attachment mechanism 110, the secondary implant 104 can couple to the primary implant 102 so that it can be rotated or oriented at any angle, for example, about longitudinal axis of the primary implant. As described with respect to other embodiments herein, the primary implant 102 can be countersunk within the SI joint. After the primary implant 102 is countersunk, the secondary implant 104 can be rotated or oriented at any angle, for example, about the longitudinal axis of the primary implant 102, to maximize contact between the anchors 106 and the ilium and sacrum for greater bone purchase.

The primary implant 102 and secondary implant 104 can be mated through a male/female design or any other design that allows the primary implant and secondary implant to move independently until secured in place by the attachment mechanism 110, which may be a fastener, such as a screw, or any other suitable locking means. As shown in the embodiment of FIGS. 58A-58F, the primary implant 102 and secondary implant 104 can rotate freely relative to one another until secured together.

FIGS. 59A-59D depict another embodiment of the SI joint implant system 100. The embodiment of FIGS. 59A-59D may include any of the same or similar features or functions as any of the other embodiments described herein and vice versa.

FIGS. 59A-D depict another embodiment of the implant system 100 in which the secondary implant 104 can rotate relative to the primary implant when coupled thereto.

FIGS. 60, 61, and 62 show the embodiment of the implant system 100 of FIGS. 59A-59D implanted within the body with the secondary implant 104 rotated at different positions relative to the primary implant 102.

FIGS. 63A-63B depict another embodiment of the SI joint implant system 100. The embodiment of FIGS. 63A-63B may include any of the same or similar features or functions as any of the other embodiments described herein and vice versa.

In certain embodiments, the secondary implant 104 can be angled or tapered from a distal end to the proximal end by an angle θ so that when the secondary implant is driven into the sacrum and ilium, it compresses the bone and in turn the SI joint. The angle θ can range from 1° to 20° depending on the amount of compression desired. For example, an embodiment of an implant 104 having a 6° taper is shown in FIGS. 63A and 63B. A width $X_1$ at the proximal end of the implant 104 can be between 19 mm and 23 mm, between 20 mm and 22 mm, about 19 mm, about 20 mm, about 21 mm, about 22 mm, about 23 mm, or any other suitable width. A width $X_2$ at the distal end of the implant 104 can be between 21.5 mm and 25.5 mm, between 22.5 mm and 24.5 mm, about 21.5 mm, about 22.5 mm, about 23.5 mm, about 24.5 mm, about 25.5 mm, or any other suitable width. In the embodiment of FIGS. 63A and 63B, a width difference between the proximal end and the distal end is 2.5 mm, which can provide about 1.25 mm of compression per side after fully inserted. The distal portion of the secondary implant 104 can be beveled or tapered to help guide the secondary implant 104. The distal portion can guide the secondary implant 104 away from the SI joint or towards the SI joint to allow for compression of bone on the primary implant 102.

FIGS. 70A-70C depict another embodiment of the SI joint implant system 100. The embodiment of FIGS. 70A-70C may include any of the same or similar features or functions as any of the other embodiments described herein and vice versa.

FIGS. 70A-70C depict another embodiment of the implant system 100 in which a primary implant portion and secondary implant portion are formed (for example, integrally formed) as a single-piece. Anchors are attached to a center-piece. The anchors can resist compression and distraction forces once implanted. As shown, in some embodiments, the center-piece does not include any threads. The implant system 100 includes barbs, which can prevent back out after the implant system 100 is implanted. The implant system 100 can be malleted into position within the SI joint. Due to the single-piece design, both the primary implant portion and secondary implant portion are implanted at the same time. The embodiment of FIGS. 70A-70C may require less instrumentation and implant components and reduce time in the operating room.

FIGS. 71A-71B depict another embodiment of the SI joint implant system 100. The embodiment of FIGS. 71A-71B may include any of the same or similar features or functions as any of the other embodiments described herein and vice versa.

FIGS. 71A-71B depict another embodiment of the implant system 100. The implant system 100 of FIGS. 71A-71B is similar to the implant system 100 of FIGS. 70A-70C, but is greater in length between a proximal end and a distal end.

FIGS. 72A-72F depict another embodiment of the SI joint implant system 100. The embodiment of FIGS. 72A-72F may include any of the same or similar features or functions as any of the other embodiments described herein and vice versa.

FIGS. 72A-72F depict another embodiment of the implant system 100 having a primary implant 102 and a secondary implant 104. The primary implant 102 includes engagement features 103 in the form of threads extending proximally from a distal end 105 towards a head 130 of the primary implant 102. The primary implant 102 also includes a smooth or threadless shank section of the shank 166 positioned proximally of the threads. The threads can extend between the smooth shank section and the distal end 105. In certain embodiments, a primary implant 102 having threads along the entire length of the primary implant 102 can lead to the threads applying counterforces to threads of the secondary implant 104, which may pull or otherwise dislodge the anchors out of the bone. A smooth or threadless shank section near the head 130 of the primary implant proximal to the threads can prevent or reduce the counterforces that can cause dislodgement of the anchors 106. For example, as the primary implant 102 is threaded down into the SI joint, the secondary implant 104 can be relieved from counter forces as it comes off the thread of the primary implant. As the primary implant 102 continues to be threaded within the SI joint, it can pull the secondary implant 104 which can pull the anchors 106 tight into the ilium and sacrum. In other embodiments, the engagement features 103 (e.g., threads) may extend over an entire length of the shank 166.

In certain embodiments, the implant system 100 can be implanted using a posterior method. In certain embodiments, the implant system 100 can be implanted through an incision made directly over the posterior SI joint from the PIIS (Posterior Inferior Iliac Spine) to the PSIS (Posterior Superior Iliac Spine). In certain embodiments, the incision may be made over the midline of the sacrum. In certain embodiments, the incision can allow access to each joint through one incision in a less invasive approach. In certain embodiments, the tissue is mobilized from the midline incision to access the SI joint for unilateral (accessing one SI joint) or bilateral (accessing both SI joints) implantation. This can help gain access to the SI joints through the midline incision. In certain embodiments, this method can prevent the need to make two separate incisions over each SI joint. In certain embodiments, the incision may be made directly over the SI joint on each side or both sides.

In certain embodiments, after the incision is made, a guidewire or rod (see FIG. 13) can be placed posteriorly into the SI joint. In certain embodiments, the guidewire or rod can be placed in the joint line between the first and second sacral foramens. This can ensure that when drilling and implantation occurs the foramen are intact and nerve injury is avoided. Positioning of the guidewire or rod in the joint line between the first and second sacral foramens can also facilitate placement of the implant system to sit flush or countersunk within the SI joint. If the implant system is placed higher, it may not sit flush or countersunk because of the PSIS prominence. Lower placement can increase the risk of nerve injury due to neighboring sciatic notch harboring nerves.

In certain embodiments, if a guidewire or rod isn't used, a more robust instrument such as a joint locator, paddle, spatula or other instrument may be used to enter the SI joint. In certain embodiments, a series of sequential dilation may be used over the guidewire or joint locator, paddle, spatula, etc. The dilators may be circular, oval, square, rectangular or any other suitable three-dimensional shape to retract tissue for drilling or implanting. In certain embodiments, after dilation occurs, a drill guide may be placed within the SI joint. The drill guide may have two tangs or more tangs to prevent migration of the drill guide. The tangs may enter the SI joint and/or grip the bone on the sacrum and ilium. After the drill guide is docked in the desired location, a drill bit or broach may be used to create a defect that matches the SI fusion implant 100. A drill may be used freehand or placed over a guidewire (cannulated drill bit) to guide the drill bit to the desired location. After drilling has occurred the drill bit may be removed. In certain embodiments, a wisp or tissue collector may be inserted down the drill guide to remove excess cartilage or other tissue that may contain chondrocytes which compete with osteocytes for bone formation. The wisp or tissue collector may be re-usable or disposable. Once the joint defect has been created the implant may be inserted.

In certain embodiments, a driver or inserter can be used to insert the primary implant 102 into the pre-determined size void created. In certain embodiments, the primary implant 102 may be countersunk within the joint for better fixation and to pack bone graft over the implant 102 or may sit flush, for example, if desired due to shallow patient anatomy preventing the countersinking method. In certain embodiments, primary implant 102 placed within the joint can resist shearing forces of the sacrum. In certain embodiments, after the primary implant 102 is placed within the SI joint, the secondary implant 104 can be anchored to the top of the primary implant 102 or otherwise coupled or positioned against the top of the primary implant 102. The secondary implant 104 can be placed in both the ilium and sacrum and can act as a tension band. The secondary implant 104 can resist forces that compress and distract the sacroiliac joint. In combination, the primary implant 102 and secondary implant 104 can act as one system to achieve multiple points of fixation and resist multiple forces. The primary and secondary implants can be placed in one step or two steps. If a system 100 having a screw or screw-like primary implant 102 (e.g., an implant having threads) and a separate secondary implant 104 is used, they can be placed in two separate steps. For example, the primary implant 102 can first be screwed into the SI joint, and then the secondary implant 104 can be secured to the primary implant 102. If another shape is used in the primary implant 102 (for example, an implant having other engagement features 103, such as fins, barbs, teeth, or blades) the implant may be placed in one step in some embodiments, for example as shown respect to FIGS. 33A-33D. In certain embodiments, a tool or instrument may be used to align the secondary implant 104 to the primary implant 102 when inside the patient.

Figure 12A:
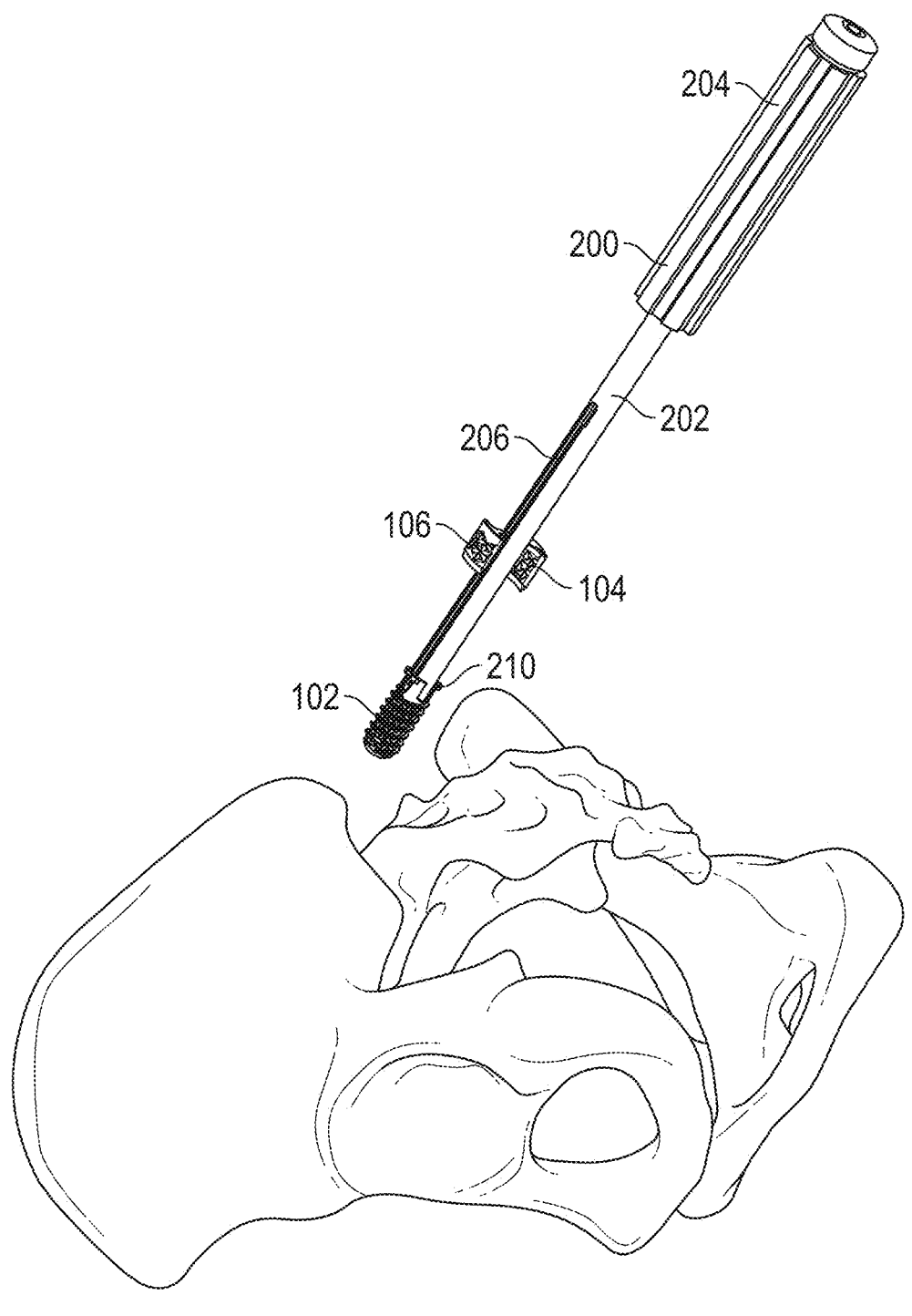
FIG. 12A illustrates a perspective view showing an embodiment of a driver coupled with an implant system by the SI joint.

FIG. 12A depicts an embodiment of a driver or inserter 200 that can be used in a method of implanting the implant system 100, as described above. The inserter 200 can include a shaft 202. The inserter 200 can include a handle 204 connected to the shaft 202. The inserter 200 can have one or more slots 206 that extend at least partially down the shaft 202. For example, the slots 206 can extend proximally from a distal portion or distal end 203 of the shaft 202 at least partially towards handle 204.

In certain embodiments, the shaft 202 can engage the primary implant 102 with a threaded rod 212 (as shown, for example, in FIG. 13) that can extend through the center of the shaft 202, for example through a lumen of the shaft 202, and enter the center of primary implant 102. The threaded rod 212 can include proximal threads 214 configured to mate with complementary internal threads within the lumen of the shaft 202. The threaded rod 212 can include distal threads 216 configured to mate with internal threads of the primary implant 102. The inserter 200 has a mating portion 210 at the distal portion or distal end 203 that engages the primary implant 102 to facilitate advancement of the primary implant 102 in the SI joint using the inserter 200. The threaded rod 212 can keep the primary implant 102 and inserter 200 held together during advancement of the primary implant 102 using the inserter 200.

The slots 206 can allow for the anchors 106 to extend laterally beyond the shaft 202 so that the secondary implant 104 can be positioned within a lumen of the shaft 202 above primary implant 102. After the primary implant 102 is coupled to the mating portion 210 of the inserter 200, the secondary implant 104 may be advanced along the slots 206 to couple with or otherwise contact the primary implant 102. In certain embodiments, the slots 206 may be shaped and/or positioned to align the secondary implant 104 with the primary implant 102.

Figure 12B:
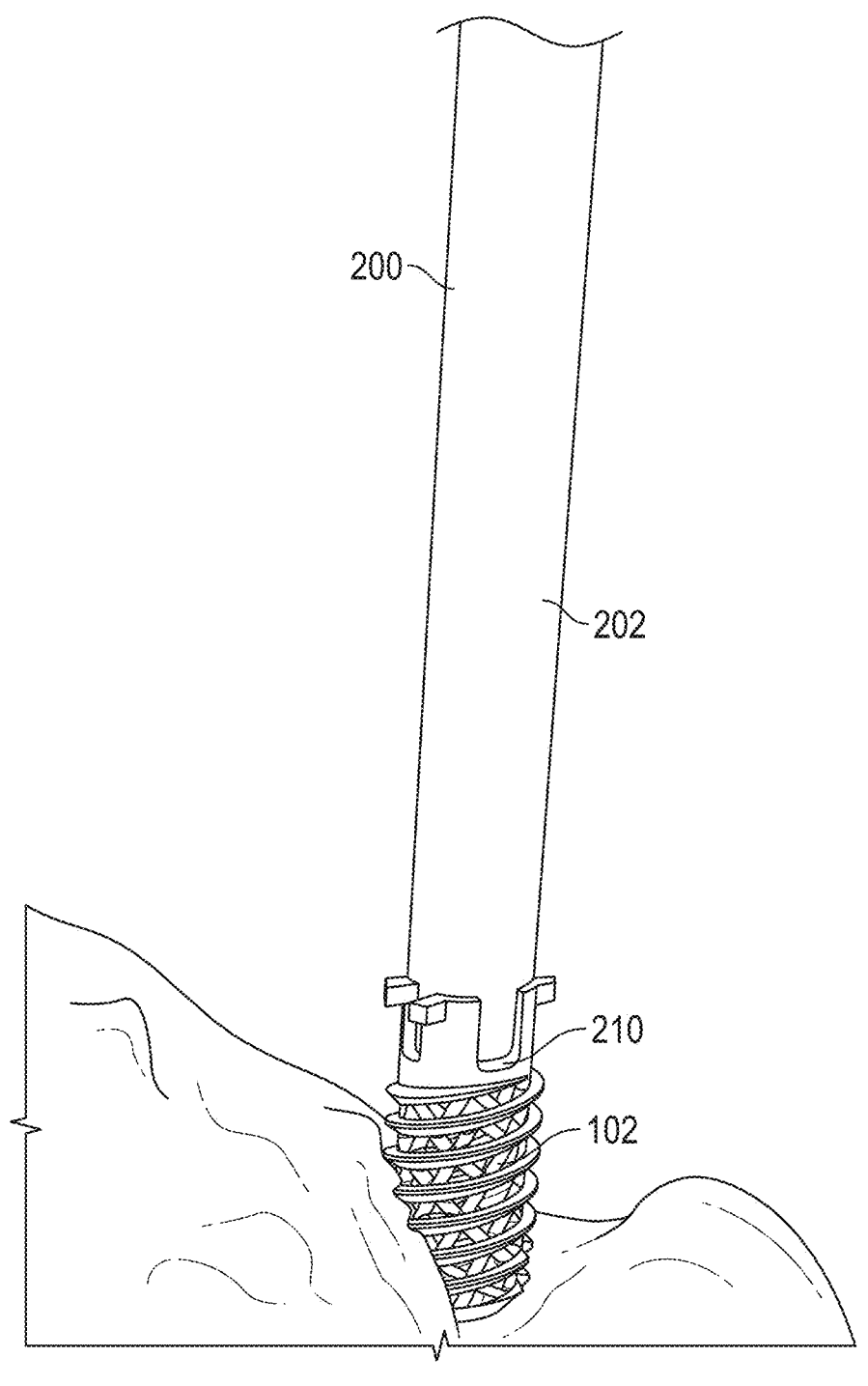
FIG. 12B illustrates a perspective view showing an embodiment of a driver coupled with an implant system within the SI joint.
Figure 12C:
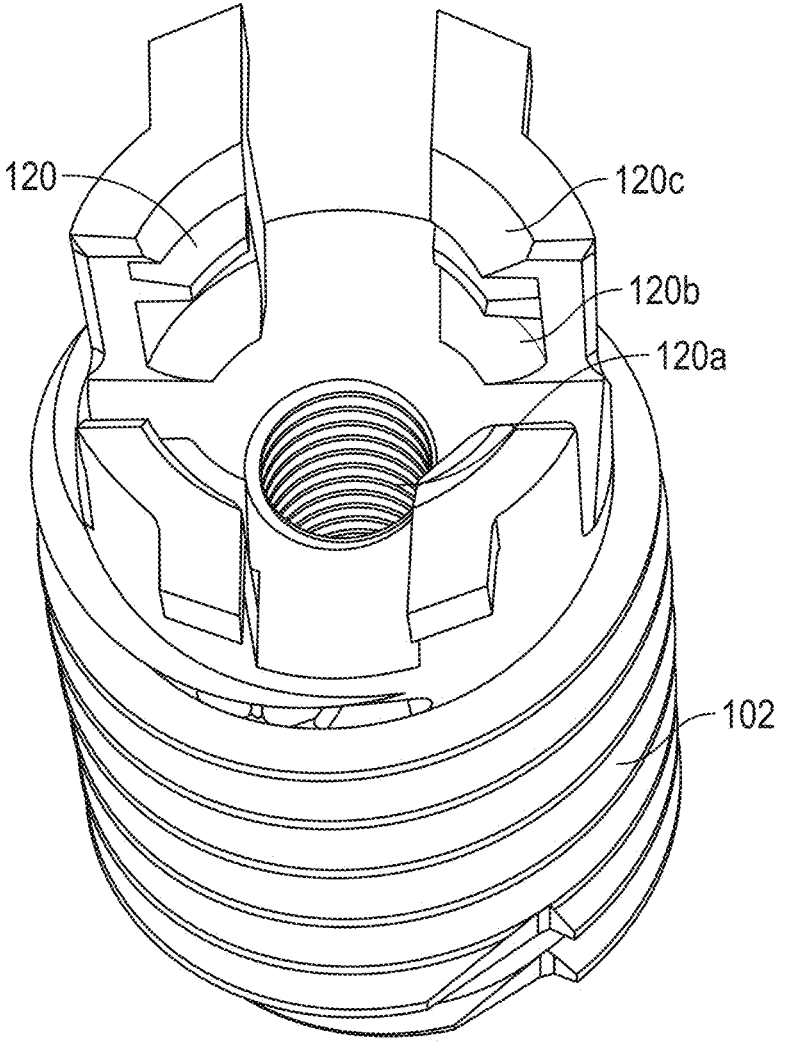
FIG. 12C illustrates a perspective view of an embodiment of the implant as pictured in FIG. 12A.
Figure 12D:
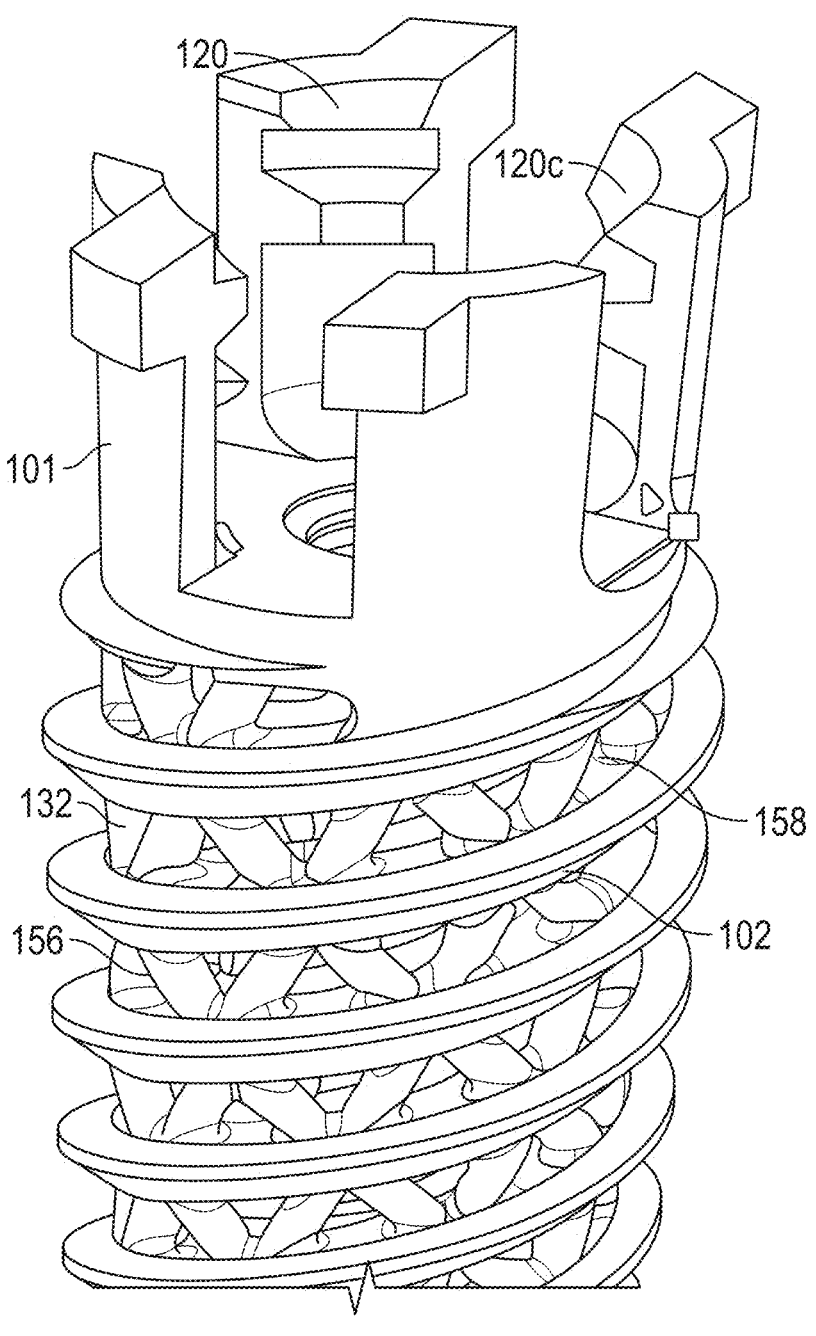
FIG. 12D illustrates a perspective view of an embodiment of the implant as pictured in FIG. 12A.

FIG. 12B illustrates shows the connection between the mating portion 210 and an embodiment of the primary implant 102. FIGS. 12C and 12D show the primary implant 102 of FIG. 12B. The embodiment of the primary implant 102 of FIGS. 12A-12D may include any of the same or similar features or functions as any of the other embodiments described herein and vice versa.

In certain embodiments, the primary implant 102 can include one or more engagement features 120. The engagement features 120 can include one or more grooves, rows, slots, etc. In certain embodiments, the inserter 200 can engage one or more of the engagement features 120 so that the inserter 200 stays engaged to the primary implant 102 during advancement of the primary implant into the SI joint.

In certain embodiments, the secondary implant 104 can be configured to engage one or more of the engagement features 120 to couple with the primary implant 102. For example, the secondary implant 104 may include corresponding engagement features that engagement features 120.

As described herein, n certain embodiments, the secondary implant 104 can be received by the primary implant 102, and an attachment mechanism 110 can couple the primary implant 102 and the secondary implant 104. In certain embodiments, the attachment mechanism 110 can engage one or more of the engagement features 120. For example, in certain embodiments, the primary implant 102 can include engagement features 120a for engaging the threaded rod 212. In certain embodiments, the primary implant 102 can include engagement features 120b for engaging the mating portion 210. In certain embodiments, the primary implant can include engagement features 120c for engaging the attachment mechanism 110.

In certain embodiments in which a threaded rod 212 is used, the threaded rod 212 can be removed from the primary implant 102 and inserter 200 to disengage the inserter 200 from the primary implant 102.

Figure 13:
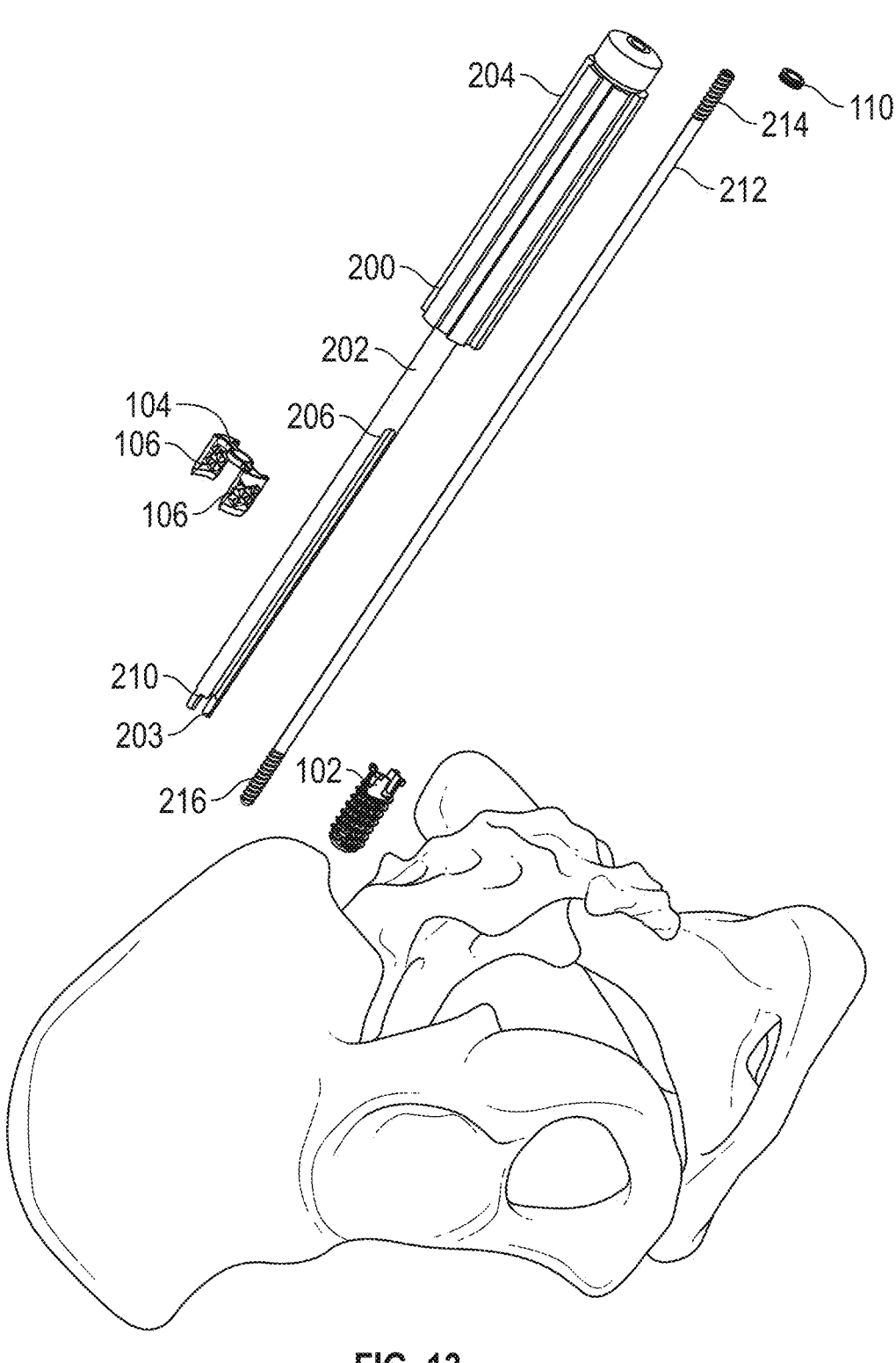
FIG. 13 illustrates a perspective view showing an embodiment of a driver, rod, and implant of an implant system for an SI joint.

FIG. 13 is an exploded view that shows the inserter 200, the threaded rod 212, the primary implant 102, the secondary implant 104, and the attachment mechanism 110.

Figure 14:
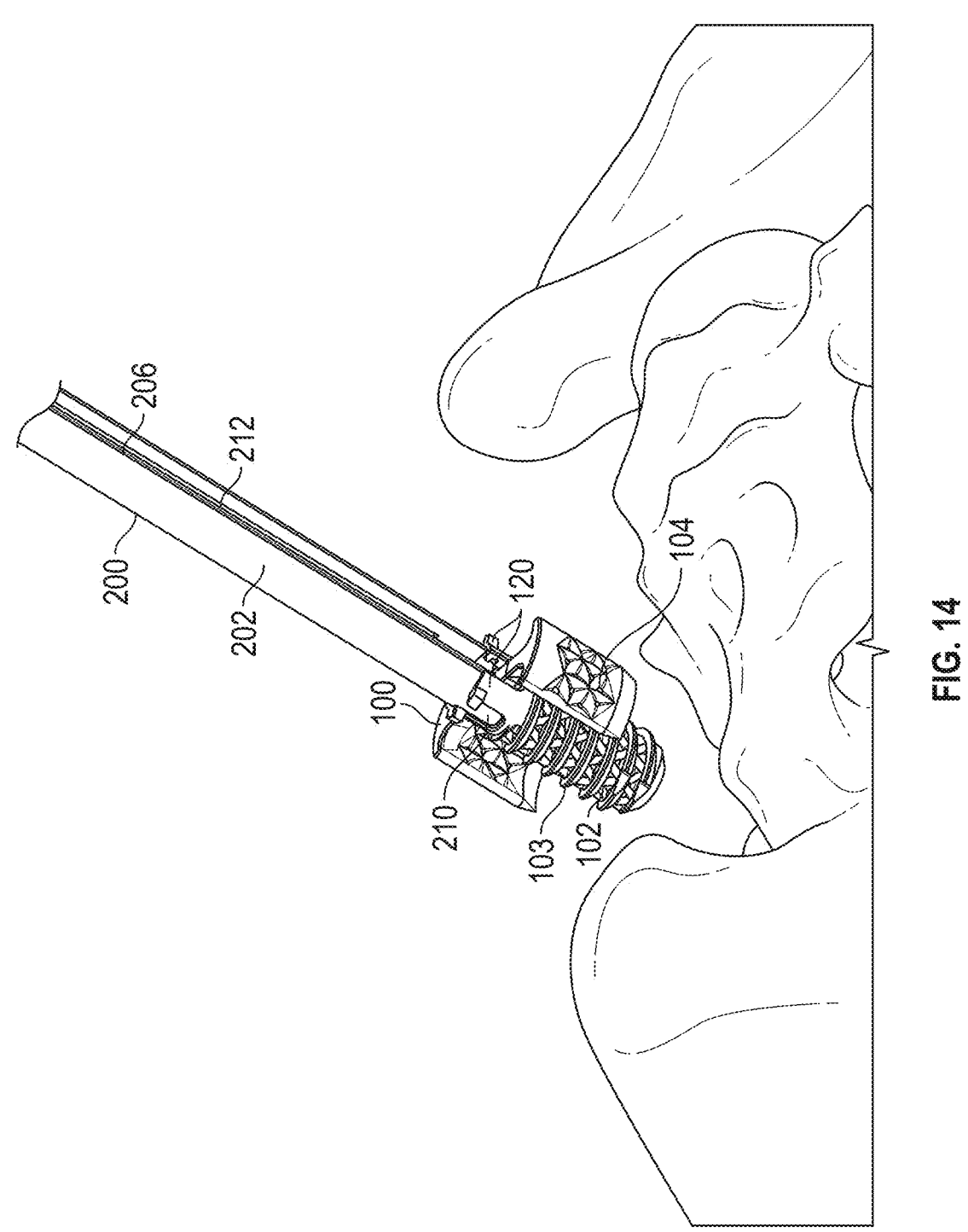
FIG. 14 illustrates a perspective view showing an embodiment of a driver, rod, and implant system by the SI joint.

FIG. 14 shows the primary implant 102, the secondary implant 104 and the inserter 200 held together although not inserted into bone.

Figure 27:
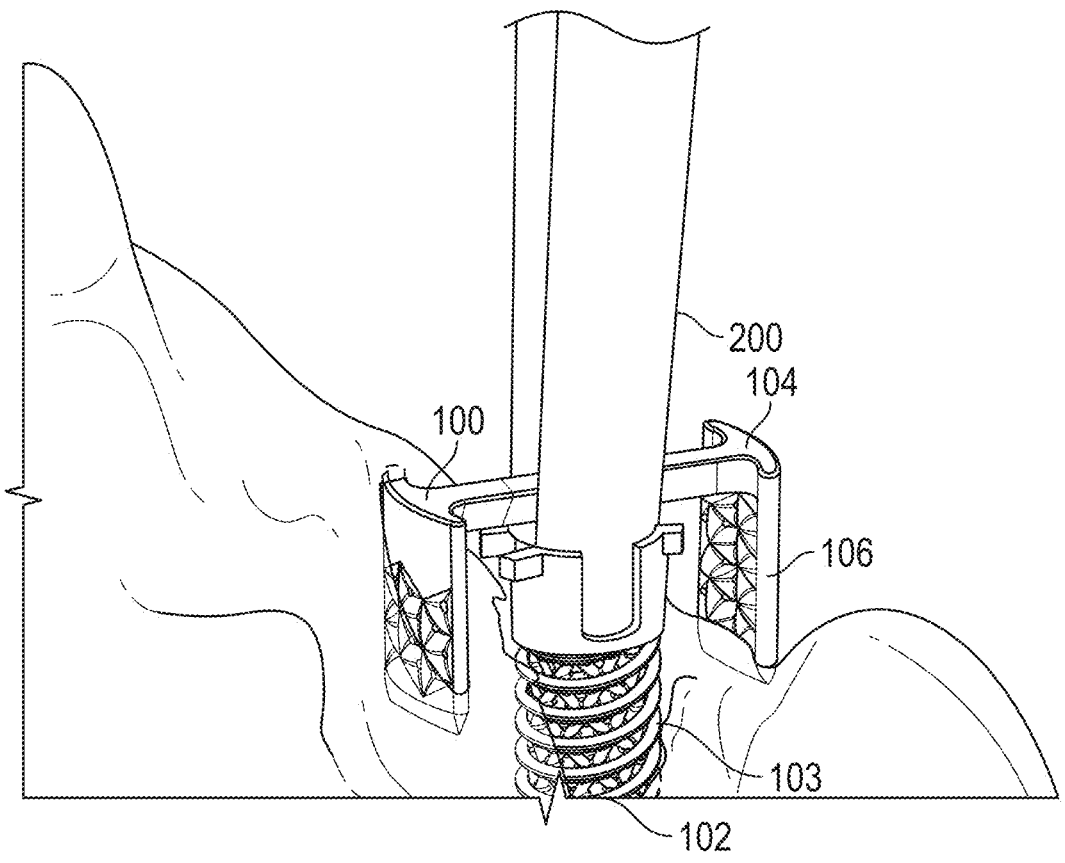
FIG. 27 illustrates a perspective view of an embodiment of the implant system inserted into the SI joint.
Figure 28:
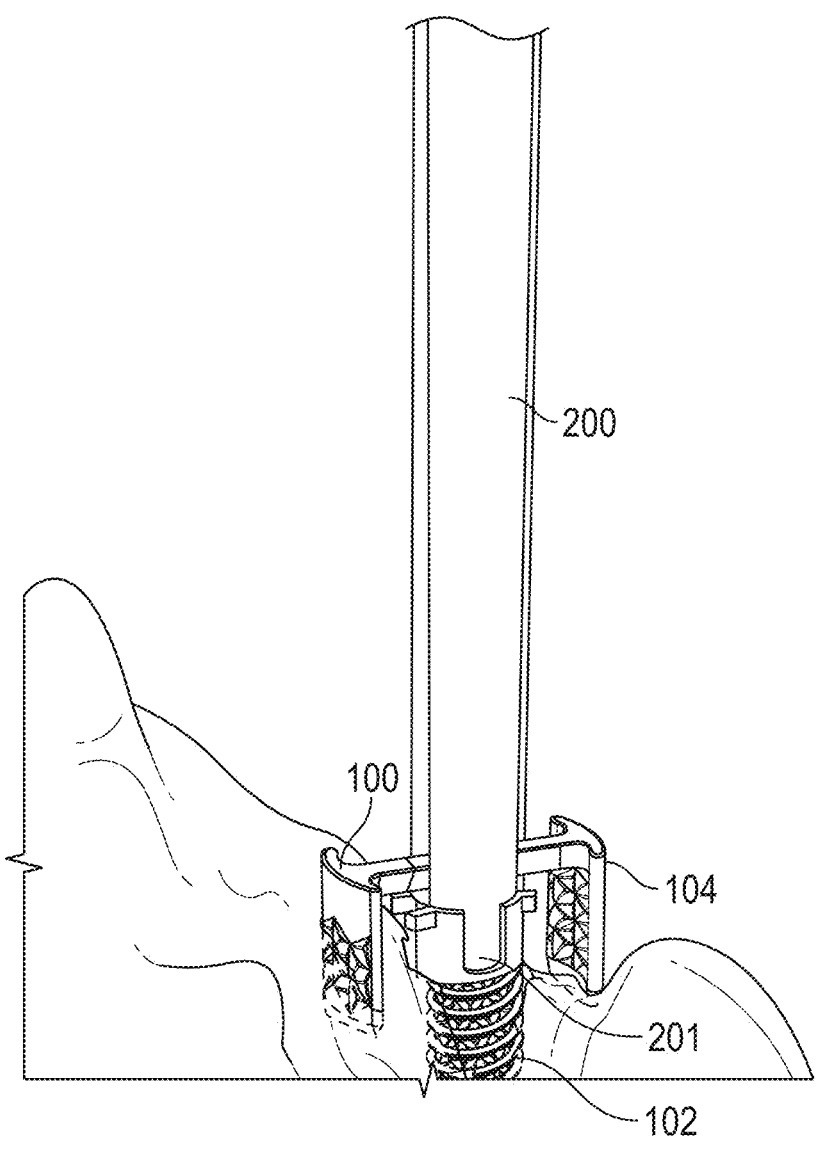
FIG. 28 illustrates a perspective view of an embodiment of the implant system inserted into the SI joint.

FIGS. 27 and 28 show the primary implant 102 and secondary implant 104 imbedded in bone together with the inserter 200 coupled to the implants. The primary implant 102 and secondary implant 104 may be proud of the SI joint, as shown in FIGS. 27 and 28, or may be countersunk to allow bone to grow over the implants.

Figure 15:
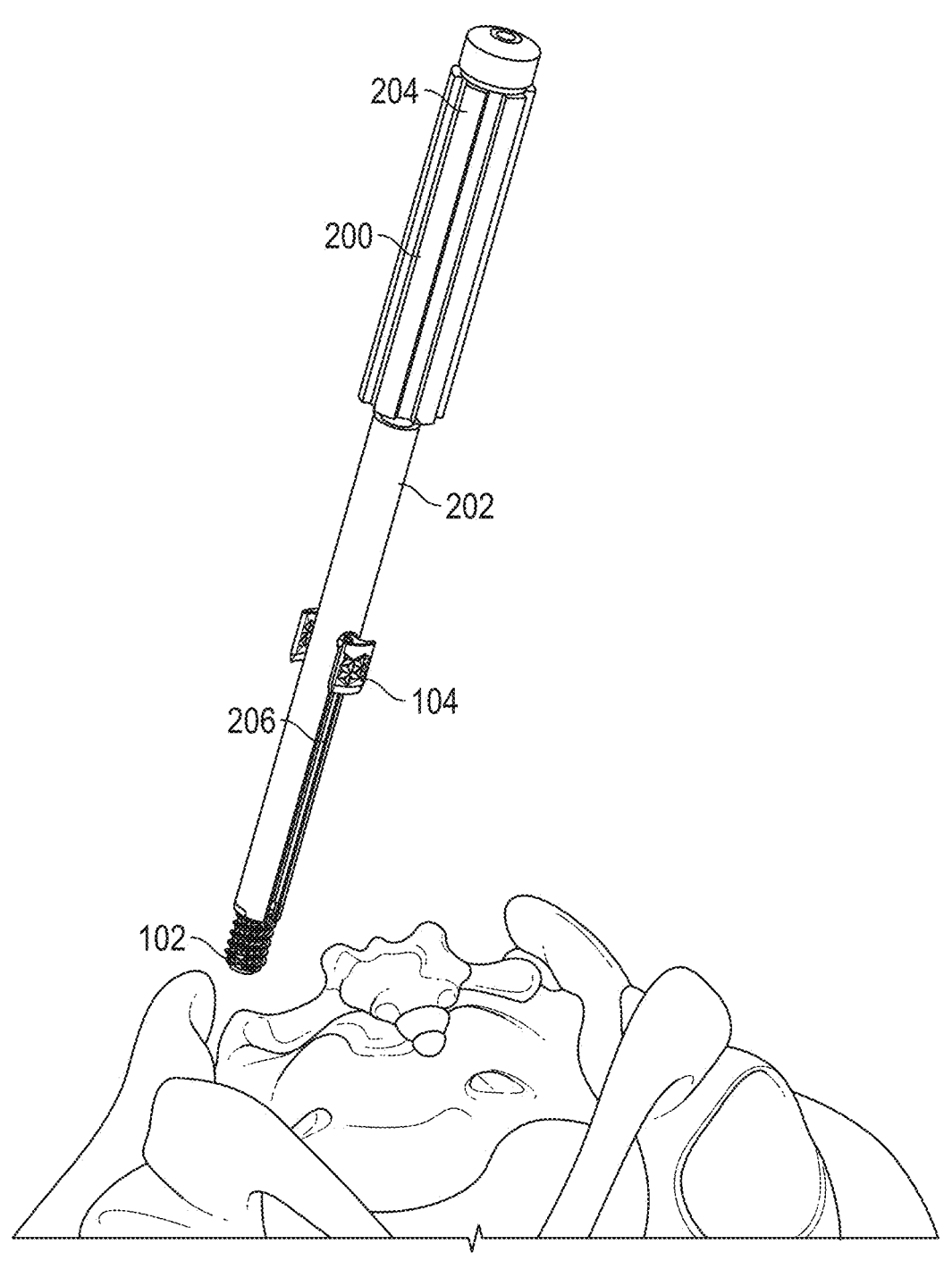
FIG. 15 illustrates a perspective view showing an embodiment of a driver coupled with an implant system for insertion into the SI joint.
Figure 16:
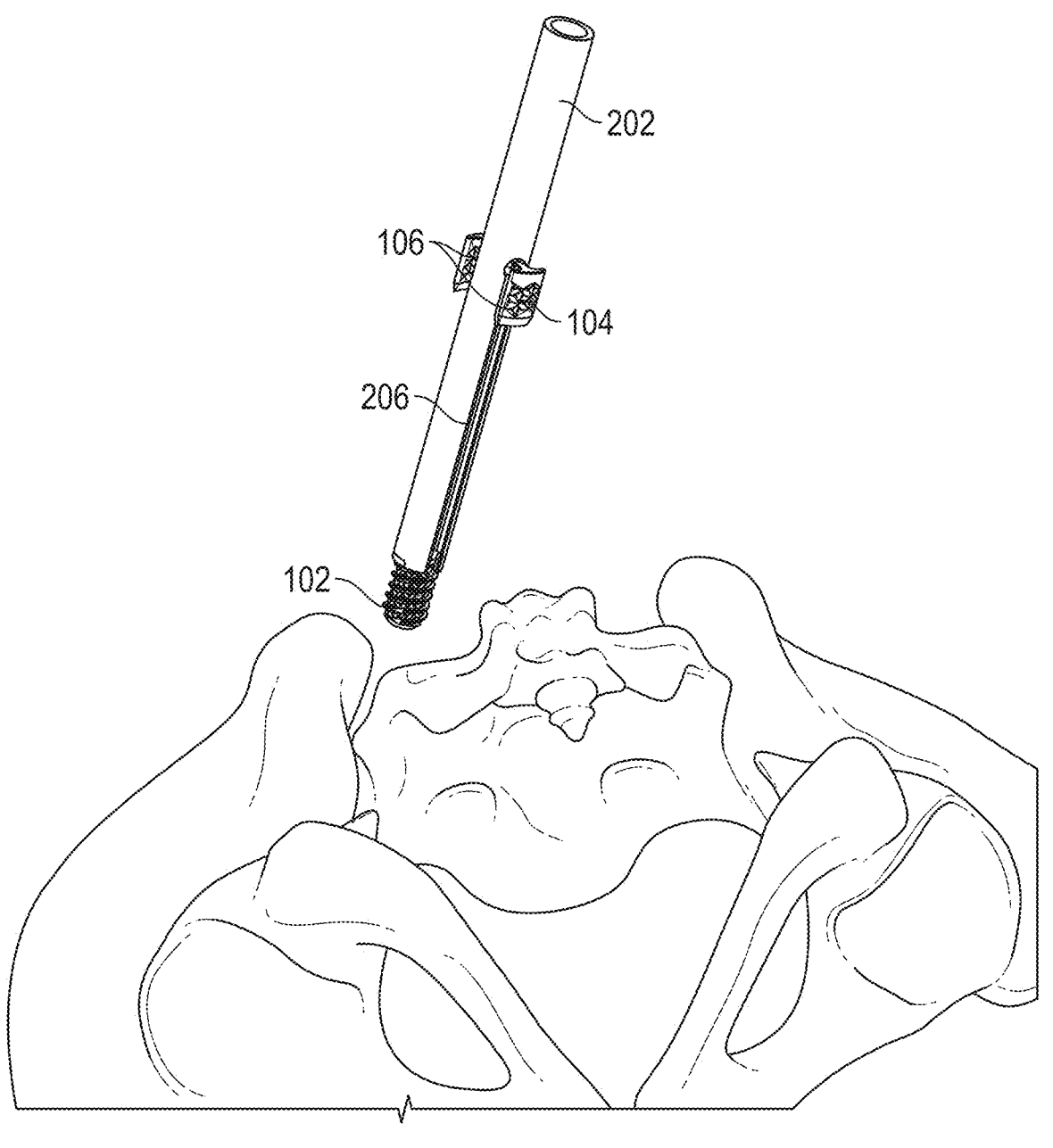
FIG. 16 illustrates a perspective view of another embodiment of the implant system for insertion into the SI joint.
Figure 17:
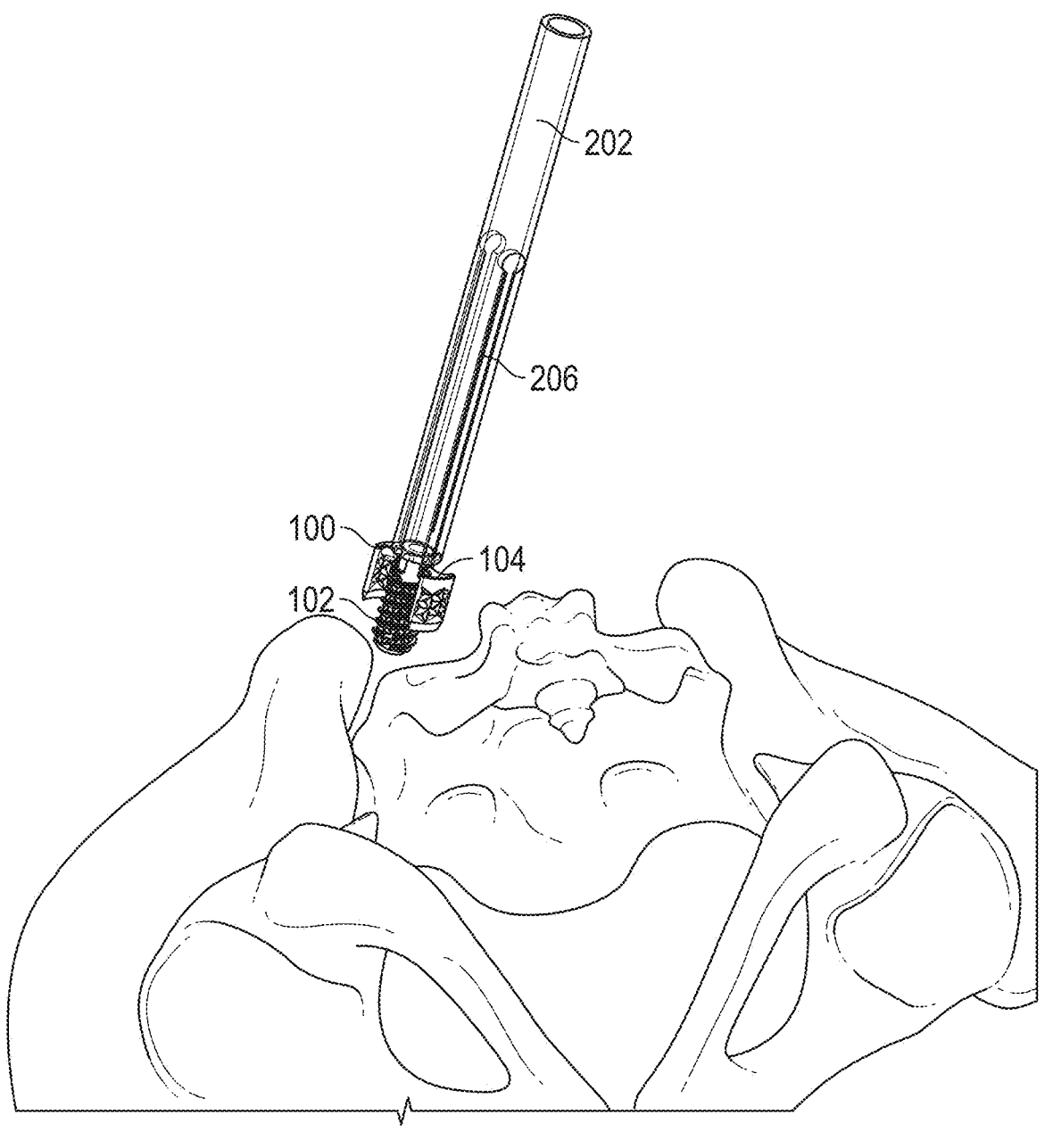
FIG. 17 illustrates a perspective view of another embodiment of the implant system for insertion into the SI joint.
Figures 18, 19:
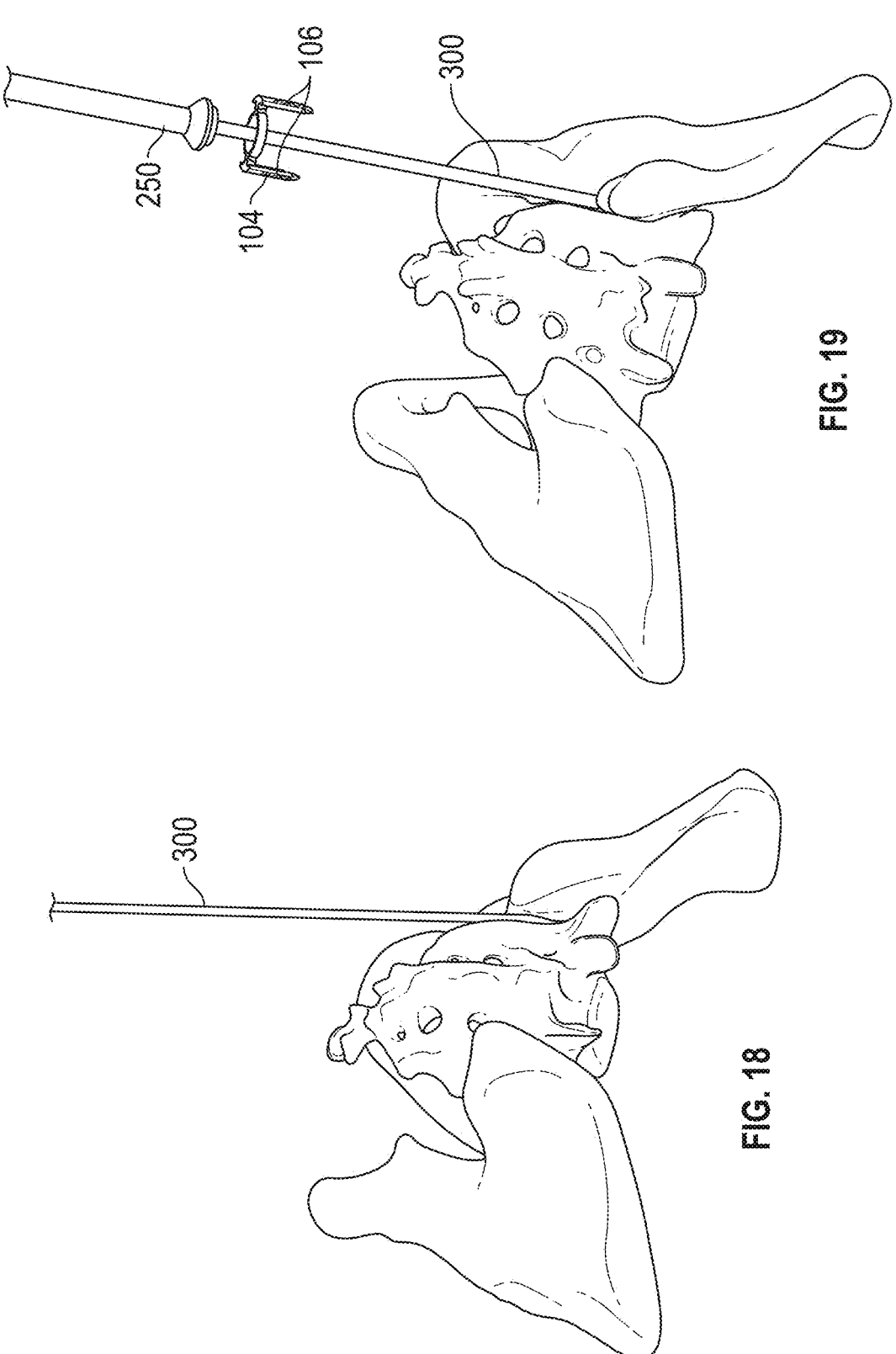
FIG. 18 illustrates a perspective view of another embodiment using a guidewire in the implant system for insertion into the SI joint.
FIG. 19 illustrates a perspective view of another embodiment using a guidewire and driver in the implant system for insertion into the SI joint.
Figure 20:
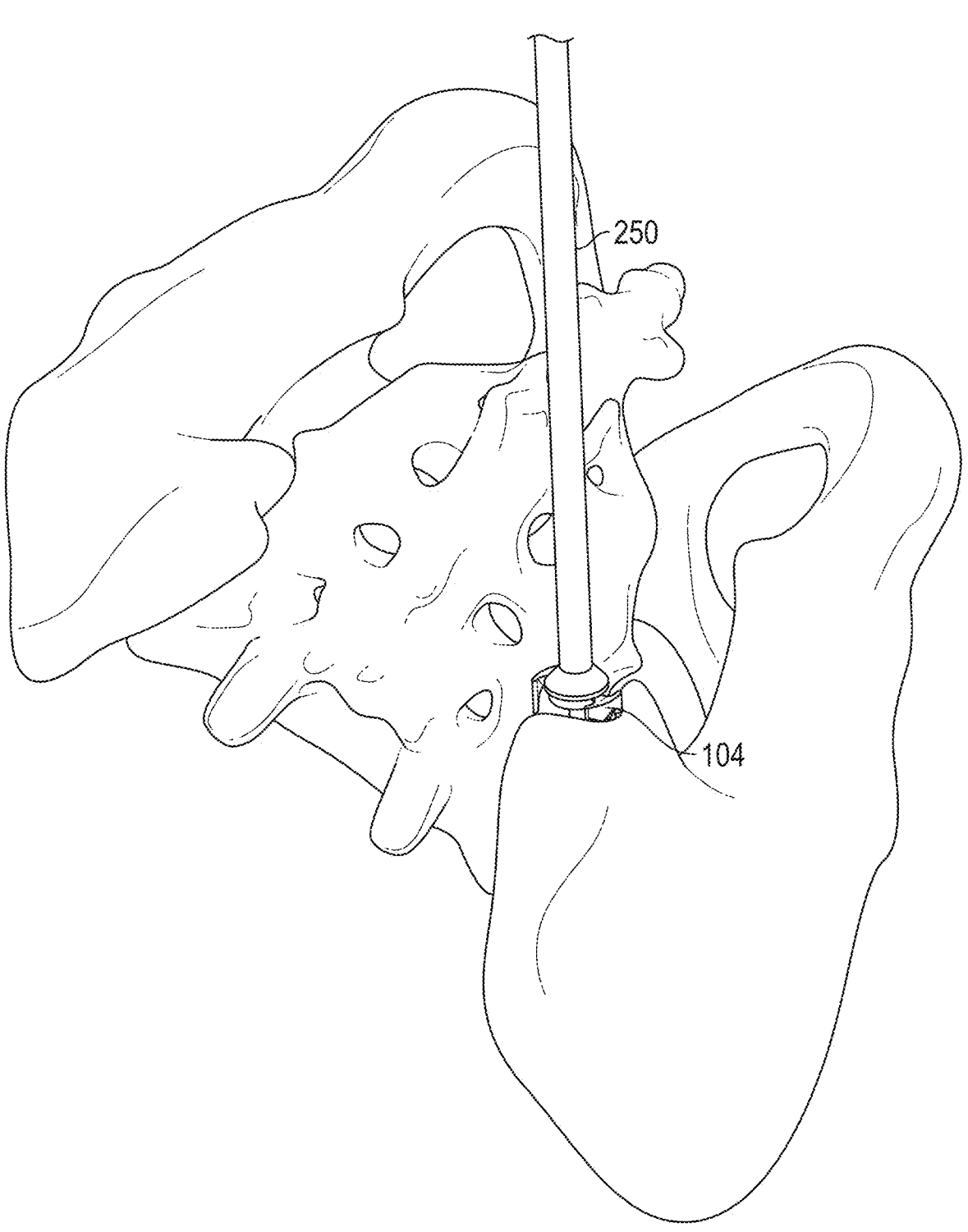
FIG. 20 illustrates a perspective view of an embodiment of the implant system using a driver and guidewire with an implant in the SI joint.
Figure 21:
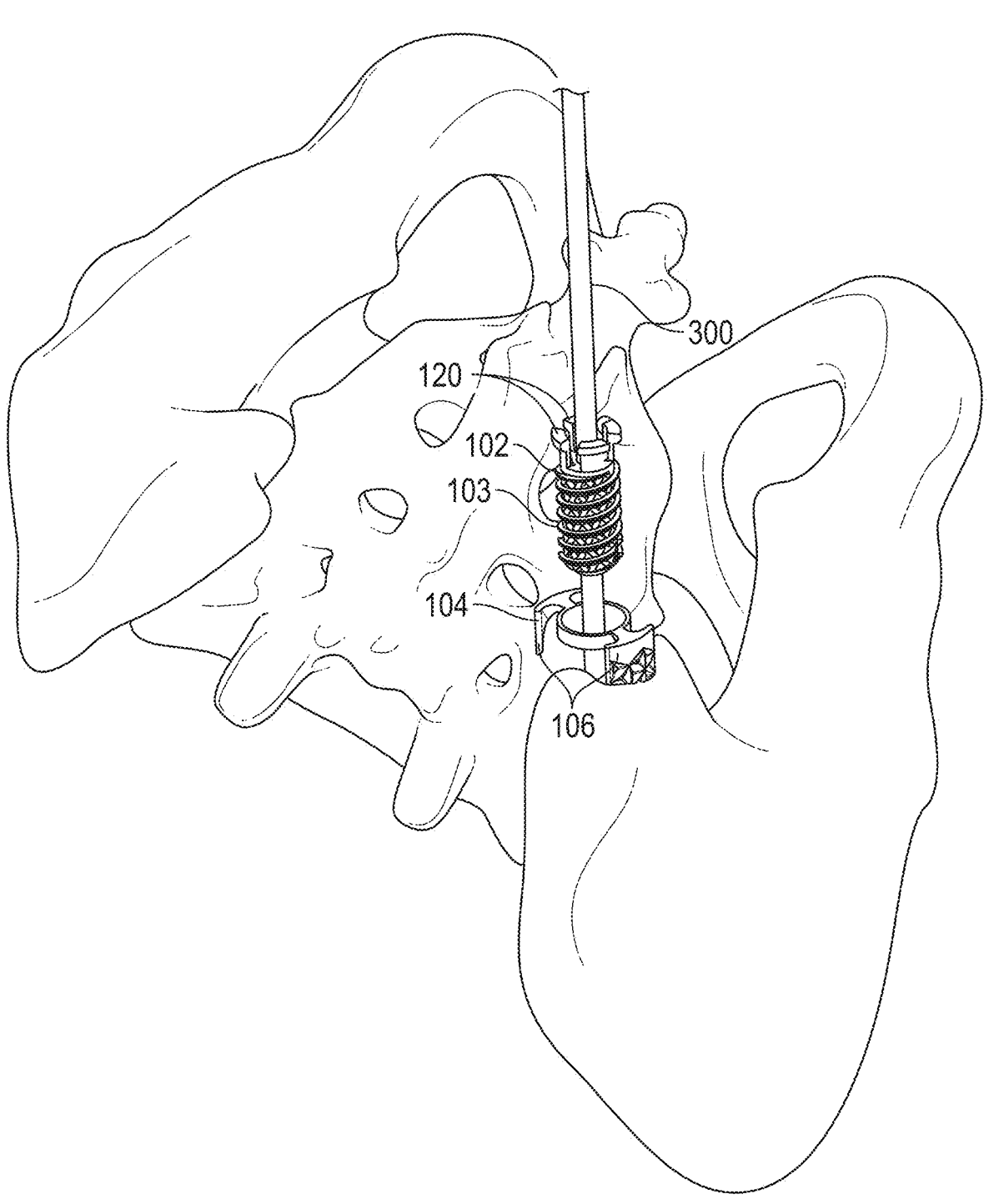
FIG. 21 illustrates a perspective view of an embodiment of the implant system inserted into the SI joint.
Figure 22:
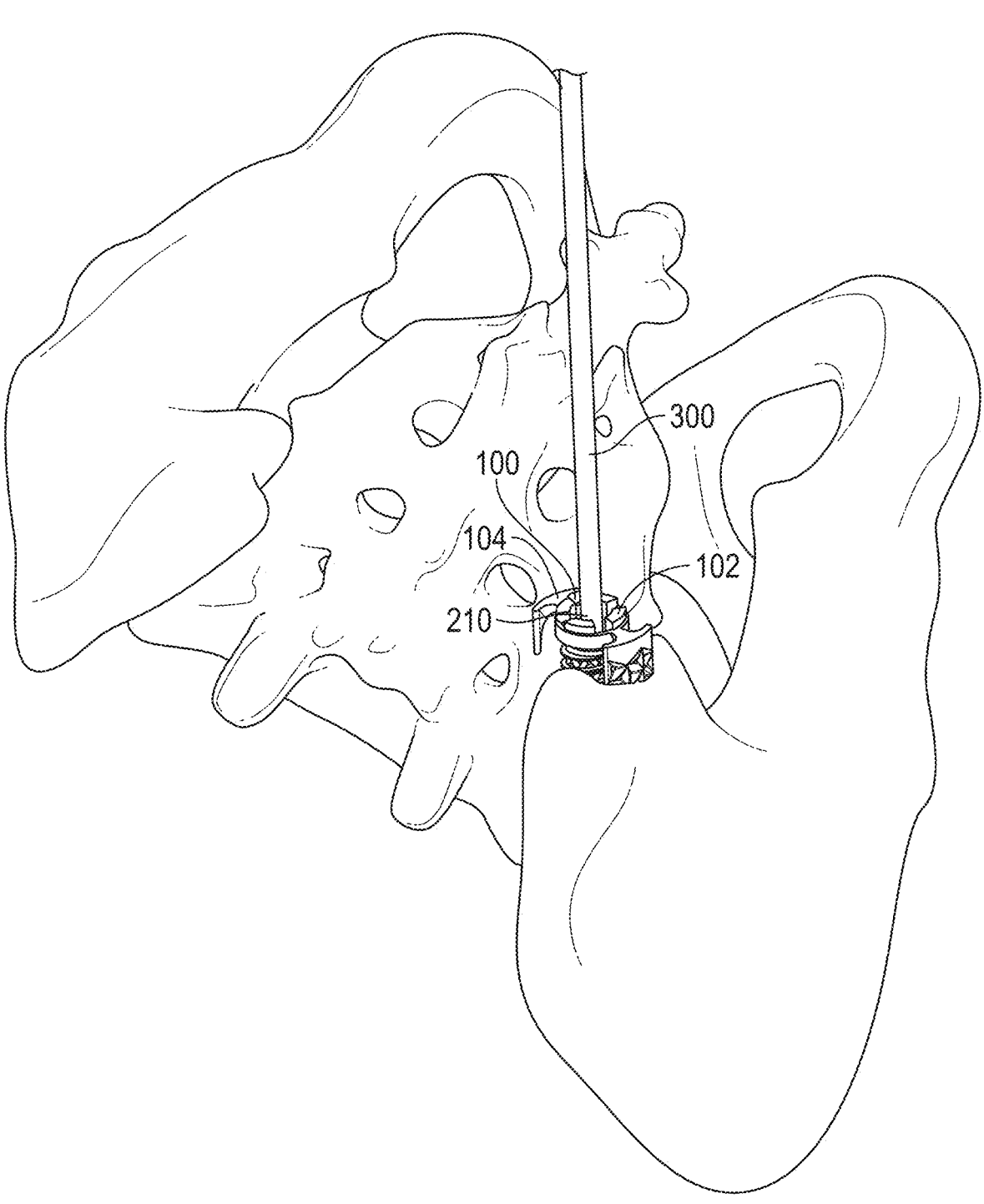
FIG. 22 illustrates a perspective view of an embodiment of the implant system during insertion into the SI joint.
Figure 23:
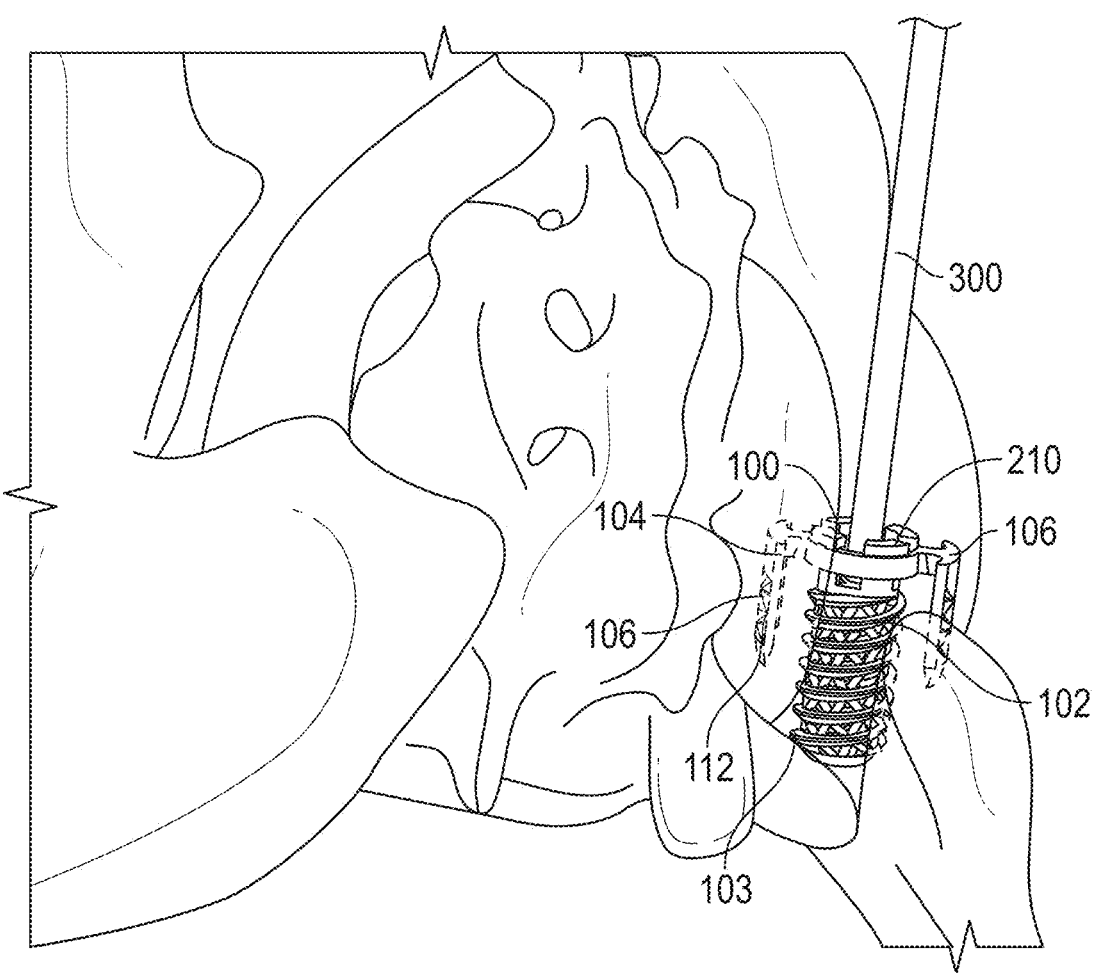
FIG. 23 illustrates a perspective view of an embodiment of the implant system during insertion into the SI joint.
Figure 24:
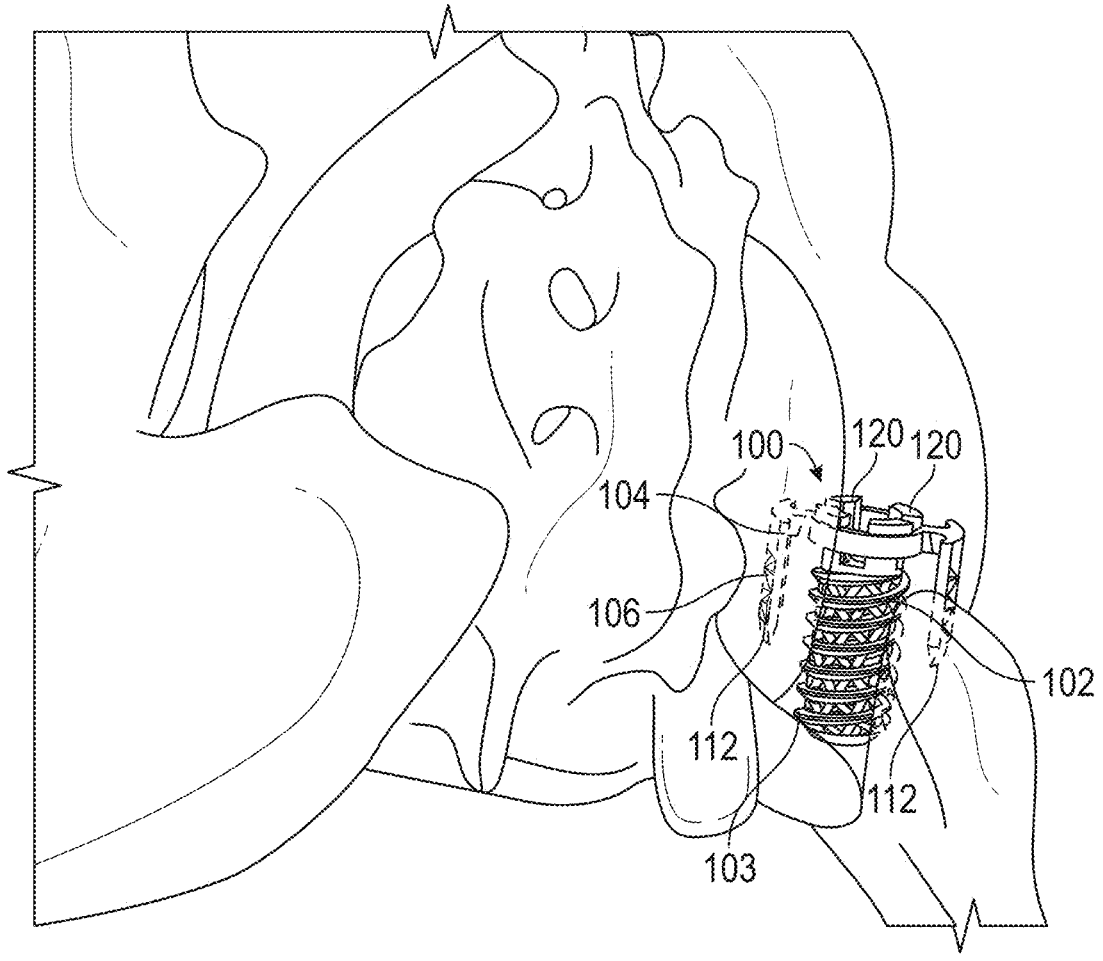
FIG. 24 illustrates a perspective view of an embodiment of the implant in the SI joint.

FIGS. 15, 16, and 17, show another version of an inserter 200 that is connected to the primary implant like a tower mechanism. The tower mechanism clips on or cinches onto the primary implant 102. The secondary implant 104 can then be driven into the bone. The tower mechanism can be released once the primary implant 102 and secondary implant 104 are inserted. A shaft 202 can grip an outer head of the primary implant 102 while a threaded rod, such as threaded rod 212 keeps the inserter 200 attached to the primary implant.

Figure 30:
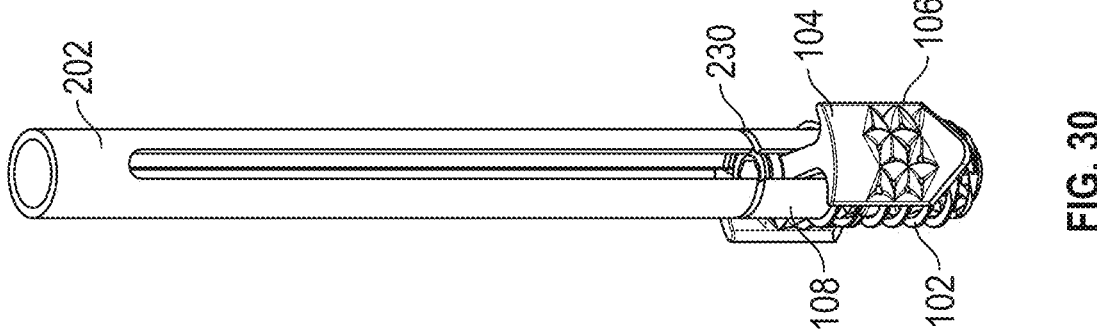
FIG. 30 illustrates a perspective view of an implant having extended tabs.
Figure 29:
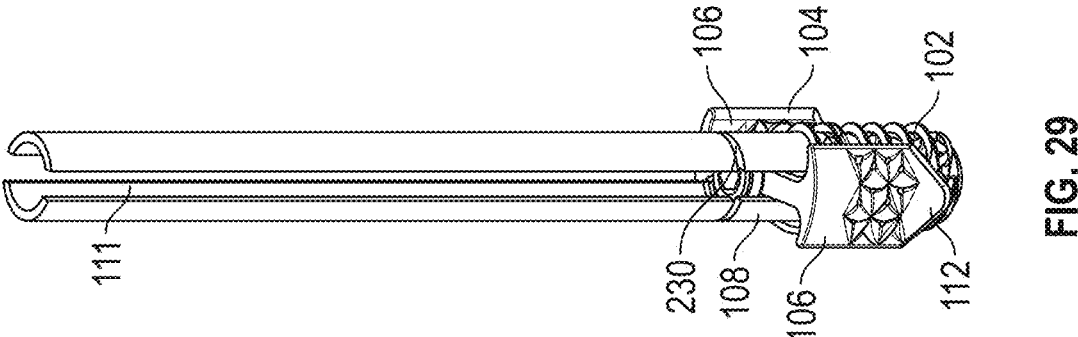
FIG. 29 illustrates a perspective view of an implant having extended tabs.

FIGS. 29 and 30 show alternative embodiments of the implant system 100 having extended tabs 108 of the primary implant including a frangible joint or break off point 230. A superior portion of the extended tabs 108 can be broken off from the tabs after the implant system 100 is positioned within the SI joint. The extended tabs 108 can serve as an inserter and minimize instrumentation required to implant the implant system. The extended tabs 108 may act as a dilator for a working channel 111 for delivery of the secondary implant, the connection mechanism 110, and/or any other components of the implant system 100. In some embodiments, a broach or punch can be placed through the channel 111 prior to the secondary implant to create a pathway for the secondary implant, for example, if bone is dense or hard. In certain embodiments, a set screw can be placed down the channel. In certain embodiments, the extended tabs can provide a channel for packing bone graft over the implant system 100. In some embodiments, the implant system 100 can be implanted within the SI joint (and countersunk in some embodiments), and bone graft can be packed over the implant system 100 through the channel formed by the extended tabs 108. After the bone graft is introduced, the extended tabs can be broken at the frangible joint or break off point 230 and the superior portion of the extended tabs can be removed.

Figure 31:
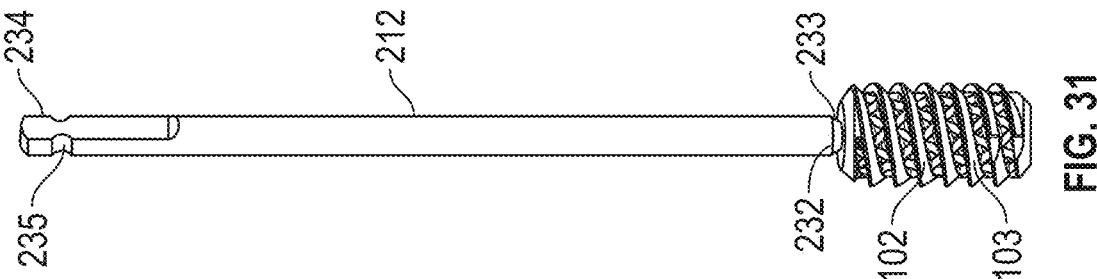
FIG. 31 illustrates a perspective view of an implant coupled to a rod.

FIG. 31 depicts an alternative embodiment of a rod 212 in which the rod 212 is coupled to the primary implant 102 by a frangible joint or break off point 232. As shown in FIG. 31, the rod 212 can have a distal end 233 and a proximal end 234, wherein the proximal end contains notches 235 for connecting to handles or for gripping. The frangible joint or break off point 232 can be formed by a sharp angle at the distal end 233 of the rod 212. The frangible joint or break off point 232 can be broken in response to bending or application of torque on the rod 212.

FIGS. 18, 19, 20, 21, 22, 23, and 24 depict an embodiment of a method of implanting an embodiment of an implant system 100 in which no fastener or attachment mechanism 110 is used to keep the primary implant 102 and secondary implant 104 together. In certain embodiments, the primary implant 102 has threads or anti backout features preventing it and the secondary implant 104 from expulsing. In certain embodiments, a guidewire or rod 300 can be used to locate the SI joint. After the SI joint is located, the secondary implant 104 can be inserted first into the ilium and sacrum, as shown, for example, in FIGS. 19 and 20. For example, an inserter or driver 250 can be used to insert the secondary implant 104. After the secondary implant 104 is inserted, a drill bit with or without a surface reamer can be used to drill or ream into the SI joint to form a pilot hole for the primary implant 102. The drill bit can be removed and the primary implant 102 can be inserted over the rod or guidewire 300, as shown for example, in FIG. 21. The primary implant 102 can be advanced until the primary implant 102 bottoms out on the secondary implant 104 preventing it from going further down the SI joint, as shown, for example, in FIGS. 22 and 23. After the implant 102 is inserted into the SI joint, the guidewire or rod 300 can be removed, as shown, for example, in FIG. 24.

In certain embodiments, a head of the primary implant 102 can have a fixed or variable orientation with respect to the secondary implant 104. In certain embodiments, the head of the primary implant 102 can rotate, for example, to make up for needed trajectory change.

Figures 25, 26:
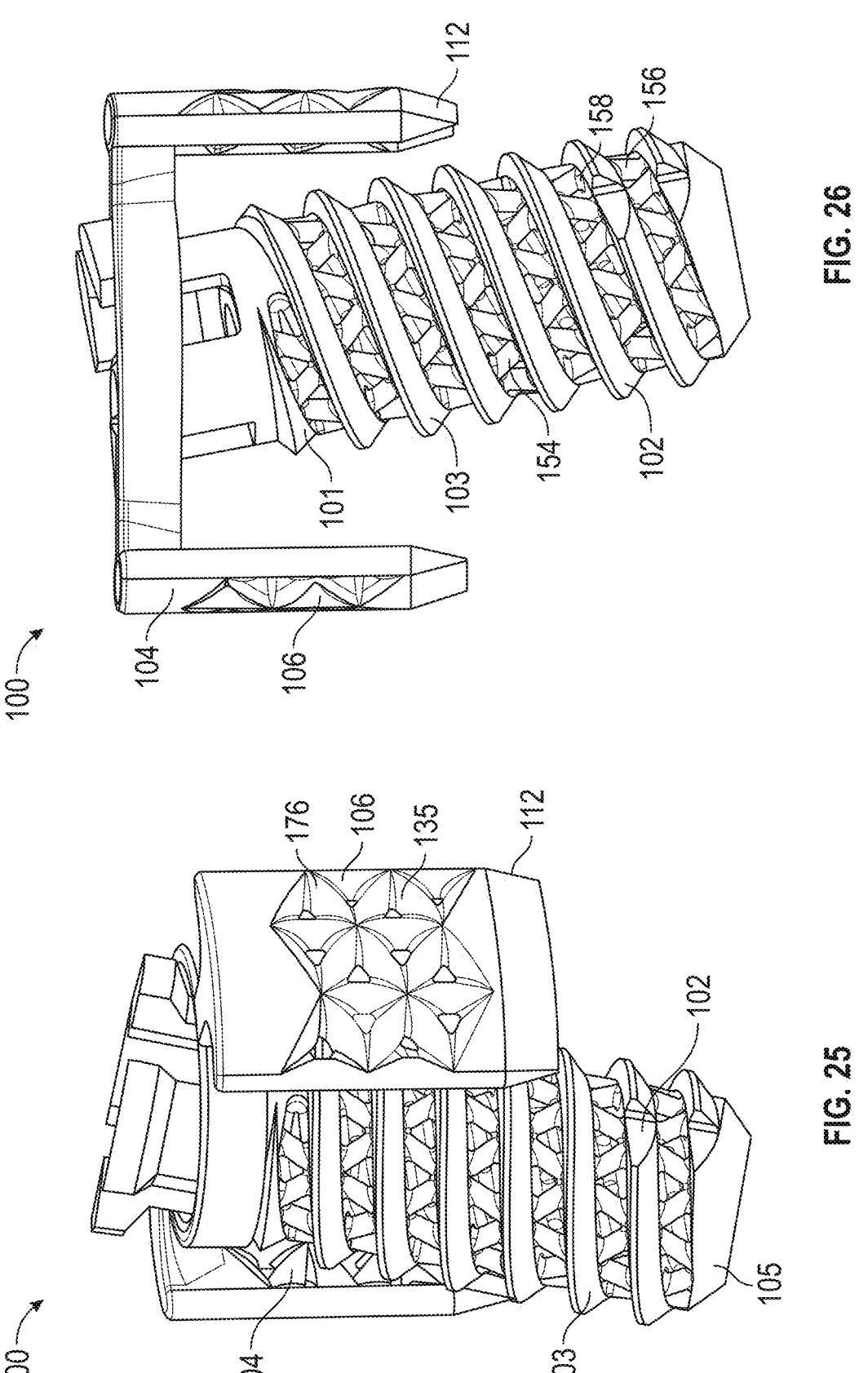
FIG. 25 illustrates a front view of an alternative rotating embodiment of the implant.
FIG. 26 illustrates a front view of an alternative rotating embodiment of the implant.

FIGS. 25 and 26 depict another embodiment of the SI joint implant system 100. The embodiment of FIGS. 25 and 26 may include any of the same or similar features or functions as any of the other embodiments described herein and vice versa. FIGS. 25 and 26 depict another embodiment of the implant system 100 in which the primary implant 102 can be received within the secondary implant 104.

FIGS. 25 and 26 show examples of rotation of the head of the primary implant 102 relative to the secondary implant 104. If the trajectory of the primary implant 102 is changed it can still seat properly in the secondary implant 104. In certain embodiments, the primary implant 102 and secondary implant 104 can have engagement features that allow the two implants to lock together. For example, the primary implant 102 and secondary implant 104 can be locked together using threads, snaps, grooves, etc.

Similarly, in certain embodiments, the secondary implant 104 of FIGS. 36A-36G can be implanted prior to the primary implant 102.

In certain embodiments, the implant system 100, as shown in FIGS. 36A-36G, can be placed using a posterior method below the posterior superior iliac spine (PSIS) to prevent instruments and the implants from being hung up during placement. The PSIS overhangs the SI joint and can be difficult for physicians to navigate. In certain embodiments, one implant system 100 can be placed in the SI joint below the PSIS. In certain embodiments, such as in a patient with weak or soft bone, a second implant system 100 can be placed above the PSIS for increased fixation.

A method for implanting the system 100, for example, as shown in FIGS. 36A-36G, is described with respect to FIGS. 37-53. Although the method is described with respect to the embodiment shown in FIGS. 36A-36G, it may be used with or modified for use with any of the other embodiments described herein. Additionally, any of the steps may be modified based on surgeon preference or anatomical variation.

As described above, the implant system 100 can be implanted using a posterior method through an incision. The incision can be approximately 1 inch in length. In certain embodiments, the incision can be made in a horizontal direction. In certain embodiments, a vertical incision may be insufficient for passage of the instruments described herein.

Figures 37A, 37B:
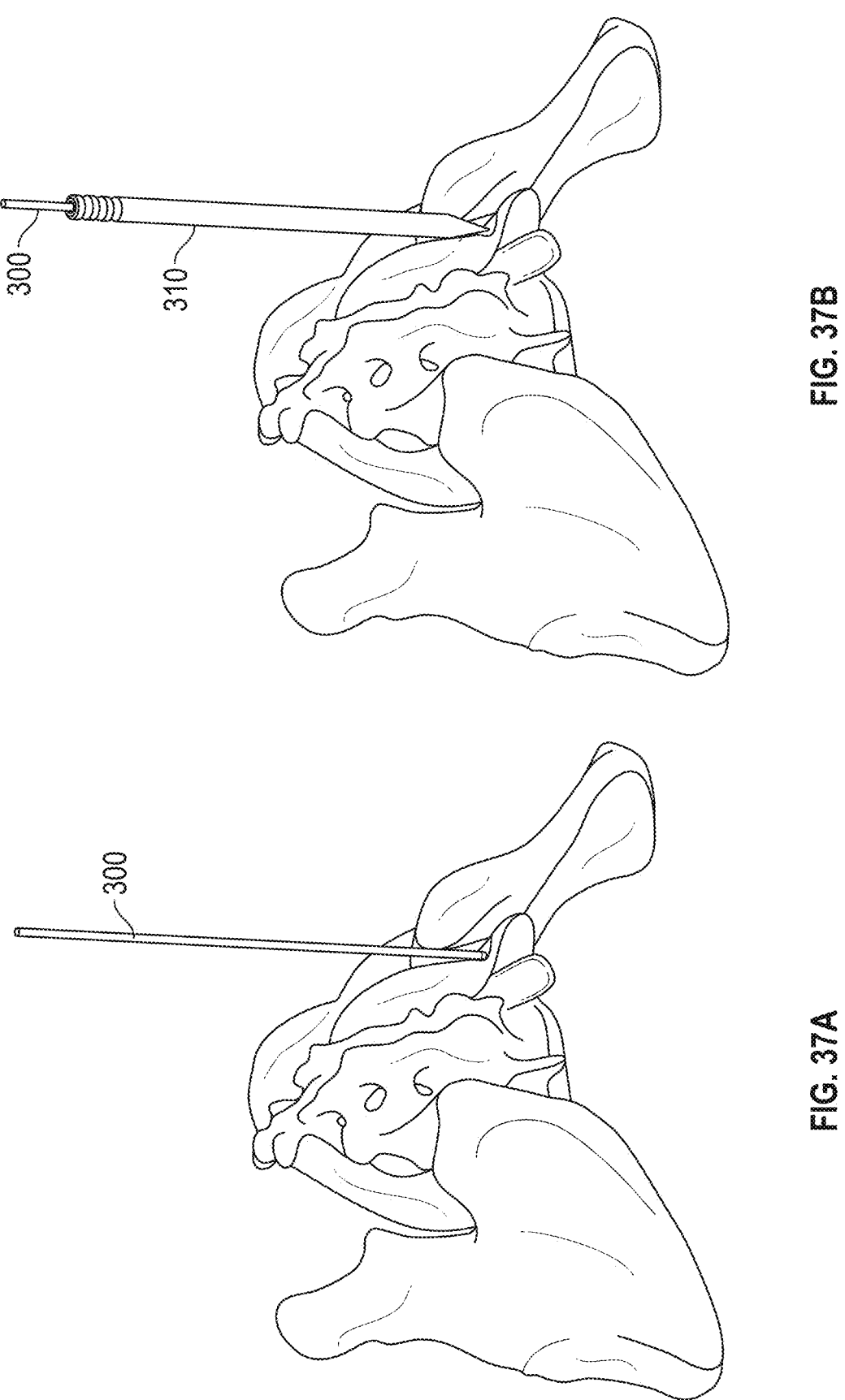
FIG. 37A illustrates a perspective view of a guidewire as part of an implant system inserted into the SI joint.
FIG. 37B illustrates a perspective view of a guidewire and SI joint locator as part of an implant system inserted into the SI joint.

As shown in FIG. 37A, in certain embodiments, a guidewire or rod 300 can be placed into the SI joint through the incision. The guidewire 300 may be placed using fluoroscopic anterior-posterior, lateral, and/or pelvic inlet views. The fluoroscopic views may be used in any order. Any of the views may be omitted if desired. The guidewire 300 can be placed using a posterior approach. The guidewire 300 can be traversed down the SI joint to ensure that the implant system 100 is placed properly and has proper fixation.

Figure 39:
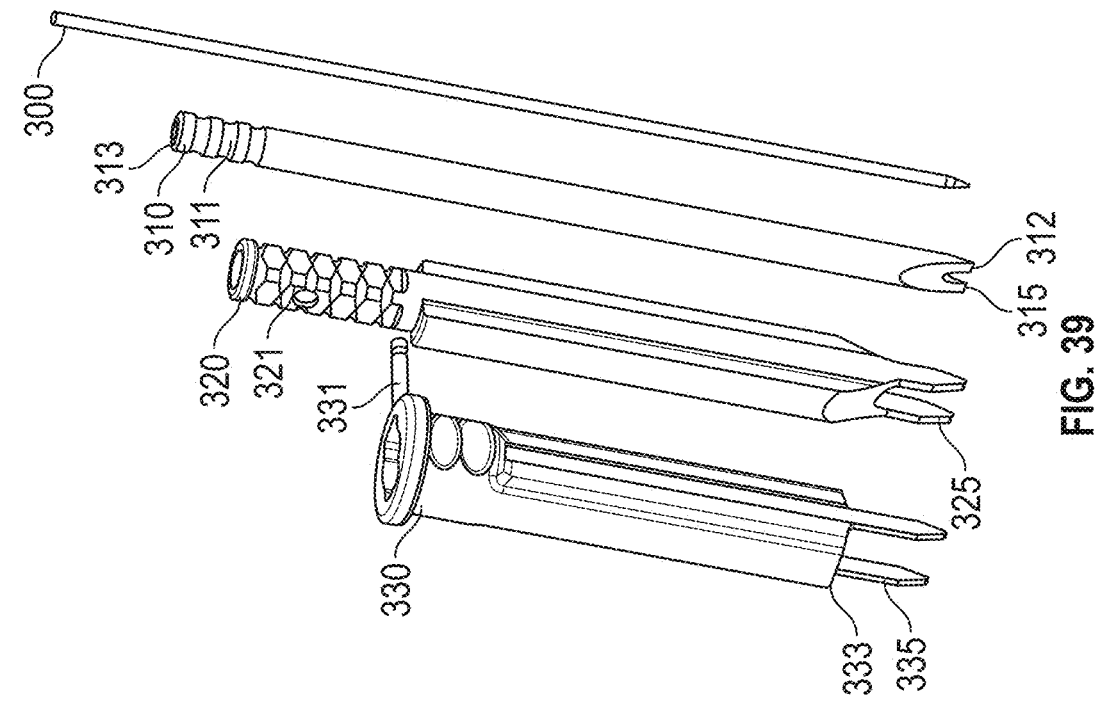
FIG. 39 illustrates the guidewire, SI joint locator, dilator, and guide as part of an implant system.

After the guidewire 300 is placed within the SI joint, an SI joint locator 310 can be placed over the guidewire 300 and into the SI joint, as shown in FIG. 37B. In some procedures, the guidewire may be omitted, and the SI joint locator 310 may be placed within the SI joint as an initial step. This may be beneficial if the SI joint is tight and prevents proper placement of the guidewire 300. The SI joint locator 310 may have a proximal end 313 and a distal end 312, wherein the distal end 312 is inserted into the joint. The SI joint locator may have ridges or a grip 311 on the distal end 312. A lumen runs through the SI joint locator so the guidewire 300 may extend therethrough. The SI locator 310 may include teeth or tangs 315 that may anchor within the SI joint, as seen in FIG. 39.

Figures 38A, 38B:
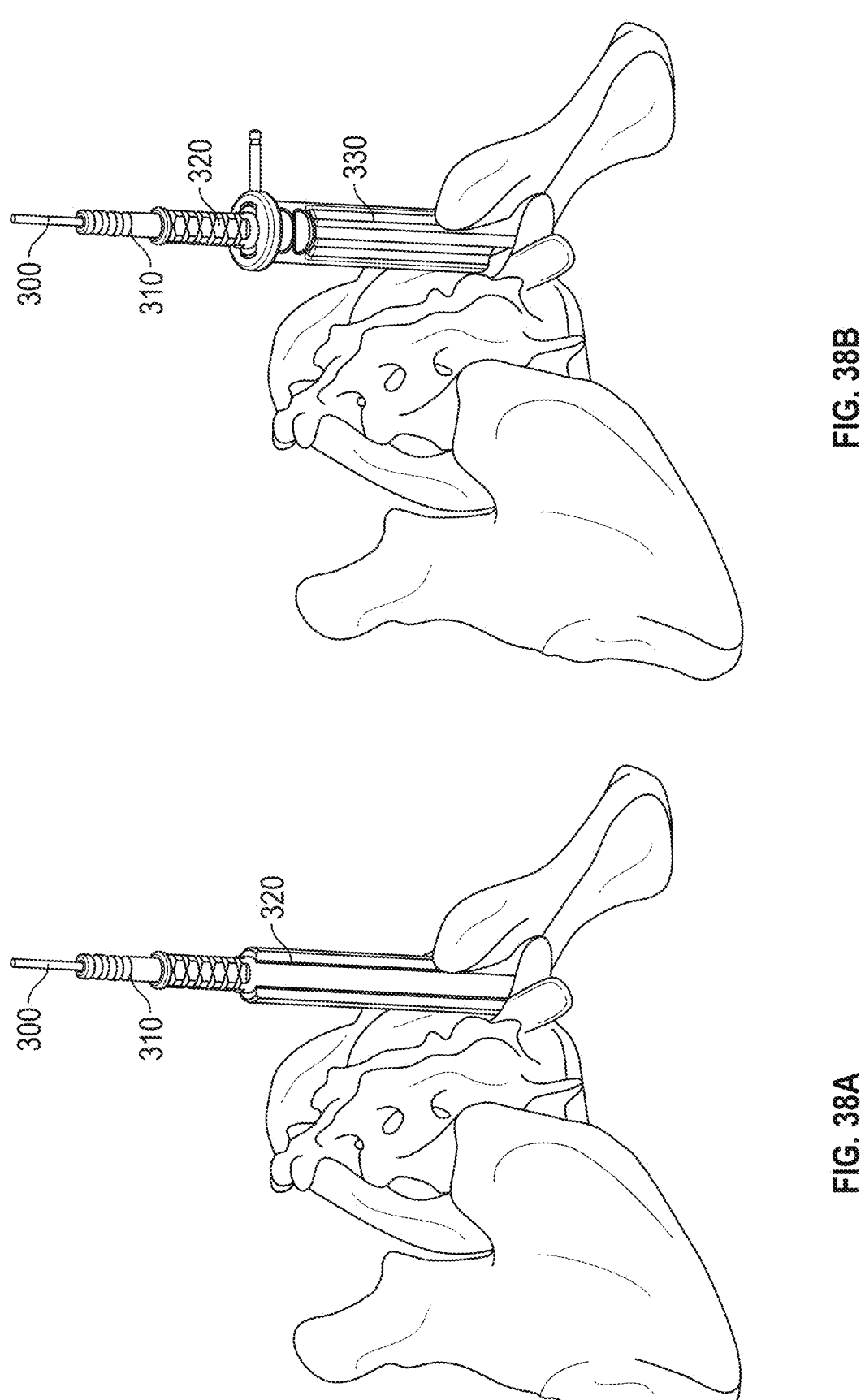
FIG. 38A illustrates a perspective view of a guidewire, SI joint locator, and a dilator as part of an implant system inserted into the SI joint.
FIG. 38B illustrates a perspective view of a guidewire, SI joint locator, dilator, and guide as part of an implant system inserted into the SI joint.

As shown in FIG. 38A, in some embodiments, after the joint locator 310 is placed, one or more dilators 320 (for example, a single dilator or a plurality of dilators in series) may be used to dilate the tissue. The one or more dilators 320 can include teeth or tangs 325 that may anchor within the SI joint. The one or more dilators may also include handles or grips 321.

In some embodiments, the one or more dilators 320 can dilate the tissue to provide a path for a guide 330, for example, as shown in FIG. 38B. The guide 330 may act as a drill guide. In some embodiments, the guide 330 may act as a guide for one or more other instructions and/or as a guide for the secondary implant 104 and/or primary implant 102. In some embodiments, the guide 330 may be the largest dilator of the one or more dilators. Each of the dilators 320 have a central lumen to allow the dilator to be placed over smaller sized dilators or the SI joint locator 310 already placed within the joint.

Figure 40:
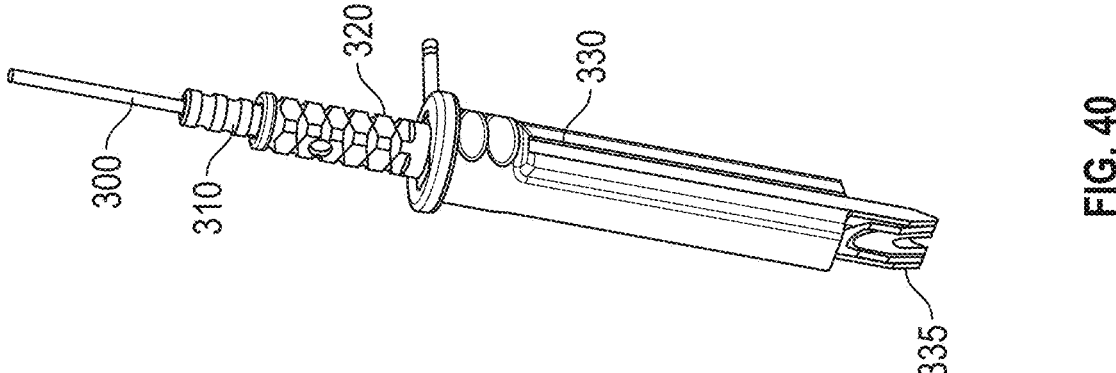
FIG. 40 illustrates a perspective view of the guidewire, SI joint locator, dilator, and guide fit together as part of an implant system.

After the one or more dilators 320 are inserted, the guide 330 can be placed within the SI joint. The guide 330 can include teeth or tangs 335 that anchor into the SI joint. The teeth or tangs may be parallel or perpendicular to the joint, for example, depending on user preference. As shown in FIGS. 39 and 40, two or more teeth or tangs 335 can be located at a base of the guide 330 to allow for anchoring and prevent slipping during drilling, broaching, bone punching and/or inserting implants. As described herein, the SI joint locator 310 and/or one or more dilators 320 may also include teeth or tangs. The guide 330 can also include a handle 331 that can be gripped during use.

Figure 41:
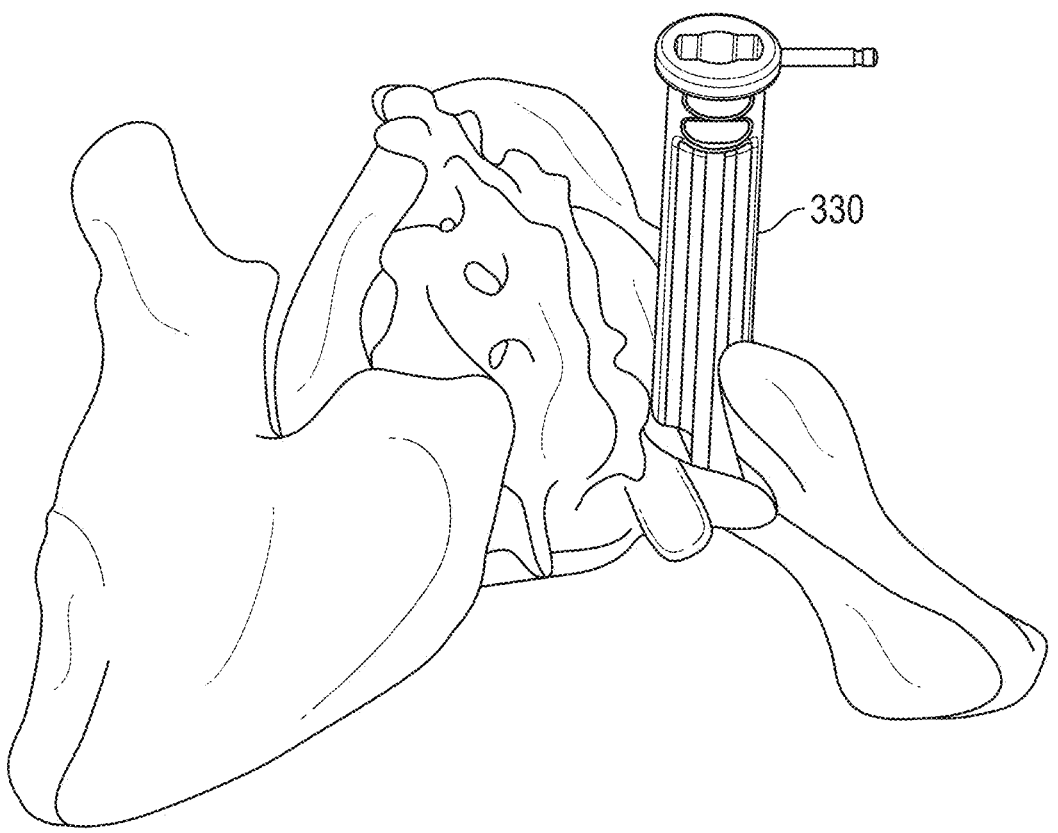
FIG. 41 illustrates a perspective view of the guide as part of the implant system in the SI joint.

Once the guide 330 is positioned within the SI joint, the guidewire 300, SI joint locator 310, and one or more dilators 320 can be removed from the guide 330 as shown, for example, as shown in FIG. 41. In some embodiments, the shape and/or dimensions of the guide 330 can be the same at the portions of a distal end 333 that contact the ilium and the sacrum. In other embodiments, the distal end 333 can have a different shape and/or dimensions on the ilium and sacral sides to match the anatomy of the patient, for example, a longer sacral side or ilium side. The distal end 333 or distal surface of the guide 330 can be shaped, dimensioned, or otherwise configured to sit flush within the SI joint on both the sacral side and ilium side, for example, to allow a drill bit and/or implant inserters to provide accurate depths for accurate implant insertion and prevent the implants from sitting proud of the SI joint or being countersunk too deep.

Figure 43:
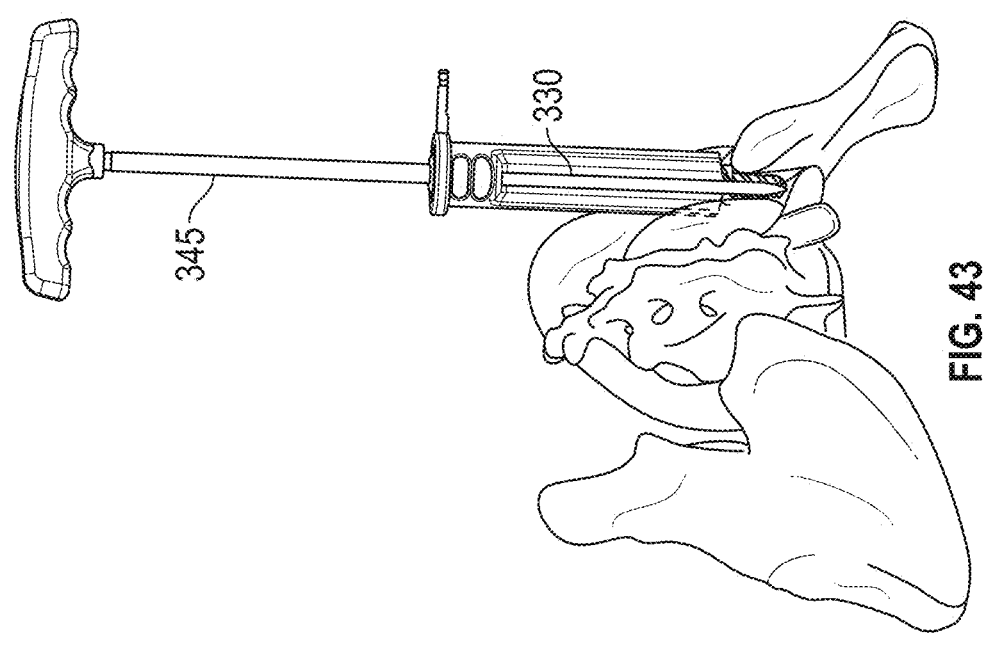
FIG. 43 illustrates a perspective view of a handle, drill tool, and implant as part of an alternative embodiment of an implant system inserted into the SI joint.
Figure 42:
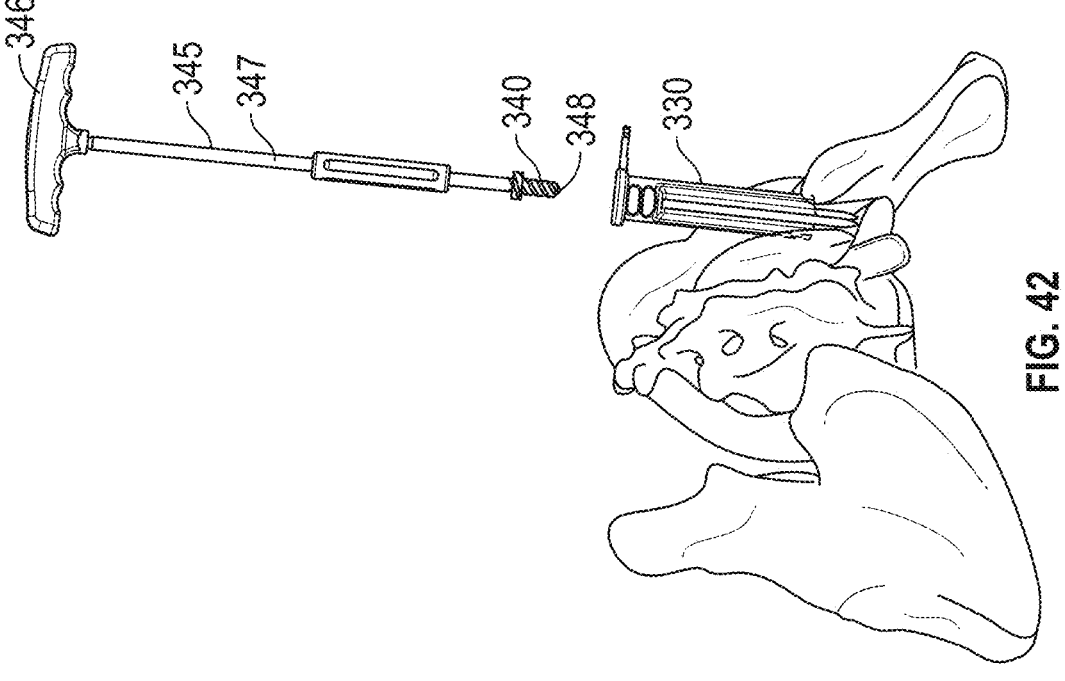
FIG. 42 illustrates a perspective view of a handle, drill tool, and implant as part of an embodiment of an implant system inserted into the SI joint.
Figure 44:
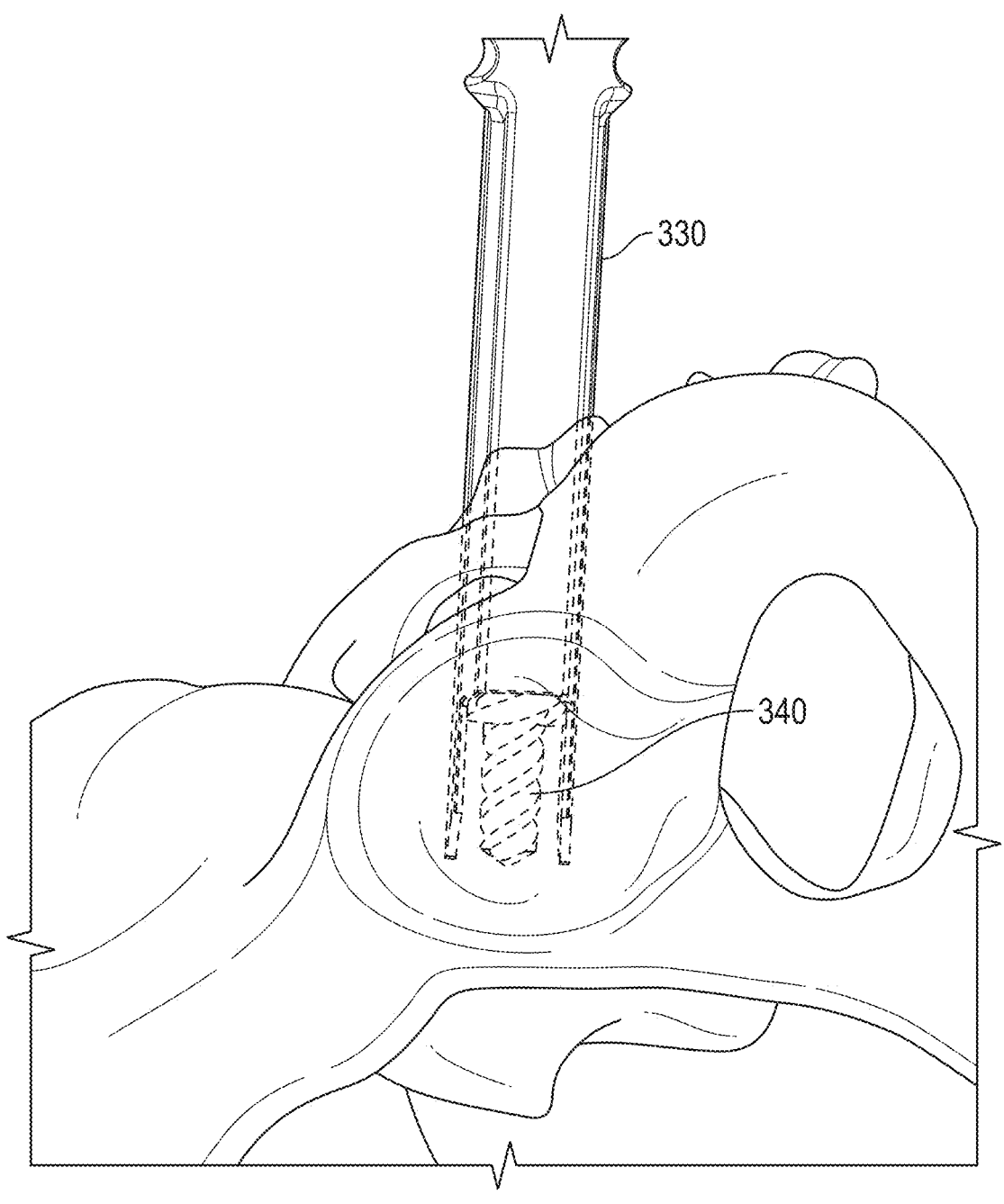
FIG. 44 illustrates a side view of a drill bit and a guide as part of an implant system in an embodiment.

After the guidewire 300, SI joint locator 310, and one or more dilators 320 are removed, a drill bit 340 of a drill tool 345 may be placed down the guide 330 to create a pilot hole for the primary implant 102, as shown in FIGS. 42-44. The drill tool 345 includes a handle 346 connected to a shaft 347 leading to a distal end 348. The guide 330 can be variable to allow for the drill bit to be angled so that a user can change trajectory. Alternatively, the guide 330 may be fixed so as to allow little or no variability in drill angle or position when inserted within the SI joint. The drill bit may be cannulated or non-cannulated.

In an alternative embodiment, an all-in-one inserter may be used. FIGS. 75A-75D illustrate an embodiment of an all-in-one inserter 420 system. The all-in-one inserter 420 saves time, makes insertion less cumbersome, and prevents cross threading or mal-insertion of the two implants. With the all-in-one inserter 420, the secondary implant 104 is tightened to the end of an inserter body 421. The primary implant 102 is threaded onto the end of a driver 422. The top of the inserter body 421 may be malleted to position the secondary implant 104. The secondary implant 104 may be bridged across the SI joint into the ilium and sacrum. Once the secondary implant 104 is flush or counter-sunk into the joint, the driver 422 coupled to the primary implant 102 is placed down the inserter body 421 to thread the primary implant 102 through the secondary implant 104.

In some embodiments, shown in FIG. 75D, there may be a nut 423 positioned on threading 424 at the top of the driver 422. The threading 424 may contain an immovable stopper 425 at the top to prevent the nut 423 from completely unthreading from the driver 422. This is to prevent the nut 423 from disengaging and getting lost during the cleaning process. When the driver 422 is positioned within the inserter body 421 and the nut 423 is threaded down towards the driver 422, shown in FIG. 75C, the driver 422 and inserter body 421 are tightened together, and the secondary implant 104 is tightened against the inserter body 421. In some embodiments, there may be more than one nut on the threading.

FIGS. 75A and 75B illustrate an all-in-one inserter 420 system with an attached handle 331 which may be used for threading the primary implant 102 into position. The handle can be twisted to insert the primary implant 102 into the joint. Once the primary implant 102 is threaded down, the all-in-one inserter 420 may be released from both implants by threading the nut 423 away from the driver 422, as shown in FIGS. 75A and 75B. Once the nut is threaded up, the driver can then be unscrewed from the primary implant. The user may use a ratcheting handle or non-ratcheting handle to thread the primary implant down.

Figure 45:
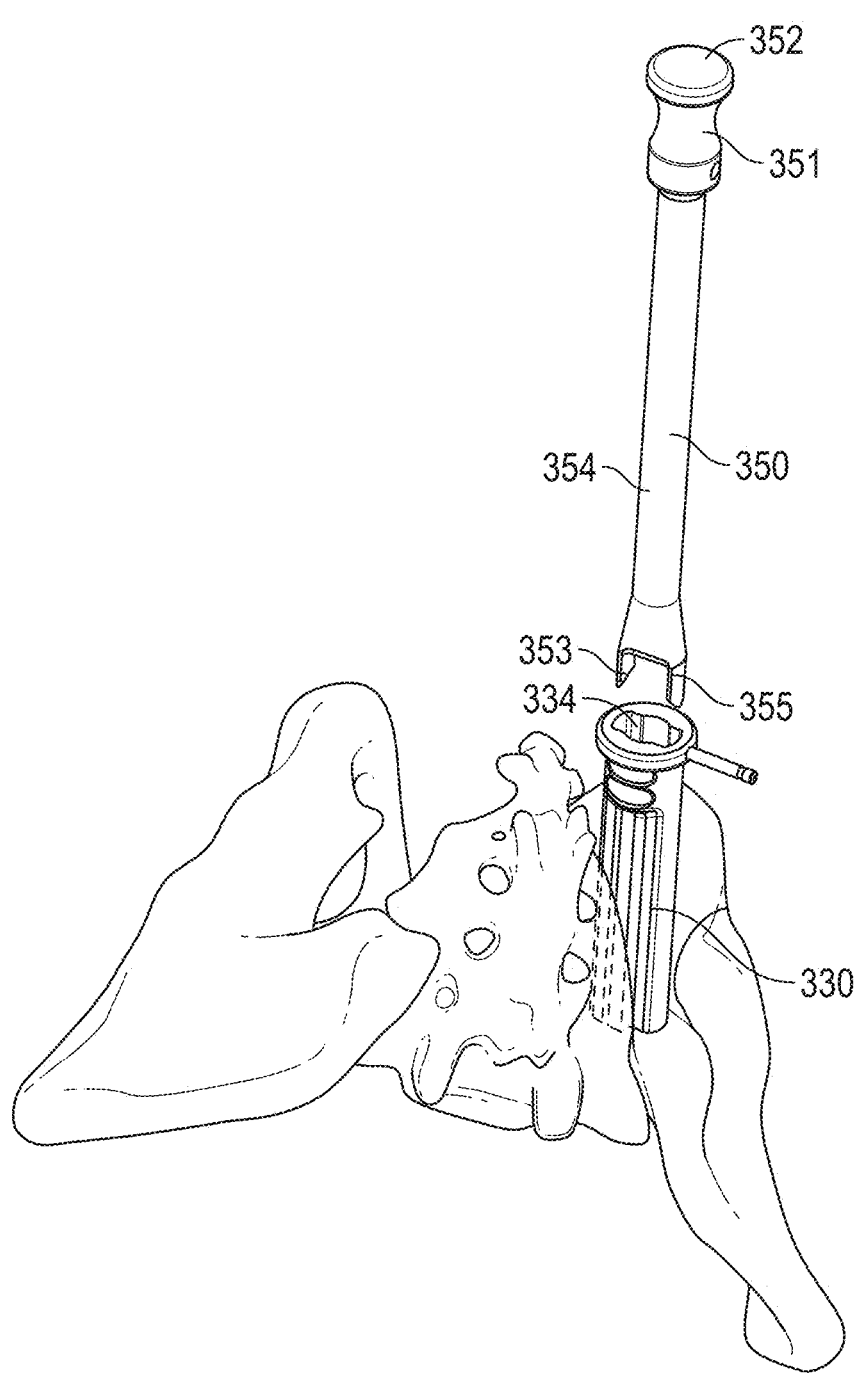
FIG. 45 illustrates a perspective view of a guide and bone punch as part of an embodiment of an implant system inserted into the SI joint.
Figure 46:
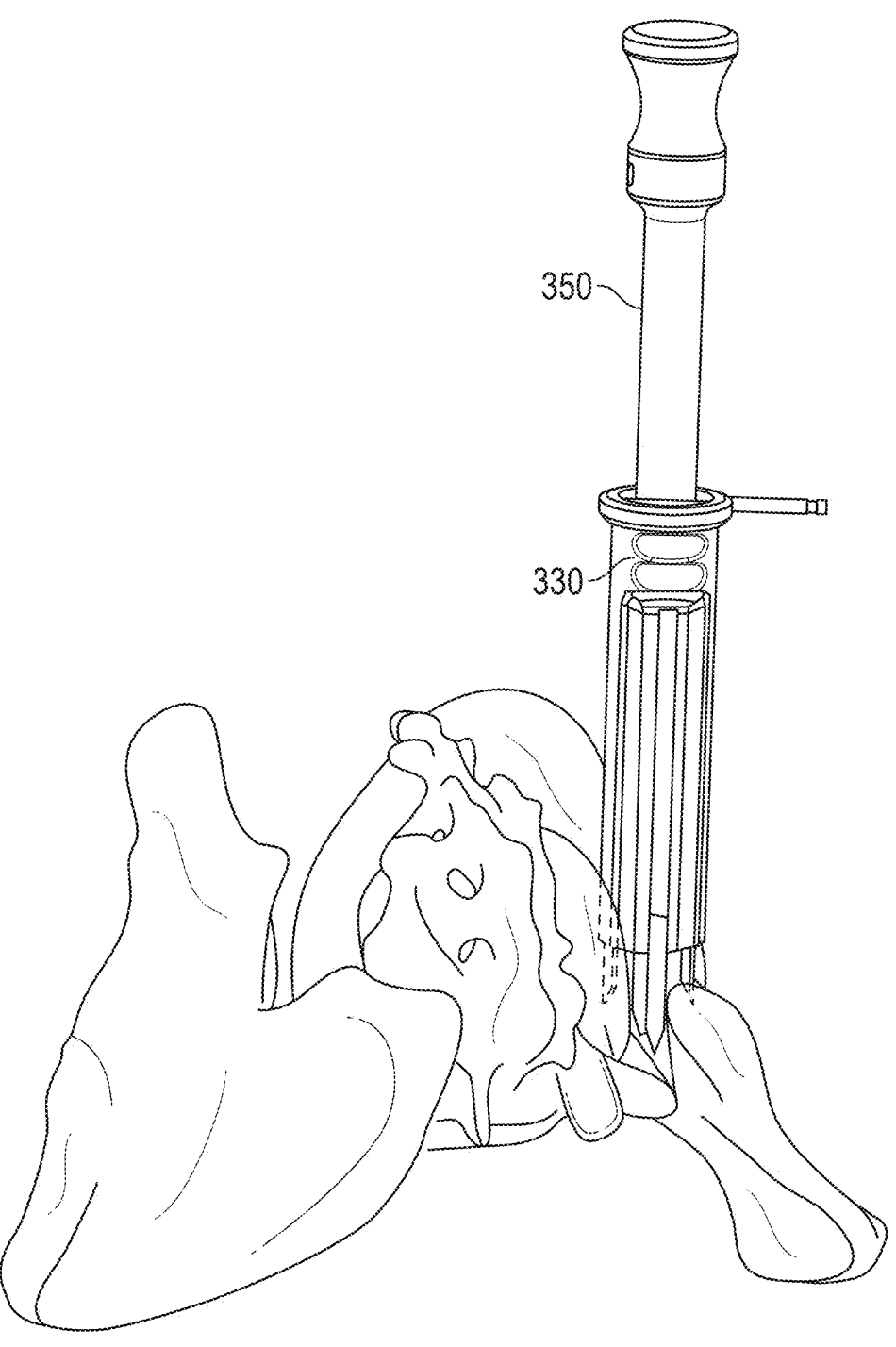
FIG. 46 illustrates a perspective view of a guide and bone punch as part of an alternative embodiment of an implant system inserted into the SI joint.

As shown in FIGS. 45 and 46, after the pilot hole is created with the drill bit 340, a bone punch 350 may inserted through the guide 330 and used to create a path for the secondary implant 104 or anchors. In some embodiments, the guide 330 may provide a pre-set trajectory for the punch to prevent variability in punch placement. The bone punch 350 includes a handle 351 at its proximal end 352, protrusions 355 at its distal end 353 for punching into bone, and a shaft 354 extending therebetween. The guide 330 may contain channels or slots 334 that receive the protrusions 355. These slots 334 can be shaped and dimensioned to prevent rotational movement of the protrusions 355 within the guide 330, for example, to maintain a pre-set trajectory of the bone punch as it is advanced through the guide 330.

Following use of the bone punch 350, the secondary implant 104 can be inserted through the guide 330. The secondary implant 104 can be inserted using an implant inserter 360, as shown in FIGS. 47A-47C. For some patients, for example if the bone is sufficiently soft, use of the bone punch instrument may be omitted. In such embodiments, the anchors or secondary implant 104 can be inserted using the implant inserter 360 without use of a bone punch.

As shown in FIG. 47A, the implant inserter 360 can include mating features 365 (for example, mating tabs or protrusions) configured to engage corresponding mating features 134 of the secondary implant 104. The mating features 134 can be in the form of one or more recesses or slots. The mating features 134 can be positioned within the ring 124 or within the anchors 106. For example, as shown in FIG. 47A, each of the anchors 106 includes a mating feature 134 in the form of a slot or recess configured to receive a complementary mating feature 365 of the implant inserter 360 in the form of a tab or protrusion. Additionally, the implant inserter 360 may have a handle or a grip that may be rubber or silicone to facilitate gripping by the surgeon.

In some embodiments, these slots 334 of the guide 330 can be configured to receive the anchors 106 of the secondary implant 104, for example, to maintain a pre-set trajectory of the anchors 106 as they are advanced through the drill guide to a surgical location (e.g., into the path created by the bone punch 350). The slots 334 can be shaped and dimensioned to prevent rotational movement of the protrusions 355 within the guide 330.

The anchors 106 may be driven into the ilium and sacrum to allow for stabilization and transfixing the SI joint from a posterior approach. In certain embodiments, one of the anchors 106 can be driven in each side of the ilium and sacrum. In certain embodiments, the anchors 106 may include windows or openings 135 for bone ingrowth and/or barbs to prevent the anchors from backing out. The secondary implant 104 can be driven until it is countersunk such that the implant 104 is not proud of the SI joint.

After the implant 104 is positioned at the desired location relative to the SI joint (e.g., countersunk such that it is not proud of the SI joint), the screw or primary implant 102 can be inserted into the SI joint through the opening 126 of the ring 124. For example, as shown in FIGS. 48-51, the primary implant 102 can be inserted using an implant inserter 370. The implant inserter 370 may contain mating hardware at the distal end to couple with the primary implant 102. In some embodiments, the primary implant 102 can be inserted through a lumen 361 within the implant inserter 360 while the implant inserter 360 is positioned within the guide 330.

In certain embodiments, the ring 124 may allow for polyaxial movement of the primary implant 102 to allow for different angles of the primary implant 102 relative to the ring 124. In other embodiments, the position of the implant 102 can be fixed to prevent any movement between the primary implant 102 and the anchors 106.

The implant inserter 370 can be used to drive the implant 102 through the opening 126 of the ring 124 until the implant 102 locks or stops. For example, the implant 102 can include threads on a collar that can thread into the ring 124 that allow for a positive stop and prevent over-inserting of the implant 102. This may also prevent stripping of the implant 102 in the bone.

After the primary implant 102 is in place, the implant inserter 370, implant inserter 360, and guide 330 can be removed. The primary implant 102 can be provided in a variety of lengths between 20 mm to 45 mm. Primary implants 102 of different lengths may be used interchangeably with the secondary implants 104. In some embodiments, a primary implant 102 having a greater length can allow for more purchase into the SI joint. FIGS. 52 and 53 depict the primary implant 102 and secondary implant 104 after implantation.

In certain embodiments, one or more of the primary implant 102, secondary implant 104, guidewire 300, joint locator 310, one or more dilators 320, guide 330, drill tool 345, bone punch 350, implant inserter 360, and implant inserter 370 can be provided in a kit. In some embodiments, one or more of the instruments used to implant the primary implant 102 and secondary implant 104, such as the guidewire 300, joint locator 310, one or more dilators 320, guide 330, drill tool 345, bone punch 350, implant inserter 360, and implant inserter 370, can be provided in a kit. The instruments may be disposable and can be provided in a kit of pre-packaged sterile disposable instruments. The pre-packaged sterile disposable instruments can reduce costs associated with autoclaves and prevent the risk of cross-contamination from blood if the same instruments are used to perform multiple surgeries. Shipping a tray of sterile instruments can be costly due to weight and size of the trays. In some embodiments, the implants 102 and 104 and the instruments used for implantation can be placed in one sterile tray together or in separate trays separating implants and instruments. In some embodiments, the instruments and implants 102 and 104 can be provided in autoclavable trays if desired, for example, to meet surgeon desires of durability and handling. Some physicians may prefer metal instruments that are heavier and more durable. In such embodiments, the implants and instruments may be placed in one tray that can be sterilized together.

Another method for implanting the SI joint implant system 100, for example, the embodiments of the SI joint implant system 100 as shown in FIG. 58A-58F, 59A-59D, or 63A-63B, is described with respect to FIGS. 64A-69C. Although the method is described with respect to the embodiments shown in FIG. 58A-58F, 59A-59D, or 63A-63B, it may be used with or modified for use with any of the other embodiments described herein. Additionally, any of the steps may be modified based on surgeon preference or anatomical variation. Further any of the instruments in the method of FIGS. 64A-69C may be provided in a kit as described with respect to the instruments described with respect to FIGS. 37-53 (for example, as pre-packaged sterile disposable instruments or instruments in an autoclavable tray).

As shown in FIGS. 64A and 64B, one or more of a guidewire 300, a joint locator 310, one or more dilators 320, and a guide 330 may be inserted into the SI joint as described herein. The guide 330 can include a handle 332. The handle 332 may be removably coupled to the guide 330.

In some embodiments, the one or more dilators 320 can include a series of dilators (for example, two or more dilators, up to five dilators, or any other suitable number of dilators). In some embodiments, guide 330 may be the largest dilator of the one or more dilators. The one or more dilators 320 and/or drill guide 330 can include slots 334 that guide the secondary implant 104 along a desired trajectory. The SI joint locator, one or more dilators 320, and/or drill guide 330 can include teeth or tangs to anchor into the SI joint, as described herein.

As shown in FIGS. 65A and 65B, the guidewire 300, SI joint locator 310, and one or more dilators 320 can be removed, and a drill bit 340 of a drill tool 345 may be placed down the guide 330 to create a pilot hole for the primary implant 102.

As shown in FIGS. 66A-66D, the primary implant 102 can be coupled to an implant inserter 370. The implant inserter 370 can include a handle 372, a shaft 374 coupled to the handle 372, and a threaded rod 376. The shaft 374 can include one or more mating features, such as tabs or protrusions 378 that can couple with the groove cuts or recesses 152 of the primary implant 102. The engagement of the tabs or protrusions 378 with the groove cuts or recesses 152 can facilitate driving of the primary implant into the SI joint. The threaded rod 376 can be positioned partially within the shaft. A threaded distal end 380 of the threaded rod 376 can extend out of the distal end of the shaft and couple with interior threads of the primary implant 102 to secure the primary implant to the implant inserter 370.

As shown in FIGS. 67A-67B, the primary implant 102 can be driven into the SI joint through the guide 330 using the implant inserter 370. After the primary implant 102 is in position, the handle 372 and shaft 374 can be decoupled from the threaded rod 376 and removed while the threaded rod 376 remains coupled to the primary implant 102. In certain embodiments, the handle 372 and shaft 374 can be decoupled from the rod 376 via a rod and spring mechanism as shown in FIG. 67C. As shown in FIG. 67C, the rod and spring mechanism can include a rod 382 that can be actuated to decouple the handle 372 and shaft 374 from the rod 376. The rod and spring mechanism can include a spring configured to bias the rod 382 to a locked configuration in which removal of the handle 372 and shaft 374 from the rod 376 is prevented.

As shown in FIG. 68A, the secondary implant 104 can be coupled to an implant inserter 360. The inserter 360 can include mating features 365 (for example, mating tabs or protrusions) configured to engage corresponding mating features 134 of the secondary implant 104. After the implant inserter 360 is coupled to the implant 104, the inserter 360 can be used to insert the implant 104 over the threaded rod 376, as shown in FIG. 68B, and over the proximal end 148 of the primary implant 102. As shown in FIG. 68B, the guide 330 includes slots 334 that can receive the anchors 106 of the secondary implant 104 and guide the secondary implant 104 along a desired trajectory.

The anchor ring 124 can be guided along the threaded rod 376 with the threaded rod 376 extending through the central opening 126. The secondary implant 104 can then be driven into the bone. In some embodiments, the secondary implant can be driven into the bone using a mallet, as shown in FIG. 68C.

After the secondary implant is driven into bone, a handle can be attached to the threaded rod 376 and used to remove the threaded rod 376, as shown in FIG. 69A. The attachment mechanism 110 can then then be inserted through a lumen of the implant inserter 360 using an implant inserter 390 and into engagement with the interior threads of the primary implant 102 to secure the secondary implant 104 and primary implant 102 together, as shown in FIGS. 69B and 69C.

After the primary implant 102 and secondary implant 104 are secured together in place, the guide 330, implant inserter 360 and implant inserter 390 can be removed.

FIGS. 73A-73E depict an embodiment of a rasp 400. The rasp 400 extends between a proximal end 402 and a distal end 404. The rasp 400 can include a rasping tip 406 having rasping surfaces 408*a* and 408*b* extending from opposing generally rectangular surfaces 410*a* and 410*b*. In certain embodiments, the surface 410*a* and the surface 410*b* can be a top surface and a bottom surface, respectively, of the rasping tip 406. The rasping tip 406 can include generally flat side surfaces 412*a* and 412*b*. The distal end 404 can be a pointed or wedge shaped distal end of the rasping tip 406.

The distal end 404 and rasping tip 406 can be dimensioned, shaped, or otherwise configured to be inserted into a SI joint. In certain embodiments, the rasp 400 can be used to decorticate bone within a SI joint. In certain embodiments, the rasp 400 can be used to decorticate bone in the SI joint prior to forming a pilot hole with a drill bit and/or implanting a primary implant 102. The rasping tip 406 can be dimensioned to be wider than a drill bit 502 of a drill 500 used in a procedure for implanting an SI joint implant system 100. The rasping surface 408*a* and/or the rasping surface 408*b* can have a width X4 that is wider than a width X3 of the drill bit 502 or any other drill bit described herein. For example, in certain embodiments, the width X4 can be about 16 mm and the width X3 can be about 10 mm. In certain embodiments, the width X4 can be between 5 mm and 7 mm and the width X3 can be between 3.5 mm and 4.5 mm. The rasping surface 408*a* and/or the rasping surface 408*b* may also be wider than the primary implant 102. A rasping surface 408*a* and/or rasping surface 408*b* that is wider than the drill bit and/or implant can create an area of decortication in the SI joint around (e.g., laterally beyond a cross-sectional area of) the primary implant 102 to promote bone fusion.

In certain embodiments, a rasp 400 may be used with a drill guide 330. FIGS. 74A-74D illustrate the rasp 400 and drill guide 330 in different configurations. A user may first take a rasp 400, as seen in FIG. 74A, and drive it down through the joint until notches 403 on opposite sides of the rasp match up with the posterior SI joint margin. The notches 403 are located on the distal end 404 of the rasp 400, proximal to the rasping surface, and help with countersinking the insertion instruments to the correct depth. The correct depth of the rasp 400 may be seen on fluoro imaging. Once the rasp 400 is driven to the correct depth within the SI joint, the drill guide 330 is placed over the rasp 400 and driven down until the notches 403 are covered and can no longer be seen on fluoro imaging. FIG. 74B shows the drill guide 330 being placed over the rasp 400 but is not yet into position since the notches 403 are still visible. FIGS. 74C and 74D illustrate the drill guide 330 positioned all the way over the rasp 400 so that the notches on the distal end 404 are no longer visible.

In some embodiments, the drill guide 330 may be shaped with a symmetrical V 336 toward the distal end, before the tip, to improve insertion into the joint between the ilium and sacrum. The symmetrical V is illustrated in FIG. 74A. In alternative embodiments, the drill guide, as well as other insertion instruments, may have an asymmetrical V shape 337 at the end to accommodate the different size and shape of the ilium and sacrum; this is illustrated on the rasp in FIG. 73C. The asymmetrical V shape 337 may help align the instruments to ensure they do not move around in the joint.

FIGS. 76A-82B depict additional embodiments and examples of SI joint implant systems, procedures for implanting SI joint implant systems 100, and related tools. The SI joint implant system of FIG. 76A can include any of the same or similar features and functions as any of the other SI joint implant systems described herein and vice versa.

As described herein, an SI joint implant system 100 can include a primary implant 102 and a secondary implant 104. In certain embodiments, the secondary implant 104 can be inserted first into the SI joint line with one anchor 106 in the ilium and one anchor 106 in the sacrum. The implant can be impacted into approximately the middle of the sacroiliac joint (e.g., between the sacrum and the ilium) for equal force distribution. This can ensure all of the forces are equally distributed across the implant. An example of an axis 600 that extends approximately in the middle of the sacroiliac joint is shown in FIG. 76B. As the secondary implant 104 is impacted into the joint a bevel at the distal tips of the anchors 106 of the secondary implant 104 can compress the sacroiliac joint. An example of a bevel 117 at the distal tips is shown in FIGS. 83A-83C. Once the secondary implant 104 is in place the primary implant 102 can be placed or engaged to the secondary implant 104, as described herein.

In certain embodiments, the implant system can resist forces on the SI joint including shear, nutation, counternutation, compression, and distraction.

In some embodiments, the primary implant 102 and secondary implant 104 may be placed in the sacroiliac joint together at one time simultaneously or separately depending on physician preference or patient anatomy. In some embodiments, a specially designed inserter that allows for simultaneous placement may be utilized for simultaneous insertion.

The ultimate resting position of the implant system may be placed at a depth near the surface of the SI joint or may be placed at a depth X5 from a posterior end of the SI joint in the middle of the SI joint (e.g., so that a proximal end of the implant system 100 is positioned at the depth X5) to equally distribute forces and provide enhanced stabilization. The implant system can be positioned near the midline of the articular surface of the joint, between the posterior portion and anterior portion of the joint. In some embodiments, the implant system can be countersunk within the SI joint at a depth in approximately the middle portion of the SI joint. In some embodiments, a drill can be advanced about 30 mm to 40 mm into the joint, which can allow the implant system to be countersunk in the middle of the articular surface of the joint. In some embodiments, the depth X5 when the implant system 100 is positioned at a depth in the middle of the SI joint can be about 8 mm, about 10 mm, or about 12 mm. In some embodiments, the depth X5 when the implant system 100 is positioned at a depth in the middle of the SI joint can be between 8 mm and 12 mm. In some embodiments, the implant system 100 can be positioned at depths of at least 6 mm, at least 8 mm, at least 10 mm, at least 12 mm, between 0 and 20 mm, between 0 mm and 18 mm, between 0 mm and 12 mm, between 6 mm and 14 mm, between 3 mm and 10 mm, between 5 mm and 10 mm, or any other suitable depth. The implant system can be between 20 mm and 40 mm in length. In some embodiments, countersinking the implant by between 5 mm and 10 mm can be advantageous for allowing bone graft material to be packed behind the implant.

Countersinking the primary implant 102 and secondary implant 104 at a depth X5 in the approximately middle portion of the SI joint can create a socket behind the implant system 100 in which bone graft can be placed. FIG. 76B depicts an example of the implant system 100 countersunk within the SI joint having bone graft 700 positioned within a socket behind the implant system 100. FIG. 76B shows a portion of the bone cut-away to provide visibility of the implant system.

In some embodiments, bone graft material may introduced into the SI joint prior to introducing the implant system 100. In some embodiments, bone graft material may be positioned bone graft material may be applied to a distal end of the secondary or primary implant prior to implantation to provide bone graft material distal to the implant system upon implantation into the SI joint.

As described herein, in certain embodiments, a drill bit or reamer may be used in a procedure for implanting an SI joint system, which may result in an area between the ilium and sacrum that has been prepared with the drill bit or reamer, which can enhance graft incorporation behind the implant system. This a potential area for fusion to occur between the ilium and sacrum. The area for bone graft to be placed can hold 2.5 cc-10 cc of bone graft material, which may include allograft, autograft, or synthetic bone grafts. The amount of bone graft material that can be placed behind an implant may depend on the patient's anatomy and the depth of countersinking of the implant. For example, in certain embodiments, 5 cc or about 5 cc of bone graft material may be placed when the implant system is positioned at a depth of about 10 mm.

In certain embodiments, the secondary implant 104 can resist all of the forces of the SI joint when it spans across the SI joint. The secondary implant 104 can be placed on the sacral side and ilium side, with one anchor 106 on each side.

In some embodiments, for stronger fixation and increased compression, a first anchor 106 of the secondary implant 104 can be placed so that the implant spans or transfixes both cortices of the ilium. In some embodiments, the other anchor 106 can be placed in the sacrum. The anchor 106 on the ilium side can be malleted directly into the ilium or can slide down the outside of the ilium and can pull the ilium and sacrum together. Examples of implant system in which the secondary implant 104 transfixes both cortices of the ilium are shown in FIGS. 77A-77B. As shown in FIG. 77B, the secondary implant can extend across three cortices (on the outside of the ilium, on the inside of the ilium, and on the inside of the sacrum. This can provide stronger fixation, increased compression, and increased stability.

In some embodiments, the arm 146 that connects the anchor 106 to the ring 124 of the secondary implant 104 can transfix completely across both cortices of the ilium and the other arm 146 that connects the anchor 106 to the ring 124 can transfix the sacrum.

In some embodiments, there are other ways that an implant can be inserted from a posterior approach and transfix or span both cortices of the ilium and transfix the sacrum. This may be accomplished by using different shapes, sizes, materials, designs, etc. This style of implant may provide fixation and compression and fixation like that provided by the secondary implant 104 described herein.

Once the secondary implant 104 is placed in the desired location the primary implant 102 may be threaded or inserted by other means through the secondary implant 104 to the desired location. The primary implant 102 can be placed to prevent secondary implant 104 or anchor 106 pullout.

The secondary implant 104 may be placed at a variety of angles as long as it engages in the ilium or sacrum. Depending on anatomy or entry point of the joint the user may place the secondary implant 104 at an angle such that the implant system 100 (e.g., a longitudinal axis of the implant system 100, a longitudinal axis of the primary implant 102, and/or a longitudinal axis of the secondary implant 104) is positioned at an angle (e.g., relative to the axis 600) and not right down the joint line. When placed at an angle, the secondary implant 104 can be configured to still span the joint to provide stability. When the anchor 106 or secondary implant 104 is placed at an angle it can cause the trajectory of the primary implant 102 or screw to extend primarily into either the ilium or sacrum. As described herein, the primary implant 102 or screw can be placed to prevent the secondary implant 104 from migrating and when in bone such as the ilium or sacrum, and can provide implant purchase to prevent migration. As long as the anchor 106 or secondary implant 104 crosses the joint the joint will be stable regardless of whether the primary implant 102 is positioned primarily in the ilium or sacrum. An example of the primary implant 102 positioned primarily in the ilium is shown in FIG. 78. An example of the primary implant 102 positioned primarily in the sacrum is shown in FIG. 79.

In certain embodiments, a method for implanting an implant system 100 in an SI joint can include placing a guidewire within the SI joint. After the guidewire is placed, one or more dilators can be used to dilate tissue. After dilation a drill guide may be placed and a drill tool/drill bit may be placed down the guide to prepare the SI joint for implantation of the implant system. The implant system 100 may then be implanted as described herein. After implantation, bone graft material (e.g., bone graft material 700) can be packed behind the implant system within the socket.

In certain embodiments, a method for implanting an implant system in an SI joint can include placing a guidewire within the SI joint. After the guidewire is placed, a rasp and/or joint finder/joint locator can be advanced to the SI joint, as described herein. The rasp may be used to create an area of decortication in the SI joint around (e.g., laterally beyond a cross-sectional area of) the primary implant 102 to promote bone fusion. Next, a drill guide may be placed and a drill tool/drill bit may be placed down the guide to prepare the SI joint for implantation of the implant system. The implant system may then be implanted as described herein. After implantation, bone graft material can be packed behind the implant system within the socket.

An embodiment of a drill guide 330 is shown in FIGS. 80A-81C. The drill guide 330 may include one or more tangs or teeth 335 that can serve as anchor points for the drill guide 330. For example, in certain embodiments, the drill guide can include 2, 3, 4, or any other suitable number of teeth or tangs 335. For example, in an embodiment with 4 teeth 335, 2 teeth 335 can be positioned in the joint line, 1 tooth 335 can be positioned in the sacrum, and 1 tooth 335 can be positioned in the ilium. In some embodiments, a drill guide may have any combination of 1 or 2 teeth 335 positioned in the joint line, 1 tooth 335 positioned in the sacrum, and 1 tooth 335 positioned in the ilium, for example, depending on surgeon preference. As shown in FIGS. 80A and 80C, in some embodiments, each of the teeth 335 can be positioned at a distal end of the drill guide.

In certain embodiments, the drill bit or reamer may have a single consistent diameter throughout the length of the drill bit or may have a wider crown to prepare the SI joint for the secondary implant 104 as it may be wider than the primary implant 102. In some embodiments, the drill bit or reamer may have a distal end that is more narrow than the proximal end the drill bit or reamer. It may be tapered from distal to proximal end or may be two separate diameters.

FIG. 82A depicts a kit that may be used to implant an SI joint implant system. The kit can include one or more of any of the following: one or more guidewires, guide pins, or rods 300; one or more rasps 400; one or more drill guides 330; an impact cap 808; a t-handle 810]; one or more drills or drill bits 500; one or more inserter main bodies 421; a one or more inserter secondary bodies 422; an inserter driver 814 (e.g., a hexalobe driver); a plastic pin puller 816; an instrument removal tool 818; a caddy 820; one or more primary implants 102; one or more secondary implants 104; a graft tamp 826; a tissue dilator 320; and a sterilization tray 830.

In some embodiments, the pin puller 816 can be used to pull a guidewire. If a guidewire is stuck, the pin puller 816 can be used to apply force so that the guidewire can be extracted.

In certain embodiments, following a drilling procedure (e.g., to prepare a surgical location), bone graft can be delivered through a drill guide 330. In some embodiments, a tamp 826 can be used to push the graft.

The caddy 820 allows implants to be loaded and keeps them aligned while loading on an all-in-one inserter.

The instrument removal tool 818 can be inserted into an instrument, such as a rasp 400 and used to remove the instrument.

FIG. 82B depicts an embodiment of an inserter 840. In certain embodiments, the inserter 840 can be an all-in-one inserter as described herein. In certain embodiments, the inserter 840 can include components of the kit of FIG. 82A. In certain embodiments, the inserter 840 can include an inserter main body 421 and an inserter secondary body 422. The inserter secondary body 422 can be coupled to a primary implant 102 and removably secure the primary implant 102. The inserter primary body 421 can engage a secondary implant 104. The inserter secondary body 422 can be advanced through the inserter primary body 421 and used to thread the primary implant 102 into the secondary implant 104 to secure the primary implant 102 and secondary implant 104 to the inserter 840. FIG. 82B depicts a cross-sectional view of the inserter 840.

After the primary implant 102 and secondary implant 104 are coupled with the inserter 840, the inserter 840 can be advanced into the body towards a treatment region (e.g., an SI joint or facet joint). Advancing both the primary implant 102 and secondary implant 104 together with an assembled inserter 840 can provide ease of use and prevent passing of different instruments and engagement issues, for example, in comparison to separate insertions using two different instruments, which may run the risk of cross-threading or other issues.

In some embodiments, an impact cap 808 can be coupled to the inserter 840 (e.g., to a proximal end of the inserter secondary body 422). The impact cap 808 can then be malleted to drive the secondary implant 104 into bone.

After the secondary implant 104 is in the desired position, a driver 814 can be used to deploy the primary implant 102. In some embodiments, the driver 814 can be used to advance (e.g., thread) the primary implant 102 into a joint (e.g., an SI joint or facet joint).

In some embodiments, the handle 810 can be coupled to the driver 814 and rotated to rotate the driver 814 and advance the primary implant 102.

After the primary implant 102 and secondary implant 104 are in position, the inserter 840 and driver 814 can be uncoupled from the implant system and removed from the body.

FIGS. 83A-83C depict another embodiment of the SI joint implant system 100. The joint implant system 100 can include any of the same or similar features and/or functions as the other joint implant systems described herein (e.g., the implant system 100 of FIGS. 72A-72F). FIG. 83A depicts a side view of the implant system 100.

The implant system 100 includes a primary implant 102 and a secondary implant 104. The primary implant 102 includes engagement features 103, which can be in the form of threads, extending proximally from a distal end towards a head of the primary implant 102. The primary implant 102 can also include a smooth or threadless shank section of the shank positioned proximally of the threads. The threads can extend between the smooth shank section and the distal end. In other embodiments, the engagement features 103 (e.g., threads) may extend over an entire length of the shank.

FIGS. 83B and 83C depict perspective views of the secondary implant 104. As shown in FIGS. 83A-83C, the anchors 106 can include a distal edge 112. The edge 112 may converge or taper to a sharp distal point. For example, the edge may converge or taper laterally inwards (e.g., from one lateral direction inwards and the opposite lateral direction inwards, wherein the lateral directions refer to left and right directions of the page with respect to FIG. 83A).

In some embodiments, the edge 112 may converge to a blunted or curved distal end generally inwards from the anterior and posterior direction (e.g., into and out of the page with reference to FIG. 83A), alternatively or in addition to converging generally laterally inwards to a sharp distal end.

In some embodiments, the edge 112 may be a beveled tip. The beveled tip can include a beveled surface 117 as shown in FIGS. 83A-83C. The beveled surface 117 may be oriented at the angle between 20 degrees and 35 degrees, between 15 degrees and 40 degrees, or any other suitable angle. In some embodiments, the angle can be 27.5 degrees. In some embodiments, the angle can be greater than 15 degrees, greater than 20 degrees, greater than 30 degrees, greater than 40 degrees, greater than 50 degrees, or any other suitable angle. As the secondary implant 104 is impacted into the SI joint the beveled surface 117 can cause compression of the sacroiliac joint (e.g., compression between the ilium and sacrum). In some embodiments, the greater the angle, the greater the compression caused.

In certain embodiments, the one or more anchors 106 can be coupled to an anchor ring 124 by one or more arms 146. The arms may include a cutting keel or edge 119 for cutting bone as the secondary implant 104 is driven into the SI joint.

In certain embodiments, the primary implant can include a hydrophilic surface 121. The hydrophilic surface can attract and hold bone marrow aspirate (BMA) and other fluids that may container growth factors. In some embodiments, the surface 121 can be an acid etched coating, a bead blasted surface, and/or a 3D printing of a roughened metal surface to allow for and promote bone ingrowth.

The primary implant 102 can include a truss or beam system 154. In some embodiments, the truss or beam system 154 can form a trellis configuration. The truss or beam system 154 can act as a scaffolding to provide increased biomechanical strength to the implant 102 and to facilitate bone growth. The truss or beam system 154 can facilitate fusion with surrounding bone. The truss or beam system 154 can also provide stability as the implant 102 fuses with the surrounding bone.

The truss or beam system 154 can be formed of a plurality of truss elements or beams 156. In some embodiments, the plurality of truss elements or beams 156 can extend between at least some of the engagement features 103. A number of windows or openings 158 can be formed between the truss elements of beams 156 of the truss or beam system 154 to facilitate fusion of the implant with surrounding bone. The openings 158 can be between 500 μm and 750 μm. The openings 158 can be positioned so that at least some of the openings 158 will contact the bone of the sacrum and the ilium regardless of the orientation of the primary implant 102 when fully seated within the SI joint to promote bony ingrowth. In certain embodiments, the primary implant may include a wall (e.g., the shank) separating the system 154 and openings 158 from an inner cannula or channel of the primary implant 102.

In certain embodiments, any of the joint implant systems described herein or components thereof may be implanted within a facet joint. Similarly, any of the implantation methods described herein or steps thereof may be used to implant a joint implant system within a facet joint. Any of the implantation tools described herein or components thereof may be used to implant a joint implant system within a facet joint.

For example, in certain embodiments, a first anchor of a secondary implant can be implanted within a superior articular facet, and a second anchor of the secondary implant can be implanted within an inferior articular facet. In certain embodiments, the anchors may have beveled edges to cause compression of the facet joint.

In certain embodiments, a primary implant can be implanted within the facet joint. In some embodiments, the primary implant can be implanted such that a longitudinal axis of the primary implant is parallel with or generally parallel with an axis that extends approximately in the middle of the facet joint (e.g., down the joint line). In other embodiments, the primary implant can be positioned at an angle with the axis extending approximately in the middle of the facet joint so that the primary implant is positioned primarily in the superior articular facet or primarily in the inferior articular facet.

In some embodiments, the primary implant can be placed through the secondary implant to prevent the secondary implant from backing out and to resist forces within the facet joint.

In some embodiments, the primary implant can be countersunk within the facet joint, and bone graft material can be packed over the proximal end of the primary implant. In some embodiments, bone graft material can be placed distal to the distal end of the primary implant. For example, in some embodiments, bone graft material can be placed distal to the distal end of the primary implant and the primary implant can be positioned proud of the facet joint.

The implant system can resist forces of the facet joint (e.g., shearing forces, external forces that compress/distract the facet joint, etc.). In some embodiments, the implant system can help prevent implant migration and allow for fusion of the facet joint.

An example of a joint implant system 100 that may be implanted in a facet joint is depicted in FIGS. 84A-84G. The joint implant system 100 can include any of the same or similar features and/or functions as the other joint implant systems described herein (e.g., the implant system 100 of FIGS. 72A-72F, the implant system 100 of FIGS. 83A-83C, etc.) and vice versa.

Figure 84B:
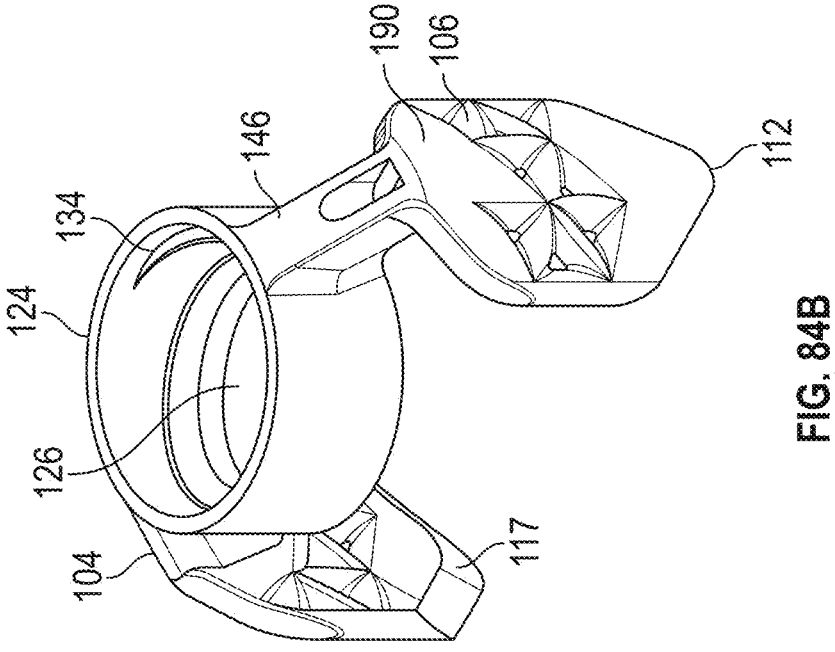
Figure 84A:
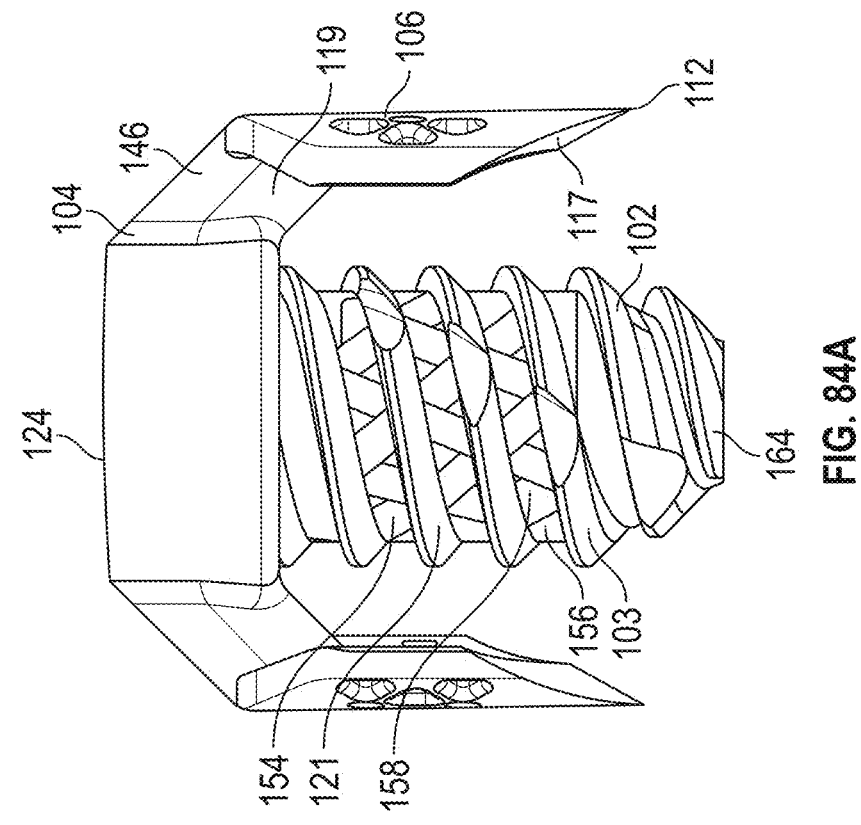
Figures 84C, 84D:
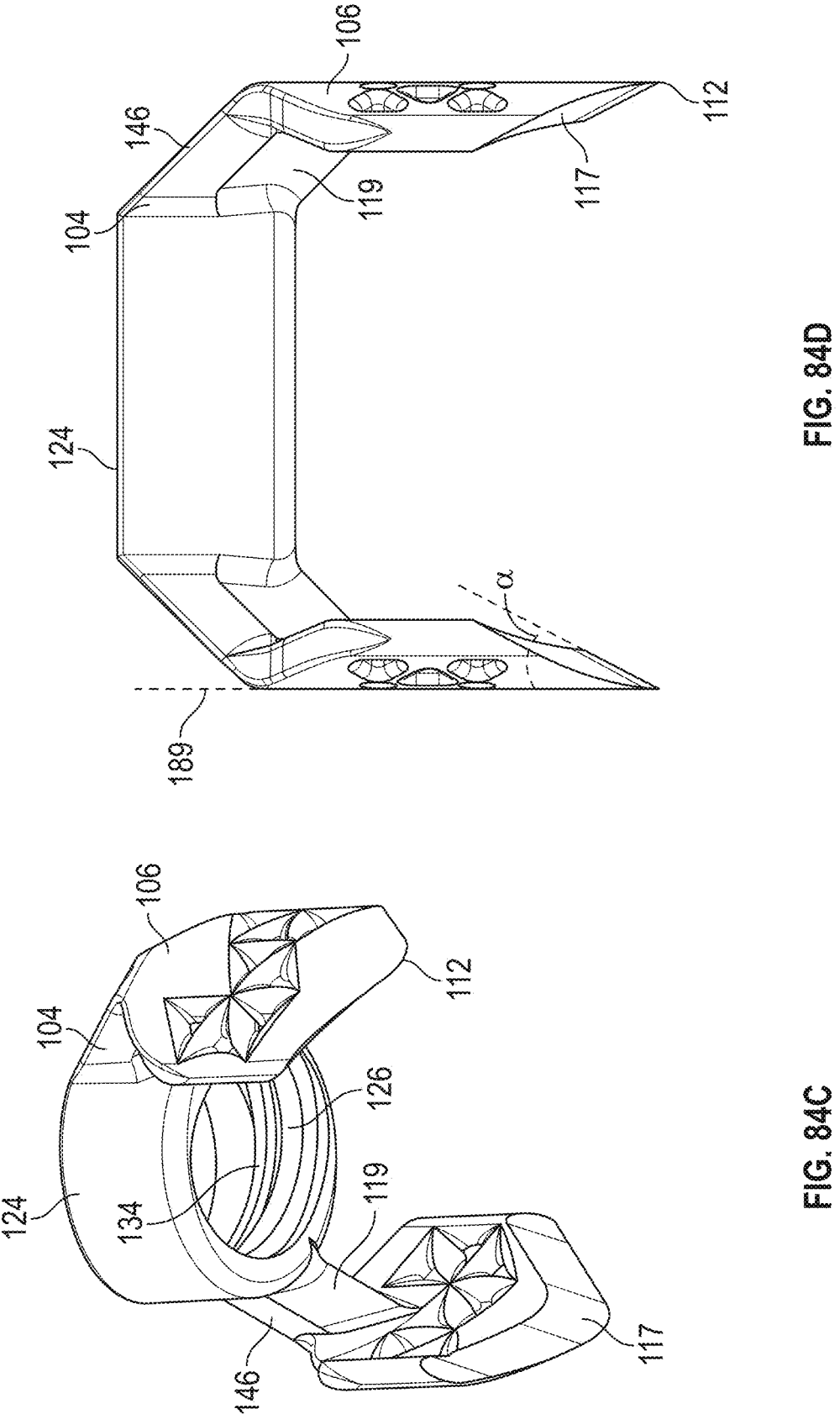
Figure 84F:
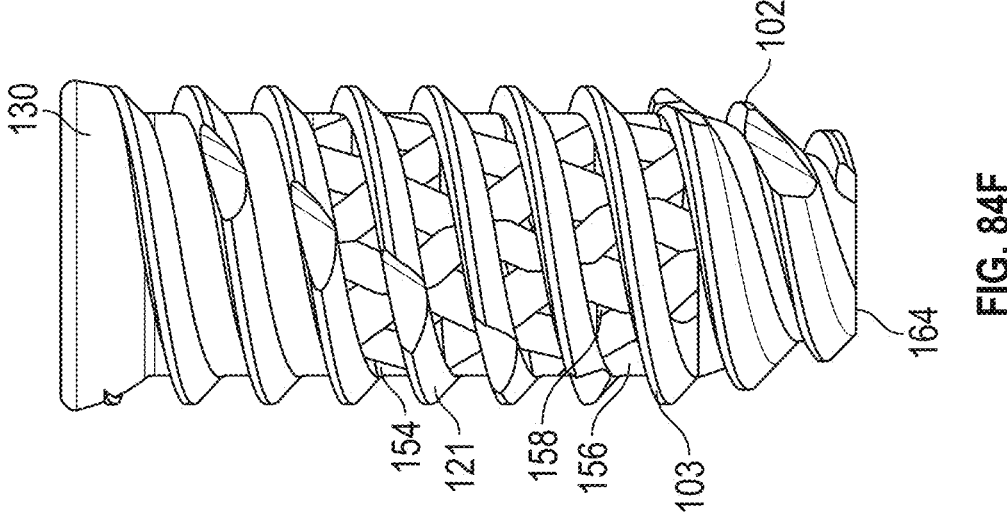
Figure 84E:
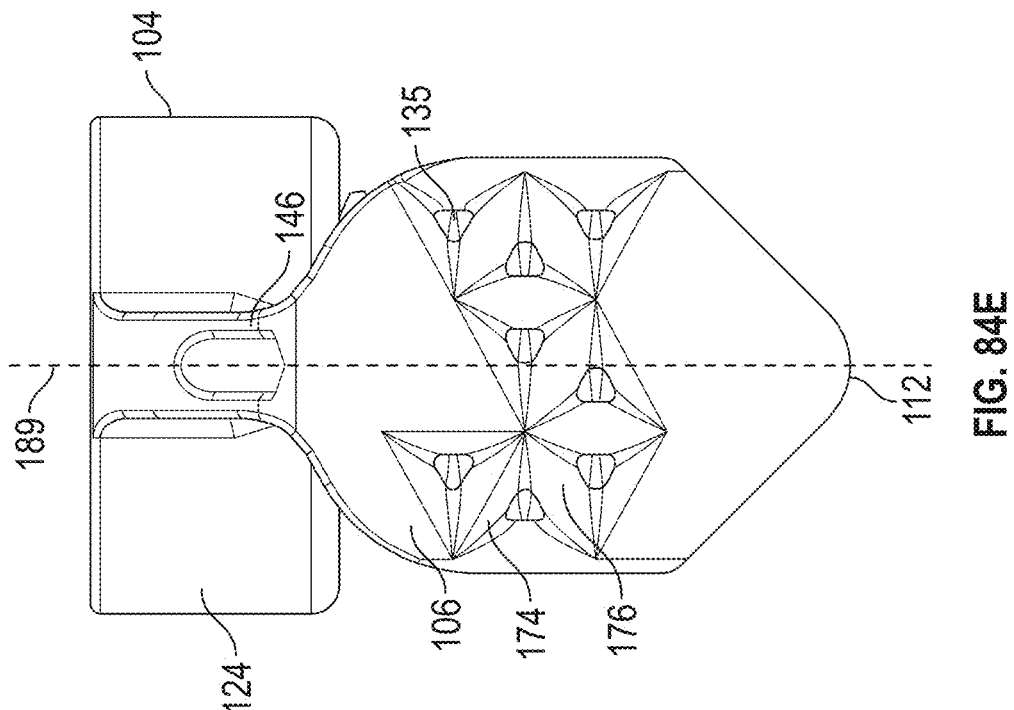
Figure 84G:
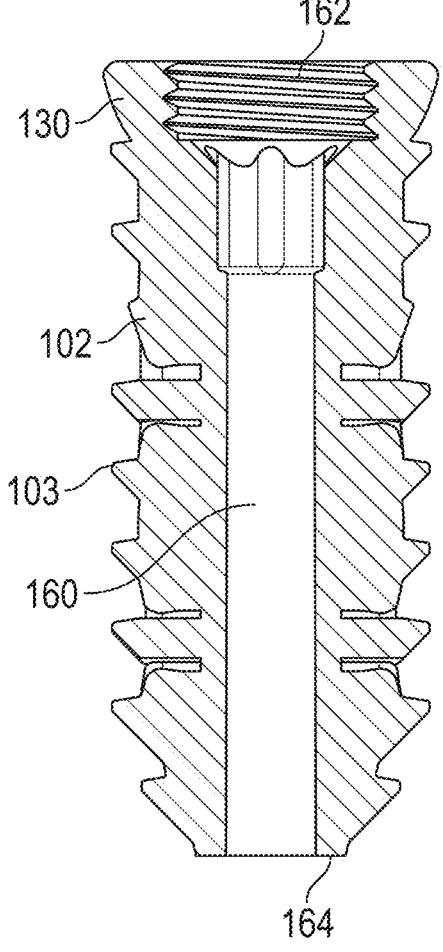

FIG. 84A depicts a side view of the implant system 100. The implant system 100 can include a primary implant 102 and a secondary implant 104. FIGS. 84B and 84C depict perspective views of the secondary implant 104. FIG. 84D and FIG. 84E depict side views of the secondary implant 104. FIG. 84F depicts a side view of the primary implant 102. FIG. 84G depicts a cross-sectional view of the primary implant 102.

In some embodiments, the primary implant 102 can be implanted within the facet joint. In some embodiments, the primary implant 102 can be implanted such that a longitudinal axis of the primary implant 102 is parallel with or generally parallel with an axis that extends approximately in the middle of the facet joint (e.g., down the joint line). In other embodiments, the primary implant 102 can be positioned at an angle with the axis extending approximately in the middle of the facet joint so that the primary implant 102 is positioned primarily in the superior articular facet or primarily in the inferior articular facet.

The primary implant 102 can include engagement features 103, which can be in the form of threads, extending proximally from a distal end towards a head of the primary implant 102. The engagement features 103 (e.g., threads) may extend over an entire length of a shank of the primary implant 102. In other embodiments, the primary implant 102 can include a smooth or threadless shank section of the shank positioned proximally of the engagement features 103. In such embodiments, the engagement features 103 can extend between the smooth shank section and the distal end.

In certain embodiments, the secondary implant 106 can be implanted across the facet joint. As shown in FIGS. 84A-84D, the secondary implant 104 can include anchors 106. In certain embodiments, a first anchor 106 can be implanted within a superior articular process of the facet joint, and a second anchor 106 can be implanted within an inferior articular process of the facet joint.

The anchors 106 can include a distal edge 112. The edge 112 may converge or taper to a sharp distal point. For example, the edge 112 may converge or taper laterally inwards (e.g., from one lateral direction inwards and the opposite lateral direction inwards, wherein the lateral directions refer to left and right directions of the page with respect to FIG. 84A).

In some embodiments, the edge 112 may converge to a blunted or curved distal end generally inwards from the anterior and posterior direction (e.g., into and out of the page with reference to FIG. 84A), alternatively or in addition to converging generally laterally inwards to a sharp distal end.

In some embodiments, the edge 112 may be a beveled tip. The beveled tip can include a beveled surface 117 as shown in FIGS. 83A-83C. The beveled surface 117, or beveled edge, can be on a portion of the inner surface of at least one of the first anchor 106 or second anchor 106. The inner surface can be the portion of the anchor facing the central axis of the secondary implant 104. The beveled surface can include an internal beveled angle $\alpha$. In certain embodiments, the beveled angle $\alpha$ can be measured relative to an insertion axis of the implant 102. In some embodiments, the beveled surface 117 may be oriented at the angle $\alpha$ relative to a proximal-distal axis 189 extending along an outer face 190 of the anchor 106. In some embodiments, the proximal-distal axis 189 can be parallel to the insertion axis. In some embodiments, the proximal-distal axis 189 can be the midline of the anchor 106. In some embodiments, the angle $\alpha$ can have a positive value between 0 degrees and 90 degrees (e.g., relative to the insertion axis). In some embodiments, the angle $\alpha$ can be between 20 degrees and 35 degrees, between 15 degrees and 40 degrees, or any other suitable angle. In some embodiments, the angle $\alpha$ can be 27.5 degrees. In some embodiments, the angle can be greater than 15 degrees, greater than 20 degrees, greater than 30 degrees, greater than 40 degrees, greater than 50 degrees, or any other suitable angle. As the secondary implant 104 is impacted into the facet joint the beveled surface 117 can cause compression of the facet joint (or SI joint in other embodiments). In some embodiments, the greater the angle $\alpha$, the greater the compression caused. In some examples, the beveled surface 117 can extend less than or equal to 75% of the length of the anchor 106. For example, the beveled surface can extend proximally from the distal end of the implant over less than or equal to 75% of the length of the anchor 106. The beveled surface 117 can extend between 30% and 75% of the length of the anchor 106 (e.g., extending proximally from the distal end of the anchor 106). The beveled surface 117 can extend between 25% and 50% of the length of the anchor 106 (e.g., extending proximally from the distal end of the anchor 106). The beveled surface 117 can extend between 10% and 40% of the length of the anchor 106 (e.g., extending proximally from the distal end of the anchor 106).

In certain embodiments, the one or more anchors 106 can be coupled to an anchor ring 124 by one or more arms 146. The arms may include a cutting keel or edge 119 for cutting bone as the secondary implant 104 is driven into the SI joint.

In certain embodiments, the primary implant can include a hydrophilic surface 121. The hydrophilic surface can attract and hold bone marrow aspirate (BMA) and other fluids that may container growth factors. In some embodiments, the surface 121 can be an acid etched coating, a bead blasted surface, and/or a 3D printing of a roughened metal surface to allow for and promote bone ingrowth.

The primary implant 102 can include a truss or beam system 154. In some embodiments, the truss or beam system 154 can form a trellis configuration. The truss or beam system 154 can act as a scaffolding to provide increased biomechanical strength to the implant 102 and to facilitate bone growth. The truss or beam system 154 can facilitate fusion with surrounding bone. The truss or beam system 154 can also provide stability as the implant 102 fuses with the surrounding bone.

The truss or beam system 154 can be formed of a plurality of truss elements or beams 156. In some embodiments, the plurality of truss elements or beams 156 can extend between at least some of the engagement features 103. A number of windows or openings 158 can be formed between the truss elements of beams 156 of the truss or beam system 154 to facilitate fusion of the implant with surrounding bone. The openings 158 can be between 500 μm and 750 μm. The openings 158 can be positioned so that at least some of the openings 158 will contact the bone of the superior articular facet and the inferior articular facet regardless of the orientation of the primary implant 102 when fully seated within the SI joint to promote bony ingrowth. In certain embodiments, the primary implant may include a wall (e.g., the shank) separating the system 154 and openings 158 from an inner cannula or channel of the primary implant 102.

In certain embodiments, the primary implant 102 can be cannulated from the proximal end to the distal end, having a channel 160 extending between the proximal end and the distal end. In some embodiments, as described in further detail herein, the channel 160 can allow for a guidewire or guide rod to extend through the implant 102.

In some embodiments, the primary implant 102 can be loaded with demineralized bone matrix (DBM), cortical fibers, synthetic bone matrix, BMP2 or BMP7, peptide graft, autograft or any combination thereof. In some embodiments, the channel 160 can be packed and/or filled with bone graft material. In some embodiments, the openings 158 and/or alternative openings may be in communication with the channel 160. When the channel 160 is packed and/or filled with bone graft material, the bone graft material can flow through the openings 158 for introduction of bone graft material within the channel 160 to the SI joint. In other embodiments, the channel 160 is separated from the openings 158 (e.g., via a wall).

The truss or beam system 154 can allow for larger volumes of bone graft material to be packed into the implant 102 while maintaining the biomechanical strength of the implant in comparison to implants without a truss or beam system 154.

In some embodiments it may be desirable for the channel 160 to have a diameter large enough to receive bone graft, but small enough to avoid or inhibit deformation of breakage due to fragility. The diameter can also be sufficiently small for the implant to fit in a desired anatomic location, such as the facet joint or SI joint.

In certain embodiments, acid etching, bead blasting, surface coating such as HA (Hydroxyapatite), or any other suitable surface technology may be utilized to enhance the surface finish to create an optimal area for bone to grow to in the primary implant 102. In certain embodiments, 3D printing may be utilized to create surfaces structures and features for bone to grow to. In certain embodiments, the surface structures may be on the nanometer or micrometer scale which can be optimal or desirable for bone to grow to.

In certain embodiments, the primary implant 102 may be CNC machined, 3D printed, or manufactured by any other suitable means. In certain embodiments, the primary implant 102 can be made of stainless steel, titanium, poly-ether-ether-ketone (PEEK), ceramic, human allograft or any other suitable implantable material strong enough to resist the forces described herein and pass biomechanical testing. In certain embodiments, the implant material can be important to achieve bony ingrowth.

In certain embodiments, the implant can be configured to be inserted with a driver, such as a hex driver, a star driver, a square driver, a torx driver, or any other suitable driver for driving the implant into bone. The proximal end of the implant 102 can include an engagement feature 162 for coupling with an inserter such as in FIG. 5A, as described herein. The engagement feature 162 may be a recess configured to couple with an inserter. The engagement feature 162 can be shaped to couple with a hex driver, a star driver, a square driver, a torx driver, or any other suitable driver for driving the implant 102 into bone.

As shown in FIG. 84F, a tip 164 of the implant can be flat. In certain embodiments, the primary implant 102, or a shank of the primary implant 102, may be conical. In certain embodiments, the primary implant 102 or the shank can be tapered. In certain embodiments, the primary implant 102 or shank can be symmetrical about a central axis with no taper. In some embodiments, the primary implant 102 or the shank can be untapered throughout the entire length of the implant or a portion of the length. For example, the shank can have a uniform cross-section or a generally uniform cross-section. In some embodiments, the engagement features 103 (e.g., threads) can extend a uniform distance or generally uniform distance from the shank throughout the length of the primary implant 102. Such untapered embodiments may further prevent or reduce migration or back out of the primary implant 102 from the SI joint in comparison to tapered implants. In some embodiments, the primary implant 102 can be self tapping or self drilling.

In some embodiments, the primary implant 102 may be only partially cannulated. For example, the channel 160 may extend from the proximal end only partially along the length of the primary implant 102 towards the distal end. In other embodiments, the primary implant 102 may not be cannulated. In other words, the implant 102 may have a solid core. A primary implant 102 that is only partially cannulated may have a higher biomechanical strength than an implant that is cannulated through its entire length. An implant that is not cannulated may have a higher biomechanical strength than a partially or fully cannulated implant.

FIGS. 85A-85B show examples of implant systems 100 implanted within the facet joints.

As shown in FIGS. 85A-85B, the implant system 100 can anchor within the superior articular process and the inferior articular process.

As shown in FIGS. 85A-85B, the secondary implant 104 can extend across the joint and be implanted into the superior articular process and the inferior articular process. The primary implant 102 can be implanted down the joint line (e.g., generally parallel with an axis that extends approximately in the middle of the facet joint) or slightly off-axis to the joint line.

The implant system 100 can prevent the facet joint from opening once implanted and can apply compression to assist with joint fusion.

In some embodiments, the primary implant 102 can be inserted prior to the secondary implant 104. In other embodiments, the secondary implant 104 can be inserted prior to the primary implant.

In some embodiments, the primary implant 102 can be countersunk within the facet joint, and bone graft material can be packed over the proximal end of the primary implant 102. In some embodiments, bone graft material can be placed distal to the distal end of the primary implant 102. For example, in some embodiments, bone graft material can be placed distal to the distal end of the primary implant 102 and the primary implant 102 can be positioned proud of the facet joint.

In some embodiments, the primary implant 102 can be placed through the secondary implant 104 to prevent the secondary implant 104 from backing out and to resist forces within the facet joint.

The implant system 100 can resist forces of the facet joint (e.g., shearing forces, external forces that compress/distract the facet joint, etc.). In some embodiments, the implant system 100 can help prevent implant migration infusion of the facet joint.

Although described primarily with respect to a facet joint, the implant system 100 of FIGS. 84A-G may be implanted within an SI joint as described herein.

In certain embodiments, any of the primary implants described herein may have windows (e.g., windows 172 as described herein). The windows may be square, rectangular, circular, oblong, oval, polygonal, irregular, or any other suitable shape. The windows can provide an interface between an inner portion of the primary implant (e.g., an inner cannula or an inner passage) and the external environment (e.g., to promote bone fusion). In certain embodiments, the windows can facilitate packing of bone graft within the interior of the primary implant and can enable fusion completely through the primary implant. This can allow the sacrum and ilium, with respect to an SI joint, or two facets, with respect to a facet joint, to fuse, completely together and/or prevent or restrict motion, which may be advantageous for a long term successful surgical outcome. There may be one large window or multiple windows.

The window(s) may penetrate all the way through from one side to the other (e.g., to form a passage between one side of the primary implant and another side of the implant). In some embodiments, the primary implant may be generally solid or uncannulated between a proximal and distal end and the window(s) may penetrate all the way through the implant to form a passage within the implant. In other embodiments, the primary implant can be generally solid or uncannulated between a proximal and distal end and the window(s) may penetrate partially through the implant. In other embodiments, the primary implant can be fully or partially cannulated between a proximal and distal end and the windows can extend to the inner cannula. In some such embodiments, the window(s) and cannula can be connected. In some such embodiments, the window(s) and cannula can be connected to provide a passage between one side of the primary implant and other side of the primary implant.

The windows can advantageously provide a fusion through the primary implant (e.g., through a passage within the implant). Fusion through the primary implant may allow the implant to be permanently fixed within the joint and/or may prevent migration. The primary implant can be shaped, sized, and/or otherwise dimensioned so that a wall thickness is sufficiently thick to withstand the appropriate biomechanical forces. Larger windows may promote more fusion, but windows that are too large may cause wall weakness. In some embodiments, a maximum window size may be selected so that the implant is able to withstand the appropriate biomechanical forces. In some embodiments, one or more windows can be positioned so that the implant is able to withstand the appropriate biomechanical forces. The forces exerted on the primary implant can include shear, compression, torque, cantilever, etc.

The window(s) and/or passage(s) can be packed with any suitable bone graft of material, such as autograft, allograft, cellular graft, synthetic bone graft or any variation or combination thereof.

In certain embodiments, a passage extending between windows within a primary implant can include an inner surface having surface structures and/or features to promote bone growth and/or provide additional stability. For example, in certain embodiments, the surface structures may attract osteocytes and/or provide for cell attachment. In certain embodiments, CNC machining, 3-D printing, acid etching, bead blasting, surface coating such as HA (Hydroxyapatite), or any other suitable surface technology may be utilized to enhance the surface finish to create an optimal area for bone to grow to in the passage. In certain embodiments, the surface structures may be on the nanometer or micrometer scale which can be optimal or desirable for bone to grow to.

An example of a primary implant 102 that may be implanted in an SI joint or a facet joint is depicted in FIGS. 86A-86C. The primary implant 102 can include any of the same or similar features and/or functions as the other primary implants described herein and vice versa.

As shown, the primary implant 102 can include one or more windows 172. The one or more windows 172 can form a channel or passage 173 through an interior of the primary implant 102. For example, in some embodiments, a passage 173 may extend through the primary implant 102 between two windows 172 on different (e.g., opposing) sides of the implant. In some embodiments, a passage 173 can connect two windows 172. In some embodiments, the two windows 172 can be spaced 180 degrees apart from one another about the circumference of the primary implant 102.

In some embodiments, the passage 173 extending through the interior of the primary implant 102 can be level. For example, in some embodiments a central axis of the passage 173 can be perpendicular or generally perpendicular to the longitudinal axis of the primary implant 102 extending between the proximal end and distal end of the primary implant 102. In some embodiments, the central axis of the passage 173 can lie on a plane perpendicular to the longitudinal axis. In some embodiments, the windows 172 on opposing lateral sides of the primary implant 102 can be disposed at the same position along the length of the primary implant 102 between its proximal and distal end. In other embodiments, a central axis of the passage 173 can extend at a non-perpendicular angle relative to the longitudinal axis of the primary implant 102.

FIG. 86D depicts an implant system 100 positioned within an SI joint showing bone growth through the primary implant 102.

An advantage of the passage 173 and the windows 172 is that fusion can be viewed through the sacrum and ilium or through the facets during a CT scan. For example, when a passage 173 extends through the interior of the primary implant 102 between two windows 172, an operator and/or physician may see one solid window of fusion through the passage 173 from one window 172 to another window 172. In certain embodiments, the passage 173 can include an inner surface 175 having surface structures and/or features to promote bone growth. For example, acid etching, bead blasting, surface coating such as HA (Hydroxyapatite), or any other suitable surface technology may be utilized to enhance the surface finish of the inner surface 175 to create an optimal area for bone to grow to in the passage. In certain embodiments, the surface structures may be on the nanometer or micrometer scale which can be optimal or desirable for bone to grow to. As shown in FIG. 86D, the implant system 100 can be countersunk beneath the joint line of the SI joint. Advantageously, the bone graft material can be packed on top of the implant system 100 without the bone graft material going over the top of the joint. Bone fusion can be viewed through the windows 172 and in the surrounding area of the primary implant 102.

In certain embodiments, any of the secondary implants described herein may have windows (e.g., windows 178 as described herein). For example, in certain embodiments, one or more of the anchors of the secondary implant can include windows. The windows may be square, rectangular, circular, oblong, oval, polygonal, irregular, or any other suitable shape. The windows can provide an interface between an inner portion of the anchor (e.g., an inner cannula or an inner passage) and the external environment (e.g., to promote bone fusion). In certain embodiments, the windows can facilitate packing of bone graft within the interior of the anchor and can enable fusion completely through the anchor.

The window(s) may penetrate all the way through from one side to the other (e.g., to form a passage between one side of an anchor and another side of the anchor). In some embodiments, The windows can advantageously provide a fusion through the anchors. The anchors can be shaped, sized, and/or otherwise dimensioned so that a wall thickness is sufficiently thick to withstand the appropriate biomechanical forces. Larger windows may promote more fusion, but windows that are too large may cause wall weakness. In some embodiments, a maximum window size may be selected so that the anchors are able to withstand the appropriate biomechanical forces. In some embodiments, one or more windows can be positioned so that the anchor is able to withstand the appropriate biomechanical forces. The forces exerted on the anchors can include shear, compression, torque, cantilever, etc.

The window(s) and/or passage(s) can be packed with any suitable bone graft of material, such as autograft, allograft, cellular graft, synthetic bone graft or any variation or combination thereof.

In certain embodiments, the windows and/or passages of the anchors of the secondary implant can be aligned with the windows and/or passage of the primary implant to promote bone fusion through both the secondary implant and primary implant (e.g., along a continuous path through the anchors and primary implant). This can allow the sacrum and ilium, with respect to an SI joint, or two facets, with respect to a facet joint, to fuse, completely together and/or prevent or restrict motion, which may be advantageous for a long term successful surgical outcome. There may be one large window or multiple windows.

In certain embodiments, a passage extending between windows within an anchor of a secondary implant can include an inner surface having surface structures and/or features to promote bone growth. For example, acid etching, bead blasting, surface coating such as HA (Hydroxyapatite), or any other suitable surface technology may be utilized to enhance the surface finish to create an optimal area for bone to grow to in the passage. In certain embodiments, the surface structures may be on the nanometer or micrometer scale which can be optimal or desirable for bone to grow to.

An example of a secondary implant 104 that may be implanted in an SI joint or a facet joint is depicted in FIGS. 87A-87C. The secondary implant 104 can include any of the same or similar features and/or functions as the other secondary implants described herein and vice versa.

As shown, one or more of the anchors 106 of the secondary implant 104 can include one or more windows 178. One or more windows 178 can form a channel or passage 180 through an interior of one of the anchors 106. For example, in some embodiments, a passage 180 may extend through one of the anchors 106 between two windows 178 on different (e.g., opposing) sides of the anchor 106. In some embodiments, a passage 180 can connect two windows 178.

In some embodiments each anchor 106 can include a passage 180. In other embodiments, one of the anchors 106 can include a passage 180.

In some embodiments, the windows 178 of the anchors 106 can be positioned to align with the windows 172 of the primary implant 102 when the primary implant 102 and secondary implant 104 are assembled together. In some embodiments, the passages 180 of the anchors 106 can be positioned to align with the passage 173 of the primary implant 102 when the primary implant 102 and secondary implant 104 are assembled together, for example, to promote bone fusion through both the secondary implant and primary implant (e.g., along a continuous path through the anchors 106 and primary implant 102). For example, the passages 180 and the passage 173 may be coaxial.

An advantage of the passage 173 and the windows 172 is that fusion can be viewed through the sacrum and ilium or through the facets during a CT scan. For example, when a passage 173 extends through the interior of the primary implant 102 between two windows 172, an operator and/or physician may see one solid window of fusion through the passage 173 from one window 172 to another window 172.

In some embodiments, any of the primary implants described herein can be formed of one or more shape memory materials (e.g., metals or metal alloys, such as nitinol, and/or other non-metal materials. In some embodiments, such a primary implant may expand and contract. In some embodiments, such a primary implant may be heated or cooled to allow for compression. A primary implant having shape memory material may be beneficial for the facet joint. In certain embodiments, for example, a primary implant formed of shape memory material may be cooled outside of the body. When inserted into the body, the primary implant can experience a higher temperature and compress and tighten.

In other embodiments, the primary implant may be formed of one or more materials that do not bend or change shape, such as stainless steel. In some embodiments, a rigid material or non-shape memory material, such as stainless steel may be beneficial. For example, such material may be stronger and heavier weight bearing. Such primary implants may be beneficial in larger joints such as the SI joint.

In some embodiments, any of the secondary implants described herein and/or anchors thereof can be rigid to prevent breakage and provide compression when driven into bone.

In certain embodiments, a joint implant system may include an implant housing one or more retractable/extendable blades. The implant may be implanted within a joint, such as an SI joint or facet joint, and after implantation, the blades may be extended out of a body of the implant to engage bone of opposing sides of the joints (e.g., to engage a sacrum and ilium, to engage a superior articular facet and an inferior articular facet, etc.). The blades may be driven into the bone to prevent migration and assist with fusion. In some embodiments, the implant system can include an actuator tool, such as a pin or screw, that can be used to extend the blades out of the body of the implant.

FIGS. 88A-88J depict an embodiment of a joint implant system 8600. The joint implant system 8600 can include an implant 8602. The implant can be dimensioned, shaped, and/or otherwise configured to be positioned within a joint. For example, the implant 8602 can be positioned within a facet joint. In some embodiments, the implant 8602 can be positioned within a sacroiliac joint.

The implant 8600 can include a plurality of blades 8610. The blades 8610 may be extendable or advanceable from a body of the implant 8600. In some embodiments, the implant 8602 can have slots 8608 from which blades 8610 can extend. In some embodiments, the blades 8610 can extend diagonally from the implant 8600.

As shown, the implant 8600 can include four blades 8610. In other embodiments, the implant 8600 can include any number of blades 8610, for example, depending on the anatomy of the joint and the amount of fixation desired to assist with stabilization and fusion.

Figure 88A:
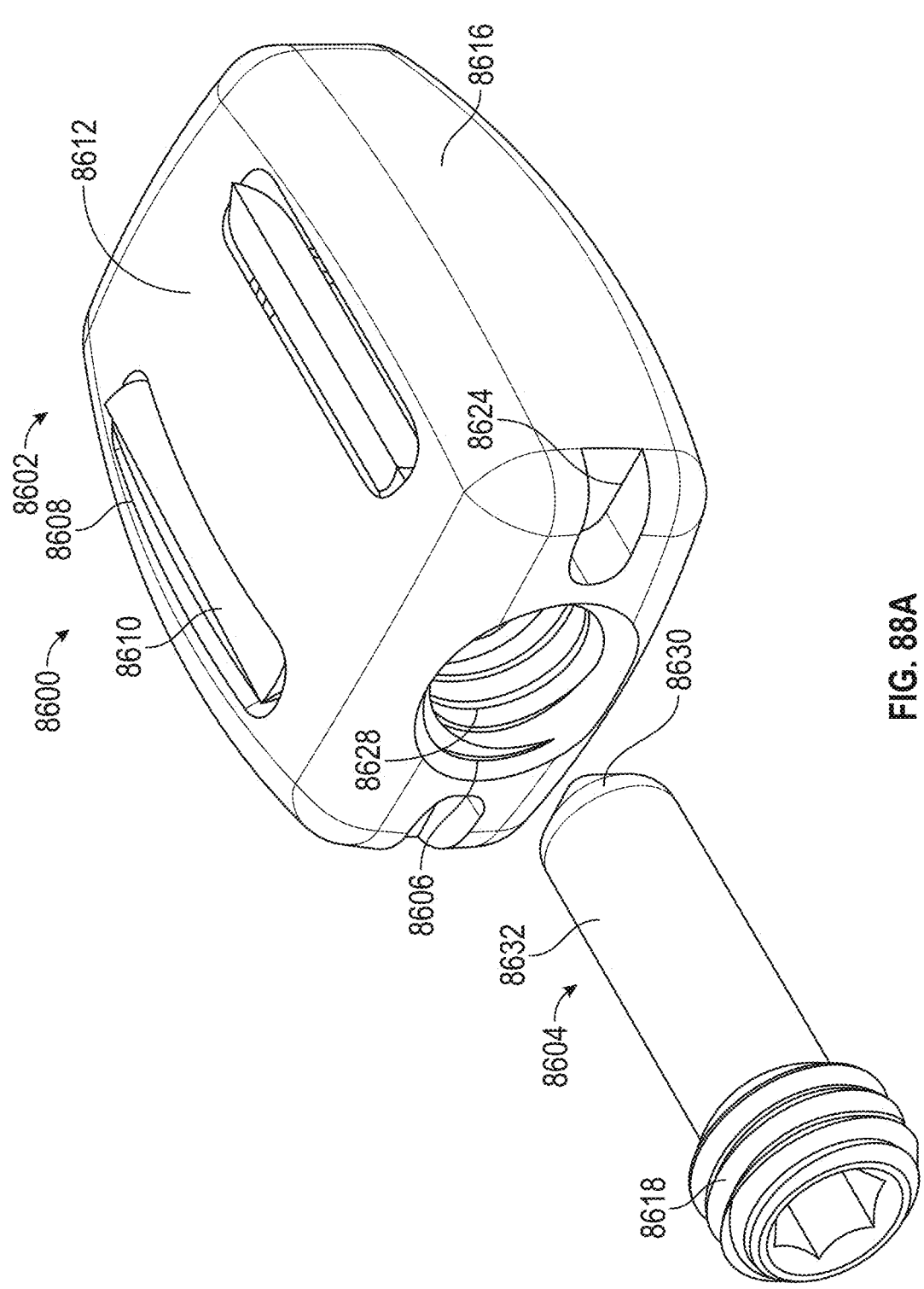
Figures 88B, 88C:
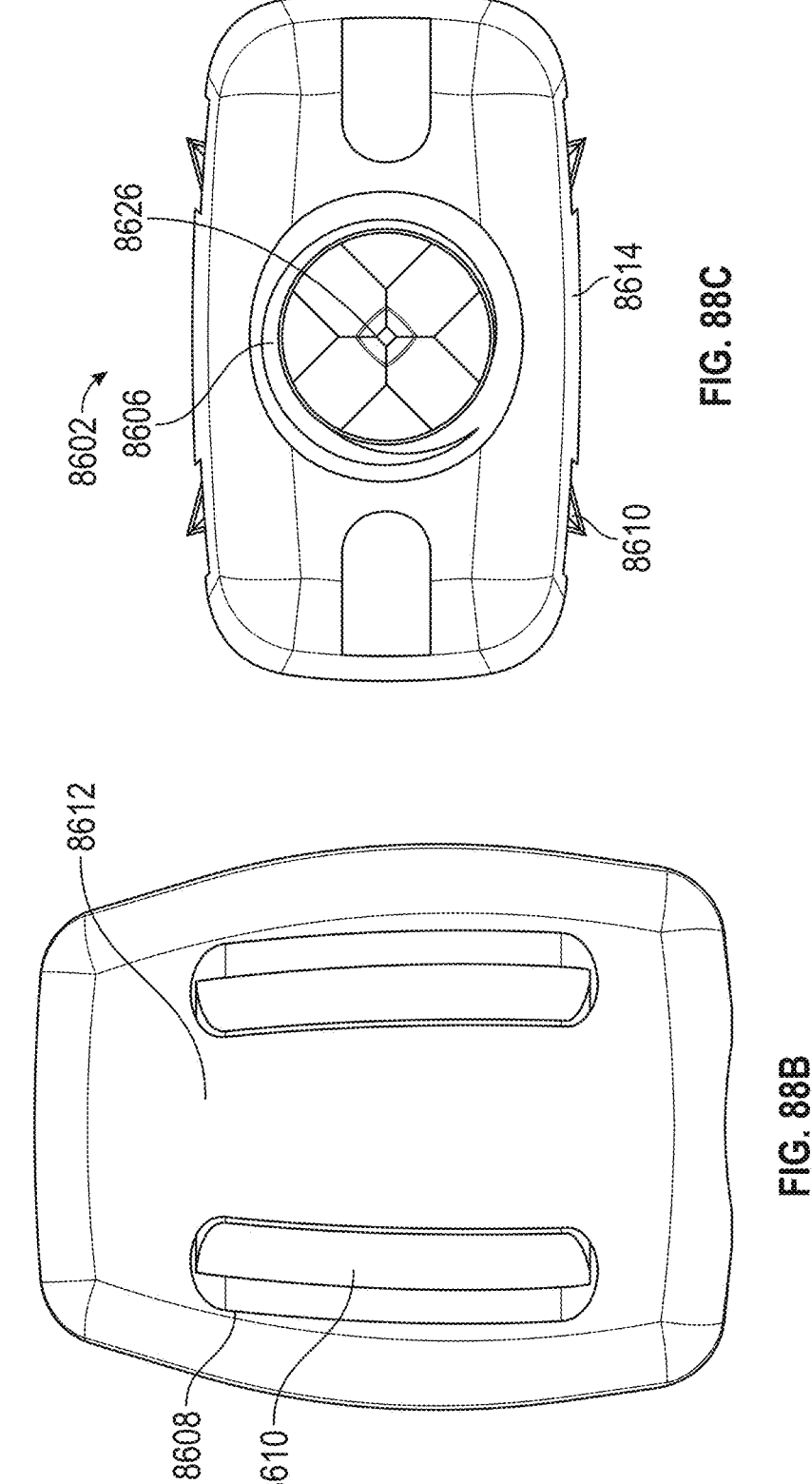
Figure 88E:
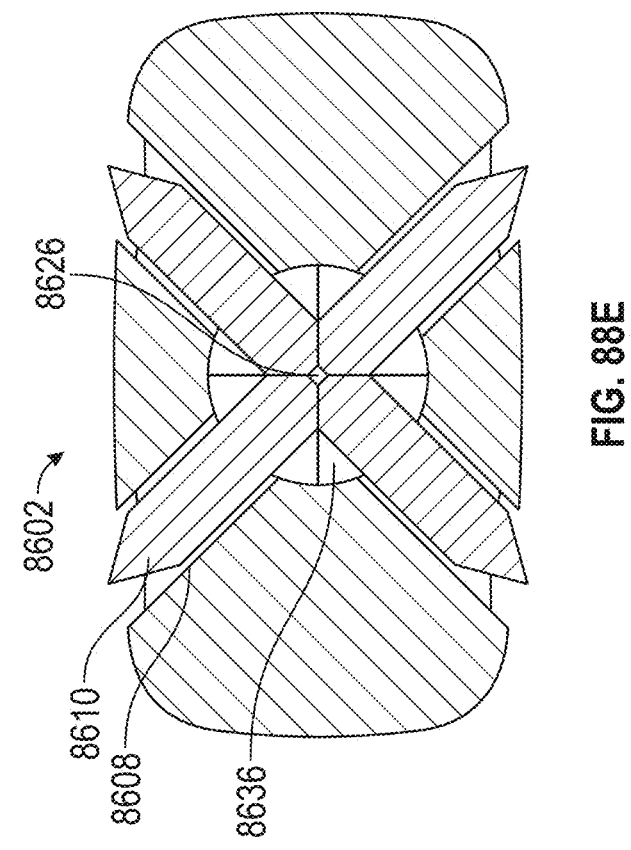
Figure 88D:
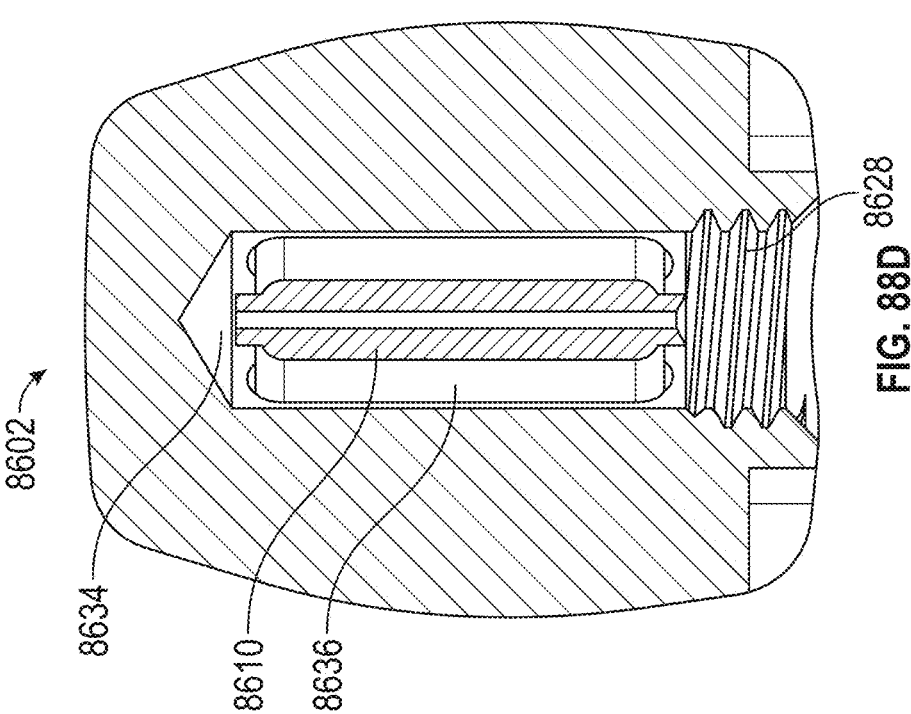

FIG. 88A depicts a perspective view of a joint implant system 8600 with blades 8610 in a retracted state. FIG. 88B depicts a top view of an implant 8602 of the joint implant system 8600 with blades 8610 in a retracted state. FIG. 88C depicts a front view of the implant 8602 of the joint implant system 8600 with blades 8610 in a retracted state. FIG. 88D depicts a cross-sectional view of the implant 8602 of the joint implant system 8600 with blades 8610 in a retracted state. FIG. 88E depicts a cross-sectional view of the implant 8602 of the joint implant system 8600 with blades 8610 in a retracted state.

Figure 88F:
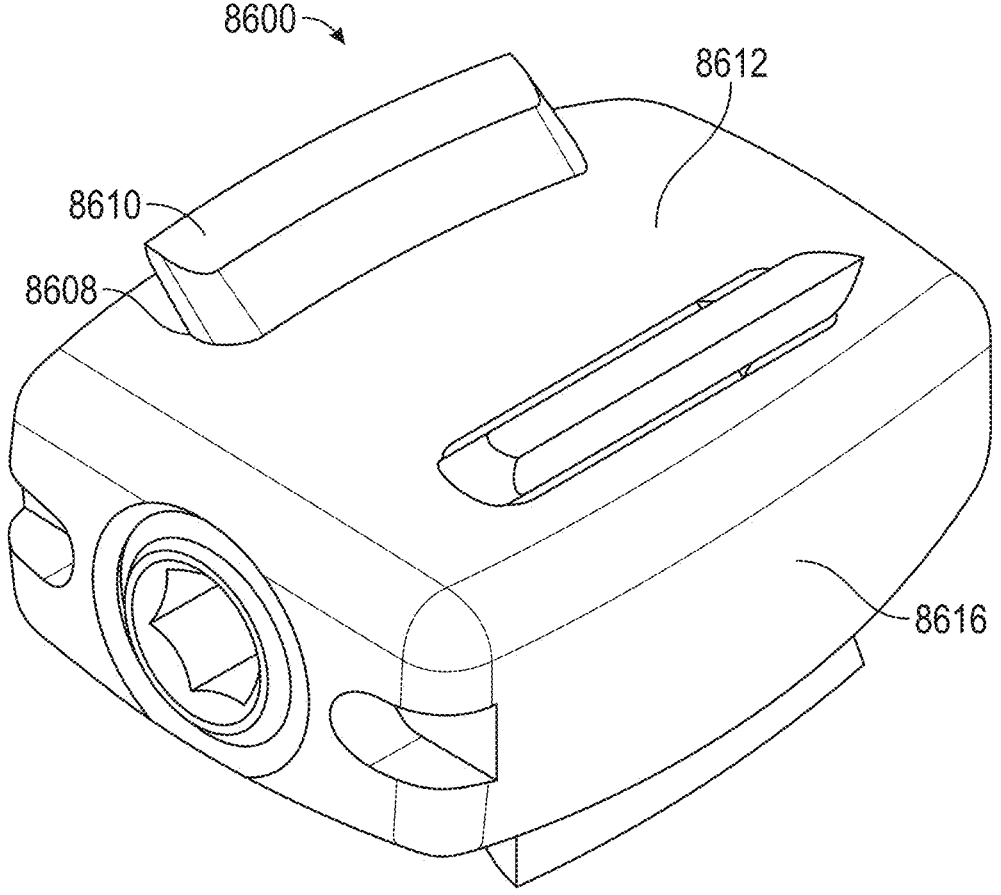
Figures 88G, 88H:
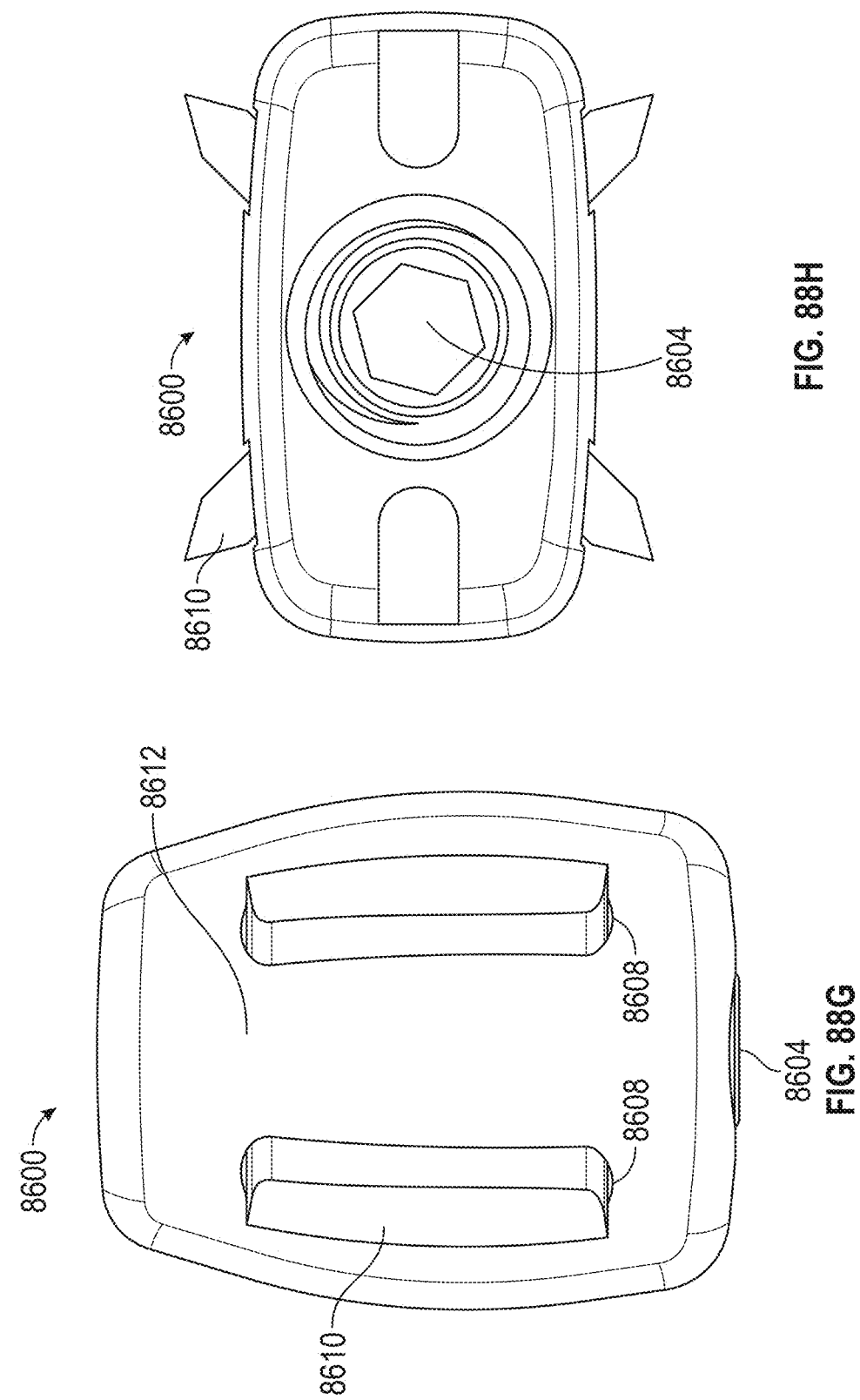
Figures 88I, 88J:
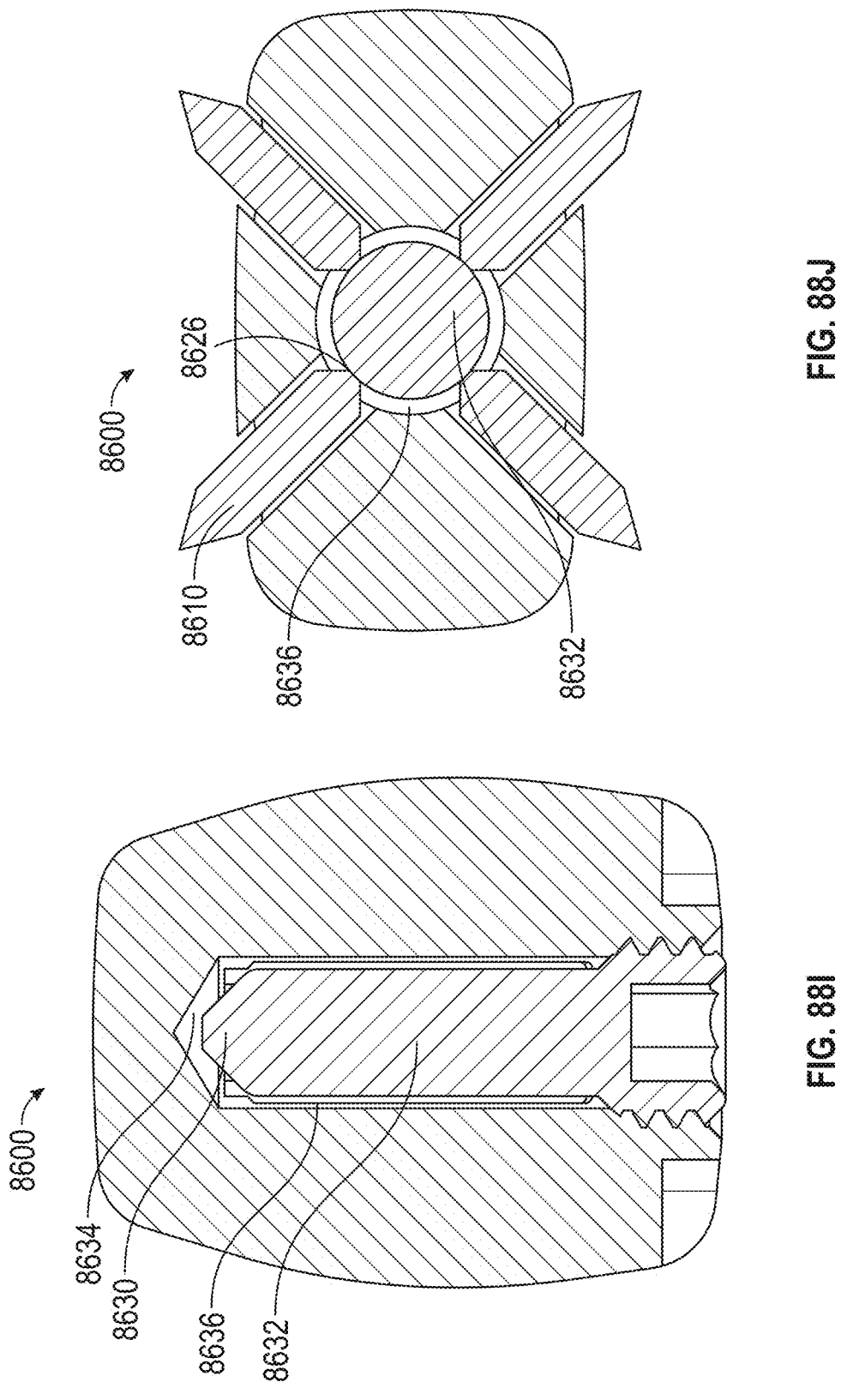

FIG. 88F depicts a perspective view of the joint implant system 8600 with blades 8610 in an engaged state or extended state. FIG. 88G depicts a top view of the joint implant system 8600 with blades 8610 in an engaged state. FIG. 88H depicts a front view of the joint implant system 8600 with blades 8610 in an engaged state or extended state. FIG. 88I depicts a cross-sectional view of the joint implant system 8600 with blades 8610 in an engaged state or extended state. FIG. 88J depicts a cross-sectional view of the joint implant system 8600 with blades 8610 in an engaged state or extended state.

In some embodiments, the blades 8610 can be anchors, screws, grips, spikes, anti-migration tabs, or arms. In some embodiments, the deployable anchors or screws may have barbs or threads to help anchor in the bone to prevent implant migration. Advantageously, the four blades 8610 can provide better fixation than an implant with less blades.

Advantageously, the four blades 8610 can have less of a risk of tissue damage than an implant with more blades.

In some embodiments, the implant system 8600 can include an actuator 8604. The actuator 8604 can be inserted into an aperture 8606 of the implant 8602 in order to shift the implant 8602 from a retracted state to an engaged state. In some embodiments, the actuator 8604 can be a pin, screw, a drive component, a rod, or a cone. In some embodiments, the blades 8610 can be driven out with force, threading, or another method of deployment or actuation upon advancing the actuator 8604 within the implant 8602. In the engaged or extended state, the blades 8610 can extend radially outward from the position of the blades 8610 in the retracted state. In some embodiments, in the retracted state, the blades 8610 can be contained within the implant 8602 or partially protrude from the implant 8602. In the retracted state, the blades 8610 can be positioned to facilitate implantation into a joint (e.g., an SI joint of facet joint) without resistance or with minimal resistance due to contact between the blades 8610 and the anatomy. The actuator 8604 can push the blades 8610 to extend radially outward by abutting an inner end of the blades 8610.

As shown in FIG. 88A, the implant 8602 can be a curved rectangular prism, for example with rounded edges and rounded corners. In some embodiments, the implant 8602 can be a cube, a sphere, a prism, or an elliptical shape. Advantageously, the lack of sharp corners can reduce the risk of tissue damage in the patient. The implant 8602 can have dents 8624 on the front, or the proximal end. The dents 8624 can engage with a device for placing the implant. In some embodiments, the dents 8624 can engage with a device for securing the implant in place.

As shown in FIG. 88A, the slots 8608 can be in fluid communication with the aperture 8606. The implant 8602 can have four slots 8608, for example two slots 8608 on the top 8612 of the implant 8602 and two slots 8608 on the bottom 8614 of the implant 8602. In some embodiments, the implant 8602 can have between one and eight slots. In some embodiments, the implant 8602 can have between one and eight blades. In some embodiments, the implant 8602 can have slots on the side 8616 of the implant 8602. In some embodiments, the blades 8610 can extend outward at an angle of 45 degrees from the central axis of the implant 8602. In some embodiments, the blades 8610 can extend outward at an angle of between 30 and 60 degrees from the central axis of the implant 8602. In some embodiments, the blades 8610 can extend outward at an angle of between 10 and 80 degrees from the central axis of the implant 8602.

As shown in FIG. 88A, the aperture 8606 of the implant 8602 can have a threaded portion 8628. The actuator 8604 can have a threaded portion 8618 that can engage the threaded portion 8628 of the aperture 8606. Screwing the threaded portion 8618 of the pin into the threaded portion 8628 of the aperture 8606 can allow the actuator 8604 to extend into the implant 8602. Screwing the threaded portion 8618 of the pin into the threaded portion 8628 of the aperture 8606 can lock the actuator 8604 in the implant 8602, and lock the implant 8602 in the engaged position. The actuator 8604 can have a tapered portion 8630 on the distal end. The tapered portion 8630 can be sloped to engage the inside edges 8626 of the blades 8610. The tapered portion 8630 can abut the inside edges 8626 of the blades 8610. As the actuator 8604 is further advanced into the aperture 8606, the inside edges 8626 of the blades 8610 can slide radially outward along the sloped or tapered portion 8630 of the actuator 8604. Optionally, the inside edges 8626 of the blades 8610 can be positioned around the shaft 8632 of the actuator 8604 when the implant 8602 is in the engaged position. The shaft 8632 can have a larger diameter than the tapered portion 8630 of the actuator 8604.

As shown in FIG. 88B, the blades 8610 can extend slightly out of the slots 8608 in some embodiments. The front of the implant 8602 can be larger than the back. The shape of the implant 8602 can be optimized for placement within a joint. In some embodiments, the blades 8610 may be recessed within the implant 8602 to prevent damage to surrounding tissue during implantation of the implant 8600.

As shown in FIGS. 88C and 88E, the inside edges 8626 of the blades 8610 can form an inner aperture. The inner aperture can have a smaller diameter than the aperture 8606. The central axis of the inner aperture can align with the central axis of the aperture 8606. The inside edges 8626 of the blades 8610 can have small surfaces which can form the inner aperture. For example, the inside edges 8626 of the blades 8610 can have small straight surfaces which can form a diamond when the blades 8610 are retracted. The inside edges 8626 of the blades 8610 can include angled portions which can fit together with the angled portions of the other inside edges 8626 of the blades 8610 when the blades 8610 are retracted. This can allow the blades 8610 to retract further, and can provide the inner aperture for the actuator 8604 to enter.

As shown in FIG. 88D, the aperture 8606 can open into a cavity 8636 within the implant 8602. The depth of the cavity 8636 can accommodate the length of the actuator 8604. Optionally, the distal end of the cavity 8636 can include a tapered portion 8634 that can accommodate the tapered portion 8630 of the actuator 8604. In some embodiments, the cavity 8638 can extend to the back of the implant 8602.

As shown in FIGS. 88F-H, the actuator 8604 can be positioned in the implant 8602 to extend the blades 8610 radially outward. In the engaged position, the blades 8610 can extend outward at an angle of 45 degrees from the central axis of the implant 8602. In some embodiments, in the engaged position, the blades 8610 can extend outward at an angle of between 30 and 60 degrees from the central axis of the implant 8602. In some embodiments, in the engaged position, the blades 8610 can extend outward at an angle of between 10 and 80 degrees from the central axis of the implant 8602. The blades 8610 can extend outside the implant 8602 between 0.1 and 0.2 inches. In some embodiments, the blades 8610 can extend outside the implant 8602 between 0.05 and 0.5 inches. In some embodiments, the blades 8610 can extend outside the implant 8602 between 0.01 and 1 inch.

As shown in FIG. 88I, the actuator 8604 can be mostly or entirely contained within the implant 8602. The tapered portion 8630 of the actuator 8604 can be contained within the tapered portion 8634 of the cavity 8636.

As shown in FIG. 88J, the inner edges 8626 of the blades 8610 can be positioned radially around the shaft 8632 of the actuator 8604 in the engaged or extended position. The small surfaces of the inner edges 8626 of the blades 8610 can contact the shaft 8632. The angled portions of the inner edges 8626 of the blades 8610 can separate from the angled portions of the inner edges 8626 of the other blades 8610 as the blades 8610 are pushed outward.

In some embodiments, the blades 8610 can be positioned in the engaged or extended state so that at least one of the blades 8610 will contact the bone on each side of the joint regardless of the orientation of the implant 8600 when fully seated within the joint. For example, the blades 8610 can be positioned in the engaged or extended state so that at least one of the blades 8610 will contact a superior articular facet and at least one of the blades 8610 will contact an inferior articular facet when fully seated within the facet joint. In some embodiments, the blades 8610 can be positioned in the engaged or extended state so that at least one of the blades 8610 will contact an ilium and at least one of the blades 8610 will contact a sacrum when fully seated within an SI joint. The implant 8602 can be placed within the facet joint (or SI joint or other joints) from an in-line or posterior approach. The implant 8602 may be positioned between the superior articular facet and inferior articular facet. In some embodiments, the implant 8602 may partially protrude through the superior articular facet and inferior articular facet. The actuator 8604 can be inserted into the implant 8602 while the implant 8602 is positioned within the facet joint. The blades 8610 can be forced outward into one or multiple facets. The blades 8610 may resist different forces and help stabilize while fusing. For example, the blades 8610 may resist shear, nutation, counter nutation, and/or expulsion forces. The blades 8610 may deploy from within the facet joint in the cervical, thoracic, or lumbar spine.

The method described herein can allow a user to access a joint line between the facets. When the implant 8602 is positioned at a desired depth in the body of the patient, the blades 8610 or fixation devices may be deployed into the facets to provide more fixation. Advantageously, this can provide greater fixation within the body. Additionally, this can provide a greater resistance to expulsion forces, for example forces in a different direction than the implant 8602 is oriented. Advantageously, the blades 8610 being contained or partially contained within the implant 8602 upon insertion can reduce the time and effort necessary for embedding the implant, enhance ease of use, prevent implants from having a difficulty with deployment, and reduce the number of instruments needed for deployment. In some embodiments, the blades 8610 may cross over one or multiple facets. In some embodiments, the blades 8610 may not cross over a facet. Crossing over the superior articular facet and inferior articular facet can create more rigidity and better prevent expulsion. Crossing over a facet can include piercing through the facet from one side to another. In some embodiments, the blades 8610 may be long enough to pierce entirely through a facet. In some embodiments, the blades 8610 may be short enough to pierce a facet without passing to the other side. In some embodiments, the blades 8610 may be short enough to pierce a facet shallowly.

In some embodiments, one or more windows or passages can extend through the implant 8602 to facilitate fusion through the implant and across a joint.

FIGS. 89A-89J depict an embodiment of a joint implant system 8700. The joint implant system 8700 can include an implant 8702. For example, the implant 8702 can be positioned within a facet joint. In some embodiments, the implant 8702 can be positioned within a sacroiliac joint.

The implant 8700 can include a plurality of blades 8710. The blades 8710 may be extendable or advanceable from a body of the implant 8700. In some embodiments, the implant 8702 can have slots 8708 from which blades 8710 can extend. In some embodiments, the blades 8710 can extend vertically from the implant.

As shown, the implant 8700 can include two blades 8710. In other embodiments, the implant 8700 can include any number of blades 8710, for example, depending on the anatomy of the joint and the amount of fixation desired to assist with stabilization and fusion.

Figure 89A:
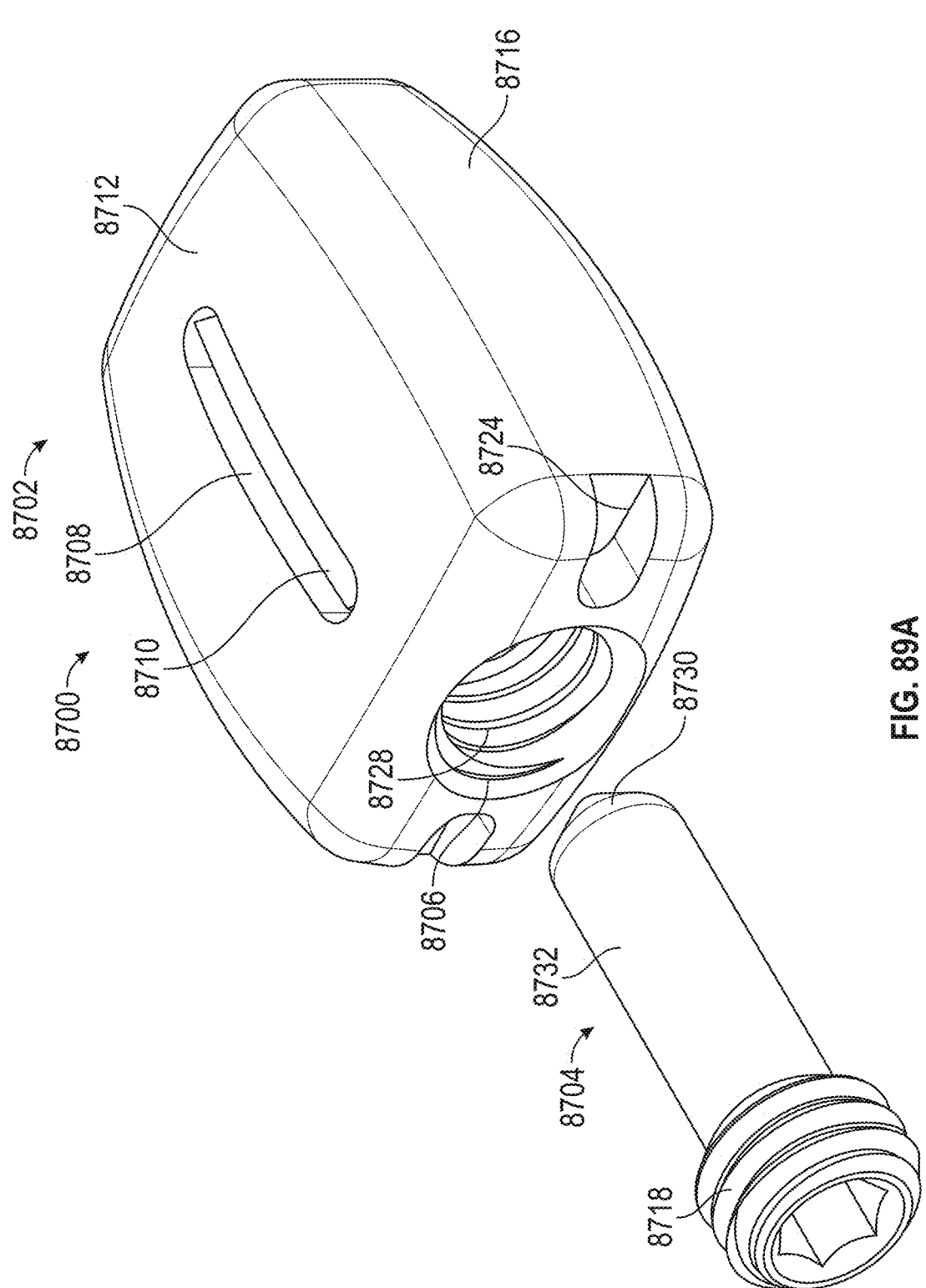
Figures 89B, 89C:
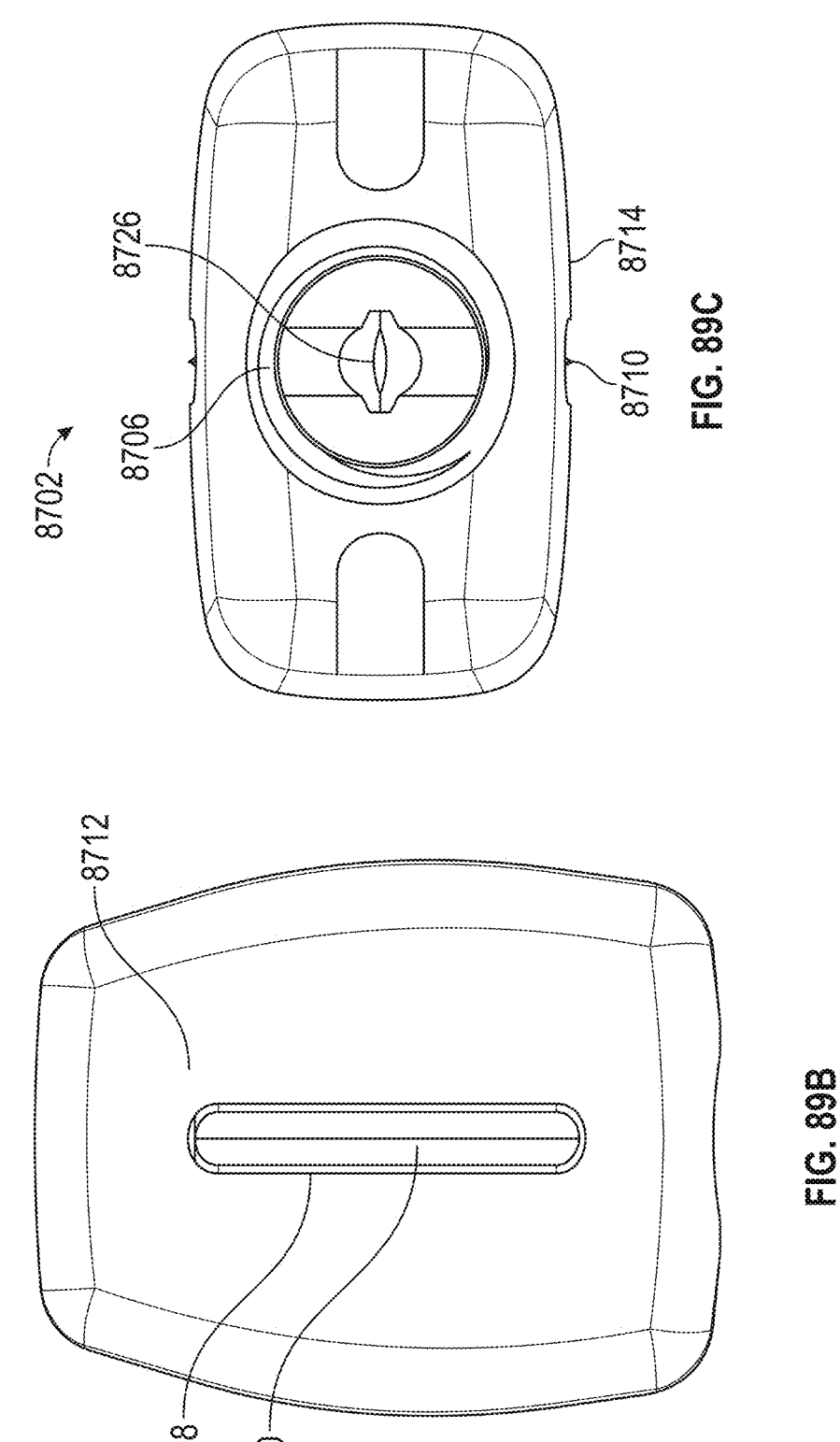
Figure 89E:
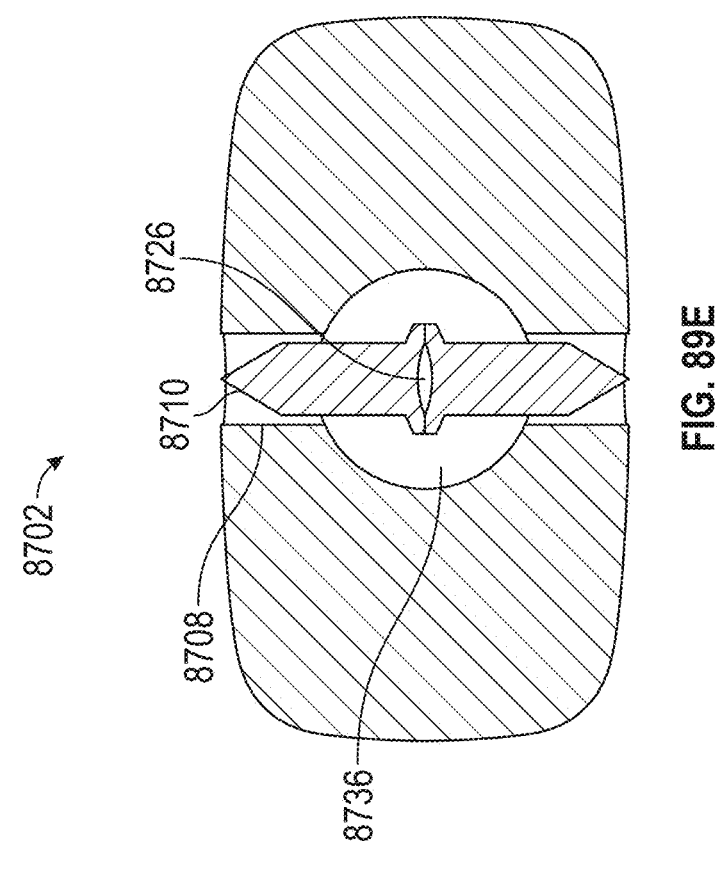
Figure 89D:
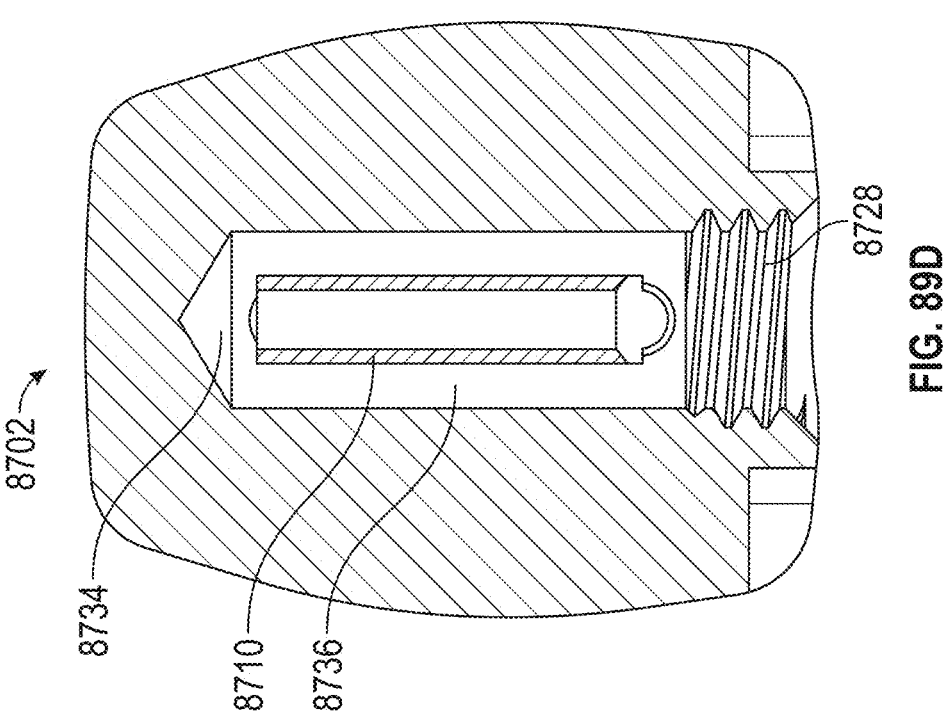

FIG. 89A depicts a perspective view of a joint implant system 8700 with blades 8710 in a retracted state. FIG. 89B depicts a top view of an implant 8702 of the joint implant system 8700 with blades 8710 in a retracted state. FIG. 89C depicts a front view of the implant 8702 of the joint implant system 8700 with blades 8710 in a retracted state. FIG. 89D depicts a cross-sectional view of the implant 8702 of the joint implant system 8700 with blades 8710 in a retracted state. FIG. 89E depicts a cross-sectional view of the implant 8702 of the joint implant system 8700 with blades 8710 in a retracted state.

Figure 89F:
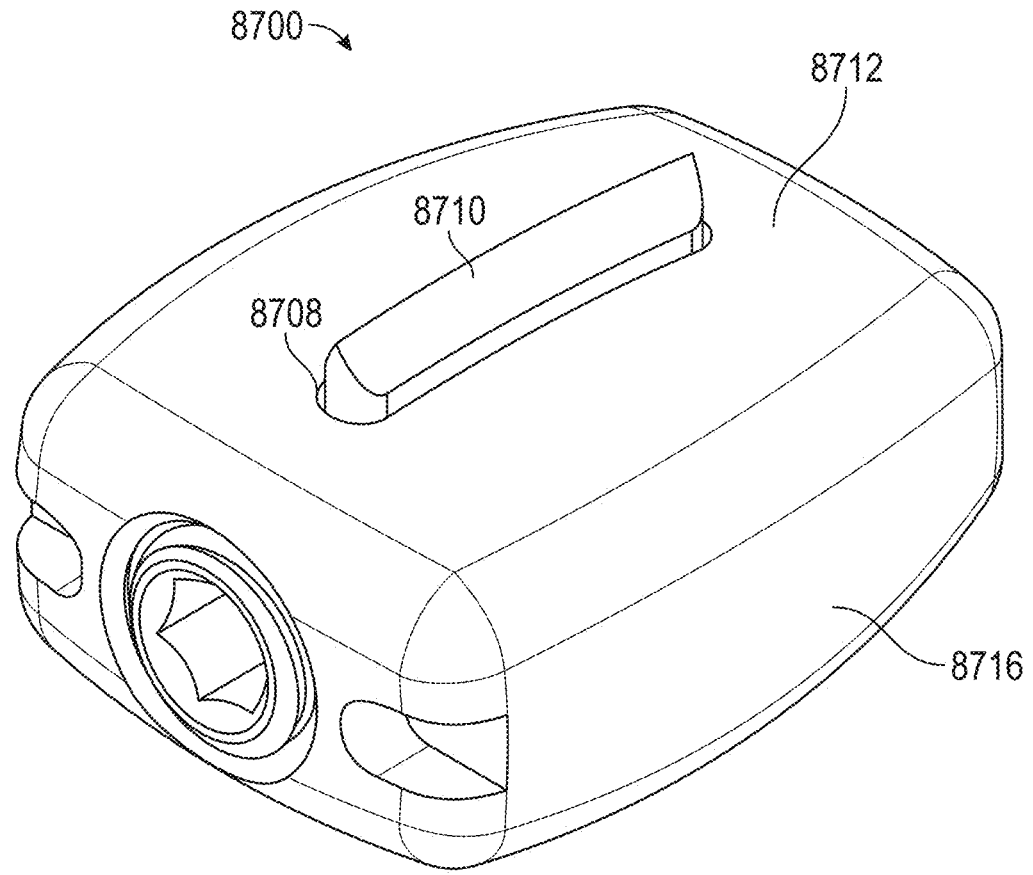
Figures 89G, 89H:
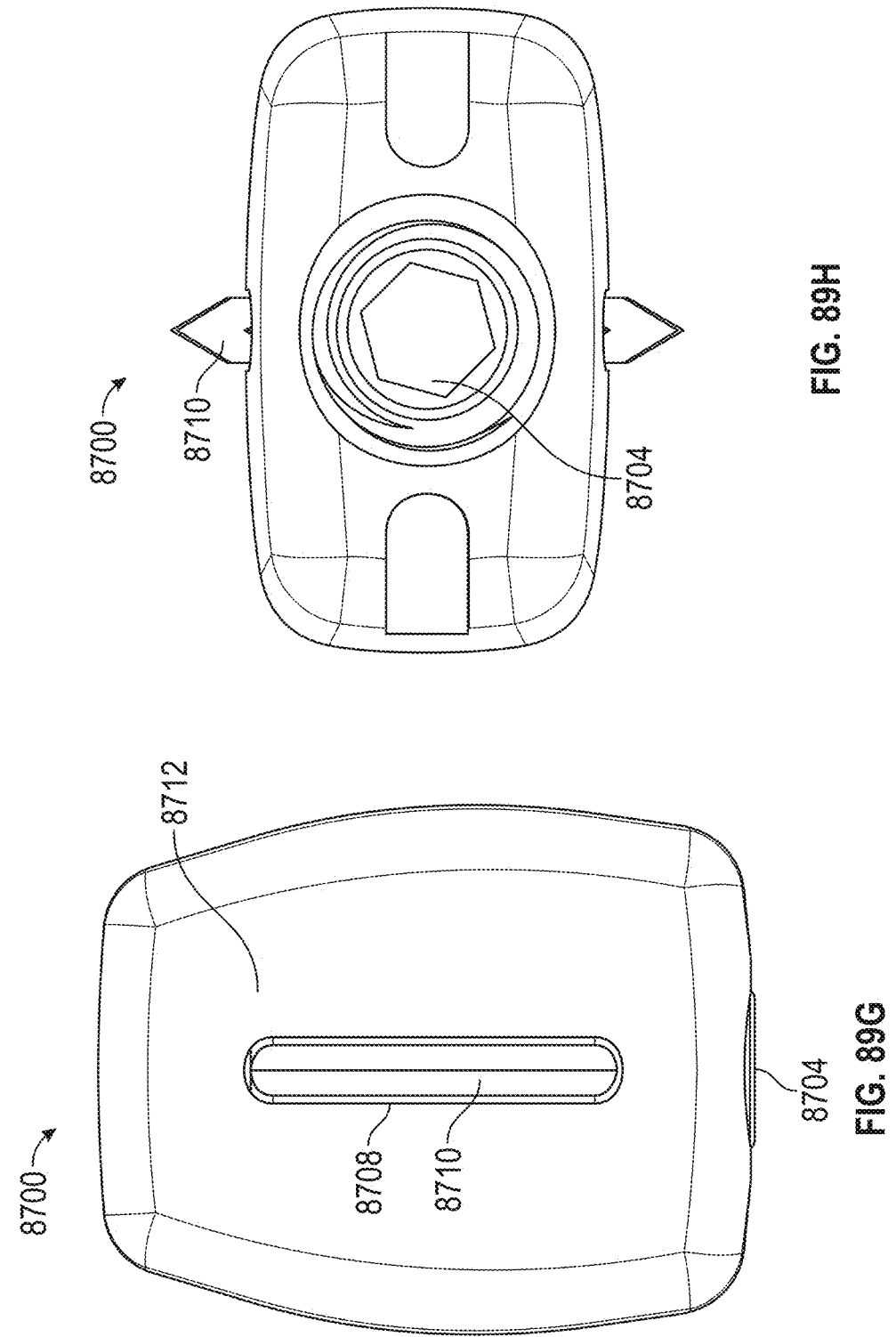
Figures 89I, 89J:
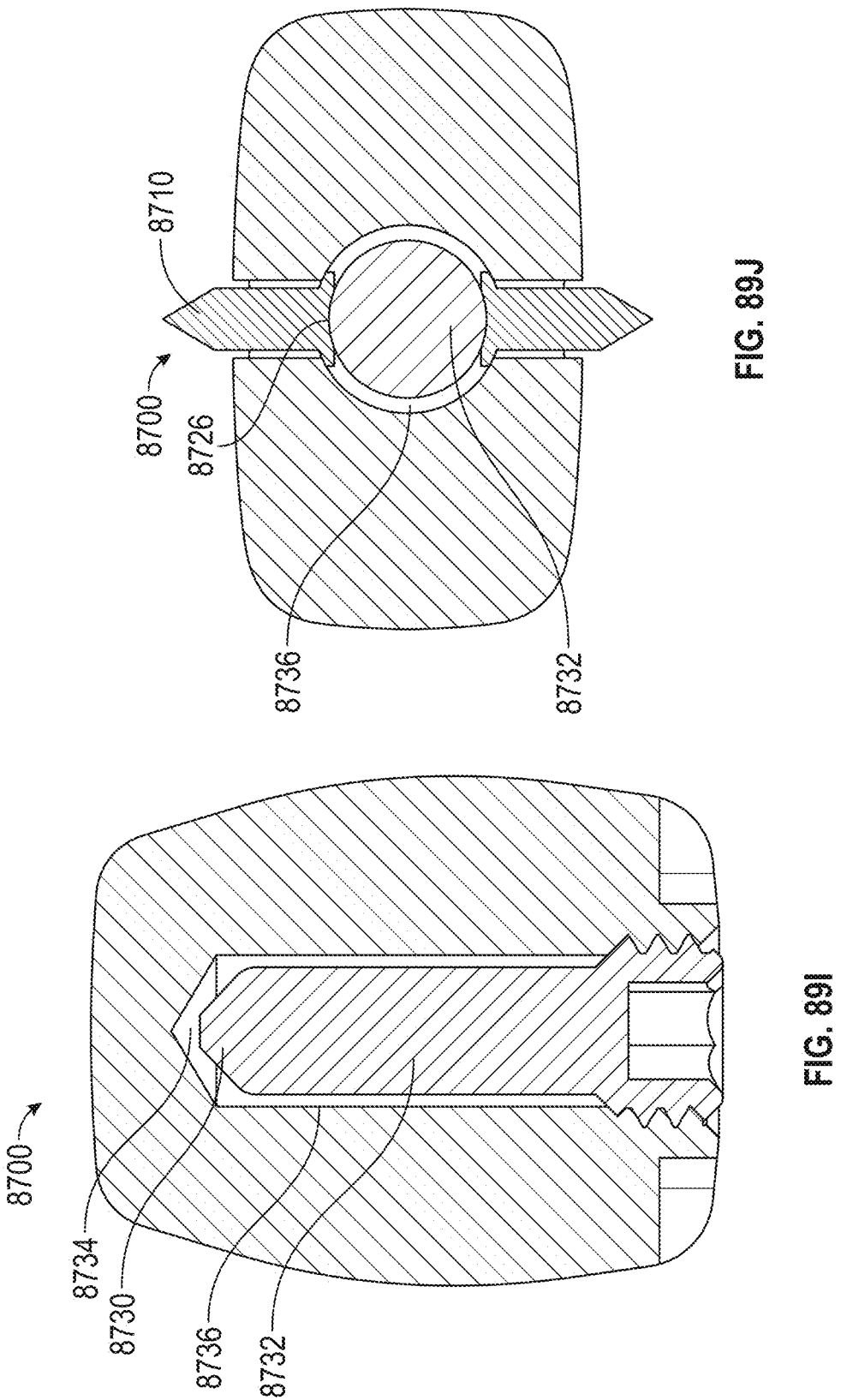

FIG. 89F depicts a perspective view of the joint implant system 8700 with blades 8710 in an engaged state. FIG. 89G depicts a top view of the joint implant system 8700 with blades 8710 in an engaged state. FIG. 89H depicts a front view of the joint implant system 8700 with blades 8710 in an engaged state. FIG. 89I depicts a cross-sectional view of the joint implant system 8700 with blades 8710 in an engaged state. FIG. 89J depicts a cross-sectional view of the joint implant system 8700 with blades 8710 in an engaged state.

In some embodiments, the blades 8710 can be anchors, screws, grips, or arms. In some embodiments, the deployable anchors or screws may have barbs or threads to help anchor in the bone to prevent implant migration. Advantageously, the two blades 8710 can provide better fixation than an implant with less blades. Advantageously, the two blades 8710 can have less of a risk of tissue damage than an implant with more blades.

In some embodiments, the implant system 8700 can include an actuator 8704. The actuator 8704 can be inserted into an aperture 8706 of the implant 8702 in order to shift the implant 8702 from a retracted state to an engaged state. In some embodiments, the actuator 8704 can be a pin, screw, a drive component, a rod, or a cone. In some embodiments, the blades 8710 can be driven out with force, threading, or another method of deployment or actuation upon advancing the actuator 8704 within the implant 8702. In the extended state, the blades 8710 can extend radially outward from the position of the blades 8710 in the retracted state. In some embodiments, in the retracted state, the blades 8710 can be contained within the implant 8702 or partially protrude from the implant 8702. The actuator 8704 can push the blades 8710 to extend radially outward by abutting an inner end of the blades 8710.

As shown in FIG. 89A, the implant 8702 can be a curved rectangular prism, for example with rounded edges and rounded corners. In some embodiments, the implant 8702 can be a cube, a sphere, a prism, or an elliptical shape. Advantageously, the lack of sharp corners can reduce the risk of tissue damage in the patient. The implant 8702 can have dents 8724 on the front, or the proximal end. The dents 8724 can engage with a device for placing the implant. In some embodiments, the dents 8724 can engage with a device for securing the implant in place.

As shown in FIG. 89A, the slots 8708 can be in fluid communication with the aperture 8706. The implant 8702 can have two slots 8708, for example one slot 8708 on the top 8712 of the implant 8702 and one slot 8708 on the bottom 8714 of the implant 8702. In some embodiments, the implant 8702 can have between one and eight slots. In some embodiments, the implant 8702 can have between one and eight blades. In some embodiments, the implant 8702 can have slots on the side 8716 of the implant 8702. The implant 8702 can have blades 8710 that extend vertically from the implant 8702. In some embodiments, the implant 8702 can have blades that extend horizontally from the implant 8702. In some embodiments, the blades 8710 can extend outward at an angle of 90 degrees from a central axis of the implant

8702. In some embodiments, the blades 8710 can extend outward at an angle of between 60 and 120 degrees from the central axis of the implant 8702. In some embodiments, the blades 8710 can extend outward at an angle of between 45 and 135 degrees from the central axis of the implant 8702.

As shown in FIG. 89A, the aperture 8706 of the implant 8702 can have a threaded portion 8728. The actuator 8704 can have a threaded portion 8718 that can engage the threaded portion 8728 of the aperture 8706. Screwing the threaded portion 8718 of the pin into the threaded portion 8728 of the aperture 8706 can allow the actuator 8704 to extend into the implant 8702. Screwing the threaded portion 8718 of the pin into the threaded portion 8728 of the aperture 8706 can lock the actuator 8704 in the implant 8702, and lock the implant 8702 in the engaged position. The actuator 8704 can have a tapered portion 8730 on the distal end. The tapered portion 8730 can be sloped to engage the inside edges 8726 of the blades 8710. The tapered portion 8730 can abut the inside edges 8726 of the blades 8710. As the actuator 8704 is further advanced into the aperture 8706, the inside edges 8726 of the blades 8710 can slide radially outward along the sloped or tapered portion 8730 of the actuator 8704. Optionally, the inside edges 8726 of the blades 8710 can be positioned around the shaft 8732 of the actuator 8704 when the implant 8702 is in the engaged position. The shaft 8732 can have a larger diameter than the tapered portion 8730 of the actuator 8704.

As shown in FIG. 89B, the blades 8710 can extend slightly out of the slots 8708 in some embodiments. The front of the implant 8702 can be larger than the back. The shape of the implant 8702 can be optimized for placement within a joint. In some embodiments, the blades 8710 may be recessed within the implant 8702 to prevent damage to surrounding tissue during implantation of the implant 8700.

As shown in FIGS. 89C and 89E, the inside edges 8726 of the blades 8710 can form an inner aperture. The inner aperture can have a smaller diameter than the aperture 8706. The central axis of the inner aperture can align with the central axis of the aperture 8706. The inside edges 8726 of the blades 8710 can have curved surfaces which can form the inner aperture. For example, the inside edges 8726 of the blades 8710 can have curved surfaces which can form a circle or ellipsis when the blades 8710 are retracted. The inside edges 8726 of the blades 8710 can include radially outward portions which can fit together with the radially outward portions of the other inside edges 8726 of the blades 8710 when the blades 8710 are retracted. This can allow the blades 8710 to retract further, and can provide the inner aperture for the actuator 8704 to enter.

As shown in FIG. 89D, the aperture 8706 can open into a cavity 8736 within the implant 8702. The depth of the cavity 8736 can accommodate the length of the actuator 8704. Optionally, the distal end of the cavity 8736 can include a tapered portion 8734 that can accommodate the tapered portion 8730 of the actuator 8704. In some embodiments, the cavity 8738 can extend to the back of the implant 8702.

As shown in FIGS. 89F-H, the actuator 8704 can be positioned in the implant 8702 to extend the blades 8710 radially outward. In the engaged position, the blades 8710 can extend outward at an angle of 90 degrees from the central axis of the implant 8702. In some embodiments, in the engaged position, the blades 8710 can extend outward at an angle of between 60 and 120 degrees from the central axis of the implant 8702. In some embodiments, in the engaged position, the blades 8710 can extend outward at an angle of between 45 and 135 degrees from the central axis of the implant 8702. The blades 8710 can extend outside the implant 8702 between 0.1 and 0.2 inches. In some embodiments, the blades 8710 can extend outside the implant 8702 between 0.05 and 0.5 inches. In some embodiments, the blades 8710 can extend outside the implant 8702 between 0.01 and 1 inch.

As shown in FIG. 89I, the actuator 8704 can be mostly or entirely contained within the implant 8702. The tapered portion 8730 of the actuator 8704 can be contained within the tapered portion 8734 of the cavity 8736.

As shown in FIG. 89J, the inner edges 8726 of the blades 8710 can be positioned radially around the shaft 8732 of the actuator 8704 in the engaged or extended position. The curved surfaces of the inner edges 8726 of the blades 8710 can contact the shaft 8732. The radially outward portions of the inner edges 8726 of the blades 8710 can separate from the radially outward portions of the inner edges 8726 of the other blades 8710 as the blades 8710 are pushed vertically or horizontally.

In some embodiments, the blades 8710 can be positioned in the engaged or extended state so that at least one of the blades 8710 will contact the bone on each side of the joint regardless of the orientation of the implant 8700 when fully seated within the joint. For example, the blades 8710 can be positioned in the engaged or extended state so that at least one of the blades 8710 will contact a superior articular facet and at least one of the blades 8710 will contact an inferior articular facet when fully seated within the facet joint. In some embodiments, the blades 8710 can be positioned in the engaged or extended state so that at least one of the blades 8710 will contact an ilium and at least one of the blades 8710 will contact a sacrum when fully seated within an SI joint.

The implant 8702 can be placed within the facet joint (or SI joint or other joints) from an in-line or posterior approach. The implant 8702 may be positioned between the superior articular facet and inferior articular facet. In some embodiments, the implant 8702 may partially protrude through the superior articular facet and inferior articular facet. The actuator 8704 can be inserted into the implant 8702 while the implant 8702 is positioned within the facet joint. The blades 8710 can be forced outward into one or multiple facets. The blades 8710 may resist different forces and help stabilize while fusing. For example, the blades 8710 can resist shear, rotational, and expulsion forces. The blades 8710 may deploy from within the facet joint in the cervical, thoracic, or lumbar spine.

The method described herein can allow a user to access a joint line between the facets. When the implant 8702 is positioned at a desired depth in the body of the patient, the blades 8710 or fixation devices may be deployed into the facets to provide more fixation. Advantageously, this can provide greater fixation within the body. Additionally, this can provide a greater resistance to expulsion forces, for example forces in a different direction than the implant 8702 is oriented. Advantageously, the blades 8710 being contained or partially contained within the implant 8702 upon insertion can reduce the time and effort necessary for embedding the implant, enhance ease of use, prevent implants from having a difficulty with deployment, and reduce the number of instruments needed for deployment. In some embodiments, the blades 8710 may cross over one or multiple facets. In some embodiments, the blades 8710 may not cross over a facet. Crossing over the superior articular facet and inferior articular facet can create more rigidity and better prevent expulsion.

In some embodiments, one or more windows or passages can extend through the implant 8702 to facilitate fusion through the implant and across a joint. FIGS. 90A-90D depict an embodiment of a joint implant 9000. The joint implant 9000 can include any of the same and/or similar features and/or functions as the joint implants or joint implant systems described herein (e.g., joint implant system 100). For example, in certain embodiments, the joint implant 9000 can include any of the same and/or similar features of both a primary implant 102 as described herein and a secondary implant 104 as described herein.

The implant 9000 can be dimensioned, shaped, and/or otherwise configured to be positioned within a joint. For example, the implant 9000 can be positioned within a facet joint. In some embodiments, the implant 9000 can be positioned within a sacroiliac joint.

In certain embodiments, the joint implant 9000 can include a central body or primary body 9002. The primary body 9002 can include any of the same and/or similar features and/or functions as the primary implant 102 described herein. In certain embodiments, the primary body 9002 can be positioned within an SI joint (e.g., advanced along a joint line of the SI joint or slightly off-axis to the joint line) to engage both the ilium and the sacrum. In certain embodiments, the primary body 9002 can be positioned within a facet joint (e.g., advanced along a joint line of the SI joint or slightly off-axis to the joint line). In certain embodiments, the primary body 9002 can resist shearing forces, such as for example, shearing forces of the sacrum, when positioned within the SI joint. In certain embodiments, the primary implant can resist rotational movement.

In certain embodiments, the implant 9000 can include one or more anchor assemblies. As shown in FIGS. 90A-D, in certain embodiments, the implant system 9000 can include an anchor assembly 9004*a* and an anchor assembly 9004*b*. As described in further detail herein, in certain embodiments, the anchor assemblies 9004*a*-*b* may each anchor within bone on opposing sides of a joint (e.g., anchor within both the ilium and the sacrum on opposing sides of the SI joint or within a superior articular process and inferior articular process of a fact joint).

In certain embodiments, the implant 9000 can achieve multiple points of fixation and resist multiple forces. For example, in certain embodiments, the implant 9000 can resist all of the forces acting on a joint, such as an SI joint or facet joint.

As described herein, the primary body 9002 can be configured to be inserted into the joint. The primary body 9002 can have a proximal end 9001 and a distal end 9005. In certain embodiments, the primary body 9002 is configured so that the distal end 9005 can be inserted within the joint without creating joint distraction.

In some embodiments, the primary body 9002 can be configured to engage bone on opposing sides of a joint (e.g., the ilium and the sacrum or superior and inferior articular processes) to secure the joint with the implant. For example, in certain embodiments, the primary body 9002 can include one or more engagement features 9003. As shown in FIGS. 90A-D, the engagement features 9003 may engage bone on opposing sides of the joint for fixation and to prevent back out. The engagement features 9003 may be in the form of barbs (e.g., anti-migration barbs) that anchor into the bone and help prevent implant migration. The barbs may be any shape or size or number suitable for positioning on the primary body 9002, to prevent migration and back out of the implant. In some embodiments the engagement features 9003 may be threads, fins, teeth, or blades. In certain embodiments, the engagement features 9003 may extend from the proximal end 9001 to the distal end 9005 of the primary body 9002 or may extend over any portion thereof.

In certain embodiments, the primary body 9002 can be cannulated from the proximal end 9001 to the distal end 9005, having a channel 9060 extending between the proximal end 9001 and the distal end 9005. In some embodiments, the channel 9060 can allow for a guidewire or guide rod to extend through the body 9002.

In some embodiments, the primary body 9002 can be loaded with demineralized bone matrix (DBM), cortical fibers, synthetic bone matrix, BMP2 or BMP7, peptide graft, autograft or any combination thereof. In some embodiments, the channel 9060 can be packed and/or filled with bone graft material.

In some embodiments it may be desirable for the channel 9060 to have a diameter large enough to receive bone graft, but small enough to avoid or inhibit deformation of breakage due to fragility. The diameter can also be sufficiently small for the implant to fit in a desired anatomic location, such as the SI joint or facet joint.

In certain embodiments, acid etching, bead blasting, surface coating such as HA (Hydroxyapatite), or any other suitable surface technology may be utilized to enhance the surface finish to create an optimal area for bone to grow to in the primary body 9002 or the anchor assemblies 9004*a-b*. In certain embodiments, 3D printing may be utilized to create surfaces structures and features for bone to grow to. In certain embodiments, the surface structures may be on the nanometer or micrometer scale which can be optimal or desirable for bone to grow to.

In certain embodiments, the implant 9000 may be a single-piece. In other embodiments, the primary body 9002 and anchor assemblies 9004*a-b* can be separate pieces that can be assembled prior to or after implantation.

In certain embodiments, the implant 9000 may be CNC machined, 3D printed, or manufactured by any other suitable means. In certain embodiments, the primary body 9002 and/or anchor assemblies 9004*a-b* can be CNC machined, 3D printed, or manufactured by any other suitable means. In certain embodiments, the implant 9000 can be made of stainless steel, titanium, poly-ether-ether-ketone (PEEK), ceramic, human allograft or any other suitable implantable material strong enough to resist the forces described herein and pass biomechanical testing. In certain embodiments, the body 9002 and/or anchor assemblies 9004*a-b* can be made of stainless steel, titanium, poly-ether-ether-ketone (PEEK), ceramic, human allograft or any other suitable implantable material strong enough to resist the forces described herein and pass biomechanical testing. In certain embodiments, the implant material can be important to achieve bony ingrowth.

In certain embodiments, the implant 9000 can be configured to be inserted with a driver, such as a hex driver, a star driver, a square driver, a torx driver, or any other suitable driver for driving the implant into bone. The proximal end 9001 of the body 902 can include an engagement feature 9062 for coupling with an inserter, such as inserter 9100 as shown in FIG. 90E. The engagement feature 9062 may be a recess configured to couple with an inserter (e.g., a threaded recess). The engagement feature 9062 can be shaped to couple with a hex driver, a star driver, a square driver, a torx driver, or any other suitable driver for driving the body 9002 into bone.

As shown in FIGS. 90A-90C, a tip 9064 of the body 9002 can be flat. In certain embodiments, the body 9002 or a portion thereof may be conical. In certain embodiments, the body 9002 or a portion thereof can be tapered.

In some embodiments, the primary body 9002 may be only partially cannulated. For example, the channel 9060 may extend from the proximal end 9001 only partially along the length of the primary body 9002 towards the distal end 9005. In other embodiments, the primary body 9002 may not be cannulated. In other words, the body 9002 may have a solid core. A primary body 9002 that is only partially cannulated may have a higher biomechanical strength than an implant that is cannulated through its entire length. An body that is not cannulated may have a higher biomechanical strength than a partially or fully cannulated body.

In certain embodiments, the anchor assemblies 9004*a-b* can each be configured to anchor within bone on opposing sides of a joint (e.g., in both the ilium and the sacrum on opposing sides of the SI joint or in both the superior articular process and inferior articular process on both sides of a facet joint). In certain embodiments, the each anchor assembly 9004*a-b* can include a plurality of anchors. For example, in certain embodiments, each anchor assembly 9004*a-b* can include a first anchor 9006*a* configured to anchor within bone on a first side of a joint and a second anchor 9006*b* configured to anchor within bone on a second side of a joint. Accordingly, in certain embodiments, the implant 9000 can include four anchors 9006*a-b*.

The anchors 9006*a-b* can be a set of tangs, circles, half circles, wedges, triangles, squares, or other three-dimensional shaped anchors. The anchors 9006 can have a curvature, for example in a half circle shape, to prevent or restrict movement of the anchors 9006 in response to shear stresses (e.g., when the implant 9000 is malleted into bone). In contrast, in some embodiments, a flat or planar anchor 9006*a-b* may slide back and forth in response to shear stresses. Each of the anchors 9006*a-b* of the may contain a blade or sharp edge 9012 at the distal leading edge to cut bone during implantation (e.g., while the implant is malleted into the bone). The edge 9012 may converge or taper to a sharp distal point. For example, the edge may converge or taper laterally inwards. In some embodiments, the edge 9012 may be a beveled tip. The beveled tip can include a beveled surface, for example, as described with respect to beveled surface 117 as shown in FIGS. 83A-83C. In certain embodiments, the beveled tips can pull the bone on opposing sides of the joint line together.

When the anchors 9006*a-b* of one of the anchor assemblies 9004*a-b* are positioned within bone on opposing sides of a joint (e.g., the ilium and the sacrum or the superior articular process and inferior articular process), the implant assembly 9004*a-b* can act as a tension band. The implant assembly 9004*a-b* can resist forces that compress/distract and forces that rotate the joint.

In certain embodiments, the primary body 9002 and the anchors 9006*a-b* can compress the facet joint for stabilization, prevent distraction, and provide a bony bed for fusion.

In certain embodiments, each of the anchor assemblies 9004*a-b* can include an arm 9046 coupled to the primary body 9002. The arms 9046 can extend laterally from the primary body 9002. The anchors 9006*a-b* of each anchor assembly 9004*a-b* can extend from its respective arm 9046. In certain embodiments, the primary body 9002 can include one or more openings for bone interdigitation. In certain embodiments, the primary body 9002 can include one or more windows and/or passages to allow for fusion and/or create a bone bridge between the bones on opposite sides of the joint (e.g., between a sacrum and an ilium or between a superior articular process and an inferior articular process. In some embodiments, the passages can be offset relative to the anchor assemblies 9004, for example, to facilitate contact with the bone on opposing sides of the joint and allow for fusion completely between the opposing sides of the joint and through the implant 9000. In some embodiments, the windows can be positioned about the central axis at an angle of about 90 degrees relative to the arms 9046.

FIG. 90E depicts an embodiment of an inserter 9100 that can be used to insert the implant 9000 into a joint (e.g., an SI joint or a facet joint). The inserter 9100 can include an inserter body 9104 and a driver 9102. The driver 9102 can be advanced within a lumen of the inserter body 9104 and engage the engagement feature 9062 of the implant 9000. In certain embodiments, a distal end of the inserter body can engage the anchor assemblies 9004*a-b*.

FIG. 90F depicts an example of the implant 9000 fully seated within a facet joint. As shown, the primary body 9002 is positioned within the facet joint between the superior articular process and inferior articular process. As shown in FIG. 90F, each of the anchor assemblies 9004*a-b* includes an anchor 9006*a* positioned within an inferior articular process and an anchor 9006*b* positioned within a superior articular process. In this configuration, the anchors 9006*a-b* of anchor assemblies 9004*a-b* can compress and stabilize the joint one each side of the primary body 9002.

In certain embodiments, the primary body 9002 can be countersunk within a joint. In some embodiments in which the primary body 9002 is countersunk, bone graft material may be packed over the top of the primary body 9002 to assist in fusion. In other embodiments, the primary body 9002 can be flush with a proximal end of the joint.

FIG. 91A is a front view of an embodiment of a joint implant system 9200. FIG. 91B is a front, cross-sectional view of the joint implant system 9200. FIG. 91C is a top perspective view of the joint implant system 9200.

The joint implant system 9200 can include any of the same and/or similar features and/or functions as the joint implants or joint implant systems described herein (e.g., joint implant system 100, joint implant 9000). For example, in certain embodiments, the joint implant system 9200 can include any of the same and/or similar features of both a primary implant 102 as described herein and a secondary implant 104 as described herein.

The joint implant system 9200 can include a joint implant 9210 having a main body 9202. The main body 9202 may have any of the same and/or similar features as the primary implant 102 as described herein.

The joint implant 9210 can include one or more channels 9292 (e.g., two channels, three channels, four channels, more than four channels, etc.). For example, as shown in FIGS. 91A-91C, the joint implant 9210 can include two channels. The channels 9292 can extend through the main body 9202 of the joint implant system 9200.

The joint implant system 9200 can include one or more implants 9290, which may also be referred to as fixation implants or fasteners. The implants 9290 may have one or more engagement features 9204 configured to engage bone for fixation and/or to prevent backout. For example, the engagement features 9204 may be in the form of threads, fins, barbs, teeth, or blades. In certain embodiments, the implants 9290 may be in the form of screws. In certain embodiments, the implants 9290 may include any of the same or similar features or functions as the primary implant 102 described herein.

The implants 9290 may include an engagement feature 9294 configured to engagement with a driver, such as a hex driver, a star driver, a square driver, a torx driver, or any other suitable driver for driving the implant into bone.

Each channel 9292 can be configured to receive an implant 9290. In some embodiments, the channels 9292 can be threaded to receive threaded implants 9290. The channels 9292 can be oriented at an angle α1 with respect to a central axis 9220 of the main body 9202. For example, a central axis 9224 (e.g., a longitudinal axis) of each of the channels 9292 can be oriented at an angle α1 of 30 degrees relative to the central axis of the main body 9202. A central axis 9224 of each of the channels 9292 can be oriented at an angle α1 of between 10 degrees and 45 degrees relative to the central axis 9220 of the main body 9202. A central axis 9224 of each of the channels 9292 can be oriented at an angle α1 of between 5 degrees and 60 degrees relative to the central axis 9220 of the main body 9202. A central axis 9224 of each of the channels 9292 can be oriented at an angle α1 of between 1 degree and 90 degrees relative to the central axis 9220 of the main body 9202. In certain embodiments, different channels 9292 may be oriented at different angles relative to the central axis 9220 of the main body 9202.

In certain embodiments, the joint implant 9210 can be placed at the target site in a joint (e.g., an SI joint or a facet joint). After the joint implant 9210 is placed, one or more implants 9290 can be placed through the one or more channels 9292. The distal ends of the implants 9290 can extend out of the main body 9202 of the joint implant 9210 and into the surrounding structures. For example, in certain embodiments, at least one implant 9210 may extend into one side of a joint (e.g., a sacrum or a superior articular facet) and at least one implant 9210 may extend into an opposing side of the joint (e.g., an ilium or an inferior articular facet). In some examples, the implants 9290 may secure the joint implant 9210 in place.

In certain embodiments, the main body 9202 can include one or more engagement features 9203. The engagement features 9203 may engage bone on opposing sides of the joint for fixation and to prevent back out. The engagement features 9203 may be in the form of barbs (e.g., anti-migration barbs) that anchor into the bone and help prevent implant migration. The barbs may be any shape or size or number suitable for positioning on the main body 9202, to prevent migration and back out of the implant. In some embodiments the engagement features 9203 may be threads, fins, teeth, or blades. In certain embodiments, the engagement features 9203 may extend from the proximal end 9201 to the distal end 9205 of the main body 9202 or may extend over any portion thereof.

In certain embodiments, the implant system 9200 can include one or more anchors 9206. The anchors 9206 may include any of the same and/or similar features and/or functions as any of the anchors described herein (e.g., the anchors 106). The anchors 9206 may be integral with or removably coupled to the main body 9202. The anchors 9206 may be part of the implant 9200.

Each of the anchors 9206 may include a blade or sharp edge 9212 at the distal leading edge to cut bone during implantation (e.g., while the implant is malleted into the bone). The edge 9212 may converge or taper to a sharp distal point. For example, the edge may converge or taper laterally inwards. In some embodiments, the edge 9212 may be a beveled tip. The edge 9212 may include any of the same and/or similar features and/or functions as the edge 112 described herein.

In certain embodiments, the main body 9202 can be advanced into a joint (e.g., along the joint line. The anchors 9206 can include a first anchor 9206 that can be anchored within the bone on a first side of a joint (e.g., within a sacrum or within a superior articular facet) and a second anchor

9206 that can be anchored within the bone on a second side of a joint (e.g., within an ilium or within an inferior articular facet).

In certain embodiments, the joint implant 9210 can be configured to be inserted with a driver, such as a hex driver, a star driver, a square driver, a torx driver, or any other suitable driver for driving the implant into bone. In some embodiments, the joint implant system 9200 can include an engagement feature 9262 for receiving a driver. In some embodiments, the engagement feature 9262 can be a threaded engagement feature for receiving the threaded end of a driver.

In some examples, the joint implant 9210 can have one or more windows or apertures that can contact the bone or bone graft. For example, in some embodiments, the main body 9202 may have one or more windows or apertures (such as windows 172 as described with respect to FIGS. 86A-86D). In some embodiments, the anchors 9206 can have one or more windows or apertures (such as the windows 178 as described with respect to FIGS. 87A-87C). The windows or apertures (e.g., windows or apertures in the main body 9202 or anchors 9206) may form one or more channels or passages extending through the implant 9210 (such as passage 173 and/or passage 180). The one or more windows or apertures and/or one or more passages can help facilitate fusion of the bone or bone graft. Once the joint implant 9210 is placed in a joint (facet or SI joint), the one or more passages can allow bone to grow through the joint implant 9210 and fuse the joint (e.g. fuse the facets of a facet joint or fuse the sacrum and ilium of an SI joint. The windows can be in the form of a slit, a hole, or other opening formed in the implant 9210.

FIG. 92 shows an embodiment of a driver 9302. The driver 9302 can include any of the same and/or similar features and/or functions as any of the other drivers described herein (e.g., driver 9102).

The driver 9302 can be advanced within a lumen of an inserter body and engage the engagement feature 9262 of the implant system 9200.

FIG. 93A shows an example of an inserter 9400 and a joint implant system 9200. FIG. 93B shows the example of the inserter 9400 engaging the joint implant system 9200 with the implants 9290 being inserted into the inserter 9400 of FIG. 93A. FIG. 93C shows the example of the inserter 9400 engaging the joint implant system 9200 with the implants 9290 fully inserted into the joint implant system 9200 of FIG. 93A.

The inserter 9400 can include any of the same and/or similar features and/or functions as the inserters described herein (e.g., inserter 9100). The inserter 9400 can include an inserter body 9494. The inserter 9400 may also include or receive the driver 9302. In some embodiments, the inserter 9400 can include windows 9496 in the inserter body 9494. The windows 9496 can allow the driver 9302 to be visible as it is inserted through the inserter body 9494.

The inserter 9400 can include channels 9491. The channels 9491 can be positioned near the distal end of the inserter body 9494. The channels 9491 can receive implants 9290 as shown in FIG. 93B. The implants 9290 can be advanced through the channels 9491 and into the channels 9292 of the joint implant 9210. The channels 9491 of the inserter 9400 can be configured to align with channels 9292 of the joint implant 9210 when the joint implant 9210 is coupled to the inserter 9400. The channels 9491 can be orientated at an angle relative to a central axis 9420 of the inserter body 9494. For example, a central axis 9424 (e.g., a longitudinal axis) of the channels 9491 can be orientated at an angle α2 relative to the central axis 9420 of the inserter body 9494 that is the same as or generally similar to the angle α1 of the central axis 9224 of the channels 9292 relative to the central axis 9220 of the joint implant system 9200. In certain embodiments, the central axis 9420 of the inserter 9400 can be collinear with the central axis 9220 of the implant 9210 when the implant 9210 is coupled to the inserter 9400.

In certain embodiments, a distal end of the inserter body 9494 can be configured to engage engagement features on the anchors 9206 of the joint implant 9210. The driver 9302 can be advanced within a lumen of the inserter body 9494 and engage the engagement feature 9262 of the joint implant 9210. The inserter 9400 can be used to drive the joint implant 9210 into a joint (e.g., a facet joint or SI joint), for example via use of a mallet while the joint implant 9210 is coupled to the inserter 9400, so that the main body 9202 is positioned within the joint and the anchors 9206 are positioned within the bone on opposing sides of the joint. After the implant 9210 is driven to a desired location within the joint, one or more of the implants 9290 may be advanced through the joint implant 9210 to provide further fixation within the joint. In some embodiments, the joint implant 9210 may be used without any implants 9290, with a single implant 9290 advanced into the bone on one side of a joint, or with two implants 9290 advanced into the bone on opposing sides of the joint. In some embodiments, the implants 9290 can be advanced through the inserter 9400 and the joint implant 9210 using a driver, such as a hex driver, a star driver, a square driver, a torx driver, or any other suitable driver for driving the implant into bone (such as driver 9300). The driver can engage a complimentary engagement feature 9294 of an implant 9290.

In some embodiments, the implant system 9200 may be countersunk within a joint as described herein.

Although use of the devices has been described with respect to example SI joint and facet joint procedure, the devices described herein can also be used in other procedures or other orthopedic applications to provide stabilization across joints other than the SI and facet joints.

Additional details regarding implants, inserters, rasps, bone graft delivery devices and systems, and related accessories that may be used in the embodiments described herein are described in U.S. patent application U.S. Pat. No. 11,116,647, issued Sep. 14, 2021, and in U.S. patent application Ser. No. 17/882,337, filed Aug. 5, 2022, each of which is incorporated by reference herein in its entirety and for all purposes.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible.

What is claimed is:

1. A sacroiliac joint implant system, comprising:
   a primary implant configured to be received in a sacroiliac joint of a patient; and
   a secondary implant configured to couple with the primary implant, the secondary implant comprising:
     a first anchor configured to be driven within a sacrum of a patient, the first anchor comprising a distal end having an inwardly facing beveled edge, the inwardly facing beveled edge of the first anchor extending distally to an outer face of the first anchor to form a sharp distal tip; and a second anchor configured to be driven within an ilium of the patient, the second anchor comprising a distal end having an inwardly facing beveled edge, the inwardly facing beveled edge of the second anchor extending distally to an outer face of the second anchor to form a sharp distal tip;

wherein the beveled edge of the first anchor and the beveled edge of the second anchor are shaped and positioned to cause compression between the sacrum and the ilium when the first anchor is driven into the sacrum and the second anchor is driven into the ilium, and wherein each of the first anchor and the second anchor comprises a curved wedge that curves radially around the primary implant when the secondary implant is coupled with the primary implant.

2. The system of claim 1, wherein the beveled edge of the first anchor and the beveled edge of the second anchor are each configured to cut bone.

3. The system of claim 1, wherein the curved wedge comprises a plurality of openings configured to facilitate bone ingrowth.

4. The system of claim 3, wherein each of the first anchor and the second anchor comprises a plurality of truss elements, the plurality of truss elements forming the plurality of openings.

5. The system of claim 1, wherein a width of the secondary implant at a proximal end is between 19 mm and 23 mm and a width of the secondary implant at a distal end is between 21.5 mm and 25.5 mm.

6. The system of claim 1, wherein the secondary implant comprises a ring configured to receive a portion of the primary implant, wherein the first anchor and the second anchor are coupled to the ring.

7. The system of claim 6, wherein the secondary implant comprises a plurality of arms extending laterally from the ring, wherein the first anchor extends from a first arm of the plurality of arms, and wherein the second anchor extends from a second arm of the plurality of arms.

8. The system of claim 6, wherein the primary implant comprises a head and a shank extending distally from the head, wherein the head of the primary implant is configured to be positioned radially within the ring of the secondary implant.

9. The system of claim 1, wherein the first anchor and the second anchor are integrally formed with one another.

10. The system of claim 1, wherein the primary implant further comprises:

a body extending from a proximal end to a distal end; and a plurality of engagement features extending from the body.

11. The system of claim 10, wherein the body of the primary implant comprises a head and a shank extending distally from the head.

12. The system of claim 11, wherein the shank of the primary implant comprises a smooth shank section proximal to the plurality of engagement features.

13. The system of claim 11, further comprising:

a first window positioned along the shank;

a second window positioned along the shank; and a first passage extending through the shank between the first window and the second window.

14. The system of claim 13, wherein the first anchor and the second anchor each comprise a passage extending therethrough.

15. The system of claim 14, wherein the passage of the first anchor and the passage of the second anchor are each configured to align with the passage of the primary implant when the primary implant is coupled to the secondary implant.

16. The system of claim 10, wherein the primary implant comprises a plurality of truss elements.

17. The system of claim 10, wherein the primary implant comprises a longitudinal interior channel configured to receive bone graft material.

18. The system of claim 1, wherein each of the inwardly facing beveled edge of the first anchor and the inwardly facing beveled edge of the second anchor have an internal beveled angle of between 20 degrees and 35 degrees, wherein the inwardly facing beveled edge of the first anchor extends at least 10% of a length of the first anchor, and wherein the inwardly facing beveled edge of the second anchor extends at least 10% of a length of the second anchor.

19. A sacroiliac joint implant system, comprising:

a primary implant configured to be received in a sacroiliac joint of a patient; and a secondary implant configured to couple with the primary implant, the secondary implant comprising:

a ring;

a plurality of arms extending laterally from the ring;

a first anchor extending from a first arm of the plurality of arms, wherein the first anchor is configured to be driven within a sacrum of a patient, the first anchor comprising a distal end having an inwardly facing beveled edge, the inwardly facing beveled edge of the first anchor extending distally to an outer face of the first anchor to form a sharp distal tip; and a second anchor extending from a second arm of the plurality of arms, wherein the second anchor is configured to be driven within an ilium of the patient, the second anchor comprising a distal end having an inwardly facing beveled edge, the inwardly facing beveled edge of the second anchor extending distally to an outer face of the second anchor to form a sharp distal tip;

wherein the beveled edge of the first anchor and the beveled edge of the second anchor are shaped and positioned to cause compression between the sacrum and the ilium when the first anchor is driven into the sacrum and the second anchor is driven into the ilium, wherein the primary implant comprises a head and a shank extending distally from the head, wherein a proximal end of the head of the primary implant is configured to be positioned radially within the ring of the secondary implant.

* * * * *